US011147984B2

(12) United States Patent
Emerson et al.

(10) Patent No.: US 11,147,984 B2
(45) Date of Patent: Oct. 19, 2021

(54) ILLUMINATION DEVICES FOR INDUCING BIOLOGICAL EFFECTS

(71) Applicant: KNOW Bio, LLC, Durham, NC (US)

(72) Inventors: David T. Emerson, Durham, NC (US); Michael John Bergmann, Atlanta, GA (US); Thomas Matthew Womble, Wake Forest, NC (US); Antony Paul van de Ven, Nongkae (TH); Nathan Stasko, Chapel Hill, NC (US); F. Neal Hunter, Durham, NC (US); Adam Cockrell, Durham, NC (US); Rebecca McDonald, Chapel Hill, NC (US)

(73) Assignee: KNOW Bio, LLC, Durham, NC (US)

( * ) Notice: Subject to any disclaimer, the term of this patent is extended or adjusted under 35 U.S.C. 154(b) by 0 days.

(21) Appl. No.: 17/117,889

(22) Filed: Dec. 10, 2020

(65) Prior Publication Data
US 2021/0290974 A1    Sep. 23, 2021

Related U.S. Application Data

(60) Provisional application No. 63/123,631, filed on Dec. 10, 2020, provisional application No. 63/075,010, (Continued)

(51) Int. Cl.
*A61N 5/06* (2006.01)
(52) U.S. Cl.
CPC .... *A61N 5/0624* (2013.01); *A61N 2005/0606* (2013.01); *A61N 2005/0632* (2013.01); (Continued)
(58) Field of Classification Search
CPC .......... A61N 5/0624; A61N 2005/0606; A61N 2005/0632; A61N 2005/0644; A61N 2005/0662; A61B 1/32; A61M 29/00
See application file for complete search history.

(56) References Cited

U.S. PATENT DOCUMENTS 2,884,926 A  *  5/1959  Grasso ................. A61N 5/0603
607/92
5,228,431 A     7/1993  Giarretto
(Continued)

FOREIGN PATENT DOCUMENTS

AU      2016100390 A4    7/2016
CN       101687101 A     3/2010
(Continued)

OTHER PUBLICATIONS

Soukos NS, Som S, Abernethy AD, Ruggiero K, Dunham J, Lee C, Doukas AG, Goodson JM. Phototargeting oral black-pigmented bacteria. Antimicrob Agents Chemother. Apr. 2005;49(4):1391-6. doi: 10.1128/AAC.49.4.1391-1396.2005. PMID: 15793117; PMCID : PMC1068628. (Year: 2005).*
(Continued)

*Primary Examiner* — Nathan J Jenness
(74) *Attorney, Agent, or Firm* — Withrow & Terranova, PLLC

(57) ABSTRACT

Illumination devices for impinging light on tissue, for example within a body cavity of a patient, to induce various biological effects are disclosed. Biological effects may include at least one of inactivating and/or inhibiting growth of one or more pathogens, upregulating a local immune response, increasing endogenous stores of nitric oxide, releasing nitric oxide from endogenous stores, and inducing an anti-inflammatory effect. Wavelengths of light are selected based on intended biological effects for one or more of targeted tissue types and targeted pathogens. Light treatments may provide multiple pathogenic biological effects, either with light of a single wavelength or with light having multiple wavelengths. Devices for light treatments are disclosed that provide light doses for inducing biological effects on various targeted pathogens and tissues with increased efficacy and reduced cytotoxicity. Particular illu-
(Continued)

mination devices are disclosed that provide safe and effective treatments for upper respiratory tract infections, including coronaviridae and orthomyxoviridae.

27 Claims, 99 Drawing Sheets

Related U.S. Application Data filed on Sep. 4, 2020, provisional application No. 63/074,970, filed on Sep. 4, 2020, provisional application No. 63/065,357, filed on Aug. 13, 2020, provisional application No. 62/991,903, filed on Mar. 19, 2020.

(52) U.S. Cl.
CPC ................. *A61N 2005/0644* (2013.01); *A61N 2005/0662* (2013.01)

(56) References Cited

U.S. PATENT DOCUMENTS 5,292,346 A * 3/1994 Ceravolo ............ A61M 35/003 600/179
5,549,639 A 8/1996 Ross
5,611,793 A 3/1997 Wilson et al.
5,616,140 A 4/1997 Prescott
5,658,148 A 8/1997 Neuberger et al.
5,683,436 A 11/1997 Mendes et al.
6,026,828 A 2/2000 Altshuler
6,096,066 A 8/2000 Chen et al.
6,171,332 B1 1/2001 Whitehurst
6,201,764 B1 3/2001 Rice et al.
6,211,626 B1 4/2001 Lys et al.
6,244,865 B1 * 6/2001 Nelson .................. A61B 5/097 128/205.29
6,251,127 B1 6/2001 Biel
6,283,956 B1 9/2001 McDaniel
6,290,496 B1 9/2001 Azar et al.
6,290,713 B1 9/2001 Russell
6,379,376 B1 4/2002 Lubart
6,443,978 B1 9/2002 Zharov
6,462,070 B1 10/2002 Hasan et al.
6,491,618 B1 12/2002 Ganz
6,497,719 B2 12/2002 Pearl et al.
6,551,346 B2 4/2003 Crossley
6,561,808 B2 5/2003 Neuberger
6,623,513 B2 9/2003 Biel
6,645,230 B2 11/2003 Whitehurst
6,663,659 B2 12/2003 McDaniel
6,676,655 B2 1/2004 McDaniel
6,887,260 B1 5/2005 McDaniel
6,890,346 B2 5/2005 Ganz et al.
6,902,397 B2 6/2005 Farrell et al.
6,918,922 B2 7/2005 Oron
6,936,044 B2 8/2005 McDaniel
6,955,684 B2 10/2005 Savage, Jr. et al.
6,977,075 B2 12/2005 Hasan et al.
6,989,023 B2 1/2006 Black
7,090,497 B1 8/2006 Harris
7,107,996 B2 9/2006 Ganz et al.
7,144,248 B2 12/2006 Irwin
7,159,590 B2 1/2007 Rife
7,201,764 B2 4/2007 Pearl et al.
7,201,765 B2 4/2007 McDaniel
7,223,270 B2 5/2007 Altshuler et al.
7,223,281 B2 5/2007 Altshuler et al.
7,226,470 B2 6/2007 Kemeny et al.
7,267,673 B2 9/2007 Pilcher et al.
7,303,578 B2 12/2007 De Taboada et al.
7,304,201 B2 12/2007 Holloway et al.
7,309,348 B2 12/2007 Streeter et al.
7,329,273 B2 2/2008 Altshuler et al.
7,329,274 B2 2/2008 Altshuler et al.
7,422,598 B2 9/2008 Altshuler et al.
7,435,252 B2 10/2008 Krespi et al.
7,467,946 B2 12/2008 Rizoiu et al.
7,494,503 B2 2/2009 McDaniel
7,544,204 B2 6/2009 Krespi et al.
D599,954 S 9/2009 Michaels et al.
7,763,058 B2 7/2010 Sterenborg et al.
D631,604 S 1/2011 Michaels et al.
D635,686 S 4/2011 Tucker et al.
7,918,229 B2 4/2011 Cumbie et al.
7,950,396 B2 5/2011 Rose et al.
D639,751 S 6/2011 Tucker et al.
D640,793 S 6/2011 Britt
8,021,148 B2 9/2011 Goodson et al.
8,021,405 B2 9/2011 White
8,025,686 B2 9/2011 Morgan
8,029,278 B1 10/2011 Levine
8,053,977 B2 11/2011 Lifka et al.
8,088,122 B2 1/2012 Li et al.
8,109,981 B2 2/2012 Gertner et al.
8,146,607 B2 4/2012 Rabin et al.
8,186,997 B2 5/2012 Binner et al.
8,192,473 B2 6/2012 Tucker et al.
8,214,958 B2 7/2012 Pinyayev et al.
8,240,312 B2 8/2012 Feuerstein et al.
8,252,033 B2 8/2012 Tucker et al.
8,398,264 B2 3/2013 Anderson et al.
8,435,273 B2 5/2013 Lum et al.
8,486,123 B2 7/2013 Vizethum et al.
8,518,029 B2 8/2013 Birmingham et al.
8,535,361 B2 9/2013 Lim et al.
8,556,951 B2 10/2013 Witt et al.
8,641,702 B2 2/2014 Pilcher et al.
8,651,111 B2 2/2014 McDaniel
8,668,727 B2 3/2014 Natale et al.
8,684,577 B2 * 4/2014 Vayser .................. A61B 1/303 362/573
8,685,466 B2 4/2014 Piergallini et al.
8,690,933 B2 4/2014 Mitchell
8,710,460 B2 4/2014 Dayton
8,721,696 B2 5/2014 Krespi et al.
8,747,446 B2 6/2014 Chen et al.
8,758,215 B2 6/2014 Legendre et al.
8,771,327 B2 7/2014 Pearl et al.
8,790,381 B2 7/2014 Pierce
8,815,931 B2 8/2014 Grafe et al.
D712,561 S 9/2014 Hagenauer
8,838,228 B2 9/2014 Beisang, III et al.
8,845,704 B2 9/2014 Dunning et al.
D716,493 S 10/2014 Michaels et al.
8,858,607 B1 10/2014 Jones
8,900,282 B2 12/2014 Brawn
8,900,283 B2 12/2014 Johnson et al.
8,940,775 B2 1/2015 Fedele et al.
9,017,391 B2 4/2015 McDaniel
9,039,966 B2 5/2015 Anderson et al.
9,040,103 B2 5/2015 Marrot et al.
9,095,704 B2 8/2015 McGuire
9,132,279 B2 9/2015 Roersma et al.
9,144,690 B2 9/2015 McDaniel
9,149,348 B2 10/2015 Wu et al.
9,162,001 B2 10/2015 Sunkara et al.
9,192,780 B2 11/2015 McDaniel
9,198,502 B2 12/2015 Barnes et al.
9,211,420 B2 12/2015 Patel et al.
9,215,921 B2 12/2015 Thiebaut et al.
9,227,082 B2 1/2016 McDaniel
D754,897 S 4/2016 Michaels et al.
9,308,389 B2 4/2016 Brawn
9,333,274 B2 5/2016 Peterson et al.
9,415,237 B2 8/2016 Wagenaar Cacciola et al.
9,439,989 B2 9/2016 Lalicki et al.
9,474,811 B2 10/2016 Sharma
9,504,752 B2 11/2016 Kanno et al.
9,504,847 B2 11/2016 Pryor et al.
D777,339 S 1/2017 Chen
9,545,524 B2 1/2017 Maass et al.
9,554,963 B2 1/2017 Pilcher et al.

(56) References Cited

U.S. PATENT DOCUMENTS

| | | |
|---|---|---|
| 9,561,077 B2 | 2/2017 | Alfano |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,700,641 B2 | 7/2017 | Hawkins et al. |
| 9,724,536 B1 | 8/2017 | Rabin et al. |
| 9,730,780 B2 | 8/2017 | Brawn et al. |
| 9,744,375 B2 | 8/2017 | Oberreiter et al. |
| D804,047 S | 11/2017 | Michaels et al. |
| 9,808,646 B2 | 11/2017 | Piergallini et al. |
| 9,808,647 B2 | 11/2017 | Rhodes et al. |
| 9,907,976 B2 | 3/2018 | Bourke, Jr. et al. |
| 9,913,994 B2 | 3/2018 | Marchese et al. |
| 10,010,718 B2 | 7/2018 | Basiony |
| 10,258,442 B2 | 4/2019 | Snyder et al. |
| 10,272,262 B2 | 4/2019 | Bourke, Jr. et al. |
| 10,328,276 B2 | 6/2019 | Williams et al. |
| 10,357,661 B2 | 7/2019 | Hellstrom et al. |
| 10,406,379 B2 | 9/2019 | Sentis et al. |
| 10,416,366 B2 | 9/2019 | Rose et al. |
| 10,525,275 B2 | 1/2020 | Stasko et al. |
| 10,561,854 B2 | 2/2020 | Kim et al. |
| 10,569,097 B2 | 2/2020 | Medendorp, Jr. et al. |
| 10,639,498 B2 | 5/2020 | Enwemeka et al. |
| 10,682,203 B2 | 6/2020 | Vazales |
| 10,729,524 B2 | 8/2020 | Brawn et al. |
| 10,780,189 B2 | 9/2020 | Randers-Pehrson et al. |
| 2002/0128648 A1 | 9/2002 | Weber et al. |
| 2003/0076281 A1 | 4/2003 | Morgan et al. |
| 2003/0130709 A1 | 7/2003 | D.C. et al. |
| 2003/0167080 A1 | 9/2003 | Hart et al. |
| 2003/0236487 A1 | 12/2003 | Knowlton |
| 2004/0044384 A1 | 3/2004 | Leber et al. |
| 2004/0052798 A1 | 3/2004 | Neuberger |
| 2004/0073079 A1 | 4/2004 | Altshuler et al. |
| 2004/0073278 A1 | 4/2004 | Pachys |
| 2004/0162596 A1 | 8/2004 | Altshuler et al. |
| 2004/0193235 A1 | 9/2004 | Altshuler et al. |
| 2004/0199227 A1 | 10/2004 | Altshuler et al. |
| 2005/0045189 A1 | 3/2005 | Jay |
| 2005/0055070 A1 | 3/2005 | Jones et al. |
| 2005/0059731 A1 | 3/2005 | Albrecht et al. |
| 2005/0064371 A1* | 3/2005 | Soukos ............... A61N 5/0601 433/217.1 |
| 2005/0256553 A1 | 11/2005 | Strisower |
| 2006/0019220 A1 | 1/2006 | Loebel et al. |
| 2006/0085052 A1 | 4/2006 | Feuerstein et al. |
| 2006/0093561 A1 | 5/2006 | Kennedy |
| 2006/0183071 A1 | 8/2006 | Hsueh |
| 2006/0194164 A1 | 8/2006 | Altshuler et al. |
| 2006/0258896 A1 | 11/2006 | Haber et al. |
| 2006/0287696 A1 | 12/2006 | Wright et al. |
| 2007/0038272 A1 | 2/2007 | Liu |
| 2007/0060819 A1 | 3/2007 | Altshuler et al. |
| 2007/0099154 A1 | 5/2007 | Johnson |
| 2007/0105063 A1 | 5/2007 | Pinyayev et al. |
| 2007/0106856 A1 | 5/2007 | Nomura et al. |
| 2007/0135874 A1 | 6/2007 | Bala |
| 2007/0185553 A1 | 8/2007 | Kennedy |
| 2007/0208396 A1 | 9/2007 | Whatcott et al. |
| 2007/0213792 A1 | 9/2007 | Yaroslavsky et al. |
| 2007/0233208 A1 | 10/2007 | Kurtz et al. |
| 2007/0260231 A1 | 11/2007 | Rose et al. |
| 2008/0021370 A1 | 1/2008 | Bornstein |
| 2008/0032252 A1* | 2/2008 | Hayman ............... A61B 5/0088 433/29 |
| 2008/0033516 A1 | 2/2008 | Altshuler et al. |
| 2008/0038685 A1 | 2/2008 | Sakaguchi et al. |
| 2008/0065175 A1 | 3/2008 | Redmond et al. |
| 2008/0096156 A1* | 4/2008 | Rose ............... A61C 1/0015 433/29 |
| 2008/0097414 A1* | 4/2008 | Li .................. A61N 5/0603 606/3 |
| 2008/0161748 A1 | 7/2008 | Tolkoff et al. |
| 2008/0214530 A1 | 9/2008 | Colles |
| 2008/0254405 A1 | 10/2008 | Montgomery et al. |
| 2008/0269849 A1 | 10/2008 | Lewis |
| 2008/0280260 A1* | 11/2008 | Belikov ............... A61C 3/00 433/215 |
| 2008/0319430 A1 | 12/2008 | Zenzie et al. |
| 2009/0035725 A1 | 2/2009 | Loebel et al. |
| 2009/0093865 A1 | 4/2009 | Krespi et al. |
| 2009/0132011 A1 | 5/2009 | Altshuler et al. |
| 2009/0143842 A1 | 6/2009 | Cumbie et al. |
| 2009/0148808 A1 | 6/2009 | Alexander et al. |
| 2009/0254156 A1 | 10/2009 | Powell et al. |
| 2009/0318802 A1 | 12/2009 | Boyden et al. |
| 2010/0004645 A1 | 1/2010 | Jeong et al. |
| 2010/0042040 A1 | 2/2010 | Arentz |
| 2010/0049180 A1 | 2/2010 | Wells et al. |
| 2010/0076526 A1 | 3/2010 | Krespi et al. |
| 2010/0076529 A1 | 3/2010 | Tucker et al. |
| 2010/0106077 A1 | 4/2010 | Rabin et al. |
| 2010/0121131 A1 | 5/2010 | Mathes |
| 2010/0136646 A1 | 6/2010 | Tsen et al. |
| 2010/0204762 A1 | 8/2010 | De Taboada et al. |
| 2010/0222852 A1 | 9/2010 | Vasily et al. |
| 2010/0242155 A1 | 9/2010 | Carullo, Jr. |
| 2010/0331928 A1 | 12/2010 | Dunning et al. |
| 2011/0015707 A1 | 1/2011 | Tucker et al. |
| 2011/0020173 A1 | 1/2011 | Pryor et al. |
| 2011/0054573 A1 | 3/2011 | Mitchell |
| 2011/0054574 A1 | 3/2011 | Felix |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0162155 A1 | 7/2011 | Wai |
| 2011/0215261 A1 | 9/2011 | Lyslo et al. |
| 2011/0264174 A1 | 10/2011 | McNeill et al. |
| 2011/0301673 A1 | 12/2011 | Hoffer et al. |
| 2012/0045738 A1* | 2/2012 | Ho ................. A61N 5/0603 433/215 |
| 2012/0059440 A1 | 3/2012 | Hamid |
| 2012/0065709 A1 | 3/2012 | Dunning et al. |
| 2012/0096657 A1 | 4/2012 | So et al. |
| 2012/0126134 A1 | 5/2012 | Deal et al. |
| 2012/0223216 A1 | 9/2012 | Flaherty et al. |
| 2012/0263625 A1 | 10/2012 | Aicher et al. |
| 2012/0270183 A1 | 10/2012 | Patel et al. |
| 2012/0310307 A1 | 12/2012 | Zhou |
| 2013/0041432 A1 | 2/2013 | Tucker et al. |
| 2013/0131762 A1 | 5/2013 | Oversluizen et al. |
| 2013/0144364 A1 | 6/2013 | Wagenaar Cacciola et al. |
| 2013/0158358 A1 | 6/2013 | Holland |
| 2013/0196284 A1 | 8/2013 | Brawn |
| 2014/0128941 A1 | 5/2014 | Williams |
| 2014/0128942 A1 | 5/2014 | Bembridge et al. |
| 2014/0148879 A1 | 5/2014 | Mersch |
| 2014/0163218 A1 | 6/2014 | Dei et al. |
| 2014/0171926 A1 | 6/2014 | Depfenhart |
| 2014/0243933 A1 | 8/2014 | Ginggen |
| 2014/0276247 A1 | 9/2014 | Hall et al. |
| 2014/0276248 A1 | 9/2014 | Hall et al. |
| 2014/0296524 A1 | 10/2014 | Jones et al. |
| 2014/0303693 A1 | 10/2014 | Haarlander et al. |
| 2014/0350643 A1 | 11/2014 | Pepitone et al. |
| 2015/0005854 A1 | 1/2015 | Said |
| 2015/0030989 A1 | 1/2015 | Soukos et al. |
| 2015/0045720 A1 | 2/2015 | Kanno et al. |
| 2015/0112411 A1 | 4/2015 | Beckman et al. |
| 2015/0164618 A1* | 6/2015 | Heacock ............... A61C 7/08 433/6 |
| 2015/0297914 A1 | 10/2015 | Hamid et al. |
| 2016/0000214 A1 | 1/2016 | Kim |
| 2016/0015840 A1 | 1/2016 | Gordon |
| 2016/0039854 A1 | 2/2016 | McFarland |
| 2016/0051835 A1 | 2/2016 | Tapper et al. |
| 2016/0059031 A1 | 3/2016 | Wescott et al. |
| 2016/0106999 A1 | 4/2016 | Michaels et al. |
| 2016/0114185 A1 | 4/2016 | Mankin |
| 2016/0129278 A1 | 5/2016 | Mayer |
| 2016/0151639 A1 | 6/2016 | Scharf et al. |
| 2016/0271415 A1* | 9/2016 | Min ................. A61C 19/066 |
| 2016/0271420 A1 | 9/2016 | Pina |

(56) References Cited

U.S. PATENT DOCUMENTS

| | | | |
|---|---|---|---|
| 2016/0317832 A1 | 11/2016 | Barneck et al. | |
| 2017/0027432 A1* | 2/2017 | Wachs | A61B 1/24 |
| 2017/0028215 A1 | 2/2017 | Medendorp, Jr. et al. | |
| 2017/0028216 A1 | 2/2017 | Medendorp, Jr. et al. | |
| 2017/0165499 A1 | 6/2017 | Blanche et al. | |
| 2017/0173358 A1 | 6/2017 | Demarest et al. | |
| 2017/0224206 A1 | 8/2017 | Vayser | |
| 2017/0225011 A1* | 8/2017 | Frost | A61N 5/062 |
| 2017/0290648 A1 | 10/2017 | Kuo | |
| 2017/0333728 A1* | 11/2017 | Sentis | A61N 5/0603 |
| 2018/0036554 A1 | 2/2018 | Krespi | |
| 2018/0146520 A1 | 5/2018 | Williams | |
| 2018/0256916 A1* | 9/2018 | Kothari | A61N 5/0603 |
| 2018/0264282 A1 | 9/2018 | Bornstein | |
| 2018/0289940 A1 | 10/2018 | Spotnitz et al. | |
| 2019/0014901 A1 | 1/2019 | Xi et al. | |
| 2019/0124888 A1 | 5/2019 | Coyle | |
| 2019/0134419 A1 | 5/2019 | Bourke, Jr. et al. | |
| 2019/0142516 A1 | 5/2019 | Boutoussov et al. | |
| 2019/0175938 A1 | 6/2019 | Rezaie et al. | |
| 2019/0201711 A1 | 7/2019 | Brawn et al. | |
| 2019/0209857 A1 | 7/2019 | Brawn et al. | |
| 2020/0101315 A1 | 4/2020 | Reinhardt | |
| 2020/0114171 A1 | 4/2020 | Tortora | |
| 2020/0155350 A1 | 5/2020 | Neev | |
| 2020/0222714 A1 | 7/2020 | Stasko et al. | |
| 2020/0298014 A1 | 9/2020 | Stasko et al. | |
| 2020/0298016 A1 | 9/2020 | Yoon et al. | |
| 2020/0353112 A1 | 11/2020 | Randers-Pehrson et al. | |
| 2020/0360124 A1* | 11/2020 | Woo | A61C 19/06 |
| 2021/0008384 A1* | 1/2021 | Lee | A61N 5/062 |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 102731405 A | 10/2012 |
| CN | 102802694 A | 11/2012 |
| CN | 103143015 A | 6/2013 |
| CN | 203169848 U | 9/2013 |
| CN | 103601727 A | 2/2014 |
| CN | 103610464 A | 3/2014 |
| CN | 103724356 A | 4/2014 |
| CN | 103930162 A | 7/2014 |
| DE | 102010010763 A1 | 9/2011 |
| DE | 102013202122 A1 | 6/2014 |
| DE | 102012224183 A1 | 7/2014 |
| EP | 2508229 A1 | 10/2012 |
| EP | 3069762 A1 | 9/2016 |
| EP | 3108931 A1 | 12/2016 |
| GB | 2499921 A | 9/2013 |
| KR | 20100124083 A | 11/2010 |
| KR | 20120090317 A | 8/2012 |
| KR | 20140014689 A | 2/2014 |
| WO | 1995010243 A1 | 4/1995 |
| WO | 2004033040 A1 | 4/2004 |
| WO | 2004084752 A2 | 10/2004 |
| WO | 2006047868 A1 | 5/2006 |
| WO | 2006063318 A1 | 6/2006 |
| WO | 2008024414 A1 | 2/2008 |
| WO | 2008041296 A1 | 4/2008 |
| WO | 2008051918 A2 | 5/2008 |
| WO | 2008066943 A2 | 6/2008 |
| WO | 2008131343 A1 | 10/2008 |
| WO | 2008144157 A1 | 11/2008 |
| WO | 2009047669 A2 | 4/2009 |
| WO | 2010098761 A1 | 9/2010 |
| WO | 2011083378 A1 | 7/2011 |
| WO | 2011083381 A1 | 7/2011 |
| WO | 2012001194 A1 | 1/2012 |
| WO | 2013036558 A1 | 3/2013 |
| WO | 2014021557 A1 | 2/2014 |
| WO | 2014089552 A1 | 6/2014 |
| WO | 2014116659 A1 | 7/2014 |
| WO | 2014136255 A1 | 9/2014 |
| WO | 2014146029 A1 | 9/2014 |
| WO | 2015006309 A1 | 1/2015 |
| WO | 2015134204 A1 | 9/2015 |
| WO | 2016039812 A1 | 3/2016 |
| WO | 2016078603 A1 | 5/2016 |
| WO | 2016081594 A1 | 5/2016 |
| WO | 2016116859 A1 | 7/2016 |
| WO | 2016178472 A1 | 11/2016 |
| WO | 2017019836 A1 | 2/2017 |
| WO | 2017044931 A1 | 3/2017 |
| WO | 2017070155 A1 | 4/2017 |
| WO | 2018026892 A1 | 2/2018 |
| WO | 2019022275 A1 | 1/2019 |
| WO | 2019127427 A1 | 7/2019 |
| WO | 2019145519 A1 | 8/2019 |
| WO | 2019156921 A1 | 8/2019 |
| WO | 2019191820 A1 | 10/2019 |
| WO | 2019234308 A1 | 12/2019 |
| WO | 2020047659 A1 | 3/2020 |
| WO | 2020081910 A1 | 4/2020 |

OTHER PUBLICATIONS

Internet webpage: https://www.facebook.com/medicsblu/ dated Oct. 1, 2020 (retrieved on Apr. 23, 2021) (Year: 2020).*

Internet webpage: https://www.youtube.com/watch?v=5Xq_KGI_djA dated Sep. 16, 2020 (retrieved on Apr. 26, 2021) (Year: 2020).*

Ahmed, Imran, et al., "Recent Patents on Light-Based Anti-Infective Approaches," Author Manuscript, Recent Patents on Anti-Infective Drug Discovery, vol. 13, Issue 1, 2018, 28 pages.

Akaberi, Dario, et al., "Mitigation of the replication of SARS-CoV-2 by nitric oxide in vitro," Redox Biology, vol. 37, Sep. 21, 2020, Elsevier B.V., 5 pages.

Author Unknown, "Assessing COVID-19-Related Symptoms in Outpatient Adult and Adolescent Subjects in Clinical Trials of Drugs and Biological Products for Covid-19 Prevention or Treatment," Guidance for Industry, US Department of Health and Human Services, Sep. 2020, 14 pages.

Baric, Ralph, "Emergence of a Highly Fit SARS-CoV-2 Variant," New England Journal of Medicine, vol. 383, Issue 27, Dec. 31, 2020, pp. 2684-2686.

Fajnzylber, Jesse, et al., "SARS-CoV-2 viral load is associated with increased disease severity and mortality," Nature Communications, vol. 11, Issue 1, Oct. 30, 2020, 9 pages.

Hamblin, Michael, "Mechanisms and Mitochondrial Redox Signaling in Photobiomodulation," Author Manuscript, Photochemistry and Photobiology, vol. 94, Issue 2, Mar. 2018, 31 pages.

Huang, NI, et al., "Integrated Single-Cell Atlases Reveal an Oral SARS-CoV-2 Infection and Transmission Axis," medrXiv, Oct. 29, 2020, 22 pages.

Kim, Peter, et al., "Therapy for Early COVID-19: A Critical Need," JAMA, vol. 324, Issue 21, Nov. 11, 2020, American Medical Association, pp. 2149-2150.

Quirk, Brendan, et al., "What Lies at the Heart of Photobiomodulation: Light, Cytochrome C Oxidase, and Nitric Oxide—Review of the Evidence," Photobiomodulation, Photomedicine, and Laser Surgery, vol. 38, Issue 9, Jul. 2020, pp. 527-530.

To, KK, et al., "Temporal profiles of viral load in posterior oropharyngeal saliva samples and serum antibody responses during infection by SARS-CoV-2: an observational cohort study," Lancet Infectious Diseases, vol. 20, Issue 5, Mar. 23, 2020, 11 pages.

Wyllie, Anne, et al., "Saliva or nasopharyngeal swab specimens for detection of SARS-Cov-2," New England Journal of Medicine, vol. 383, Issue 13, Sep. 24, 2020, 4 pages.

Xu, Hao, et al., "High expression of ACE2 receptor of 2019-nCoV on the epithelial cells of oral mucosa," International Journal of Oral Science, vol. 12, Issue 8, Feb. 24, 2020, 5 pages.

Zein, Randa, et al., "Review of light parameters and photobiomodulation efficacy: dive into complexity," Journal of Biomedical Optics, vol. 23, Issue 12, Dec. 2018, 17 pages.

Zupin, Luisa, et al., "Antiviral properties of blue laser in an in vitro model of HSV-1 infection," Microbial Immunal, Letter to the Editor, vol. 62, 2018, pp. 477-479.

(56) References Cited

OTHER PUBLICATIONS

Zupin, Luisa, et al., "Photobiomodulation therapy reduces viral load and cell death in ZIKV-infected glioblastoma cell line," Lasers in Medical Science, vol. 33, Jul. 2018, Springer Nature, pp. 2011-2013.
International Search Report and Written Opinion for PCT/US2016/044400, dated Oct. 4, 2016, 8 pages.
International Preliminary Report on Patentability for PCT/US2016/044400, dated Feb. 8, 2018, 7 pages.
Non-Final Office Action for U.S. Appl. No. 15/222,199, dated Jan. 11, 2019, 9 pages.
Non-Final Office Action for U.S. Appl. No. 15/222,243, dated Jan. 11, 2019, 10 pages.
International Preliminary Report on Patentability for PCT/US2016/044403, dated Feb. 8, 2018, 7 pages.
Final Office Action for U.S. Appl. No. 15/222,199, dated Jul. 29, 2019, 9 pages.
Notice of Allowance and Applicant-Initiated Interview Summary for U.S. Appl. No. 15/222,199, dated Sep. 18, 2019, 11 pages.
Final Office Action for U.S. Appl. No. 15/222,243, dated Jul. 29, 2019, 12 pages.
Notice of Allowance and Applicant-Initiated Interview Summary for U.S. Appl. No. 15/222,243, dated Dec. 19, 2019, 11 pages.
Non-Final Office Action for U.S. Appl. No. 16/709,550, dated Apr. 30, 2020, 13 pages.
Hamblin, Michael, "Mechanisms of Low Level Light Therapy," Aug. 14, 2008, 22 pages, photobiology.info/Hamblin.html.
Hamblin, Michael R., "The Role of Nitric Oxide in Low Level Light Therapy," Proceedings of SPIE, vol. 6846, 2008, pp. 684602-1 to 684602-14.
Hessling, Martin, et al., "Selection of parameters for thermal coronavirus inactivation—a data-based recommendation," GMS Hygiene and Infection Control, vol. 15, 2020, 7 pages.
Horby, Peter, et al., "Dexamethasone in Hospitalized Patients with Covid-19—Preliminary Report," New England Journal of Medicine, Jul. 17, 2020, 11 pages.
Jackson, George, et al., "Prevalidation of an Acute Inhalation Toxicity Test Using the EpiAirway In Vitro Human Airway Model," Applied In Vitro Toxicology, vol. 4, Issue 2, 2018, Mary Ann Liebert, Inc., pp. 149-158.
Jensen, Caleb, et al., "Is it Time to Start Transitioning From 2D to 3D Cell Culture," Frontiers in Molecular Biosciences, Review, vol. 7, Mar. 2020, 15 pages.
Jin, Jin, et al., "Noncanonical NF-KB Pathway Controls the Production of Type I Interferons in Antiviral Innate Immunity," Immunity, vol. 40, Mar. 2014, Elsevier Inc., pp. 342-354.
Karu, Tiina I., "Low-Power Laser Therapy," Biomedical Photonics Handbook, Chapter 48, CRC Press, 2003, pp. 48-1 to 48-25.
Kelm, Malte, "Nitric oxide metabolism and breakdown," Review, Biochimica et Biophysica Acta, vol. 1411, 1999, Elsevier Science B.V., pp. 273-289.
Kingsley, David, et al., "Oxygen-dependent laser inactivation of murine norovirus using visible light lasers," Virology Journal, Jul. 31, 2018, 8 pages.
Kirima, Kazuyoshi et al., "Evaluation of systemic blood number dynamics by EPR spectroscopy: HbNO as an endogenous index of NO," American Journal of Physiology Heart and Circulatory Physiology, vol. 285, No. 2, Aug. 2003, pp. H589-H596.
Kitchel, Elaine, "The Effects of Blue Light on Ocular Health," Journal of Visual Impairment and Blindness, Jun. 2000, AFB, pp. 399-403.
Klein, Eili, et al., "The frequency of influenza and bacterial coinfection: a systematic review and meta-analysis," Influenza and Other Respiratory Viruses, vol. 10, Issue 5, May 2016, John Wiley & Sons Ltd., pp. 394-403.
Kovacs, Izabella et al., "Nitric oxide-based protein modification: formation and site-specificity of protein S-nitrosylation," Frontiers in Plant Science, vol. 4, Article 137, May 14, 2013, 10 pages.

Leong, Mimi, "Effects of Light-Emitting Diode Photostimulation on Burn Wound Healing," Thesis, The University of Texas Graduate School of Biomedical Sciences at Galveston, May 2006, 92 pages.
Li, Jie, et al., "Involvement of the Toll-Like Receptor/Nitric Oxide Signaling Pathway in the Pathogenesis of Cervical Cancer Caused by High-Risk Human Papillomavirus Infection," Biomed Research International, 2017, Hindawi, 9 pages.
Lubart, et al., "A Possible Mechanism for the Bactericidal Effect of Visible Light," Review Article, Laser Therapy, vol. 20, 2011, pp. 17-22.
Mandel, Arkady, et al., "A renaissance in low-level laser (light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Marullo, Rosella, et al., "HPV16 E6 and E7 proteins induce a chronic oxidative stress response via NOX2 that causes genomic instability and increased susceptibility to DNA damage in head and neck cancer cells," Carcinogenesis, vol. 36, Issue 11, 2015, Oxford University Press, pp. 1397-1406.
Moseley, Harry, et al., "Population reference intervals for minimal erythemal doses in monochromator phototesting," Photodermatology, Photoimmunology & Photomedicine, vol. 25, 2009, pp. 8-11.
Narita, Kouji, et al., "Chronic irradiation with 222-nm UVC light induces neither DNA damage nor epidermal lesions in mouse skin, even at high doses," Research Article, PLOS One, doi.org/10.1371/journal.pone.0201259, Jul. 25, 2018, 9 pages.
Narita, Kouji, et al., "Disinfection and healing effects of 222-nm UVC light on methicillin-resistant *Staphylococcus aureus* infection in mouse wounds," Dissertation, Hirosaki University Graduate School of Medicine, 2017, Elsevier, 36 pages.
Narita, Kouji, et al., "Ultraviolet C light with wavelength of 222 nm inactivates a wide spectrum of microbial pathogens," Journal of Hospital Infection, vol. 105, Mar. 31, 2020, Elsevier Ltd., pp. 459-467.
Perdiz, Daniel, et al., "Distribution and Repair of Bipyrimidine Photoproducts in Solar UV-irradiated Mammalian Cells," Journal of Biological Chemistry, vol. 275, Issue 35, Sep. 2000, pp. 26732-26742.
Pfeifer, Gerd, et al., "UV wavelength-dependent DNA damage and human non-melanoma and melanoma skin cancer," Author Manuscript, Journal of Photochemistry and Photobiology, vol. 11, Issue 1, Jan. 2012, 14 pages.
Phurrough, Steve et al., "Decision Memo for Infrared Therapy Devices (CAG-00291N)," Centers for Medicare & Medicaid Services, Oct. 24, 2006, 37 pages.
Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.
Ramakrishnan, Praveen, et al., "Cytotoxic responses to 405 nm light exposure in mammalian and bacterial cells: Involvement of reactive oxygen species," Toxicology in Vitro, vol. 33, Feb. 2016, Elsevier B.V., pp. 54-62.
Ravanant, Jean-Luc, et al., "Direct and indirect effects of UV radiation on DNA and its components," Journal of Photochemistry and Photobiology, vol. 63, 2001, pp. 88-102.
Richardson, Tobias, et al., "Inactivation of murine leukaemia virus by exposure to visible light," Virology, vol. 341, 2005, Elsevier Inc., pp. 321-329.
Sabino, Caetano, et al., "Light-based technologies for management of COVID-19 pandemic crisis," Journal of Photochemistry and Photobiology, Aug. 2020, Elsevier B.V., 8 pages.
Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.
Saura, Marta, et al., "An Antiviral Mechanism of Nitric Oxide: Inhibition of a Viral Protease," Immunity, vol. 10, Jan. 1999, Cell Press, 8 pages.
Serrage, Hannah, et al., "Under the spotlight: mechanisms of photobiomodulation concentrating on blue and green light," Photochemical and Photobiological Sciences, Jun. 2019, 43 pages.

(56) References Cited

OTHER PUBLICATIONS

St. Denis, Tyler, et al., "Killing Bacterial Spores with Blue Light: When Innate Resistance Meets the Power of Light," Photochemistry and Photobiology, vol. 89, Issue 1, Sep. 2012, Wiley Preiodicals, Inc., 7 pages.
Tomb, Rachael, et al., "Inactivation of Streptomyces phage φC31 by 405 nm light," Bacteriophage, vol. 4, Jul. 2014, Landes Bioscience, 7 pages.
Tomb, Rachael, et al., "New Proof-of-Concept in Viral Inactivation: Virucidal Efficacy of 405 nm Light Against Feline Calicivirus as a Model for Norovirus Decontamination," Food Environ Virol, Dec. 2016, pp. 159-167.
Tomoroni, et al., "A Novel Laser Fiberscope for Simultaneous Imaging and Phototherapy of Peripheral Lung Cancer," Chest, vol. 156, Issue 3, Sep. 2019, 8 pages.
Tsen, KT, et al., "Inactivation of viruses by coherent excitations with a low power visible femtosecond laser," Virology Journal, Jun. 2007, BioMed Central Ltd., 5 pages.
Tsen, Shaw-Wei, et al., "Chemical-free inactivated whole influenza virus vaccine prepared by ultrashort pulsed laser treatment," Journal of Biomedical Optics, vol. 20, Issue 5, May 2015, 8 pages.
Tsen, Shaw-Wei, et al., "Inactivation of enveloped virus by laser-driven protein aggregation," Journal of Biomedical Optics, vol. 17, Issue 12, Dec. 2012, 8 pages.
Tsen, Shaw-Wei, "Pathogen Reduction in Human Plasma Using an Ultrashort Pulsed Laser," PLOS One, vol. 9, Issue 11, Nov. 2014, 8 pages.
Tsen, Shaw-Wei, et al., "Prospects for a novel ultrashort pulsed laser technology for pathogen inactivation," Journal of Biomedical Science, Jul. 2012, 11 pages.
Tsen, Shaw-Wei, et al., "Studies of inactivation mechanism of non-enveloped icosahedral virus by a visible ultrashort pulsed laser," Virology Journal, vol. 11, Issue 20, Feb. 2014, BioMed Central Ltd., 9 pages.
Vatansever, Fatma, et al., "Antimicrobial strategies centered around reactive oxygen species—bactericidal antibiotics, photodynamic therapy, and beyond," FEMS Microbiology Reviews, vol. 37, Issue 6, 2013, pp. 955-989.
Wei, Xue-Min, et al., "Relationship between nitric oxide in cervical microenvironment and different HPV types and effect on cervical cancer cells," Zhonghua Fu Chan Ke Za Zhi, vol. 46, Issue 4, Apr. 2011, pp. 260-265 (Abstract Only).
Williams, Vonetta, et al., "Human Papillomavirus Type 16 E6* Induces Oxidative Stress and DNA Damage," Journal of Virology, vol. 88, Issue 12, Jun. 2014, pp. 6751-6761.
Willoughby, Jamin, "Predicting Respiratory Toxicity Using a Human 3D Airway (EpiAirway) Model Combined with Multiple Parametric Analysis," Applied In Vitro Toxicology, vol. 1, Issue 1, 2015, pp. 55-65.
Wolf, Yuri, et al., "Origins and Evolution of the Global RNA Virome," mBio, vol. 9, Issue 6, Nov. 2018, 31 pages.
Abeyakirthi, Sharnika, "Nitric oxide," DermNet NZ, 2009, 4 pages, www.dermnetnz.org/topics/nitric-oxide/.
Adamskaya, Natalia et al., "Light therapy by blue LED improves wound healing in an excision model in rats," Injury, 2010, 5 pages.
Adusumilli, Nagasai, et al., "Harnessing nitric oxide for preventing, limiting and treating the severe pulmonary consequences of COVID-19," Nitric Oxide, vol. 103, Jul. 2020, Elsevier Inc., 5 pages.
Akerstrom, Sara, et al., "Nitric Oxide Inhibits the Replication Cycle of Severe Acute Respiratory Syndrome Coronavirus," Journal of Virology, vol. 79, Issue 3, Feb. 2005, pp. 1966-1969.
Akerstrom, Sara, et al., "Dual effect of nitric oxide on SARS-CoV replication: Viral RNA production and palmitoylation of the S protein are affected," Virology, vol. 395, Oct. 2009, Elsevier Inc., 9 pages.
Andrew, Penelope J. et al., "Enzymatic function of nitric oxide synthases," Cardiovascular Research, vol. 43, No. 3, Aug. 15, 1999, pp. 521-531.
Author Unknown, "Brilliant Light Therapy," In Light Wellness Systems, eBrochure, Date Unknown, 5 pages.

Author Unkown, "dpl Oral Care—For Healthy Teeth & Gums," Product Brief, Revive Light Therapy, revivelighttherapy.com/product/dpl-oral-care-light-therapy-system-teeth-whitening/, accessed Jan. 31, 2021, 5 pages.
Author Unknown, "Healed by Light," Digi-Key Electronics, Jul. 1, 2014, 4 pages, www.digikey.com/es/articles/techzone/2014/jul/healed-by-light.
Author Unknown, "illuMask," La Lumière, Date Unknown, 2 pages, http://www.illumask.com/dimming/.
Author Unknown, "IPL Hair Removal," Spectrum Science & Beauty, Spectrum Blog, Sep. 16, 2014, 3 pages, www.spectrumsciencebeauty.com.au/ipl-hair-removal/#prettyPhoto.
Author Unknown, "Near—IR Photoluminescent Dyes for Molecular Labeling," NanoQuantum, Technology, 2013, 7 pages, www.nanoquantum.com/Technology.html.
Author Unknown, "Safety and Efficacy of UVC to Fight Covid-19," Gilbert W. Beebe Webinar Series, Program Agenda, Sep. 16, 2020, 6 pages.
Author Unknown, "Theradome Laser Helmet Review—A 120 Day Continuous Journal," Prevent Hair Loss Products, Jan. 14, 2014, retrieved Jun. 27, 2017, web.archive.org/web/20140610024017/http://preventhairlossproducts.com:80/theradome-laser-helmet-review-120-day-continuous-journal/, pp. 1-4.
Author Unknown, "Ultraviolet Light Therapy," Wound Care Centers, Date Unknown, 3 pages, www.woundcarecenters.org/article/wound-therapies/ultraviolet-light-therapy.
Author Unknown, "Vio Orb—Antimicrobial Light Ball," Product Brief, Revive Light Therapy, revivelighttherapy.com/product/envirohygiene-orb-antimicrobial-light-ball/, accessed Jan. 31, 2021, 6 pages.
Author Unknown, "What is Light Therapy used for?" Rio, The Dezac Group, Ltd, Date Unknown, 4 pages, www.lightmask.com/uses_for_it.htm#top.
Avci, Pinar et al., "Low-Level Laser (Light) Therapy (LLLT) for Treatment of Hair Loss," Lasers in Surgery and Medicine, vol. 46, 2014, pp. 144-151.
Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.
Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.
Barolet, Daniel, "Light-Emitting Diodes (LEDs) in Dermatology," Seminars in Cutaneous Medicine and Surgery, vol. 27, No. 4, Dec. 1, 2008, pp. 227-238.
Bashkatov et al., "Optical properties of human skin, subcutaneous and mucous tissues in the wavelength range from 400-2000 nm," Journal of Physics D: Applied Physics, vol. 38, Jul. 2005, IOP Publishing Ltd, pp. 2543-2555.
Beck, Sara, et al., "Comparison of UV-Induced Inactivation and RNA Damage in MS2 Phage across the Germicidal UV Spectrum," Applied and Environmental Microbiology, vol. 82, Issue 5, Mar. 2016, pp. 1468-1474.
Beigel, JH, et al., "Remdesivir for the Treatment of Covid-19—Final Report," New England Journal of Medicine, vol. 383, Issue 19, Nov. 5, 2020, pp. 1813-1826.
Besaratinia, Ahmad, et al., "DNA lesions induced by UV A1 and B radiation in human cells: Comparative analyses in the overall genome and in the p53 tumor suppressor gene," PNAS, vol. 102, Issue 29, Jul. 2005, pp. 10058-10063.
Buonnano, Manuela, et al., "Far-UVC light (222 nm) efficiently and safely inactivates airborne human coronaviruses," Scientific Reports, Jun. 24, 2020, 8 pages.
Buonnano, Manuela, et al., "Germicidal Efficacy and Mammalian Skin Safety of 222-nm UV Light," Radiation Research, vol. 187, 2017, Radiation Research Society, 2017, pp. 493-501.
Cals-Grierson, M.-M. et al., "Nitric oxide function in the skin," Nitric Oxide, vol. 10, No. 4, Jun. 2004, pp. 179-193.
Chaves, Maria Emília De Abreu et al., "Effects of low-power light therapy on wound healing: Laser x LED," Anais Brasileiros de Dermatologia, vol. 89, No. 4, Jul./Aug. 2014, pp. 616-623.

(56) References Cited

OTHER PUBLICATIONS

Chen, Luni, et al., "Inhalation of Nitric Oxide in the Treatment of Severe Acute Respiratory Syndrome: A Rescue Trial in Beijing," Brief Report, Clinical Infectious Diseases, vol. 39, Oct. 2004, pp. 1531-1535.

Creagh-Brown, Benedict, et al., "Bench-to-bedside review: Inhaled nitric oxide therapy in adults," Critical Care, vol. 13, Issue 3, May 2009, BioMed Central Ltd, 8 pages.

Dai, Tianhong, et al., "Blue light for infectious diseases: Propionibacterium acnes, Helicobacter pylori, and beyond?," NIH-PA, Author Manuscript, 2012, Elsevier Ltd., 31 pages.

Darnelll, Miriam, et al., "Evaluation of inactivation methods for severe acute respiratory syndrome coronavirus in noncellular blood products," Transfusion, vol. 46, Oct. 2006, 8 pages.

De Marco, Federico, "Oxidative Stress and HPV Carcinogenesis," Viruses, vol. 5, Feb. 2013, pp. 708-731.

Donnarumma, G., et al., "Inhibition of HSV-1 Replication by Laser Diode-Irradiation: Possible Mechanism of Action," Journal of Immunopathology and Pharmacology, vol. 23, Issue 4, 2010, Biolife, pp. 1167-1176.

Dorrington, Michael, et al., "NF-KB Signaling in Macrophages: Dynamics, Crosstalk, and Signal Integration," Frontiers in Immunology, vol. 10, Apr. 9, 2019, 12 pages.

Eadie, Ewan, et al., "Extreme Exposure to Filtered Far-UVC: A Case Study," Ninewells Hospital and Medical School, Sep. 25, 2020, 14 pages.

Enwemeka, Chukuka, et al., "Blue 470-nm Light Kills Methicillin-Resistant *Staphylococcus aureus* (MRSA) in Vitro," Photomedicine and Laser Surgery, vol. 27, Issue 2, 2009, 6 pages.

Enwemeka, Chukuka, et al., "Light as a potential treatment for pandemic coronavirus infections: A perspective," Journal of Photochemistry & Photobiology, B: Biology, vol. 207, May 2020, 7 pages.

Enwemeka, Chukuka, et al., "Visible 405 nm SLD Light Photo-Destroys Methicillin-Resistant *Staphylococcus aureus* (MRSA) In Vitro," Lasers in Surgery and Medicine, vol. 40, 2008, pp. 734-737.

Farivar, Shirin et al., "Biological Effects of Low Level Laser Therapy," Journal of Lasers in Medical Sciences, vol. 5, No. 2, Spring 2014, pp. 58-62.

Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.

Ferrari-Light, Dana, et al., "The Utility of Near-Infrared Fluorescence and Indocyanine Green During Robotic Pulmonary Resection," Frontiers in Surgery, Review, vol. 6, Aug. 2019, 7 pages.

Finsen, Niels, "The Red Light Treatment of Small-Pox," The British Medical Journal, Dec. 7, 1895, pp. 1412-1414.

Garza, Felix, et al., "Visible Blue Light Therapy: Molecular Mechanisms and Therapeutic Opportunities," Current Medical Chemistry, 2018, vol. 25, Bentham Science Publishers, pp. 5564-5577.

Glazer-Hockstein, "Could Blue Light-Blocking Lenses Decrease the Risk of Age-Related Macular Degeneration," Retina, vol. 26, 2006, 4 pages.

Gupta, Asheesh et al., "History and Fundamentals of Low-Level Laser (Light) Therapy," Handbook of Photomedicine, Chapter 5, CRC Press, 2014, pp. 43-52.

Hamblin, Michael, et al., "Can light-based approaches overcome antimicrobial resistance?," Drug Development Research, Jul. 2018, Wiley Periodicals, Inc., 20 pages.

Hamblin, Michael, et al., "Mechanisms of Low Level Light Therapy," Proceedings of the SPIE, vol. 6140, Feb. 10, 2006, pp. 614001-1 to 641001-12.

Ankhzaya, "Airway management," slideshow, www.slideshare.net/gasilu/airway-management-111268937, Aug. 24, 2018, 87 pages.

Liu, et al., "Creation of a standardized geometry of the human nasal cavity," Journal of Applied Physiology, vol. 106, Jan. 2009, pp. 784-795.

International Search Report and Written Opinion for International Patent Application No. PCT/US2021/019785, dated Jun. 15, 2021, 18 pages.

Final Office Action for U.S. Appl. No. 16/709,550, dated Feb. 17, 2021, 12 pages.

Non-Final Office Action for U.S. Appl. No. 16/709,550, dated Jul. 12, 2021, 12 pages.

Non-Final Office Action for U.S. Appl. No. 16/898,385, dated Aug. 16, 2021, 12 pages.

* cited by examiner

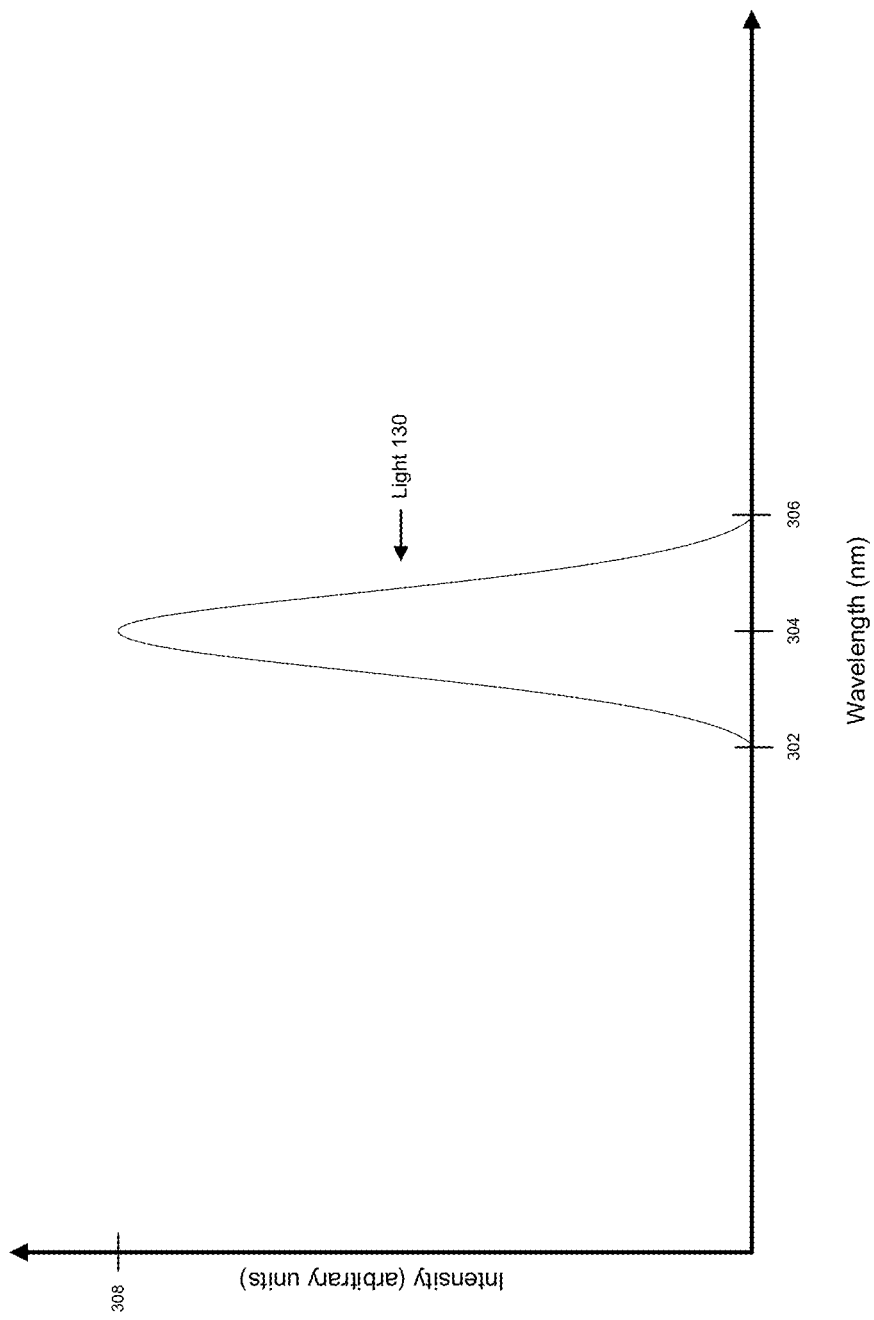

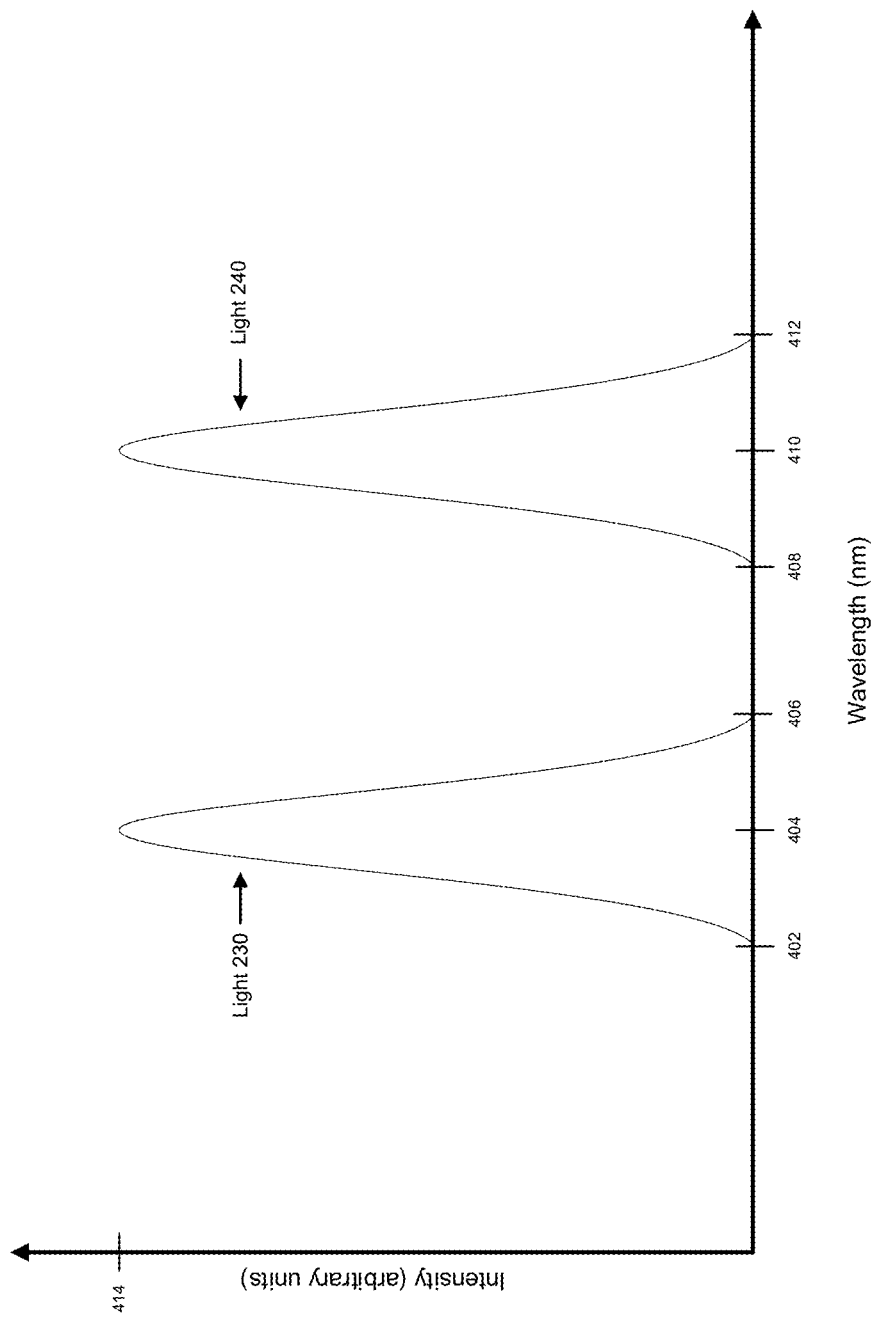

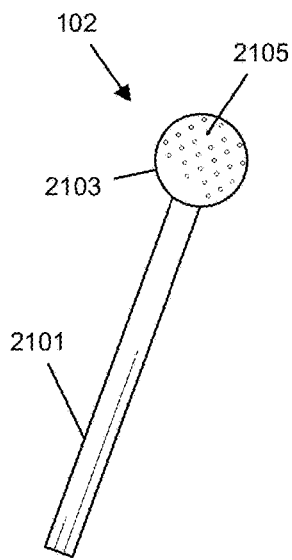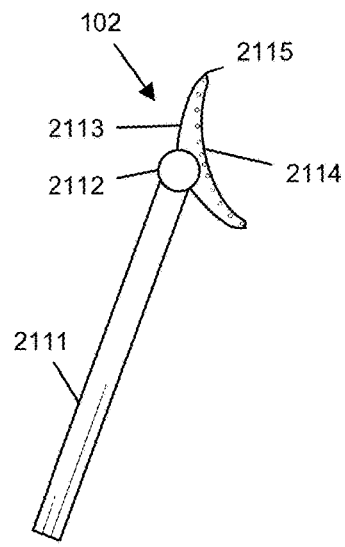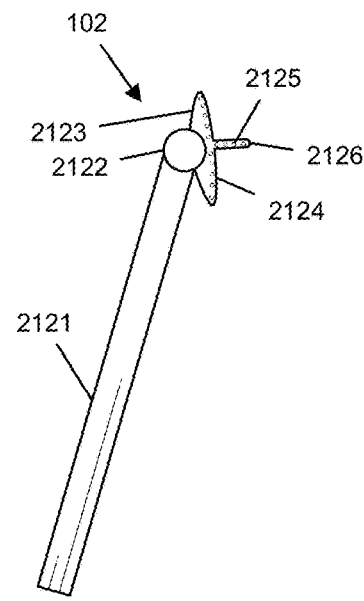
FIG. 21A  FIG. 21B  FIG. 21D
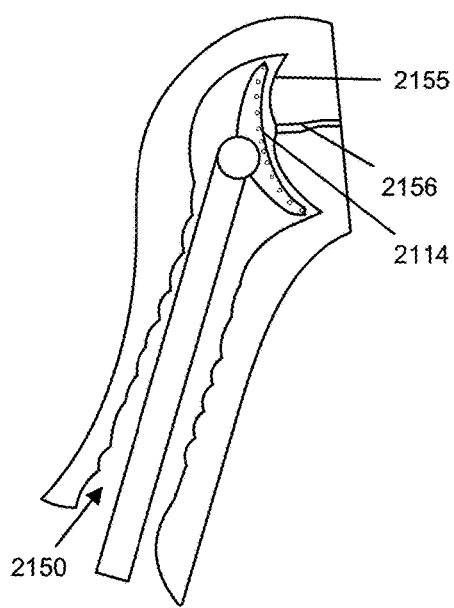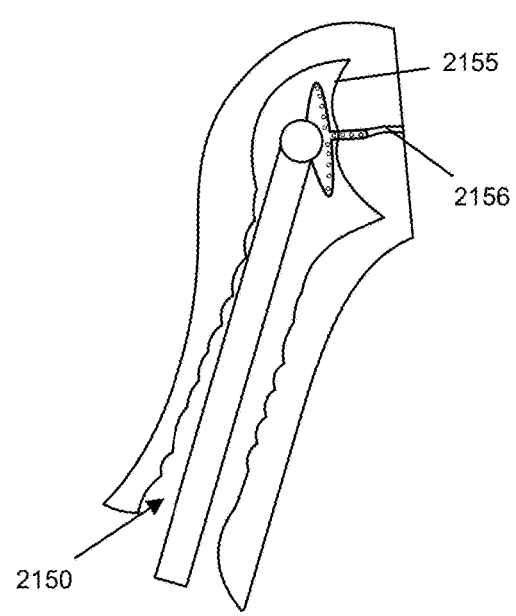
FIG. 21C  FIG. 21E

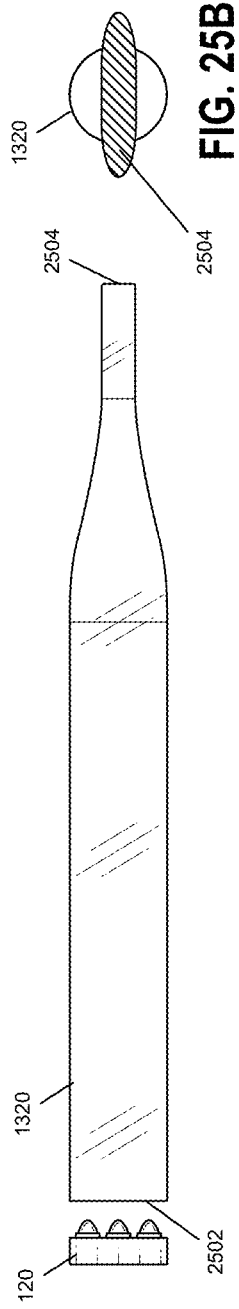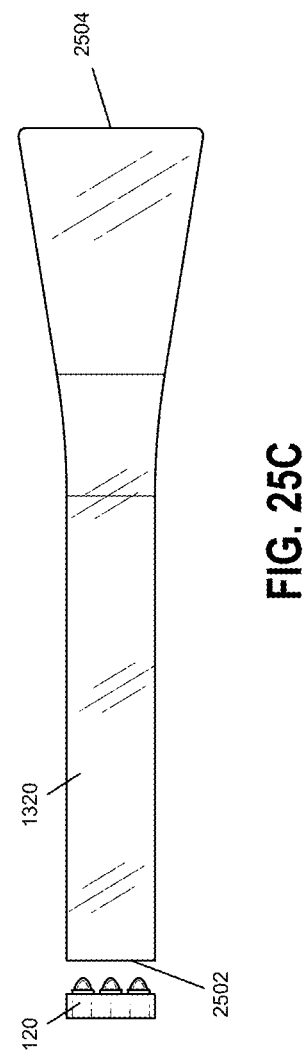

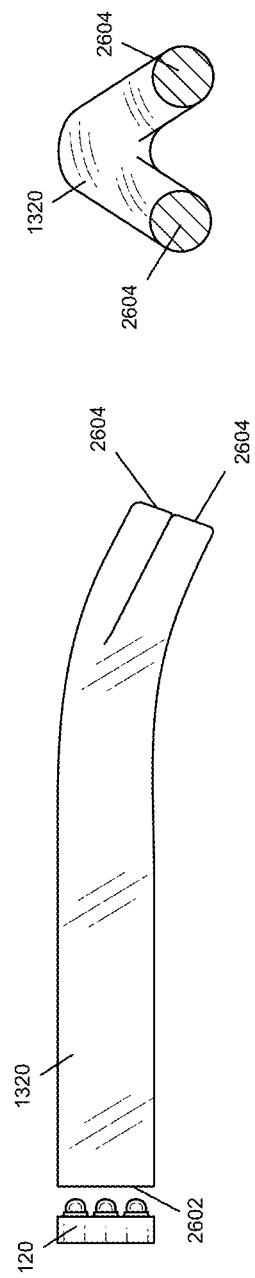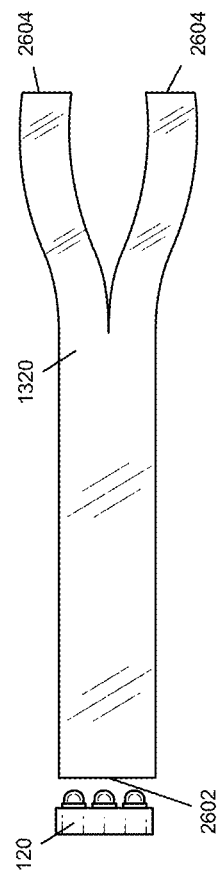
FIG. 26A  FIG. 26B  FIG. 26C

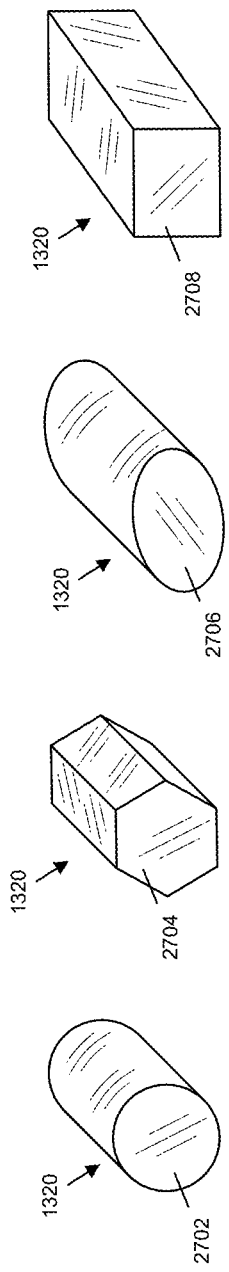
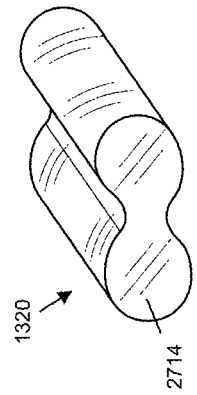
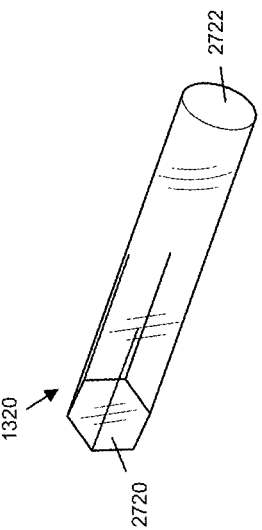
FIG. 27A – FIG. 27J

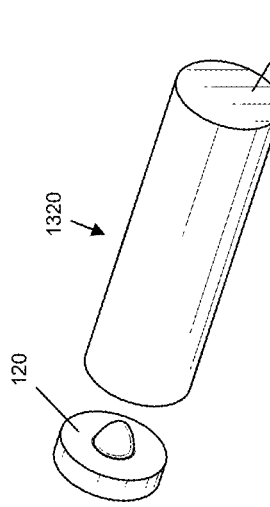
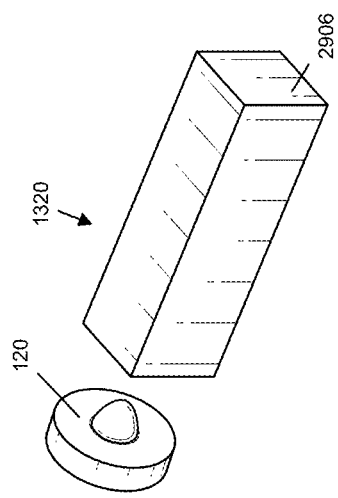
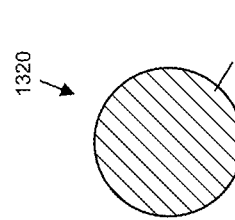
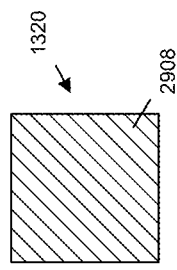
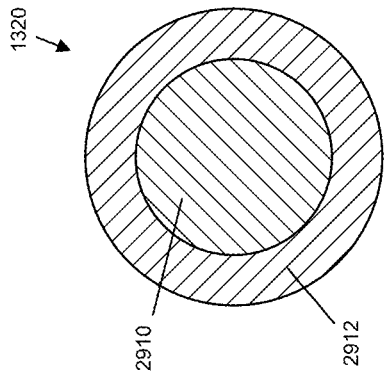
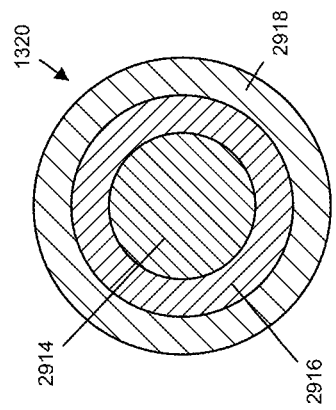

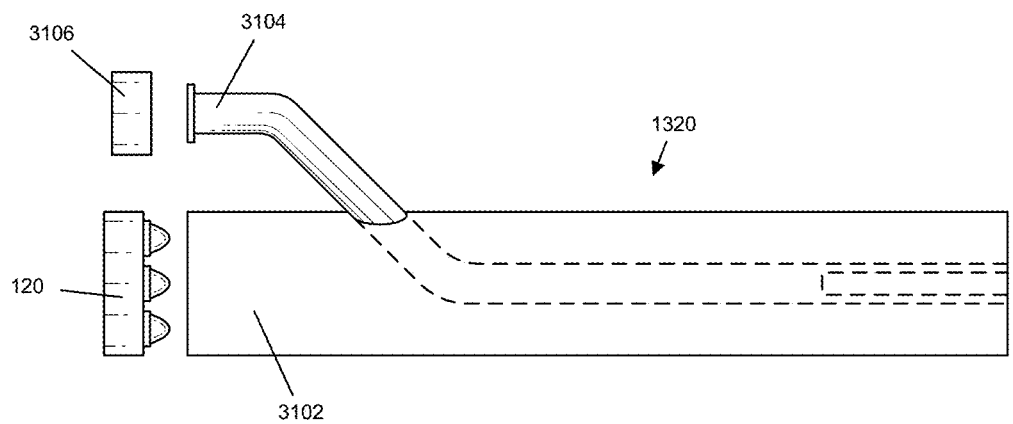
FIG. 31A
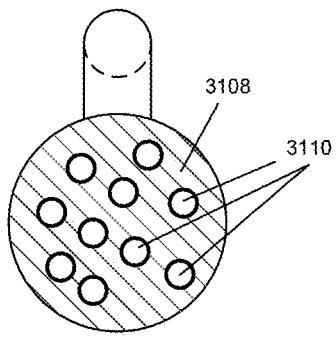 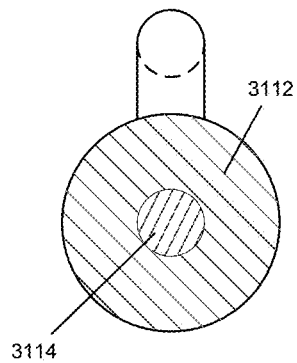 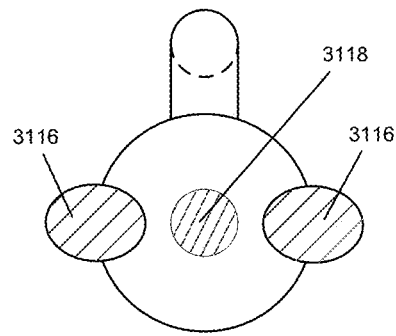
FIG. 31B  FIG. 31C  FIG. 31D

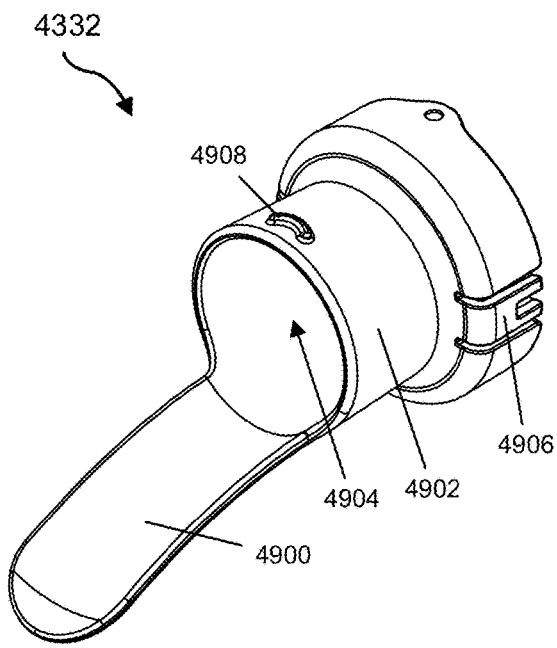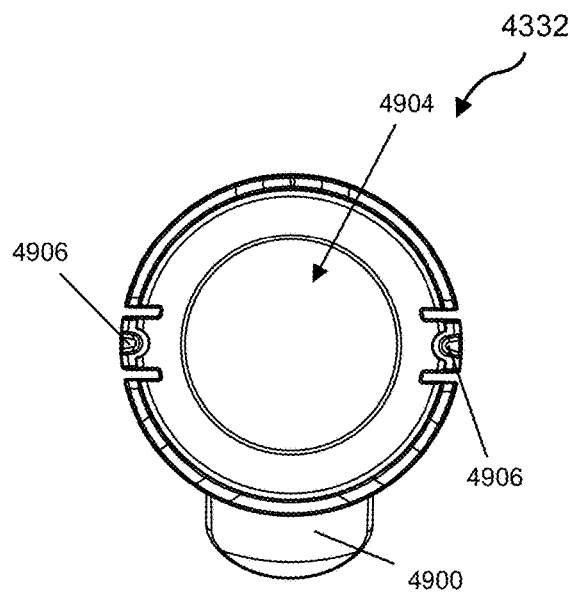
FIG. 49A  FIG. 49B
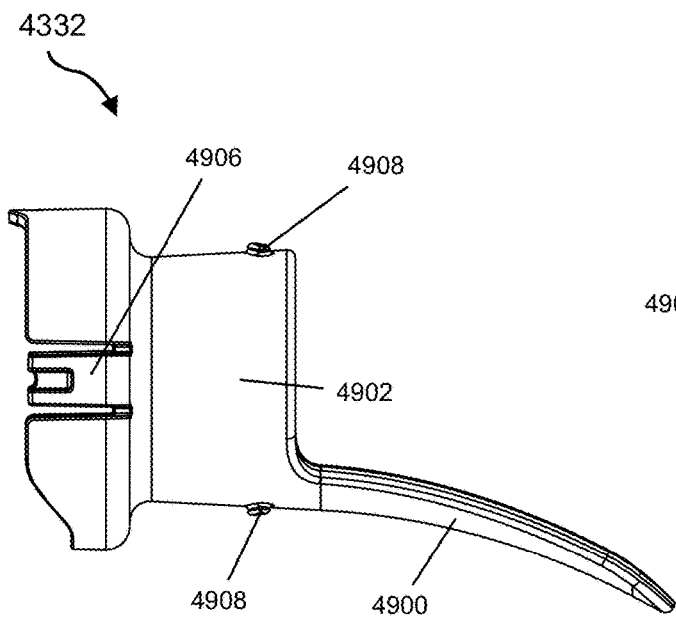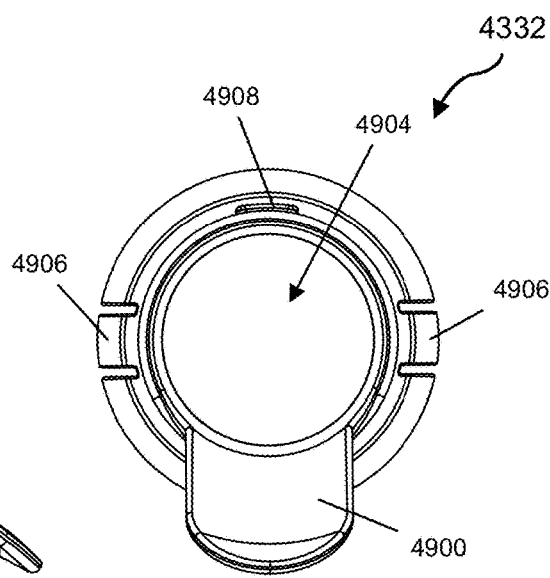
FIG. 49C  FIG. 49D

Anatomy of the Oral Cavity

Active Spike Protein → Nitric Oxide (NO) → Inactive Spike Protein

FIG. 58

Light Dose-Dependent Reduction in SARS-CoV-2 RNA at MOI 0.01

| Dose (J/cm$^2$) | 24 Hours Post-Infection | | | | 48 Hours Post-Infection | | | |
|---|---|---|---|---|---|---|---|---|
| | Average Cq Value | Standard Deviation of Cq | b Fold Decrease | c % Reduction | Average Cq Value | Standard Deviation of Cq | b Fold Decrease | c % Reduction |
| 0 | 18.35 | 0.90 | 1.00 | --- | 13.58 | 0.48 | 1.00 | --- |
| 7.5 | 17.99 | 0.34 | 0.78 | a 0.00 | 13.65 | 0.32 | 1.05 | 4.74 |
| 15 | 21.57 | 2.32 | 9.36 | 89.32 | 15.50 | 0.09 | 3.78 | 73.51 |
| 30 | 24.92 | 1.06 | 95.01 | 98.95 | 18.54 | 0.86 | 30.98 | 96.77 |
| 45 | 25.59 | 0.46 | 151.52 | 99.34 | 22.01 | 0.03 | 343.30 | 99.71 |
| 60 | 25.33 | 0.78 | 126.82 | 99.21 | 22.03 | 0.10 | 349.71 | 99.71 | a Values Less than 0 are Represented as 0%
b Fold Decrease Relative to 0 J/cm$^2$
c % SARS-CoV-2 Reduction Relative to 0 J/cm$^2$

FIG. 63C

| Wavelength | MOI 0.01 | | | | MOI 0.001 | | | |
|---|---|---|---|---|---|---|---|---|
| | $CC_{50}$ on Vero E6 Cells | $EC_{50}$ on Vero E6 Cells | SI on Vero E6 Cells | $Ic_{25}$ on Primary Human Trachial/Bronchial Tissue | LTI | $CC_{50}$ on Vero E6 Cells | $EC_{50}$ on Vero E6 Cells | SI on Vero E6 Cells | $Ic_{25}$ on Primary Human Trachial/Bronchial Tissue | LTI |
| 425nm | ~30.2 | ~1 | ~30 | ~157 | ~46 | ~30.2 | ~3.4 | ~9 | ~157 | ~46 |
| 450nm | >60 | ~7.2 | >8 | ~330 | ~46 | >60 | ~4.1 | >15 | ~330 | ~80 |

FIG. 72

| | | | $IC25_{405nm} = 120$ J/cm² | | $IC25_{425nm} = 160$ J/cm² | |
| | | | 405 nm | | 425 nm | |
| SPECIES | STRAIN | PHENOTYPE | BACTERICIDAL DOSE (J/CM²) | LTI | BACTERICIDAL DOSE (J/CM²) | LTI |
|---|---|---|---|---|---|---|
| PSEUDOMONAS AERUGINOSA | PAK | LAB STRAIN | 58 | 2.07 | 68 | 2.35 |
| PSEUDOMONAS AERUGINOSA | N0047 | MDR, CARBR, TOBRAR | 67 | 1.79 | 88 | 1.82 |
| PSEUDOMONAS AERUGINOSA | N0059 | XDR, CARBR, TOBRAR | 60 | 2.00 | 90 | 1.78 |
| PSEUDOMONAS AERUGINOSA | N0054 | MUCOID. DRUG-SUSCEPTIBLE | 53 | 2.26 | 83 | 1.93 |
| STAPHYLOCOCCUS AUREUS | N0040 | CLINICAL ISOLATE; MDR, MRSA, VANCO-S | 62 | 1.94 | >120 | <1.33 |
| STAPHYLOCOCCUS AUREUS | N0007 | MSSA; WOUND ISOLATE | >81 | <1.48 | >120 | <1.33 |
| STAPHYLOCOCCUS AUREUS | AR0215 | VISA | 60 | 2.00 | >120 | <1.33 |
| STAPHYLOCOCCUS AUREUS | AR0216 | VISA | 62 | 1.94 | >120 | <1.33 |
| HAEMOPHILUS INFLUENZAE | N0097 | RESISTANT TO CHLOR, TET, AND AMP | 18 | 6.67 | 27 | 5.93 |
| STREPTOCOCCUS PYOGENES | N0098 | ERYTHROMYCIN RESISTANT | 66 | 1.82 | 70 | 2.29 |

FIG. 81

| STRAIN ID | SPECIES | STRAIN NAME | MUCOIDY | ANTIBIOTIC CLASSIFICATION | ANTIBIOTIC RESISTANCES | SOURCE |
|---|---|---|---|---|---|---|
| N0047 | PSEUDOMONAS AERUGINOSA | AR-BANK #0103 | NON-MUCOID | MDR | AMK-I, ATM-I, FEP-R, CAZ-R, CZA-R, CIP-R, DOR-R, GEN-R, IPM-R, LVX-R, MEM-R, TOB-R | AR ISOLATE BANK |
| N0049 | PSEUDOMONAS AERUGINOSA | PAK | NON-MUCOID | | | SCHOENFISH LAB |
| N0054 | PSEUDOMONAS AERUGINOSA | AU26773 | MUCOID | | LVX-R | BCRLR |
| N0059 | PSEUDOMONAS AERUGINOSA | AR-BANK # 0054 | NON-MUCOID | XDR | ATM-I, FEP-R, CAZ-R, CZA-R, CIP-R, DOR-I, GEN-R, IPM-R, LVX-R, MEM-R, TZP-R, TOB-R | AR ISOLATE BANK |
| N0069 | PSEUDOMONAS AERUGINOSA | AR-BANK # 0090 | NON-MUCOID | XDR | AMK-I, ATM-R, FEP-R, CAZ-R, CZA-R, CIP-R, DOR-R, GEN-R, IPM-R, LVX-R, MEM-R, TZP-R, TOB-R | AR ISOLATE BANK |
| N0070 | PSEUDOMONAS AERUGINOSA | AR-BANK # 0092 | NON-MUCOID | XDR | AMK-R, ATM-R, FEP-R, CAZ-R, CZA-R, CIP-R, DOR-R, GEN-R, IPM-R, LVX-R, MEM-R, TZP-R, TOB-R | AR ISOLATE BANK |
| N0050 | PSEUDOMONAS AERUGINOSA | AR-BANK # 0095 | NON-MUCOID | MDR | ATM-R, CIP-R, DOR-I, IPM-R, LVX-R, MEM-R, TZP-I | AR ISOLATE BANK |
| N0006 | STAPHYLOCOCCUS AUREUS | STRAIN 328; ATCC 33591 | N/A | | MRSA | SCHOENFISH LAB |
| AR-0215 | STAPHYLOCOCCUS AUREUS | | N/A | | VISA | AR ISOLATE BANK |
| AR-0216 | STAPHYLOCOCCUS AUREUS | | N/A | | VISA | AR ISOLATE BANK |
| N0098 | STREPTOCOCCUS PYOGENES | ATCC BAA-946 | N/A | | ERYTHROMYCIN-RESISTANT | ATCC |
| N0097 | HAEMOPHILUS INFLUENZAE | ATCC 33929 | N/A | | RESISTANT TO CHLORAMPHENICOL, TETRACYCLINE, AND AMPICILLIN | ATCC |

FIG. 84B

| SPECIES | STRAIN | PHENOTYPE | BID BACTERICIDAL DOSE (J/CM2) | BID MBC DOSE (J/CM2) | BID MIC DOSE (J/CM2) |
|---|---|---|---|---|---|
| PSEUDOMONAS AERUGINOSA | N0049 | LAB STRAIN PAK | <10 | 50 | 50 |
| PSEUDOMONAS AERUGINOSA | N0047 | MDR, CARBR, TOBRAR | 30 | 20 | 20 |
| PSEUDOMONAS AERUGINOSA | N0054 | NOT MDR, CARBS, TOBRAS, MUCOID | 40 | 50 | 50 |
| PSEUDOMONAS AERUGINOSA | N0059 | XDR, CARBR, TOBRAR | 30 | 30 | 30 |
| PSEUDOMONAS AERUGINOSA | N0050 | MDR, CARBR, TOBRAS | 20 | 20 | 30 |
| PSEUDOMONAS AERUGINOSA | N0069 | XDR, CARBR, TOBRAR | 20 | 20 | 20 |
| PSEUDOMONAS AERUGINOSA | N0070 | XDR, CARBR, TOBRAR | 20 | 40 | 40 |
| STAPHYLOCOCCUS AUREUS | N0006 | 328; ATCC 33591; MRSA | 10 | >60 | >60 |
| STAPHYLOCOCCUS AUREUS | AR-0215 | VISA | 10 | >60 | >60 |
| STAPHYLOCOCCUS AUREUS | AR-0216 | VISA | 10 | >60 | >60 |

FIG. 84C

ILLUMINATION DEVICES FOR INDUCING BIOLOGICAL EFFECTS

STATEMENT OF RELATED APPLICATIONS

This application claims the benefit of provisional patent application Ser. No. 63/123,631, filed Dec. 10, 2020, the disclosure of which is hereby incorporated herein by reference in its entirety.

This application claims the benefit of provisional patent application Ser. No. 63/075,010, filed Sep. 4, 2020, the disclosure of which is hereby incorporated herein by reference in its entirety.

This application claims the benefit of provisional patent application Ser. No. 63/074,970, filed Sep. 4, 2020, the disclosure of which is hereby incorporated herein by reference in its entirety.

This application claims the benefit of provisional patent application Ser. No. 63/065,357, filed Aug. 13, 2020, the disclosure of which is hereby incorporated herein by reference in its entirety.

This application claims the benefit of provisional patent application Ser. No. 62/991,903, filed Mar. 19, 2020, the disclosure of which is hereby incorporated herein by reference in its entirety.

TECHNICAL FIELD

The present disclosed subject matter relates generally to devices and methods for impinging light on tissue (e.g., phototherapy or light therapy) to induce one or more biological effects. Additionally, disclosed are methods and devices for delivering light as a therapeutic treatment for tissue that comes into contact with or is infected by pathogens.

BACKGROUND

Viral infections pose a great challenge to human health, particularly respiratory tract infections of the Orthomyxoviridae (e.g. influenza) and Coronaviridae (e.g. SARS-CoV-2) families. Additionally, DNA virus including the Papovaviridae family (e.g. human papillomavirus (HPV)) have extremely wide prevalence that result in low risk papillomas of the skin and high risk papillomas of mucosal epithelial tissue. Infection by the human papillomavirus (HPV) is currently the most common sexually transmitted disease (STD).

Various light therapies (e.g., including low level light therapy (LLLT) and photodynamic therapy (PDT)) have been publicly reported or claimed to provide various health related medical benefits—including, but not limited to: promoting hair growth; treatment of skin or tissue inflammation; promoting tissue or skin healing or rejuvenation; enhancing wound healing; pain management; reduction of wrinkles, scars, stretch marks, varicose veins, and spider veins; treating cardiovascular disease; treating erectile dysfunction; treating microbial infections; treating hyperbilirubinemia; and treating various oncological and non-oncological diseases or disorders.

Various mechanisms by which phototherapy has been suggested to provide therapeutic benefits include: increasing circulation (e.g., by increasing formation of new capillaries); stimulating the production of collagen; stimulating the release of adenosine triphosphate (ATP); enhancing porphyrin production; reducing excitability of nervous system tissues; modulating fibroblast activity; increasing phagocytosis; inducing thermal effects; stimulating tissue granulation and connective tissue projections; reducing inflammation; and stimulating acetylcholine release.

Phototherapy has also been suggested to stimulate cells to generate nitric oxide. Various biological functions attributed to nitric oxide include roles as signaling messenger, cytotoxin, antiapoptotic agent, antioxidant, and regulator of microcirculation. Nitric oxide is recognized to relax vascular smooth muscles, dilate blood vessels, inhibit aggregation of platelets, and modulate T cell-mediate immune response.

Nitric oxide is produced by multiple cell types in tissue, and is formed by the conversion of the amino acid L-arginine to L-citrulline and nitric oxide, mediated by the enzymatic action of nitric oxide synthases (NOSs). NOS is a NADPH-dependent enzyme that catalyzes the following reaction:

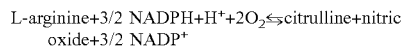

In mammals, three distinct genes encode NOS isozymes: neuronal (nNOS or NOS-I), cytokine-inducible (iNOS or NOS-II), and endothelial (eNOS or NOS-III). iNOS and nNOS are soluble and found predominantly in the cytosol, while eNOS is membrane associated. Many cells in mammals synthesize iNOS in response to inflammatory conditions.

Skin has been documented to upregulate inducible nitric oxide synthase expression and subsequent production of nitric oxide in response to irradiation stress. Nitric oxide serves a predominantly anti-oxidant role in the high levels generated in response to radiation.

Nitric oxide is a free radical capable of diffusing across membranes and into various tissues; however, it is very reactive, with a half-life of only a few seconds. Due to its unstable nature, nitric oxide rapidly reacts with other molecules to form more stable products. For example, in the blood, nitric oxide rapidly oxidizes to nitrite, and is then further oxidized with oxyhaemoglobin to produce nitrate. Nitric oxide also reacts directly with oxyhaemoglobin to produce methaemoglobin and nitrate. Nitric oxide is also endogenously stored on a variety of nitrosated biochemical structures including nitrosoglutathione (GSNO), nitrosoalbumin, nitrosohemoglobin, and a large number of nitrosocysteine residues on other critical blood/tissue proteins. The term "nitroso" is defined as a nitrosated compound (nitrosothiols (RSNO) or nitrosamines (RNNO)), via either S- or N-nitrosation. Examples of nitrosated compounds include GSNO, nitrosoalbumin, nitrosohemoglobin, and proteins with nitrosated cysteine residue. Metal nitrosyl (M-NO) complexes are another endogenous store of circulating nitric oxide, most commonly found as ferrous nitrosyl complexes in the body; however, metal nitrosyl complexes are not restricted to complexes with iron-containing metal centers, since nitrosation also occurs at heme groups and copper centers. Examples of metal nitrosyl complexes include cytochrome c oxidase (CCO-NO) (exhibiting 2 heme and 2 copper binding sites), cytochrome c (exhibiting heme center binding), and nitrosylhemoglobin (exhibiting heme center binding for hemoglobin and methemoglobin), embodying endogenous stores of nitric oxide.

SUMMARY

Aspects of the present disclosure relate to devices and methods for impinging light on a tissue, for example within a mammalian body and/or a body cavity of a patient, where the light may include at least one characteristic that exerts or induces at least one biological effect within or on the tissue. Biological effects may include at least one of inactivating and inhibiting growth of one or more combinations of microorganisms and pathogens, including but not limited to viruses, bacteria, fungi, and other microbes, among others. Biological effects may also include one or more of upregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissue and the targeted microorganisms or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Because of the relative costs, both economically and on the health and well-being of patients, new treatments to inhibit or eradicate viral infections in tissues, particularly the mucosal epithelial surfaces like the cervix, mouth, nose, throat and anus, are greatly needed. Such treatments and devices therefore are provided for herein.

Phototherapy has attracted significant attention as a therapeutic treatment for various maladies and conditions. Devices for delivering phototherapy to inhibit or eradicate viral infections and methods of using the same are disclosed herein. Irradiances of light represented in milliwatts per centimeter squared ($mW/cm^2$) have been proposed at a specific wavelength for a threshold time over a given duration to yield therapeutic dosages represented in joules per centimeter squared ($J/cm^2$) which are effective for inactivating virus or treating viral infections while maintaining the viability of epithelial tissues. These treatments can be tailored to the particular tissue being treated, as well as to the various fluids in the media, such as blood, sputum, saliva, cervical fluid, and mucous. The total dosage ($J/cm^2$) to treat an infection can be spread out over multiple administrations, with each dose applied over seconds or minutes, and with multiple doses over days or weeks, at individual doses that treat the infection while minimizing damage to the particular tissue.

In one aspect, an illumination device comprises: at least one light source arranged to irradiate light on tissue within a body cavity, the light configured to induce a biological effect, the biological effect comprising at least one of altering a concentration of one or more pathogens within the body cavity and altering growth of the one or more pathogens within the body cavity; a light guide configured to receive the light from the at least one light source; and a light guide positioner that is configured to secure the light guide for providing the light to the tissue within the body cavity. In certain embodiments, the biological effect comprises both altering the concentration of the one or more pathogens within the body cavity and altering the growth of the one or more pathogens within the body cavity. In certain embodiments, the one or more pathogens comprise at least one of a virus, a bacteria, and a fungus. In certain embodiments, the one or more pathogens comprise coronaviridae. In certain embodiments, the coronaviridae comprises SARS-CoV-2. In certain embodiments, the biological effect further comprises at least one of upregulating a local immune response within the body cavity, stimulating at least one of enzymatic generation of nitric oxide to increase endogenous stores of nitric oxide, and releasing nitric oxide from endogenous stores of nitric oxide. In certain embodiments, the biological effect comprises inactivating the one or more pathogens that are in a cell-free environment in the body cavity. In certain embodiments, the biological effect comprises inhibiting replication of the one or more pathogens that are in a cell-associated environment in the body cavity.

In certain embodiments, the light guide positioner comprises a mouthpiece that is configured to engage with one or more surfaces of an oral cavity of a user. In certain embodiments, the mouthpiece comprises one or more bite guards for protecting and securing the light guide. In certain embodiments, the illumination device further comprises a tongue depressor that is configured to depress the user's tongue for providing the light to the oropharynx. In certain embodiments, the tongue depressor is formed by a portion of the light guide. In certain embodiments, the illumination device further comprises a housing that includes the at least one light source and wherein the light guide and the light guide positioner are configured to be removably attached to the housing. In certain embodiments, the illumination device further comprises a port that is configured to at least one of charge the illumination device and access data that is stored in the illumination device.

In certain embodiments, the light includes a first light characteristic comprising a peak wavelength in a range of 410 nanometers (nm) to 440 nm. In certain embodiments, irradiating the light on the tissue within the body cavity comprises administering a dose of light in a range from 0.5 joules per square centimeter ($J/cm^2$) to 100 $J/cm^2$. In certain embodiments, irradiating the light on the tissue within the body cavity comprises administering a dose of light with a light therapeutic index in a range from 2 to 250, the light therapeutic index being defined as a dose concentration that reduces tissue viability by 25% divided by a dose concentration that reduces cellular percentage of the one or more pathogens by 50%.

In another aspect, an illumination device comprises: at least one light source arranged to irradiate light on tissue of an oropharynx of a user to induce a biological effect, the biological effect comprising at least one of altering a concentration of one or more pathogens and altering growth of the one or more pathogens; and a mouthpiece that is configured to engage with one or more surfaces of an oral cavity of the user to provide the light to the oropharynx. In certain embodiments, the biological effect comprises altering the concentration of the one or more pathogens and altering the growth of the one or more pathogens. In certain embodiments, the one or more pathogens comprise at least one of a virus, a bacteria, and a fungus. In certain embodiments, the one or more pathogens comprise coronaviridae. In certain embodiments, the coronaviridae comprises SARS-CoV-2.

In certain embodiments, the biological effect further comprises at least one of upregulating a local immune response, stimulating at least one of enzymatic generation of nitric oxide to increase endogenous stores of nitric oxide, and releasing nitric oxide from endogenous stores of nitric oxide. In certain embodiments, the mouthpiece is configured to expand the oral cavity of the user. In certain embodiments, the illumination device further comprises a light guide that is configured to receive the light from the at least one light source. In certain embodiments, the mouthpiece is configured to be removably attached to the light guide. In certain embodiments, the mouthpiece comprises one or more bite guards for protecting and securing the light guide. In certain embodiments, a portion of the light guide forms a tongue depressor that is configured to depress the user's tongue for providing the light to the oropharynx. In certain embodiments, the light comprises a peak wavelength is a range from 410 nm to 440 nm and irradiating the light on the tissue of the oropharynx comprises administering a dose of light in a range from 0.5 J/cm$^2$ to 100 J/cm$^2$. In certain embodiments, the one or more pathogens comprise coronaviridae and irradiating the light on the tissue of the oropharynx comprises administering a dose of light with a light therapeutic index in a range from 2 to 250, the light therapeutic index being defined as a dose concentration that reduces tissue viability by 25% divided by a dose concentration that reduces cellular percentage of the one or more pathogens by 50%.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF DRAWINGS

The accompanying drawing figures incorporated in and forming a part of this specification illustrate several aspects of the disclosure, and together with the description serve to explain the principles of the disclosure.

FIG. 3 is a spectral diagram showing intensity versus wavelength for exemplary nitric-oxide modulating light, according to some embodiments.

FIG. 4 is a spectral diagram showing intensity versus wavelength for exemplary endogenous-store increasing light and exemplary endogenous-store releasing light, according to some embodiments.

FIG. 21A is a schematic elevation view of at least a portion of an exemplary illumination device for delivering nitric-oxide modulating light to tissue in an internal cavity of a patient, according to one embodiment.

FIG. 21B is a schematic elevation view of at least a portion of a light emitting device including a concave light emitting surface for delivering nitric-oxide modulating light to cervical tissue of a patient, according to one embodiment.

FIG. 21C illustrates the device of FIG. 21B inserted into a vaginal cavity to deliver nitric-oxide modulating light to cervical tissue of a patient.

FIG. 21D is a schematic elevation view of at least a portion of a light emitting device including a probe-defining light emitting surface for delivering nitric-oxide modulating light to cervical tissue of a patient according to another embodiment.

FIG. 21E illustrates the device of FIG. 21D inserted into a vaginal cavity, with a probe portion of the light-emitting surface inserted into a cervical opening, to deliver nitric-oxide modulating light to cervical tissue of a patient.

FIG. 25A is a side view of an exemplary tapered light guide, according to at least one embodiment.

FIG. 25B is a front view of the exemplary tapered light guide of FIG. 25A, according to at least one embodiment.

FIG. 25C is a top view of the exemplary tapered light guide of FIG. 25A, according to at least one embodiment.

FIG. 26A is a side view of an exemplary split light guide, according to at least one embodiment.

FIG. 26B is a front view of the exemplary split light guide of FIG. 26A, according to at least one embodiment.

FIG. 26C is a top view of the exemplary split light guide of FIG. 26A, according to at least one embodiment.

FIG. 27A is a perspective view of an exemplary light guide having a circular cross-sectional area and circular faces, according to at least one embodiment.

FIG. 27B is a perspective view of an exemplary light guide having a hexagonal cross-sectional area and hexagonal faces, according to at least one embodiment.

FIG. 27C is a perspective view of an exemplary light guide having an elliptical cross-sectional area and elliptical faces, according to at least one embodiment.

FIG. 27D is a perspective view of an exemplary light guide having a rectangular cross-sectional area and rectangular faces, according to at least one embodiment.

FIG. 27E is a perspective view of an exemplary light guide having a pentagonal cross-sectional area and pentagonal faces, according to at least one embodiment.

FIG. 27F is a perspective view of an exemplary light guide having an octagonal cross-sectional area and octagonal faces, according to at least one embodiment.

FIG. 27G is a perspective view of an exemplary light guide having an oval cross-sectional area and oval faces, according to at least one embodiment.

FIG. 27H is a perspective view of an exemplary light guide having a triangular cross-sectional area and triangular faces, according to at least one embodiment.

FIG. 27I is a perspective view of an exemplary light guide having a semicircular cross-sectional area and semicircular faces, according to at least one embodiment.

FIG. 27J is a perspective view of an exemplary light guide having differently shaped cross-sectional areas and faces, according to at least one embodiment.

FIG. 29A is another perspective view of an exemplary light guide having a circular cross-sectional area and circular faces, according to at least one embodiment.

FIG. 29B is a cross-sectional view of the light guide of FIG. 29A having an uncladded core, according to at least one embodiment.

FIG. 29C is a perspective view of an exemplary light guide having a square cross-sectional area and square faces, according to at least one embodiment.

FIG. 29D is a cross-sectional view of the light guide of FIG. 29C having an uncladded core.

FIG. 29E is a cross-sectional view of an exemplary light guide having a cladded core, according to at least one embodiment.

FIG. 29F is another cross-sectional view of an exemplary light guide having a cladded core, according to at least one embodiment.

FIG. 31A is a side view of an exemplary multicore light guide, according to at least one embodiment.

FIG. 31B is a front view of an exemplary configuration of the multicore light guide of FIG. 31A, according to at least one embodiment.

FIG. 31C is a front view of an exemplary configuration of the multicore light guide of FIG. 31A, according to at least one embodiment.

FIG. 31D is a front view of an exemplary configuration of the multicore light guide of FIG. 31A, according to at least one embodiment.

FIG. 49A is a perspective view of the exemplary light guide of FIG. 43, according to some embodiments.

FIG. 49B is a rear view of the exemplary light guide of FIG. 43, according to some embodiments.

FIG. 49C is a side view of the exemplary light guide of FIG. 43, according to some embodiments.

FIG. 49D is a front view of the exemplary light guide of FIG. 43, according to some embodiments.

FIG. 52 is a side view of another exemplary configuration of the exemplary illumination device of FIG. 1, according to some embodiments.

FIG. 53 is a side view of another exemplary configuration of the exemplary illumination device of FIG. 1, according to some embodiments.

FIG. 54A is a front perspective view of an exemplary handheld configuration of an illumination device for delivering light to living tissue within or near a user's oral cavity, including the oropharynx.

FIG. 54B is a back perspective view of the illumination device of FIG. 54A.

FIG. 54C is a front view of the illumination device of FIG. 54A.

FIG. 54D is a side view of the illumination device of FIG. 54A.

FIG. 54E is a top view of the of the illumination device of FIG. 54A.

FIG. 55 is an illustration of an oral cavity.

FIG. 56A is a perspective view of an exemplary cheek retractor according to certain embodiments.

FIG. 56B is a perspective view of a cheek retractor that includes a material, such as a filter, that is configured to block certain wavelengths of light during a phototherapy treatment.

FIG. 57 is a perspective view of a device for securing a light source to a user's nostrils.

FIG. 58 is an illustration of nitric oxide inactivation of active spike (S) proteins used by coronaviruses to facilitate endocytosis into human cells.

Figure 59A:
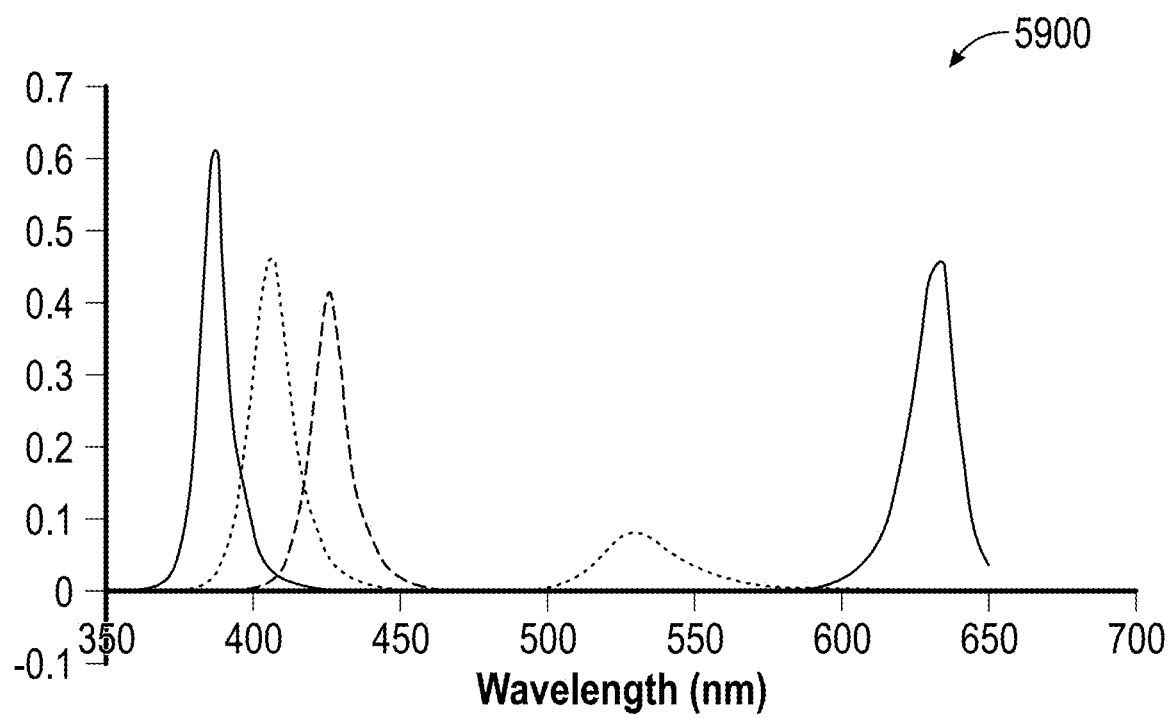

FIG. 59A is a chart illustrating measured spectral flux relative to wavelength for different exemplary LED arrays.

Figure 59B:
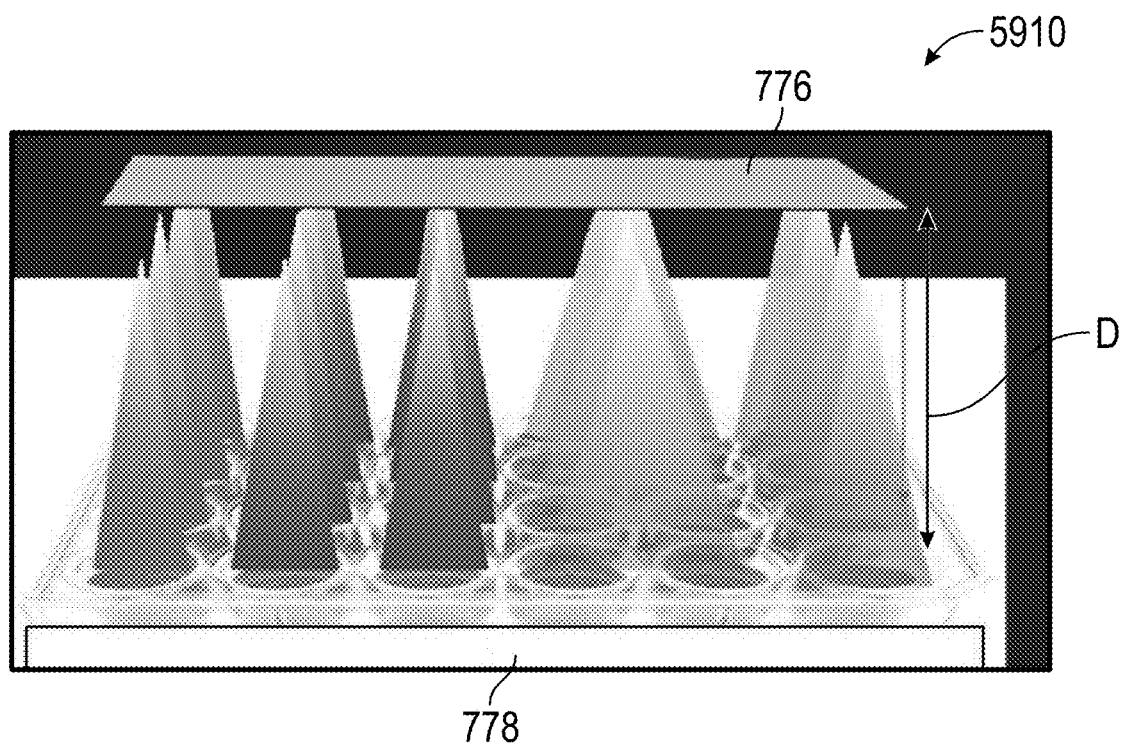

FIG. 59B illustrates a perspective view of a testing set-up for providing light from one or more LED arrays to a biological test article.

Figure 60A:
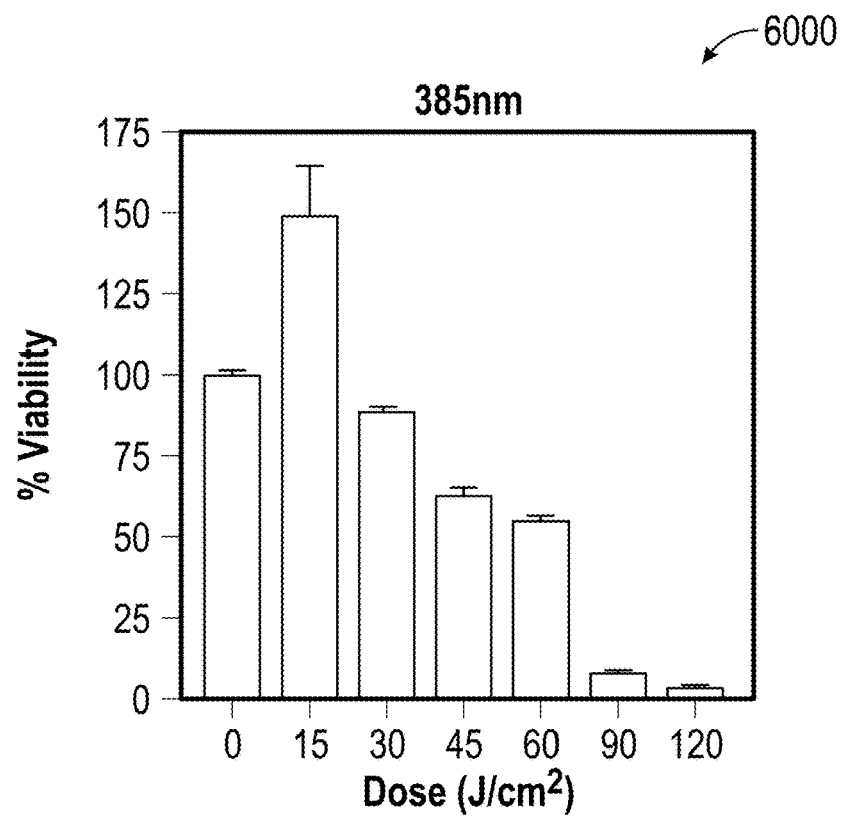

FIG. 60A is a chart illustrating a percent viability for a peak wavelength of 385 nm for a range of doses.

FIG. 60B is a chart illustrating a percent viability for a peak wavelength of 405 nm for the same doses of FIG. 60A.

Figure 60B:
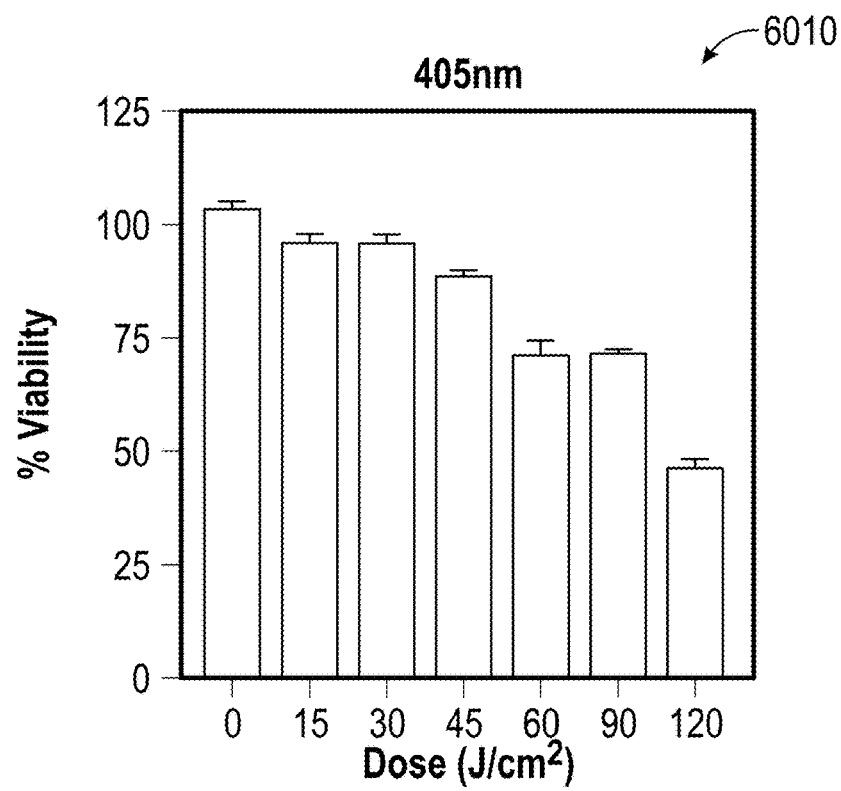
Figure 60C:
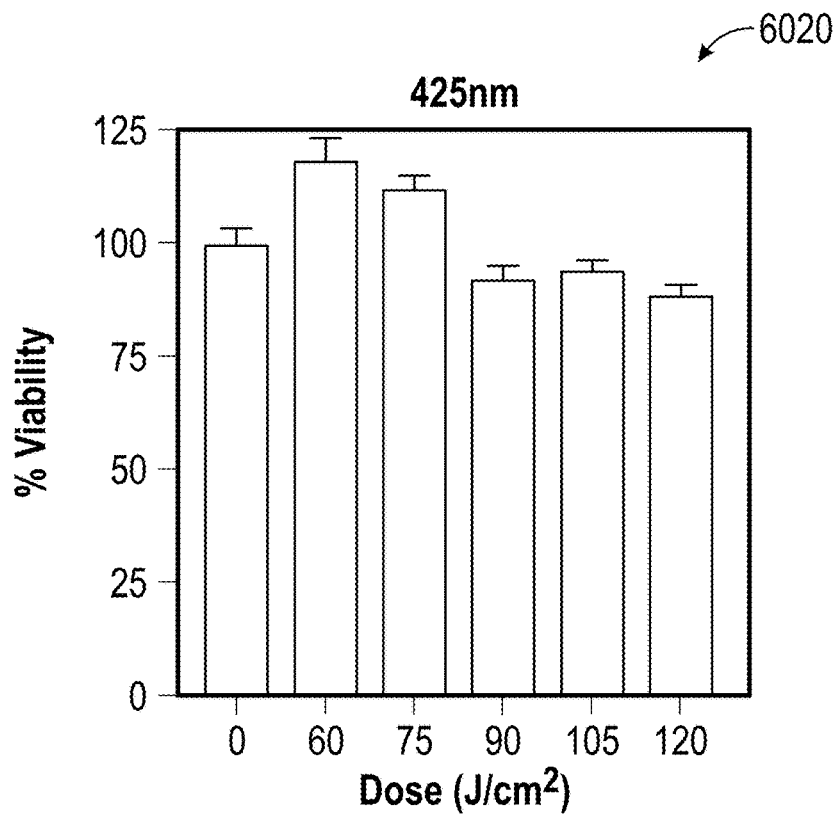

FIG. 60C is a chart illustrating a percent viability for a peak wavelength of 425 nm for the same doses of FIG. 60A.

Figure 61A:
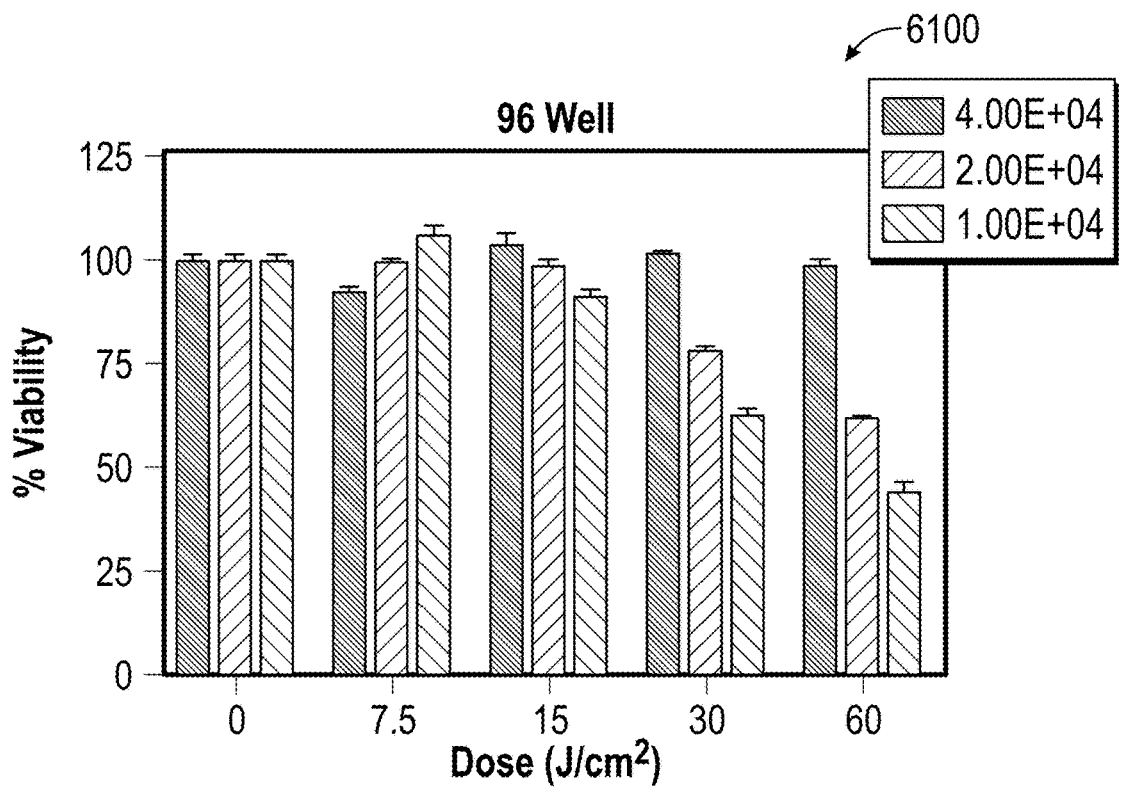

FIG. 61A is a chart illustrating percent viability for Vero E6 cells for antiviral assays performed on ninety-six well plates at various cell seeding densities.

Figure 61B:
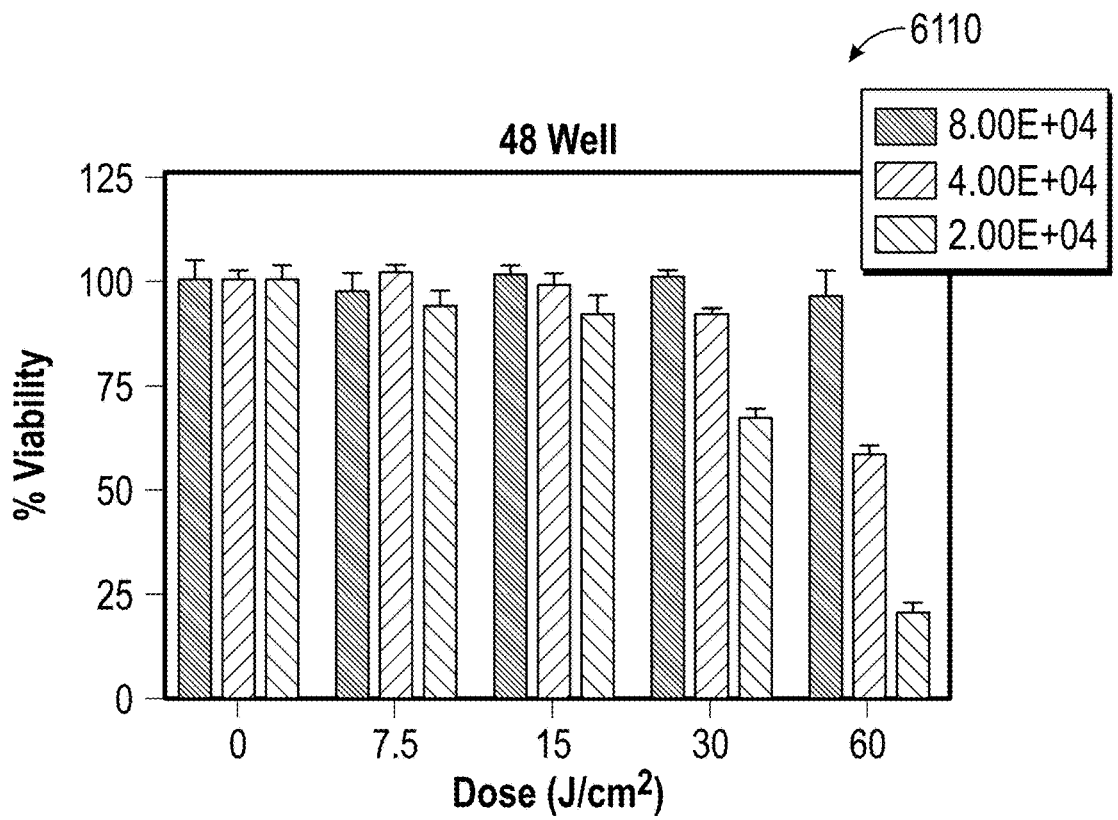

FIG. 61B is a chart illustrating percent viability for Vero E6 cells for antiviral assays performed on forty-eight well plates at various cell seeding densities.

Figure 61C:
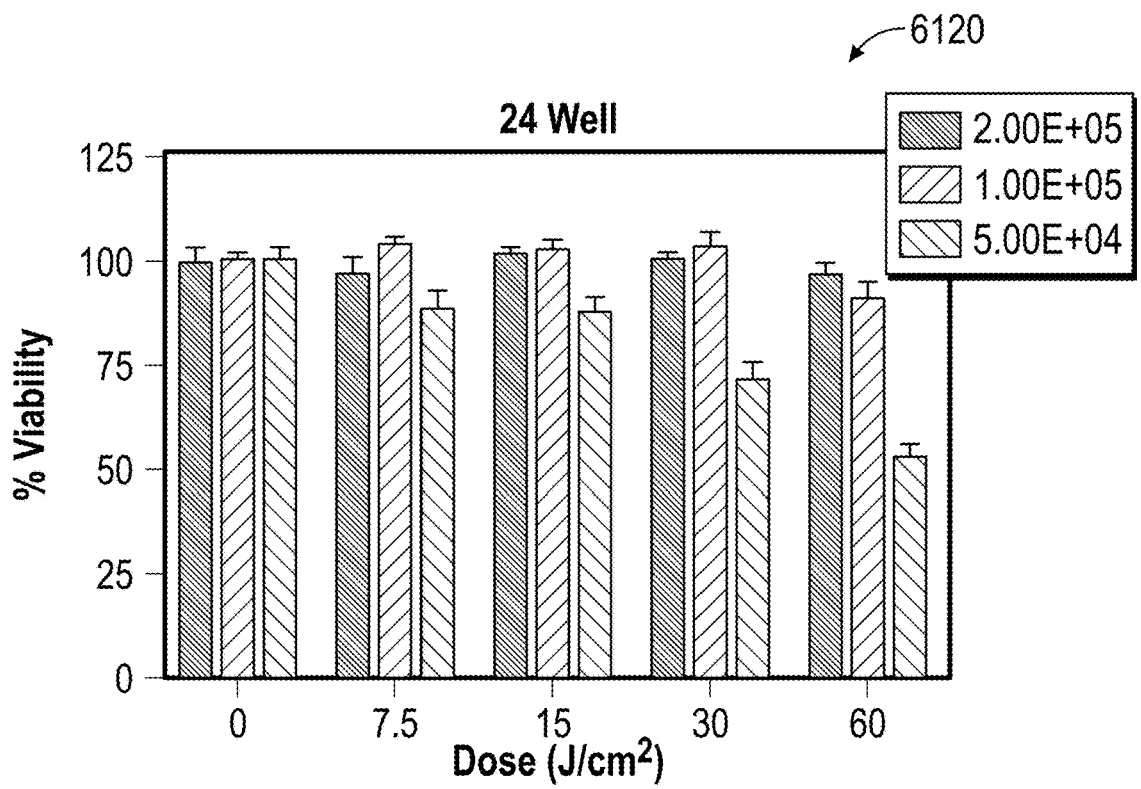

FIG. 61C is a chart illustrating percent viability for Vero E6 cells for antiviral assays performed on twenty-four well plates at various cell seeding densities.

Figure 62A:
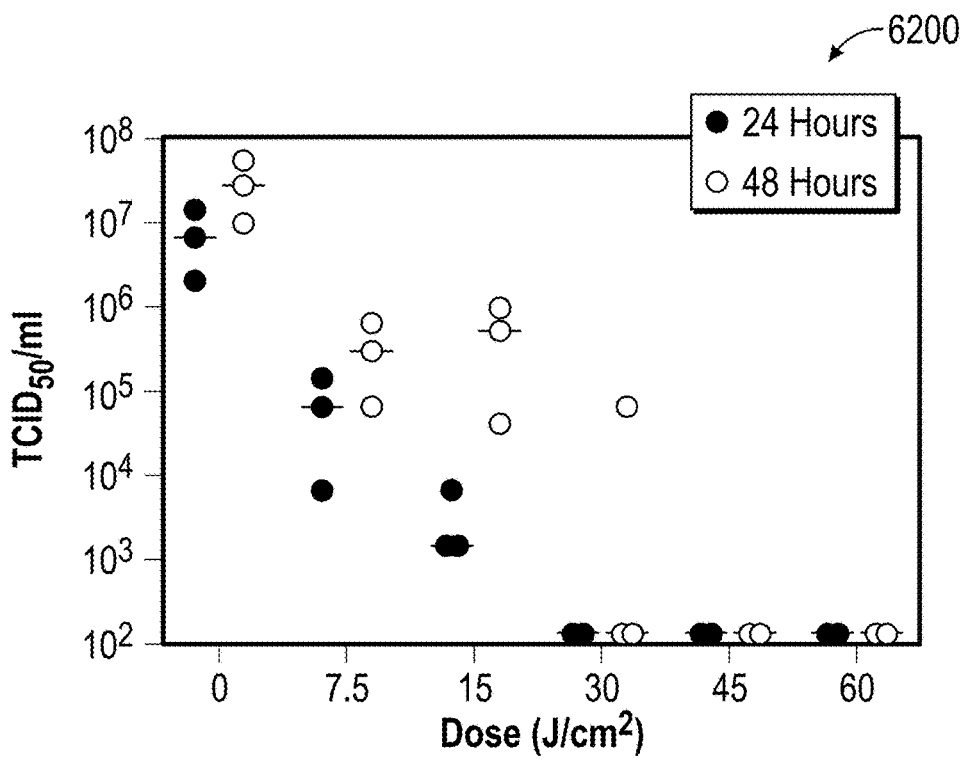

FIG. 62A is a chart illustrating tissue culture infectious dose ($TCID_{50}$) per milliliter (ml) for the 425 nm light at the various dose ranges for Vero E6 cells infected with a MOI of 0.001 SARS-CoV-2 isolate USA-WA1/2020 for 1 hour.

Figure 62B:
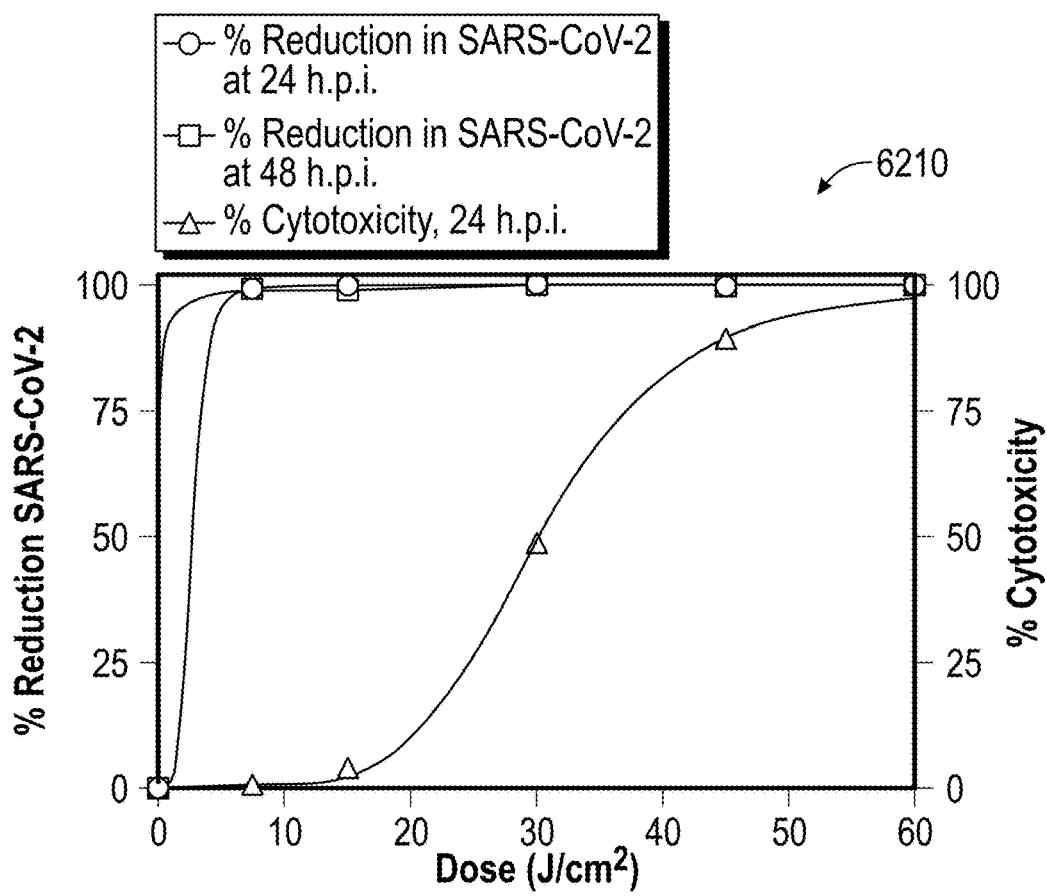

FIG. 62B is a chart illustrating percent reduction in SARS-CoV-2 replication versus percent cell cytotoxicity for the doses of light as illustrated in FIG. 62A.

Figure 63A:
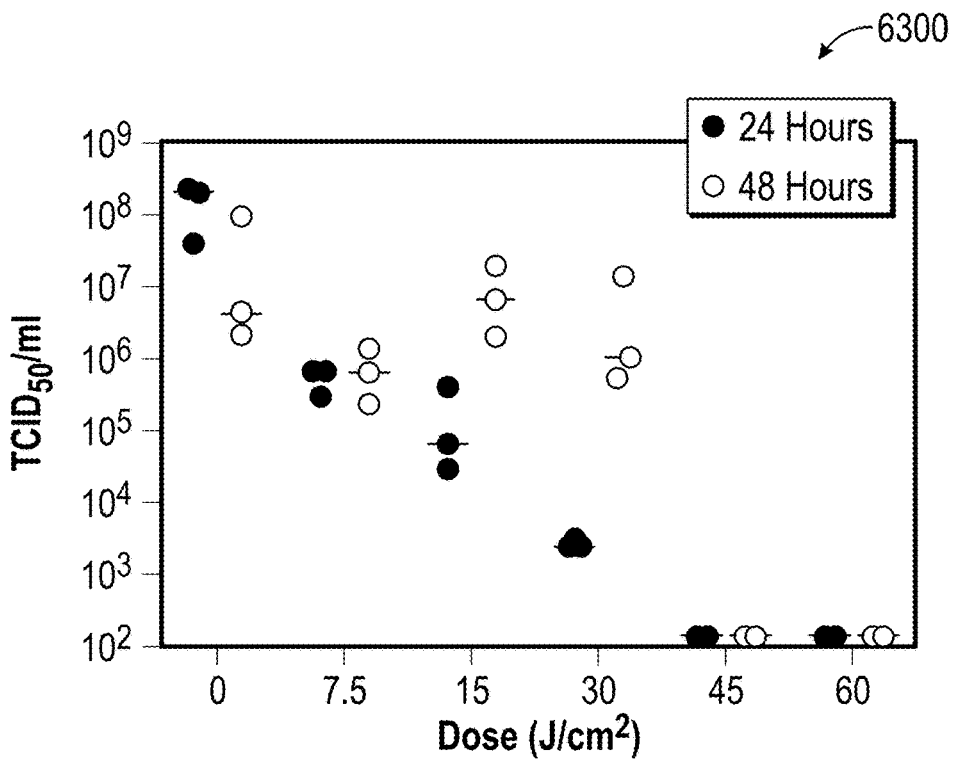

FIG. 63A is a chart illustrating $TCID_{50}$/ml for 425 nm light at various dose ranges for Vero E6 cells infected with a MOI of 0.01 SARS-CoV-2 isolate USA-WA1/2020 for 1 hour.

Figure 63B:
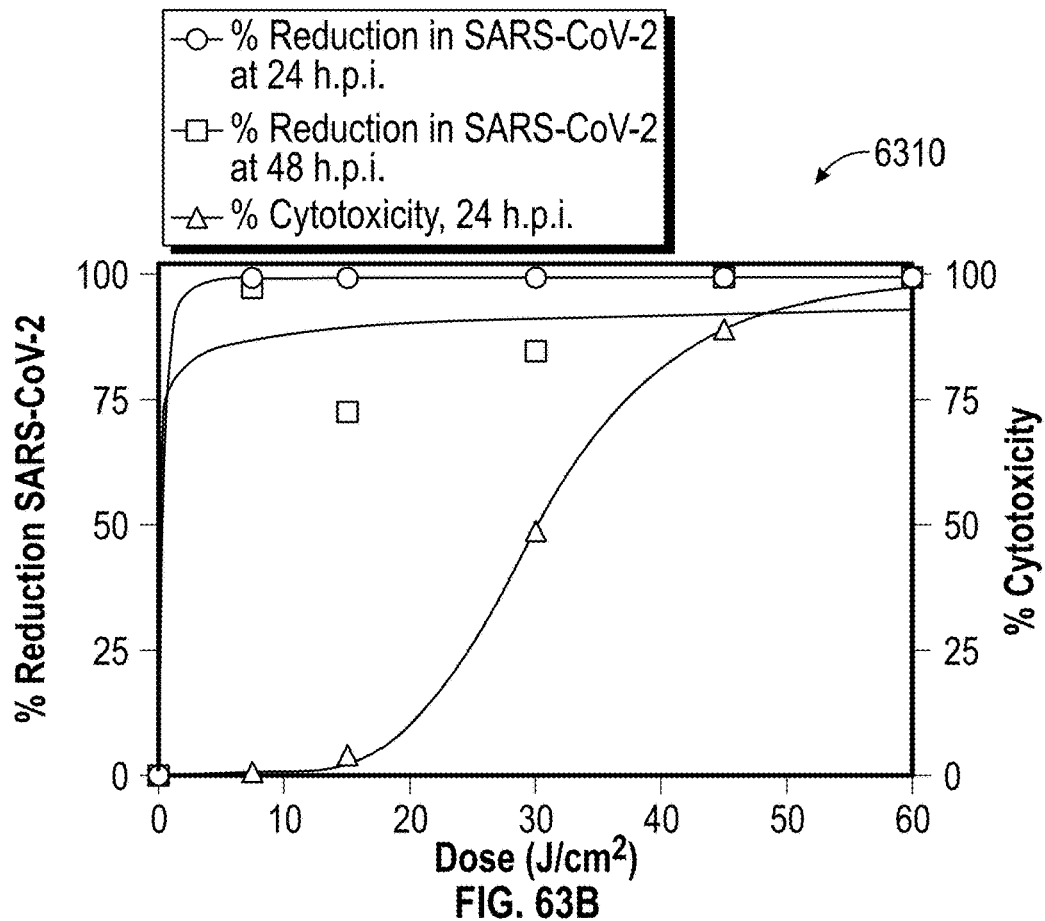

FIG. 63B is a chart illustrating percent reduction in SARS-CoV-2 replication versus percent cell cytotoxicity for the doses of light as illustrated in FIG. 63A.

FIG. 63C is a table showing an evaluation of SARS-CoV-2 RNA with reverse transcription polymerase chain reaction (rRT-PCR) for samples collected for the $TCID_{50}$ assays of FIGS. 63A-63B.

Figure 64A:
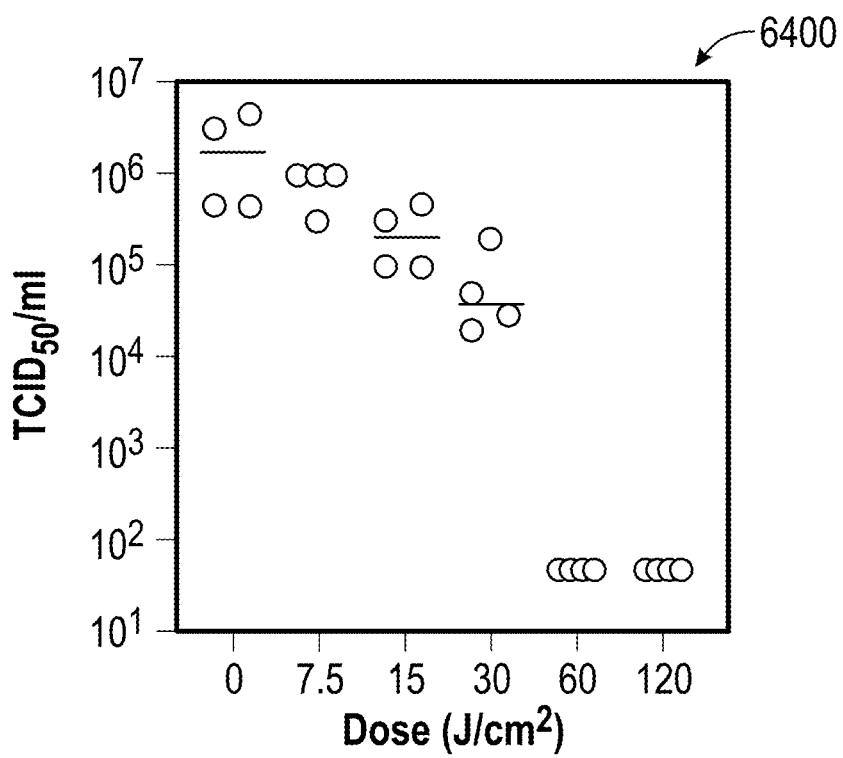

FIG. 64A is a chart illustrating $TCID_{50}$/ml for 425 nm light at various dose ranges for Vero 76 cells infected with a MOI of 0.01 SARS-CoV-2.

Figure 64B:
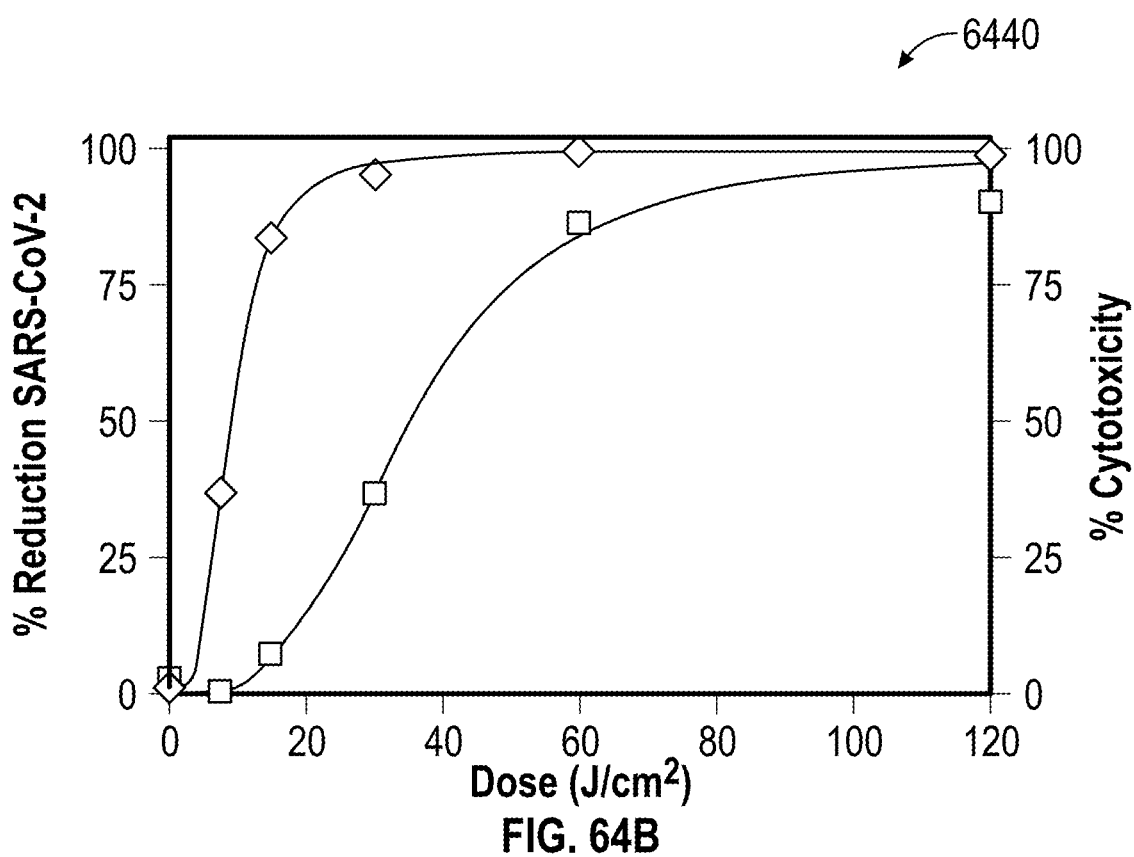

FIG. 64B is a chart illustrating percent reduction in SARS-CoV-2 replication versus percent cell cytotoxicity for the doses of light as illustrated in FIG. 64A.

Figure 65:
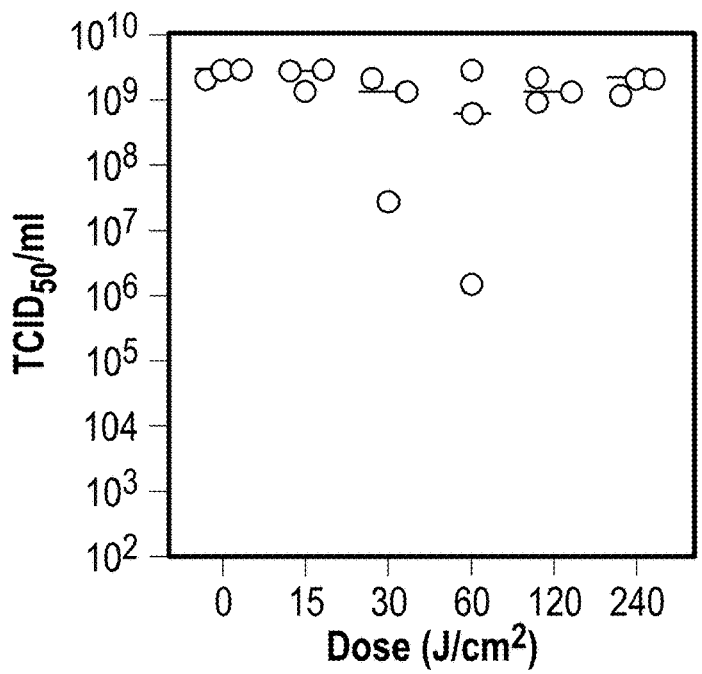

FIG. 65 is a chart illustrating $TCID_{50}$/ml versus various doses of 625 nm red light for Vero E6 cells infected with a MOI of 0.01.

Figure 66A:
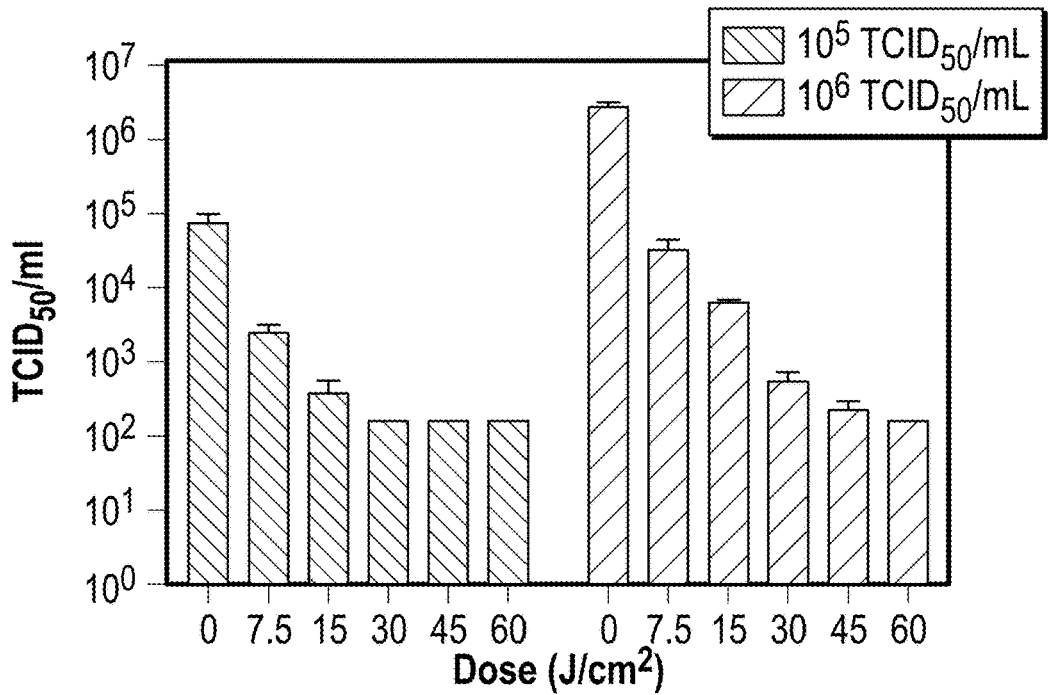

FIG. 66A is a chart illustrating a virus assay by $TCID_{50}$ on Vero E6 cells for SARS-CoV-2 from a first laboratory.

Figure 66B:
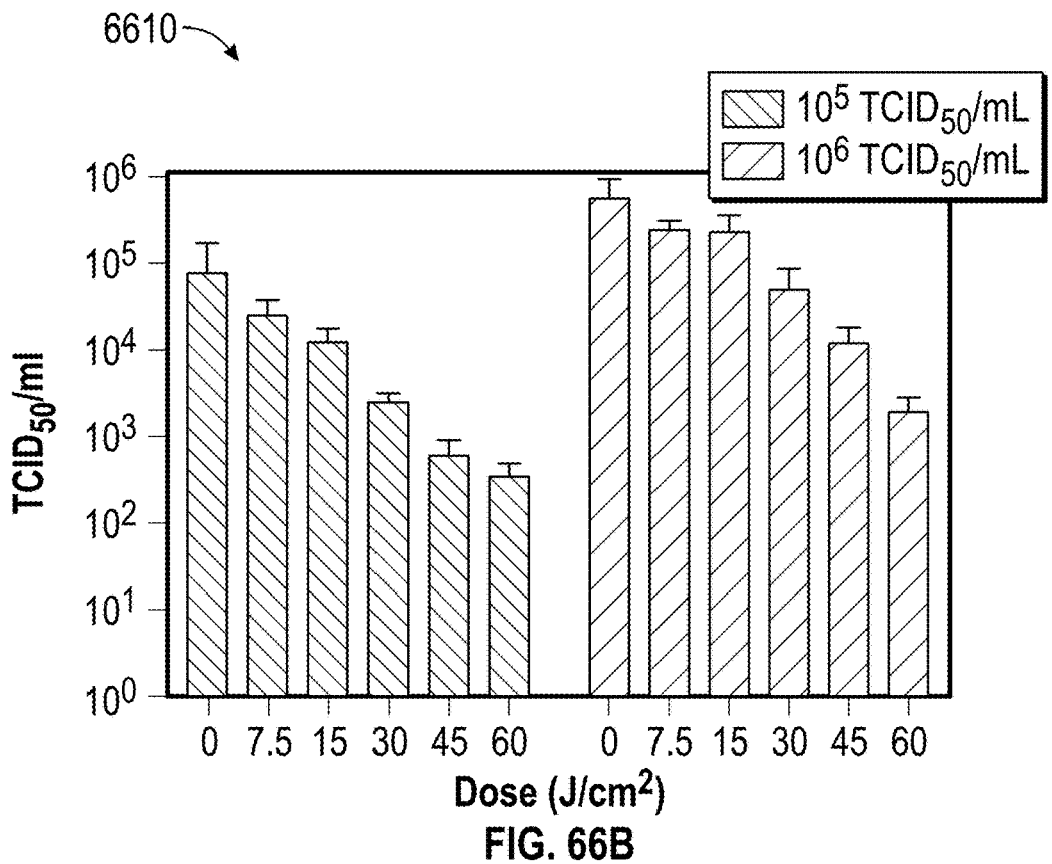
Figure 79A:
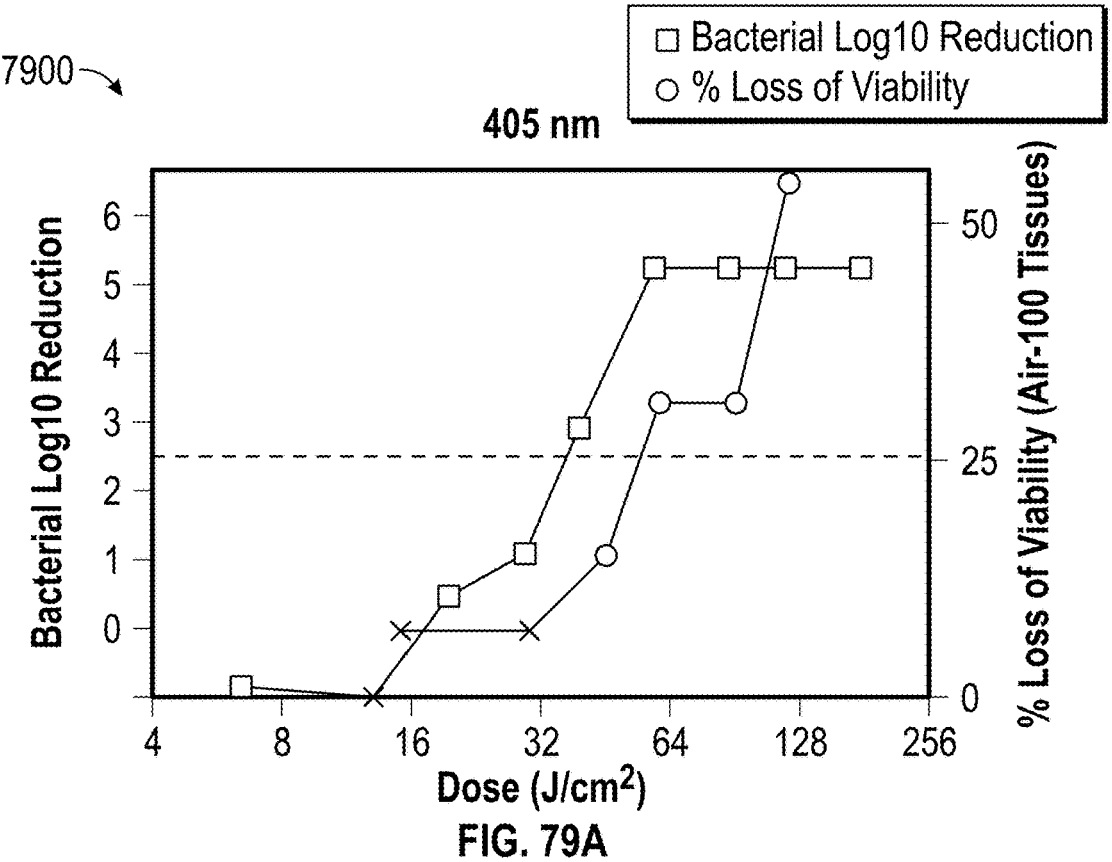

FIG. 66B is a chart illustrating a virus assay by $TCID_{50}$ on Vero E6 cells for SARS-CoV-2 from a first laboratory.

FIG. 67A is a chart indicating that Vero E6 cells do not show decreased viability under 530 nm light at doses ranging from 0-180 J/$cm^2$.

FIG. 67B is a chart indicating that Vero E6 cells do not show decreased viability under 625 nm light at doses ranging from 0-240 J/$cm^2$.

FIG. 68A is a chart showing raw luminescence values (RLU) for different seedings of Vero E6 cell densities and various doses of light (J/$cm^2$).

FIG. 68B is a chart showing percent viability for the different seedings of Vero E6 cell densities and various doses of light of FIG. 68A.

FIG. 68C is a chart comparing RLU versus total cell number to show that CTG is an effective reagent for measuring cell densities of above $10^6$ Vero E6 cells.

FIG. 69A is a chart of $TCID_{50}$/ml versus dose at 24 hours and 48 hours post infection for Calu-3 cells infected with SARS-CoV-2.

FIG. 69B is a chart showing the percent reduction in SARS-Cov-2 compared with percent cytotoxicity, for the Calu-3 cells of FIG. 69A.

FIG. 70A is a chart illustrating percent reduction in SARS-CoV-2 replication versus percent cell cytotoxicity for Vero E6 cells infected with a MOI of 0.01 after various doses of light at 425 nm.

FIG. 70B is a chart illustrating percent reduction in SARS-CoV-2 replication versus percent cell cytotoxicity for Vero E6 cells infected with a MOI of 0.001 after various doses of light at 425 nm.

FIG. 70C is a chart representing percent viability at various doses for primary human tracheal/bronchial tissue from a single donor after various doses of light at 425 nm.

FIG. 71A is a chart illustrating percent reduction in SARS-CoV-2 replication versus percent cell cytotoxicity for Vero E6 cells infected with a MOI of 0.01 after various doses of light at 450 nm.

FIG. 71B is a chart illustrating percent reduction in SARS-CoV-2 replication versus percent cell cytotoxicity for Vero E6 cells infected with a MOI of 0.001 after various doses of light at 450 nm.

FIG. 71C is a chart representing percent viability at various doses for primary human tracheal/bronchial tissue from a single donor after various doses of light at 450 nm.

FIG. 72 is a table summarizing the results illustrated in FIGS. 70A-70C and 71A-71C.

FIG. 73A is a chart showing the titer of WT influenza A virus based on remaining viral loads for different initial viral doses after treatment with different doses of 425 nm light.

FIG. 73B is a chart showing the titer of Tamiflu-resistant influenza A virus based on remaining viral load for a single initial viral dose after treatment of different doses of 425 nm light.

FIG. 74A is a chart showing the $TCID_{50}$/ml versus energy dose for WT-influenza A treated with light at 425 nm at various doses with a MOI for the WT-influenza A of 0.01.

FIG. 74B is a chart showing the percent reduction in viral loads of WT-influenza A and percent cytotoxicity against the treated cells when influenza A-infected Madin-Darby Canine Kidney (MDCK) cells were exposed to 425 nm light at various doses and a MOI for the WT-influenza A was provided at 0.01.

FIG. 74C illustrates the $TCID_{50}$ of cells infected with WT-influenza A and treated with 425 nm light at various doses with a MOI for the WT-influenza A of 0.1.

FIG. 74D illustrates the percent reduction in viral loads of WT-influenza A and percent cytotoxicity against the treated cells when influenza A-infected Madin-Darby Canine Kidney (MDCK) cells were exposed to 425 nm light at various doses and a MOI for the WT-influenza A was provided at 0.1.

FIG. 75A is a chart showing the effectiveness of light at 405, 425, 450, and 470 nm and administered with a dose of 58.5 J/$cm^2$, in terms of hours post-exposure, at killing *P. aeruginosa.*

FIG. 75B is a chart showing the effectiveness of light at 405, 425, 450, and 470 nm, and administered with a dose of 58.5 J/$cm^2$, in terms of hours post-exposure, at killing *S. aeurus.*

FIG. 76A is a chart showing the effectiveness of light at 425 nm and administered with doses ranging from 1 to 1000 J/$cm^2$ at killing *P. aeruginosa.*

FIG. 76B is a chart showing the effectiveness of light at 425 nm and administered with doses ranging from 1 to 1000 J/$cm^2$ at killing *S. aureus.*

FIG. 77A is a chart showing the effectiveness of light at 405 nm and administered with doses ranging from 1 to 1000 J/$cm^2$ at killing *P. aeruginosa.*

FIG. 77B is a chart showing the effectiveness of light at 405 nm and administered with doses ranging from 1 to 1000 J/$cm^2$ at killing *S. aureus.*

FIG. 78 is a chart showing the toxicity of 405 nm and 425 nm light in primary human aortic endothelial cells (HAEC).

FIG. 79A is a chart showing the bacterial $\log_{10}$ reduction and the % loss of viability of infected AIR-100 tissues following exposure of the tissue to doses of light ranging from 4 to 512 J/cm² at 405 nm.

Figure 79B:
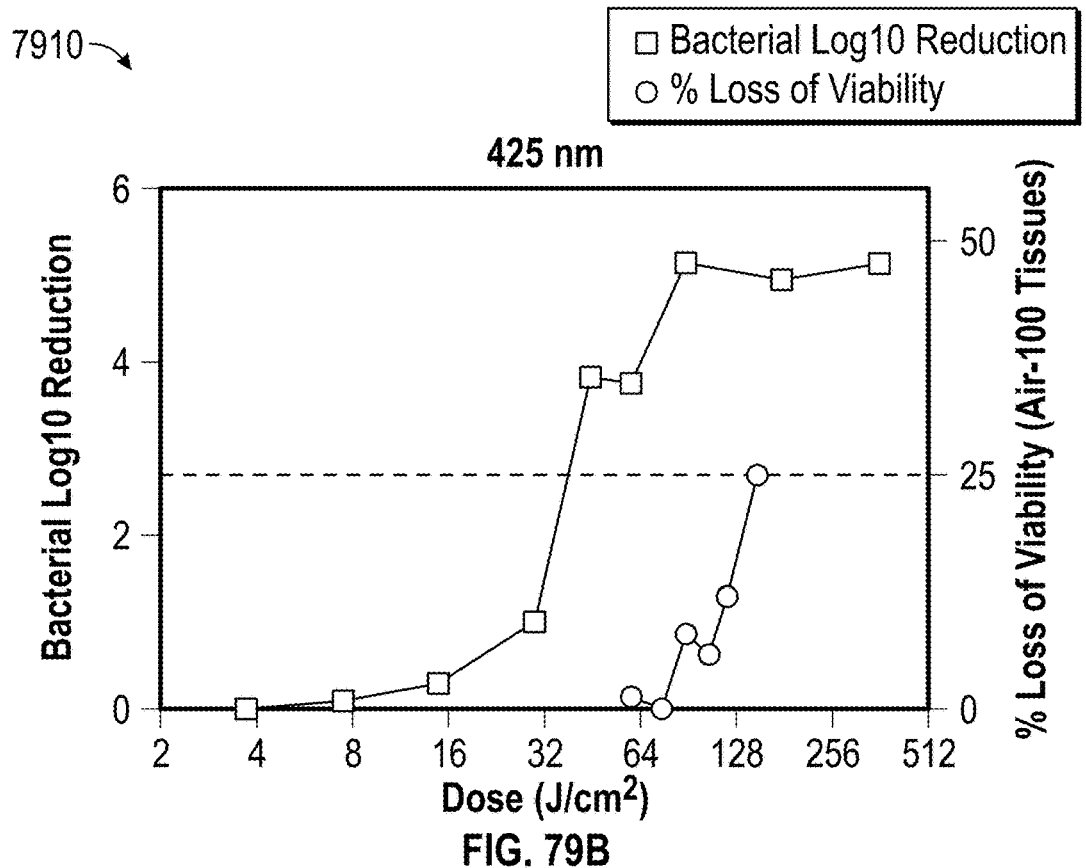

FIG. 79B is a chart showing the bacterial $\log_{10}$ reduction and the % loss of viability of infected AIR-100 tissues following exposure of the tissue to doses of light ranging from 4 to 512 J/cm² at 425 nm.

Figure 79C:
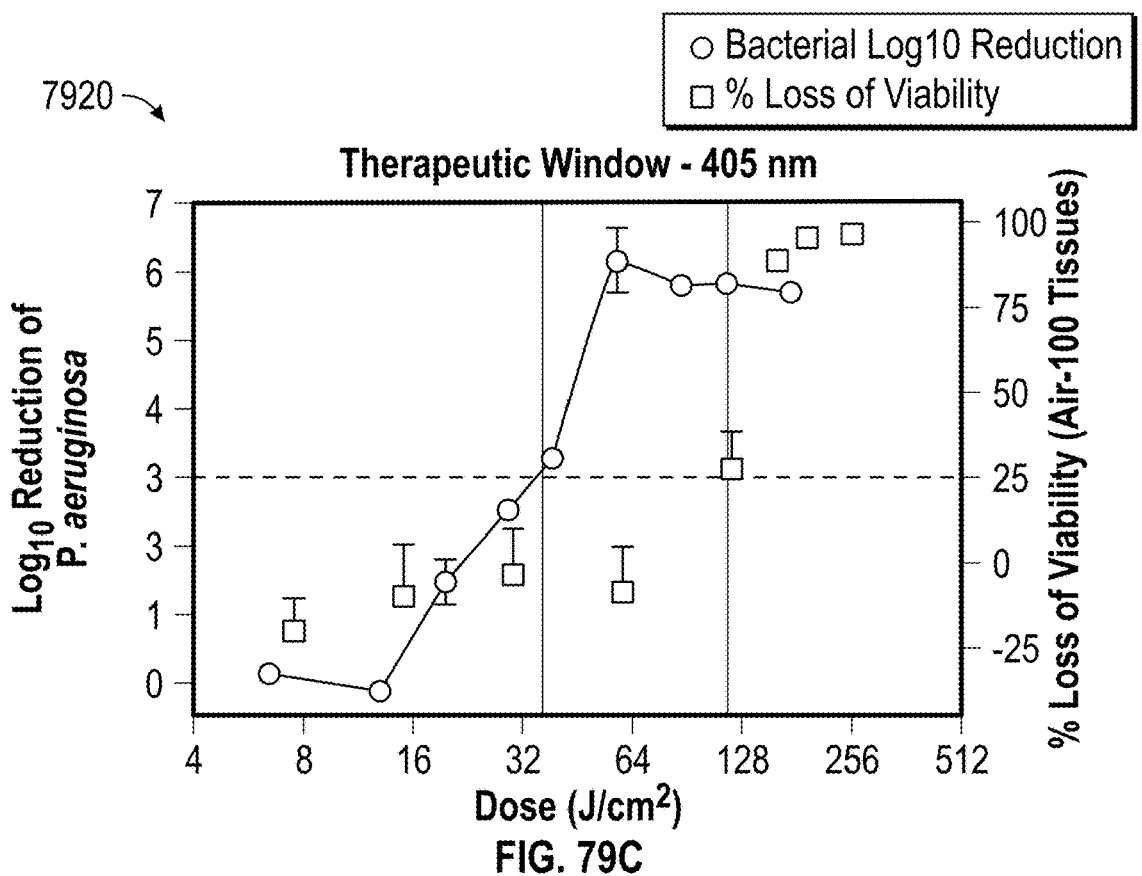

FIG. 79C is a chart showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm² at 405 nm.

Figure 79D:
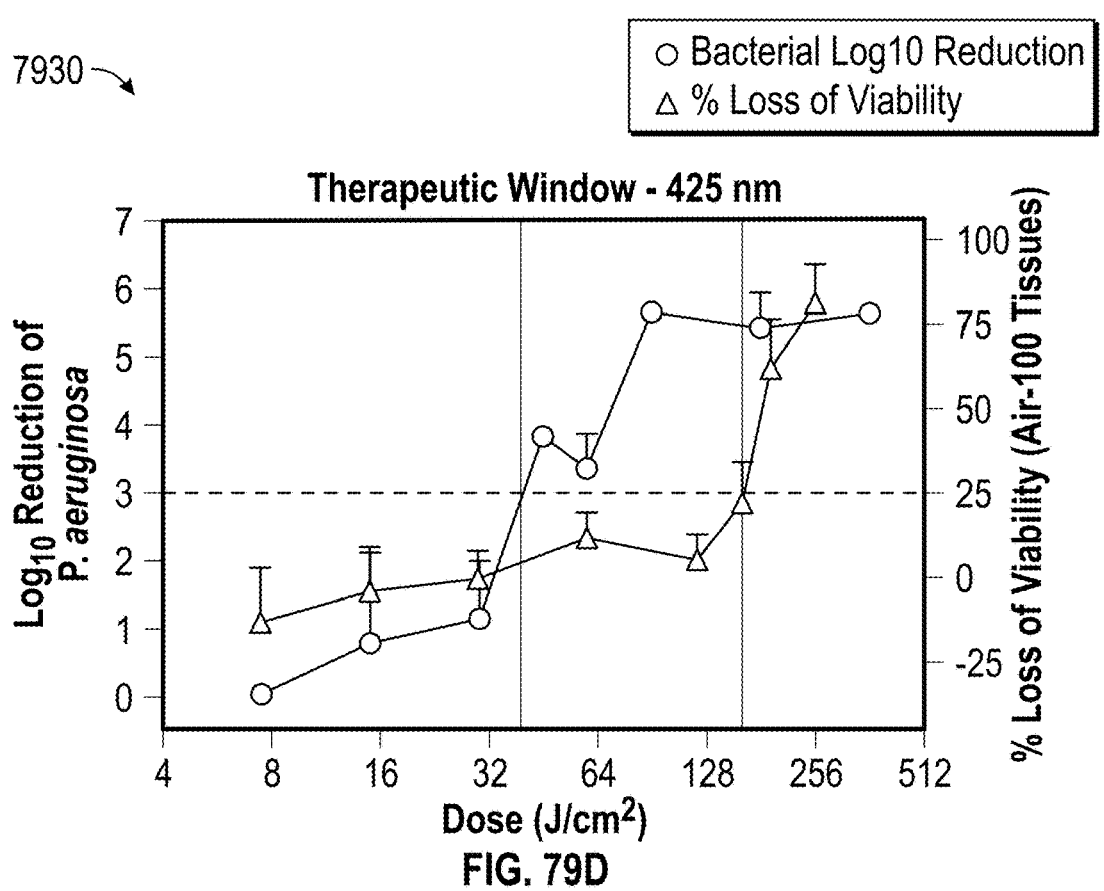

FIG. 79D is a chart showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm² at 425 nm.

Figure 79E:
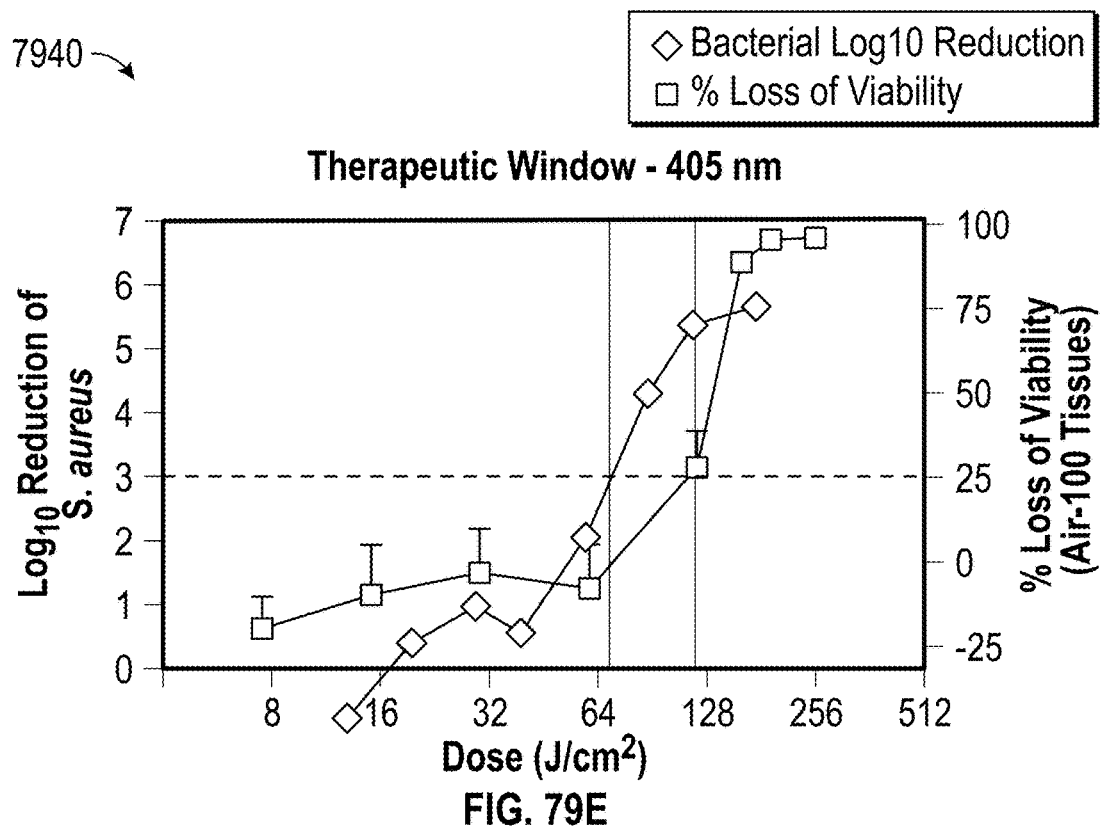

FIG. 79E is a chart showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm² at 405 nm.

Figure 79F:
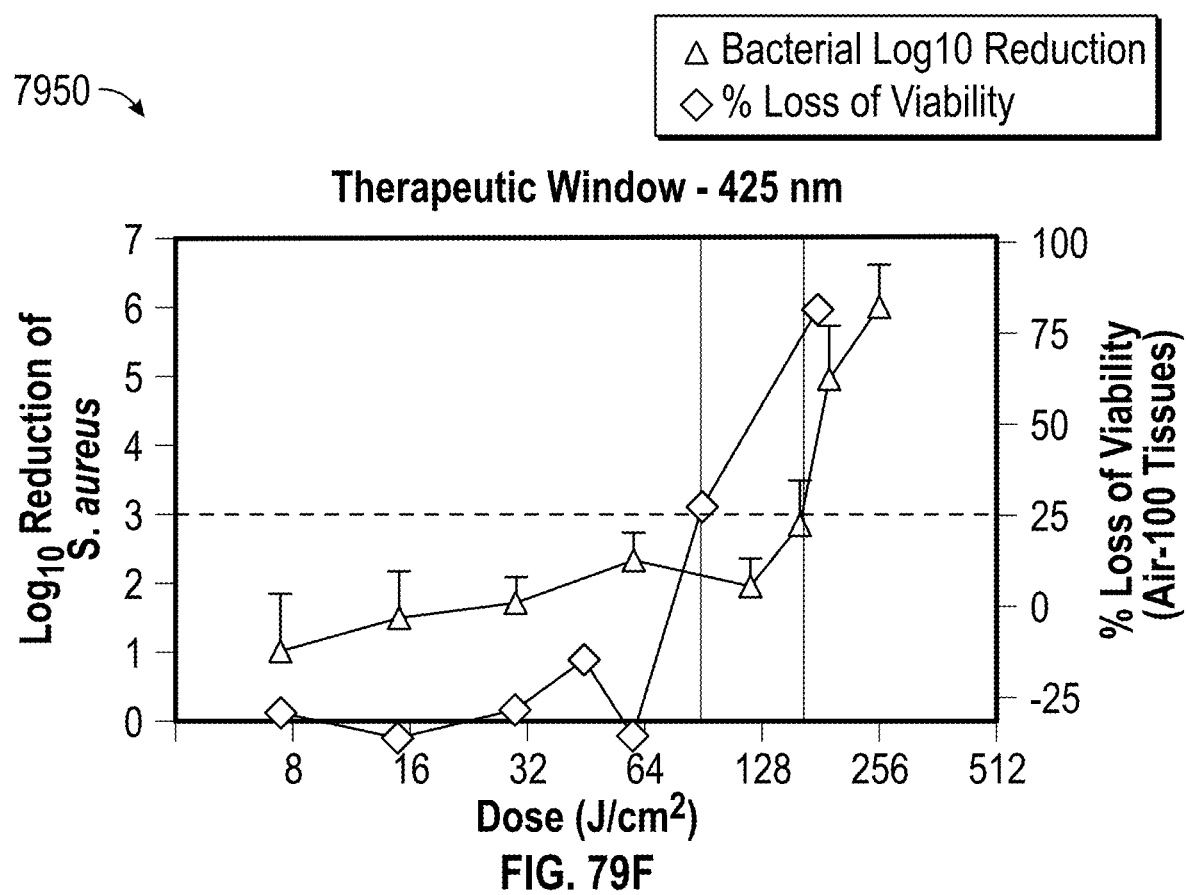
Figure 80A:
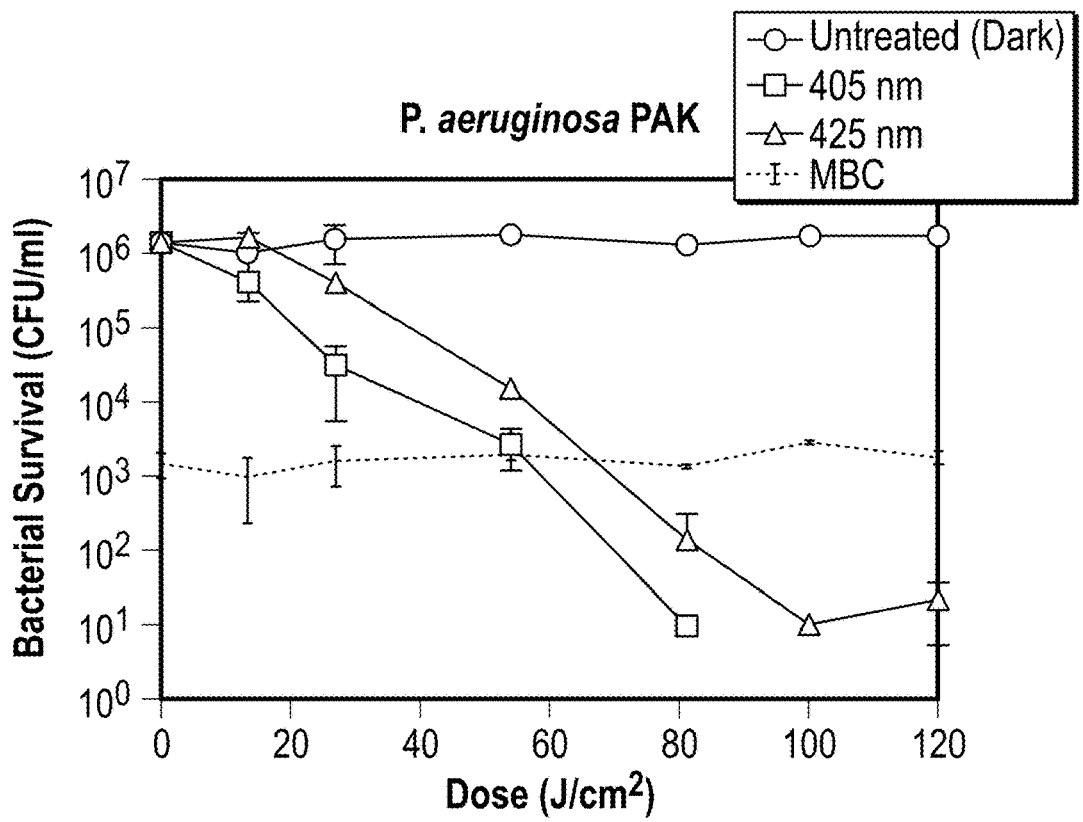
Figure 80B:
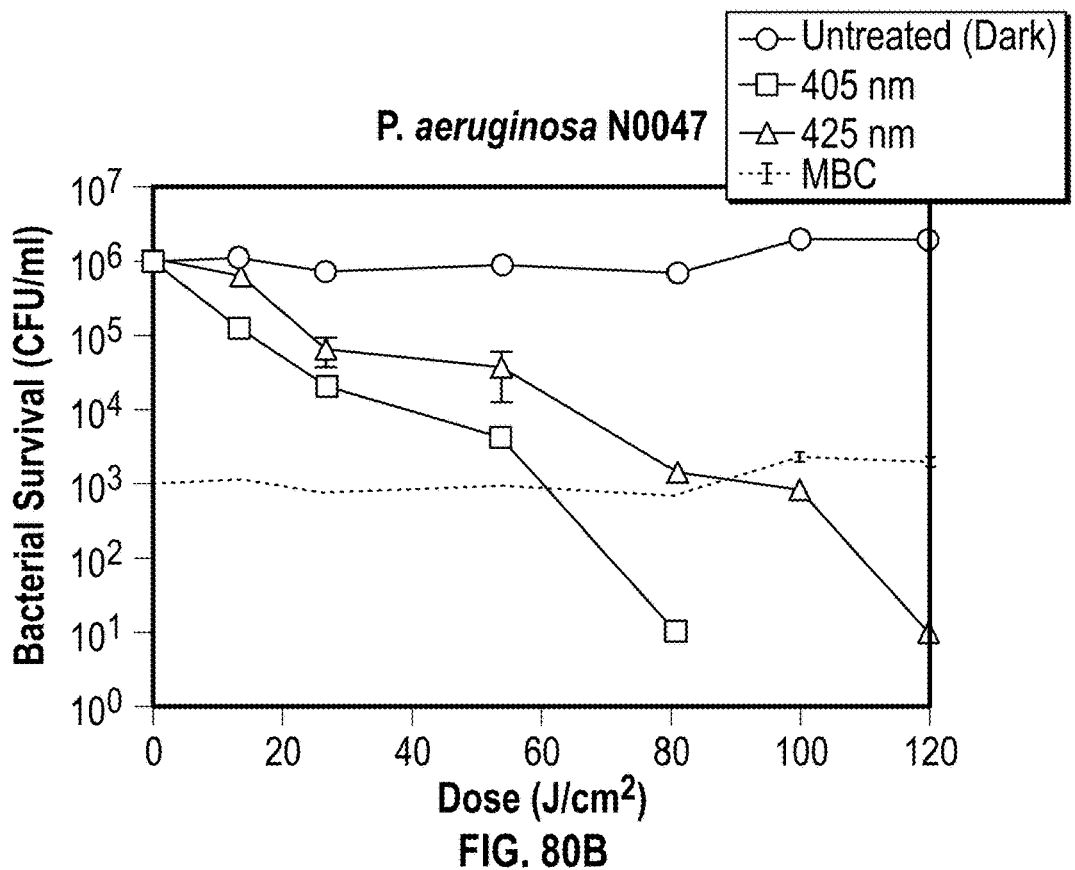
Figure 80C:
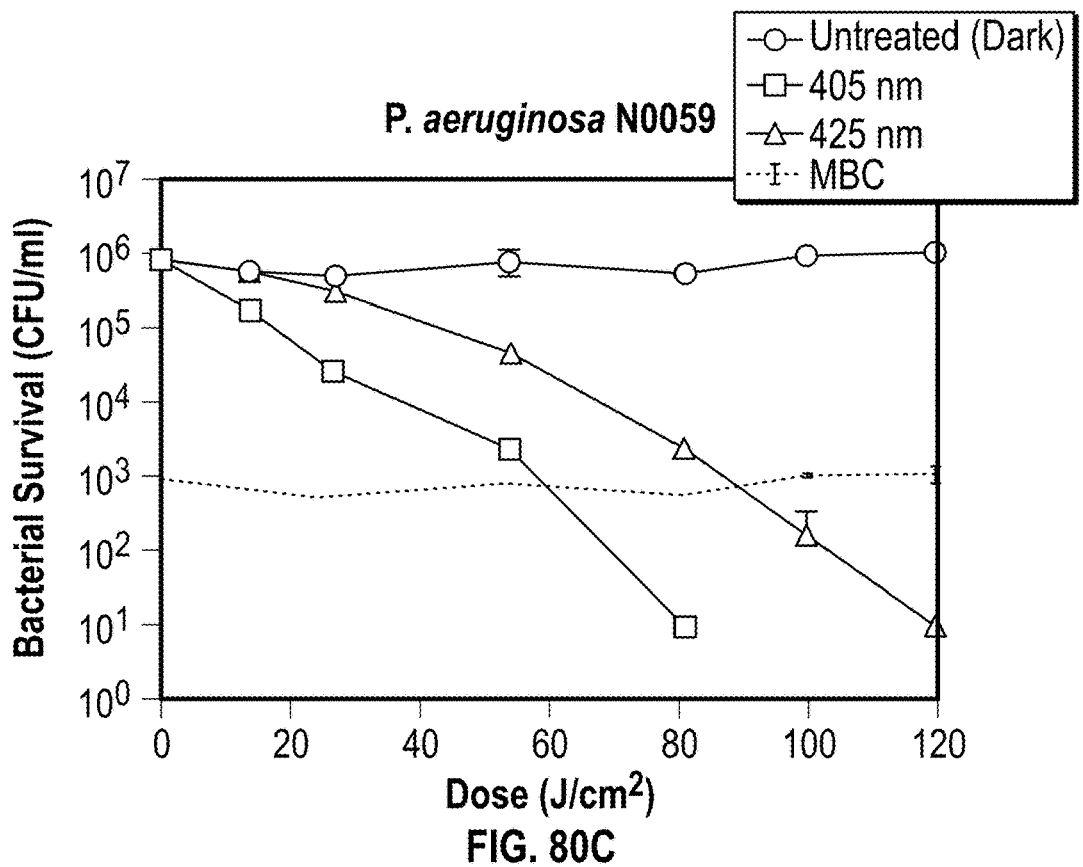
Figure 80D:
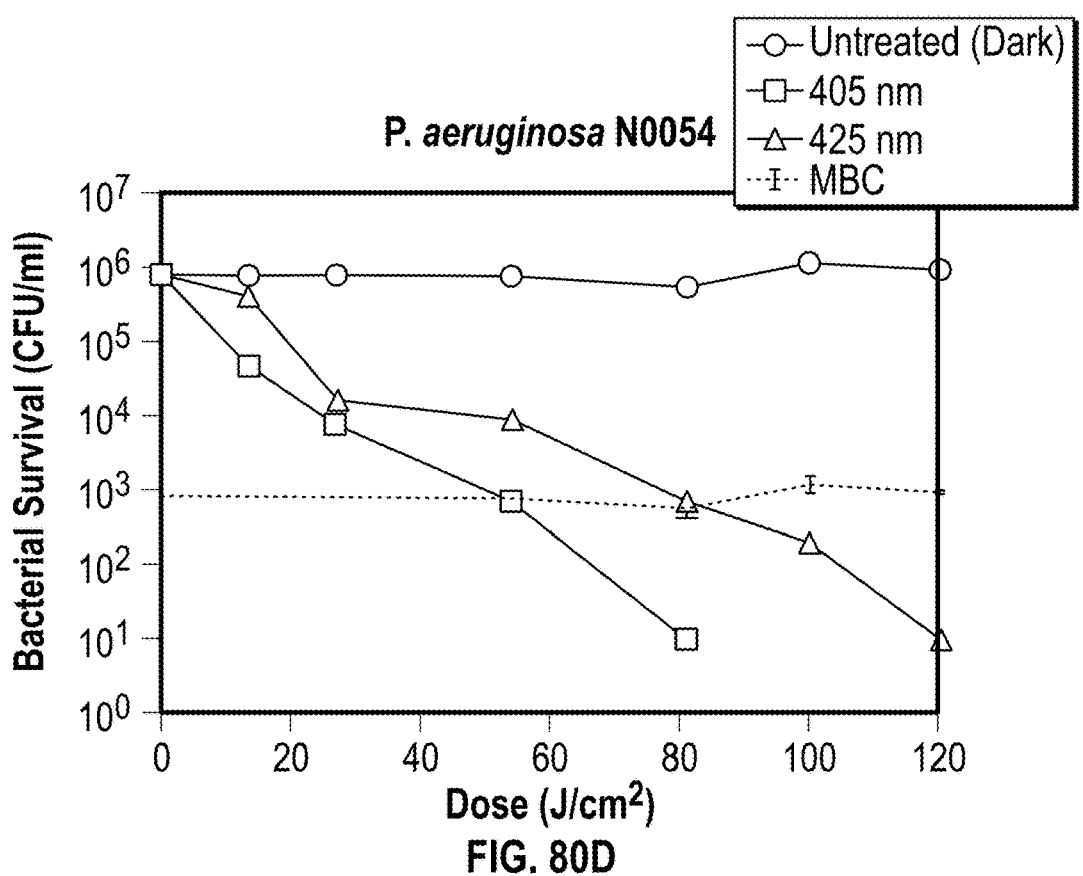
Figure 80E:
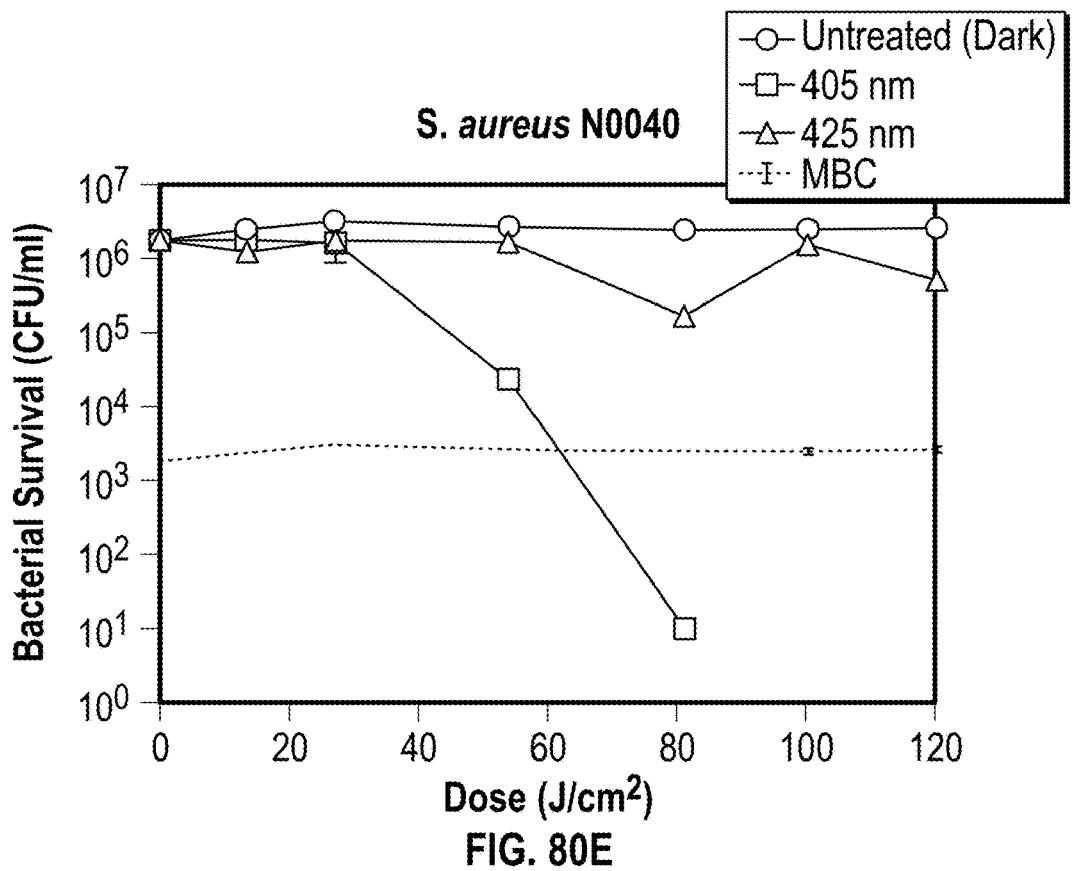
Figure 80F:
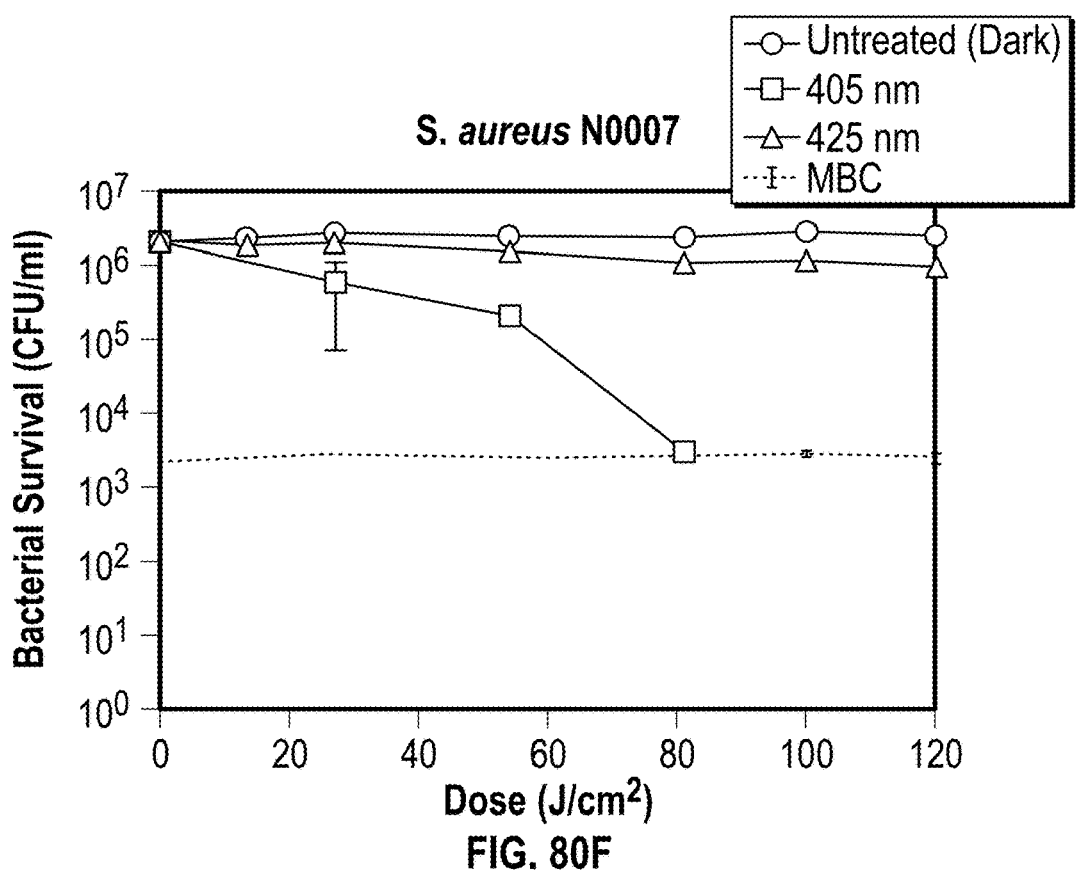
Figure 80G:
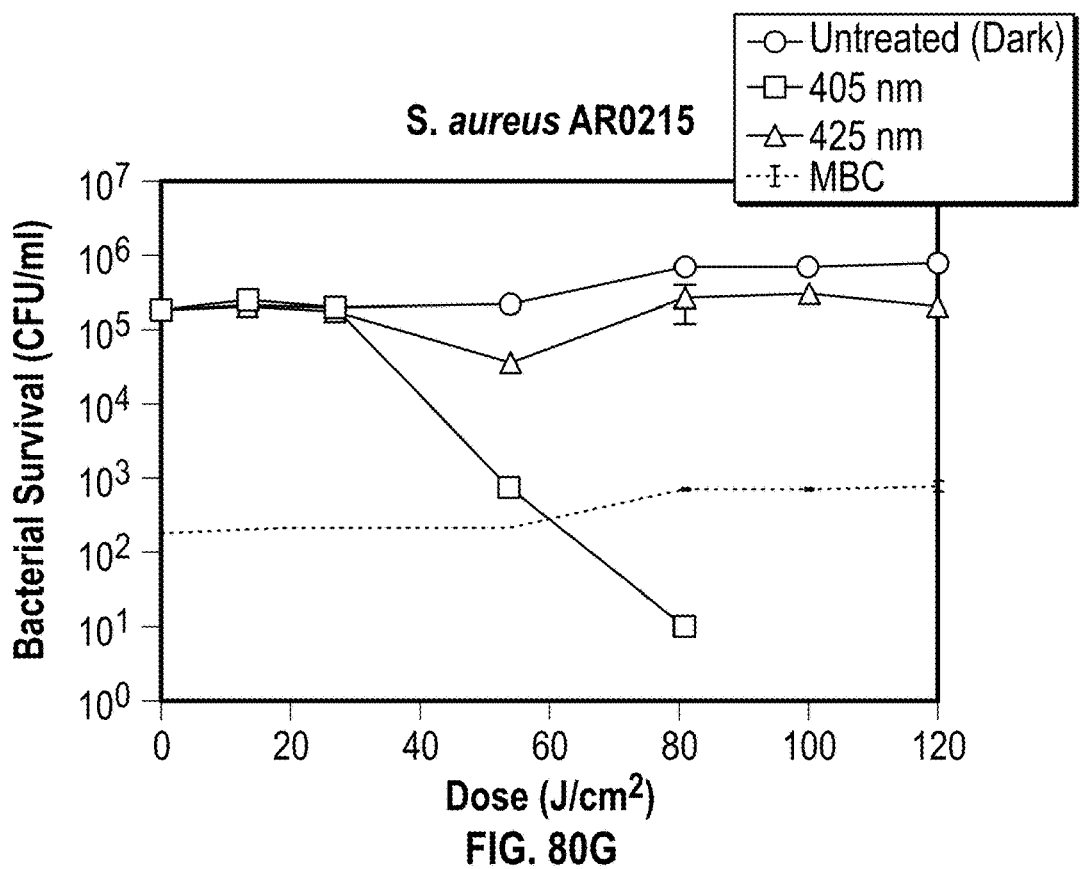
Figure 80H:
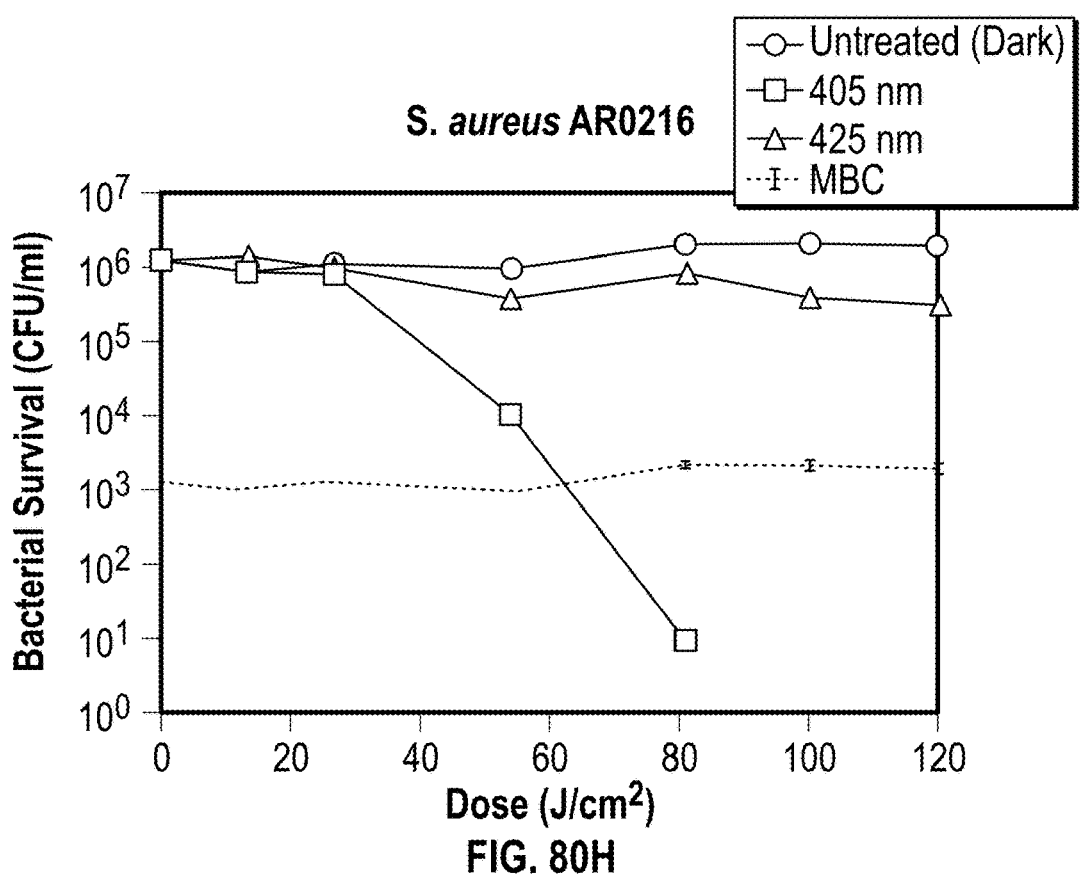
Figure 80I:
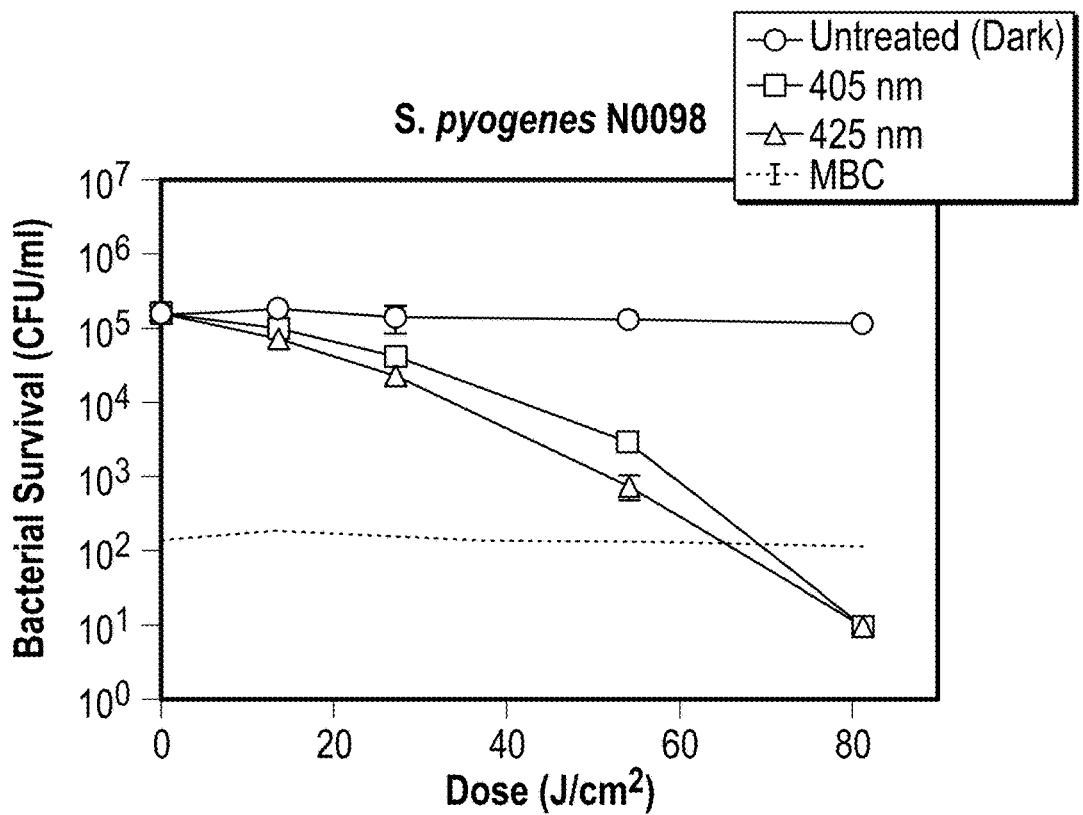
Figure 80J:
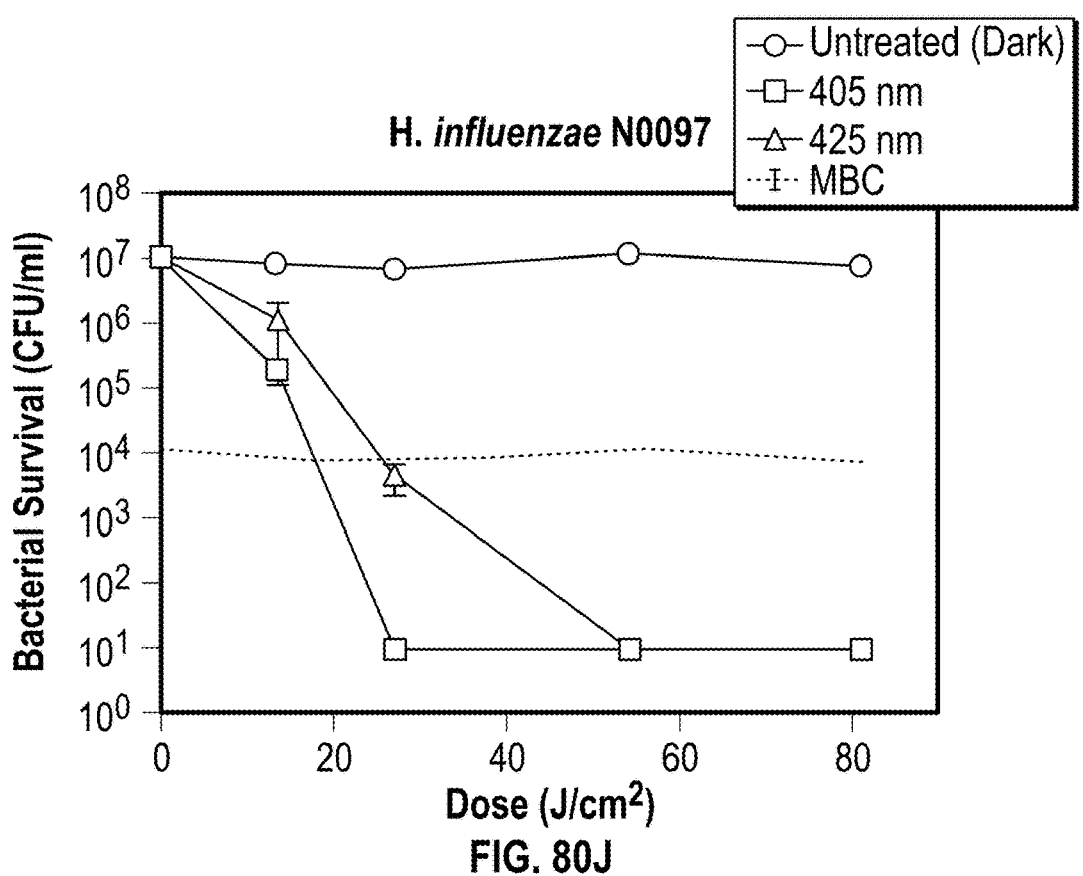

FIG. 79F is a chart showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm² at 425 nm.

FIGS. 80A-80J are a series of charts showing the effect of light at 405 nm and 425 nm, at differing dosage levels, in terms of bacterial survival vs. dose (J/cm²) for both *P. aeruginosa* and *S. aureus* bacteria.

FIG. 81 is a table summarizing the light therapeutic index (LTI) calculations and corresponding bactericidal doses for the bacterial experiments illustrated in FIGS. 79A-80.

Figure 82:
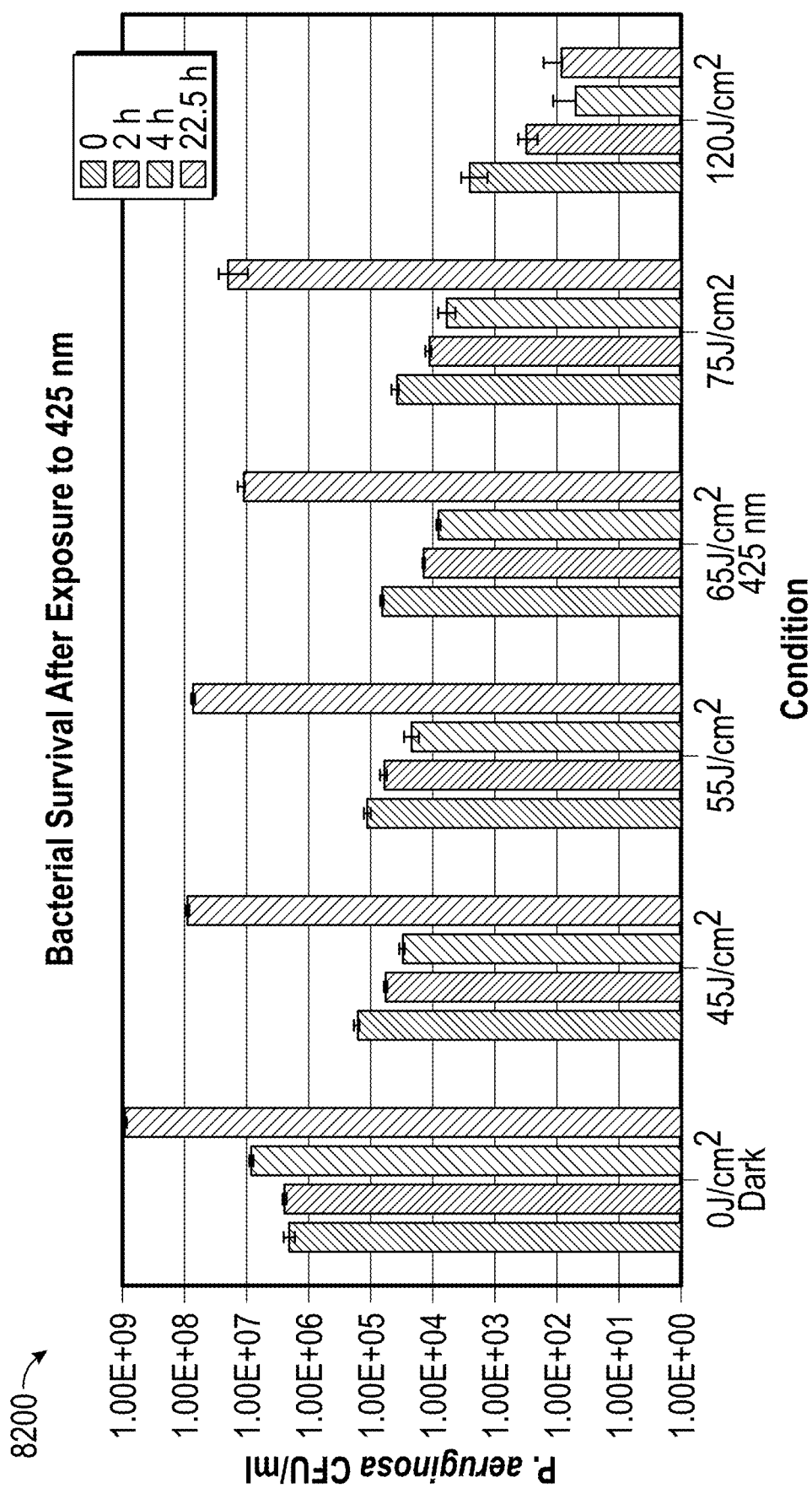

FIG. 82 is a chart showing the effect of 425 nm light at various doses at killing *P. aeuriginosa* over a period of time from 0 hours, 2 hours, 4 hours, and 22.5 hours.

Figure 83:
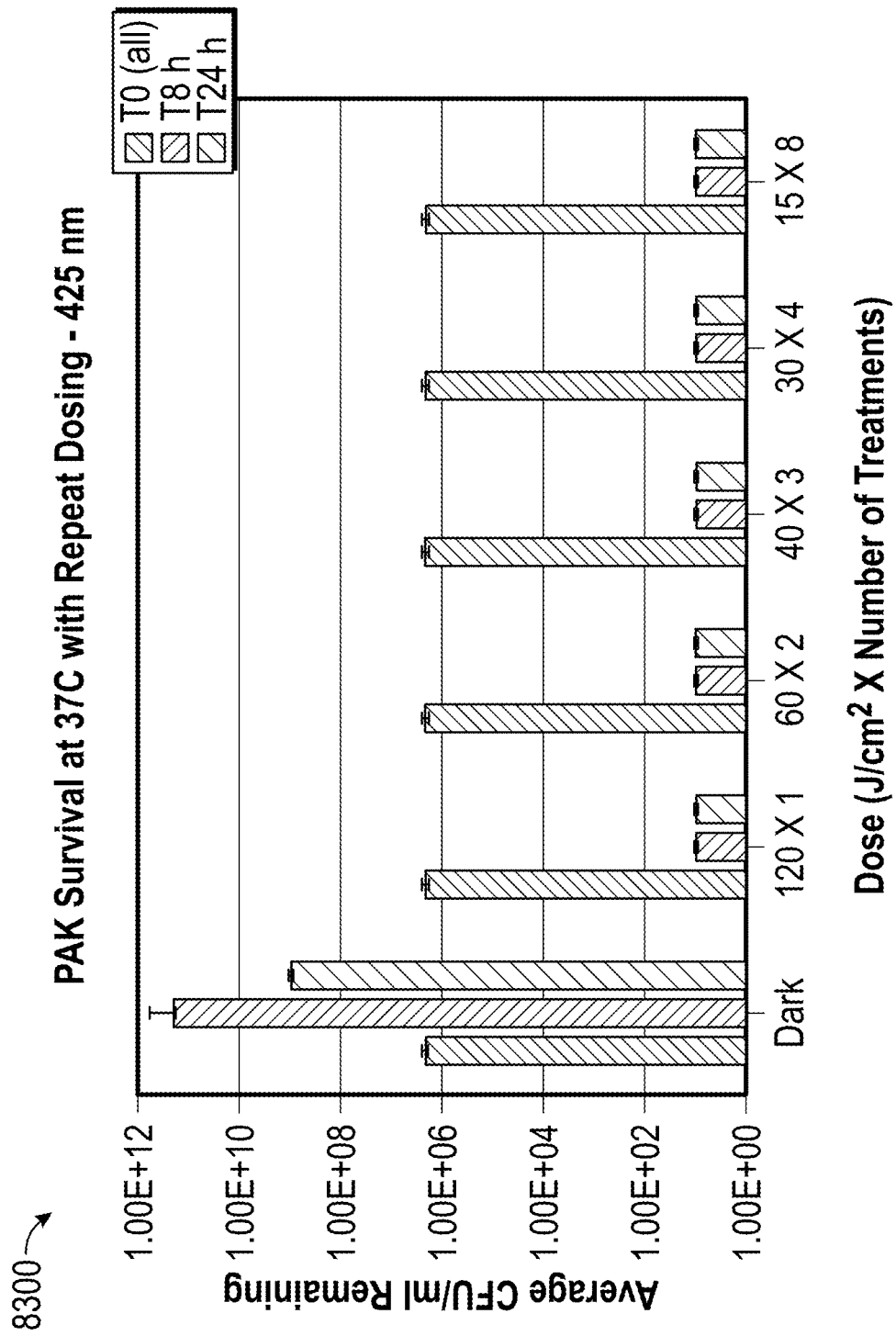

FIG. 83 is a chart showing that whether all of the light (J/cm²) is administered in one dose or in a series of smaller doses, the antimicrobial effect (average CFU/ml) vs. dose (J/cm²×number of treatments) is largely the same, at 8 hours and 48 hours post-administration.

Figure 84A:
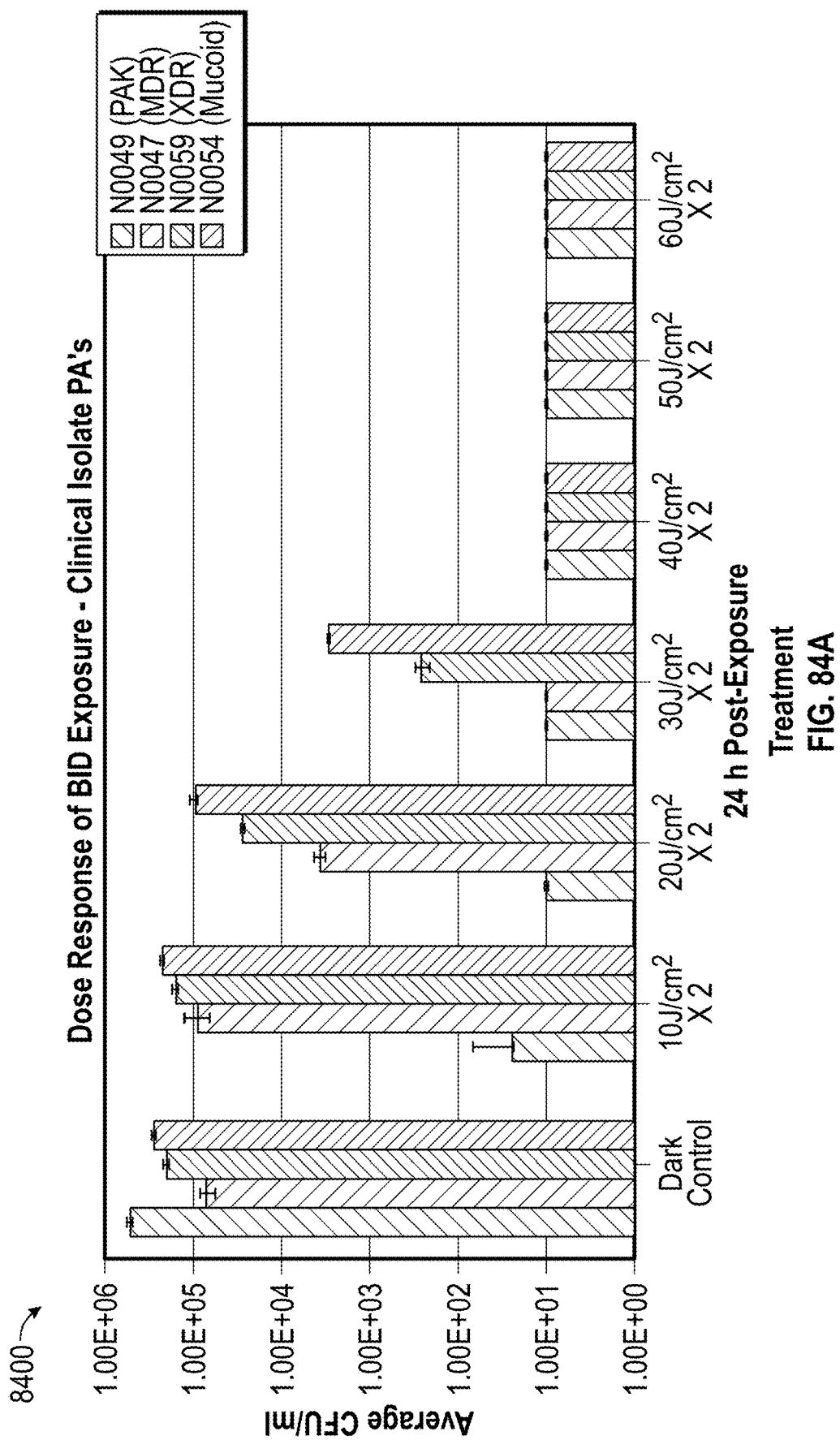

FIG. 84A is a chart showing the treatment of a variety of drug-resistant bacteria (Average CFU/ml) vs. dose (J/cm²) at 24 hours post-exposure.

FIG. 84B is a table summarizing the tested bacteria species and strains.

FIG. 84C is a table that summarizes the efficacy of twice daily dosing of 425 nm light against difficult-to-treat clinical lung pathogens.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

Aspects of the present disclosure relate to devices and methods for impinging light on a mammalian tissue, for example within a body and/or a body cavity of a patient, where the light may include at least one characteristic that exerts or induces at least one biological effect within or on the tissue. Biological effects may include at least one of inactivating and inhibiting growth of one or more combinations of microorganisms and pathogens, including but not limited to viruses, bacteria, fungi, and other microbes, among others. Biological effects may also include one or more of upregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissue and the targeted microorganisms or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Microorganisms, including disease-causing pathogens, typically invade tissues of the human body via two primary routes: mucosal surfaces within body cavities, such as the mucous membranes or mucosae of the respiratory tract, and epithelial surfaces outside of the body. There are a number of respiratory infections with disease-causing agents, including viruses and bacteria. Examples include Orthomyxoviridae (e.g., influenza), colds, coronaviridae (e.g., coronavirus), and picornavirus infections, tuberculosis, pneumonia, and bronchitis. Most infections begin when a subject is exposed to pathogen particles, which enter the body through the mouth, nose, and ears. For viral infections, three requirements typically must be satisfied to ensure successful infection in an individual host. Namely, a sufficient amount of the virus must be available to initiate infection, cells at the site of infection must be accessible, susceptible, and permissive for the virus, and local host anti-viral defense systems must be absent or initially ineffective.

Conventional treatments for respiratory infections typically involve systemic administration of antimicrobials, which can, unfortunately, lead to drug resistance and gastrointestinal distress. Devices and methods for treating, preventing, or reducing the biological activity of pathogens while they are in the mouth, nose, and/or ears, and before they travel to the lungs or elsewhere in the body, in contrast, would be particularly beneficial. In particular, such devices and methods could prevent infection by reducing microbial load before pathogens enter the lungs, decreasing the ability for penetration into cells at the site of infection, and amplifying host defense systems, all of which may minimize or avoid the need for traditional antimicrobial medicines.

The present disclosure is generally directed to illumination devices, apparatus, and methods for impinging light onto living tissue in order to induce one or more therapeutic biological effects. In various aspects, induced biological effects may include least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, the light may be referred to as nitric-oxide modulating light to increase concentrations of unbound nitric oxide within living tissue. As will be explained in greater detail below, embodiments of the present disclosure may administer light at one or more wavelengths as a Pre-Exposure Prophylaxis (PrEP) or a Post-Exposure Prophylaxis (PEP) in order to (1) eliminate pathogens in or on tissue of the ears, nose, mouth, throat, or other body cavities and/or (2) amplify host defense systems. Embodiments of the present disclosure may be used to prevent and/or treat respiratory infections and other infectious diseases. For example, in one embodiment, a hand-held illumination device may administer light at one or more wavelengths as a prophylactic measure to reduce viral infectivity and incidence of COVID-19 in individuals who have been infected or believe they may have been exposed to SARS-CoV-2 virus. In certain aspects, illumination devices of the present disclosure may be provided or referred to as phototherapeutic and/or phototherapy devices.

The term "phototherapy" relates to the therapeutic use of light. As used herein, phototherapy is used to treat or prevent microbial infections, including viral infections of the body including mucosal epithelial tissues in the vaginal cavity, anal canal, oral cavity, the auditory canal, the upper respiratory tract and esophagus.

The mechanisms by which the wavelengths of light are effective can vary, depending on the wavelength that is administered. Biological effects, including antimicrobial effects, can be provided over a wide range of wavelengths, including UV ranges, visible light ranges, and infrared ranges. The effects vary depending on the mechanism by which the light is antimicrobial, and the wavelengths that bring about these mechanisms.

An illumination device for the treatment of pathogen infected tissues and/or for inducing one or more biological effects may take any form suitable for delivering light to the infected tissue. The device will contain a light source capable of emitting a suitable light profile that can provide one or more direct or indirect biological effects. A light profile can be represented with a graph of emission intensity versus wavelength of light for any particular light source. Disclosed herein are light sources with light profiles in the visible spectrum, for example with light emissions with peak wavelengths primarily in a range from 400 nm to 700 nm. Depending on the target application, light profiles may also include infrared or near-infrared peak wavelengths at or above 700 nm, or ultraviolet peak wavelengths at or below 400 nm. In certain embodiments, light emissions may have a single peak wavelength in a range from 200 nm to 900 nm, or in a range from 400 nm to 490 nm, or in a range from 400 nm to 435 nm, or in a range from 400 nm to 420 nm, or in a range from 410 nm to 440 nm, or in a range from 420 nm to 440 nm, or in a range from 450 nm to 490 nm, or in a range from 500 nm to 900 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in a range from 320 nm to 400 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects. Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color LEDs in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad spectrum LED may provide certain wavelengths that induce one or more biological effects while also providing broad spectrum emissions to the target area for illumination. In this regard, light impingement on tissue for single and/or multiple microorganisms and/or multiple pathogenic biological effects may be provided with light of a single peak wavelength or a combination of light with more than one peak wavelength.

Doses of light to induce one or more biological effects may be administered with one or more light characteristics, including peak wavelengths, radiant flux, and irradiance to target tissues. Irradiances to target tissues may be provided in a range from 0.1 milliwatts per square centimeter (mW/cm$^2$) to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in another range specified herein. Depending on the configuration of one or more of the light source, the corresponding illumination device, and the distance away from a target tissue, the radiant flux value for the light source may be higher than the irradiance value at the tissue.

While certain peak wavelengths for certain target tissue types may be administered with irradiances up to 1 W/cm$^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 W/cm$^2$ to 10 W/cm$^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered over a number of times to provide a cumulative or total dose over a cumulative time period. By way of example, a single dose of light as disclosed herein may be provided over a single time period, such as in a range from 10 microseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter (J/cm$^2$) to 100 J/cm$^2$, or in a range from 0.5 J/cm$^2$ to 50 J/cm$^2$, or in a range from 2 J/cm$^2$ to 80 J/cm$^2$, or in a range from 5 J/cm$^2$ to 50 J/cm$^2$, while corresponding cumulative doses may be provided in a range from 1 J/cm$^2$ to 1000 J/cm$^2$, or in a range from 1 J/cm$^2$ to 500 J/cm$^2$, or in a range from 1 J/cm$^2$ to 200 J/cm$^2$, or in a range from 1 J/cm$^2$ to 100 J/cm$^2$, or in a range from 4 J/cm$^2$ to 160 J/cm$^2$, or in a range from 10 J/cm$^2$ to 100 J/cm$^2$, among other discloses ranges. In a specific example, a single dose may be administered in a range from 10 J/cm$^2$ to 20 J/cm$^2$, and the single dose may be repeated twice a day for four consecutive days to provide a cumulative dose in a range from 80 J/cm$^2$ to 160 J/cm$^2$. In another specific example, a single dose may be administered at about 30 J/cm$^2$, and the single dose may be repeated twice a day for seven consecutive days to provide a cumulative dose of 420 J/cm$^2$.

In still further aspects, light for inducing one or more biological effects may include administering different doses of light to a target tissue to induce one or more biological effects for different target pathogens. As disclosed herein, a biological effect may include altering a concentration of one or more pathogens within the body and altering growth of the one or more pathogens within the body. The biological effect may include at least one of inactivating the first pathogen in a cell-free environment, inhibiting replication of the first pathogen in a cell-associated environment, upregulating a local immune response in the mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. As further disclosed herein, a pathogen may include a virus, a bacteria, and a fungus, or other any other types of microorganisms that can cause infections. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at a time, one to a few times a day, and the beneficial effect of the phototherapy may continue in between treatments.

Light sources may include one or more of LEDs, OLEDs, lasers and other lamps according to aspects of the present disclosure. Lasers may be used for irradiation in combination with optical fibers or other delivery mechanisms. A disadvantage of using a laser is that it may require sophisticated equipment operated by highly skilled professionals to ensure proper laser radiation protection, thereby increasing costs and reducing accessibility. LEDs are solid state electronic devices capable of emitting light when electrically activated. LEDs may be configured across many different targeted emission spectrum bands with high efficiency and relatively low costs. In this regard, LEDs are comparatively simpler devices that operate over much wider ranges of current and temperature, thereby providing an effective alternative to expensive laser systems. Accordingly, LEDs may be used as light sources in photonic devices for phototherapy applications. Light from an LED is administered using a device capable of delivering the requisite power to a targeted treatment area or tissue. High power LED based devices can be employed to fulfill various spectral and power needs for a variety of different medical applications. LED-based photonic devices described herein may be configured with suitable power to provide irradiances as high as 100 mW/cm$^2$, or 200 mW/cm$^2$ in the desired wavelength range. An LED array in this device can be incorporated into an irradiation head, hand piece and or as an external unit. When incorporated into a hand piece or irradiation head, risk of eye or other organs being exposed to harmful radiation may be avoided.

According to aspects of the present disclosure, exemplary target tissues and cells light treatments may include one or more of epithelial tissue, mucosal tissue, connective tissue, muscle tissue, cervical tissue, dermal tissue, mucosal epithelial tissues in the vaginal cavity, anal canal, oral cavity, the auditory canal, the upper respiratory tract and esophagus, keratinocytes, fibroblasts, blood, sputum, saliva, cervical fluid, and mucous. Light treatments may also be applied to and/or within organs, to external body surfaces, and within any mammalian body and/or body cavity, for example the oral cavity, esophageal cavity, throat, and vaginal cavity, among others.

Features from any of the embodiments described herein may be used in combination with one another in accordance with the general principles described herein. These and other embodiments, features, and advantages will be more fully understood upon reading the following detailed description in conjunction with the accompanying drawings and claims.

Figure 1:
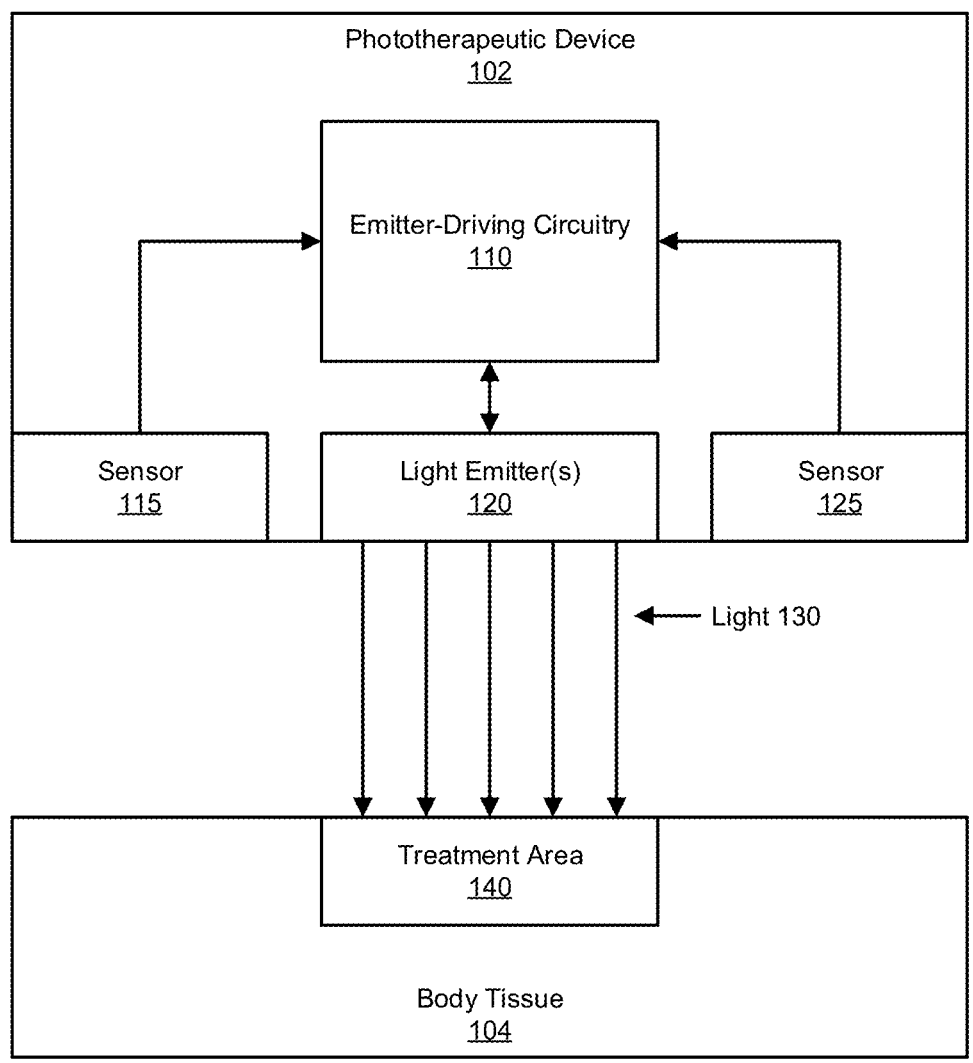
FIG. 1 is a block diagram of an exemplary illumination device for increasing concentrations of unbound nitric oxide within living tissue, according to some embodiments.

FIG. 1 is an illustration of an exemplary configuration 100 of an illumination device 102 for delivering light 130 to body tissue 104 to induce at least one biological effect. As previously described, induced biological effects may include least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, the light 130 may be configured as nitric-oxide modulating light in order to increase concentrations of unbound nitric oxide within body tissue 104. As shown in FIG. 1, the illumination device 102 may include one or more light emitter(s) 120 operable to emit the light 130 onto a treatment area 140 of the body tissue 104. The light emitter(s) 120 may be positioned so that one or more portions of the light 130 impinge the treatment area 140 with an angle of incidence of 90 degrees with a tolerance of plus or minus 10 degrees, although other angles of incidence may also be employed. The light emitter(s) 120 may also be configured to provide a beam uniformity of the light 130 of no more than about 20%, or no more than about 15%, or no more than about 10% of a range over mean at the treatment area 140. Such beam uniformity values may be determined based on selection of optics and/or waveguides for the light emitter(s) 120. In certain embodiments, the light emitter(s) 120 may be capable of providing an irradiance to the treatment area 140 of up to about 45 mW/cm$^2$ when positioned at a distance of about 96 mm from the treatment area 140, or up to about 60 mW/cm$^2$ when positioned at a distance of about 83 mm from the treatment area 140, or up to about 80 mW/cm$^2$ when positioned at a distance of about 70 mm from the treatment area 140. The above irradiance values are provided as an example. In practice the irradiance values may be configured in other ranges based on the application. The light emitter(s) 120 may include any light source capable of emitting or stimulating one or more of the biological effects. Examples of light emitter(s) 120 may include, without limitation, light-emitting diodes (LEDs), organic light-emitting diodes (OLEDs), superluminescent diodes (SLDs), lasers, and/or any combinations thereof. Where a light emitter is described as emitting light of a wavelength or a range of wavelengths, and where light is referred to as having a wavelength (e.g., a wavelength of 415 nanometers (nm)), because most light emitters (particularly those other than laser diodes) may emit light of different wavelengths within a range of wavelengths, it should be understood that the wavelength value may refer to the dominant wavelength of the light, the peak wavelength of the light, the centroid wavelength of the light, and/or a wavelength that is within 3 nm of at least 50 percent of an emission spectrum of the light. Unless otherwise specified in the present disclosure, various embodiments are provided below with reference to peak wavelengths.

The illumination device 102 may further include (1) emitter-driving circuitry 110 operable to control output of light emitter(s) 120 and (2) one or more sensors (e.g., sensors 115 and 125) operable to sense or measure attributes of illumination device 102, light emitter(s) 120, nitric-oxide modulating light 130, treatment area 140, body tissue 104, and/or the environment within which illumination device 102 operates. As will be explained in greater detail below, emitter-driving circuitry 110 may control the output of light-emitter(s) 120 based on information collected via sensors 115 and 125. Examples of sensors 115 and 125 include, without limitation, temperature sensors, photo sensors, image sensors, proximity sensors, blood pressure or other pressure sensors, chemical sensors, biosensors (e.g., heart rate sensors, body temperature sensors, sensors that detect the presence or concentration of chemical or biological species, or other conditions), accelerometers, moisture sensors, oximeters, such as pulse oximeters, current sensors, voltage sensors, and the like. In certain embodiments, the operation of methods disclosed herein may be responsive to one or more signals generated by one or more of sensors 115 and/or 125 or other elements.

Figure 2:
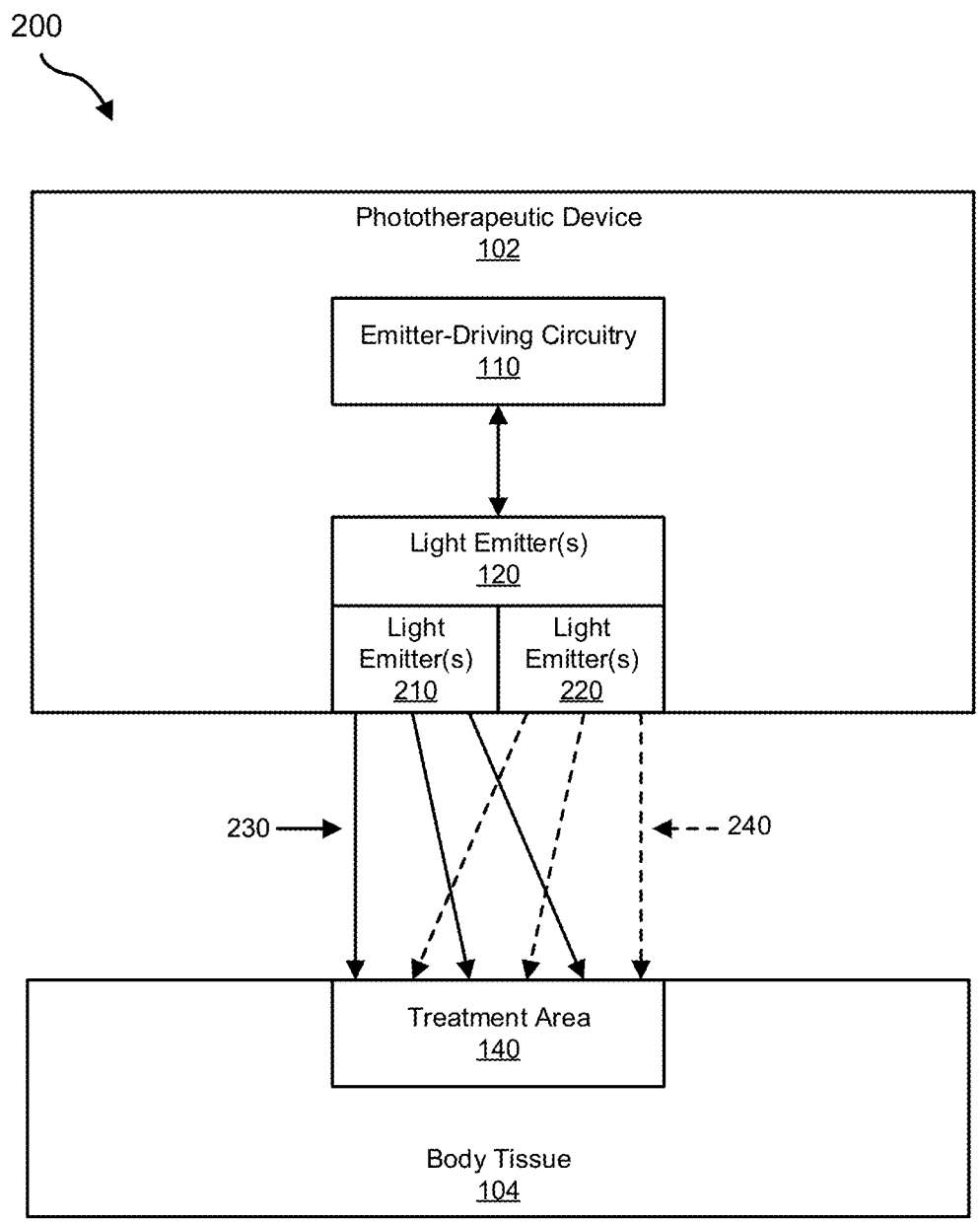
FIG. 2 is another block diagram of the exemplary illumination device of FIG. 1, according to some embodiments.

FIG. 2 is an illustration of an exemplary configuration 200 of illumination device 102 for delivering two types of light 230, 240 to body tissue 104. The two types of light 230, 240 may be configured to induce at least two biological effects, for example at least two of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. The two types of light 230, 240 may also be configured to provide a similar biological effect, such as two different types of nitric-oxide modulating light in order to increase concentrations of unbound nitric oxide within the body tissue 104. Additionally, the two types of light 230, 240 may be configured to provide the same or different biological effect for different types of microorganisms and/or pathogens that may be present in the body tissue 104.

In certain embodiments, light emitter(s) 120 may include one or more light emitter(s) 210 operable to emit endogenous-store increasing light 230 and one or more light emitter(s) 220 operable to emit endogenous-store releasing light 240. Light emitter(s) 210 and 220 may include any light source capable of emitting suitable light. Examples of light emitter(s) 210 and 220 may include, without limitation, LEDs, OLEDs, SLDs, lasers, and/or any combinations thereof.

FIG. 3 is a spectral diagram showing intensity versus wavelength for the exemplary light 130 of FIG. 1 that may be configured to induce any of the above-described biological effects, including nitric-oxide modulating light. FIG. 4 is a spectral diagram showing intensity versus wavelength for the exemplary light 230, 240 of FIG. 2 that may be respectively be configured to induce any of the above-described biological effects, such as an endogenous-store increasing light 230 and an endogenous-store releasing light 240. By way of example, the light 130 is illustrated as having a peak intensity 308 at a peak wavelength 304, the light 230 is illustrated as having a peak intensity 414 at a peak wavelength 404, and the light 230 is illustrated as having a peak intensity 414 at a peak wavelength 410. In these examples, peak wavelength 304 may be any wavelength within a range from wavelength 302 to wavelength 306, peak wavelength 404 may be any wavelength within a range from wavelength 402 to wavelength 406, and peak wavelength 410 may be any wavelength within a range from wavelength 408 to wavelength 412.

The specific peak wavelengths illustrated in FIGS. 3 and 4 are provided by way of non-limiting examples. In practice the light 130 of FIG. 1 and the light 230, 240 of FIGS. 3 and 4 may be provided in many different peak wavelength ranges depending on the target application, the one or more target microorganisms and/or pathogens, and the target tissue type. Exemplary wavelength ranges include from 200 nm to 900 nm, or from 400 nm to 900 nm, or from 400 nm to 700 nm, or from 400 nm to 450 nm, or from 400 nm to 435 nm, or from 400 nm to 420 nm, or from 420 nm to 440 nm, or from 450 nm to 490 nm, or from 500 nm to 900 nm, or from 490 nm to 570 nm, or from 510 nm to 550, or from 520 nm to 540 nm, or from 525 nm to 535 nm, or from 528 nm to 532 nm, or from 200 nm to 280 nm, or from 260 nm to 270 nm, or from 280 nm to 320 nm, or from 320 nm to 350 nm, or from 320 nm to 400 nm, or from 350 nm to 395 nm, or from 600 nm to 900 nm, or from 600 nm to 700 nm, or from 620 nm to 670 nm, or from 630 nm to 660 nm depending on the target application and the target tissue type. Specific exemplary wavelength ranges are provided below in the context of specific target applications according to principles of the present disclosure.

As used herein, the term "light" generally refers to electromagnetic radiation of any wavelength or any combination of wavelengths and/or to one or more photons. Accordingly, the term "light," as used herein, can refer to visible light or to non-visible light (in particular, ultraviolet light, or infrared light). The term "light," as used herein, may refer to a single photon of a single wavelength, or it can refer to a plurality of photons that may be of the same wavelength, or one or more photons of each of two or more wavelengths. The term "impinge," as used herein in the context of light impinging on an object (e.g., in the expression "at least one first solid state light-emitting device configured to impinge light having the first peak wavelength on skin tissue") may indicate that the light is incident on the object.

The term "peak wavelength" is generally used herein to refer to the wavelength that is of the greatest irradiance of the light emitted by a light emitter. The term "dominant wavelength" is generally used herein to refer to the perceived color of a spectrum, i.e., the single wavelength of light which produces a color sensation most similar to the color sensation perceived from viewing light emitted by the light source (i.e., it is roughly akin to "hue"), as opposed to "peak wavelength", which commonly refers to the spectral line with the greatest power in the spectral power distribution of the light source. Because the human eye does not perceive all wavelengths equally (e.g., it perceives yellow and green light better than red and blue light), and because the light emitted by many solid state light emitters (e.g., LEDs) is actually a range of wavelengths, the color perceived (i.e., the dominant wavelength) is not necessarily equal to (and often differs from) the wavelength with the highest power (peak wavelength). A truly monochromatic light such as a laser may have the same dominant and peak wavelengths.

As used herein, the term "nitric-oxide modulating light" generally refers to light that, when impinged onto living tissue, increases concentrations of unbound nitric oxide within the living tissue. The term "nitric-oxide modulating light" may encompass endogenous nitric-oxide increasing and/or endogenous nitric-oxide releasing light. The term "nitric-oxide modulating light" may refer to specific wavelengths of light that stimulate natural production of nitric oxides (e.g., through a process similar to those illustrated in FIGS. 5A and 5B) and/or instantaneous release of nitric oxide reserves found within living tissue (e.g., through a process similar to that illustrated in FIGS. 6A and 6B). The term "nitric-oxide modulating light" may additionally or alternatively refer to any light capable of stimulating at least one of (1) enzymatic generation of unbound nitric oxide within living tissue (e.g., through a process similar to that illustrated in FIGS. 5A and 5B) or (2) release of nitric oxide from endogenous stores of bound nitric oxide within living tissue (e.g., through a process similar to that illustrated in FIGS. 6A and 6B).

Figure 5A:
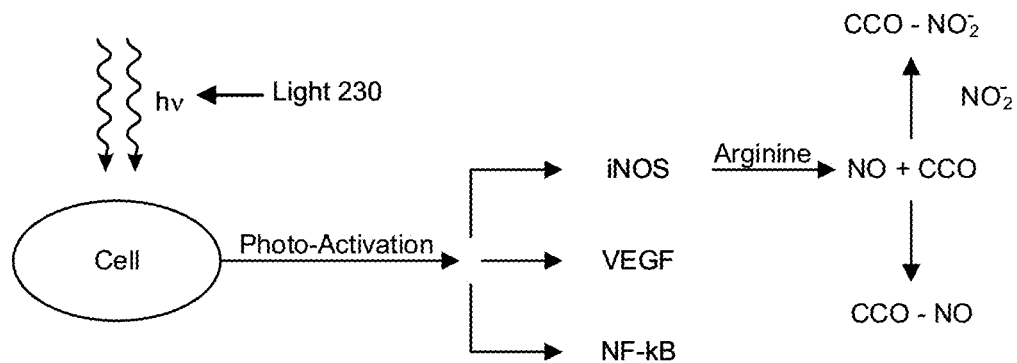
FIG. 5A is a reaction sequence showing photoactivated production of nitric oxide (NO) catalyzed by iNOS, followed by binding of NO to CCO.
Figure 5B:
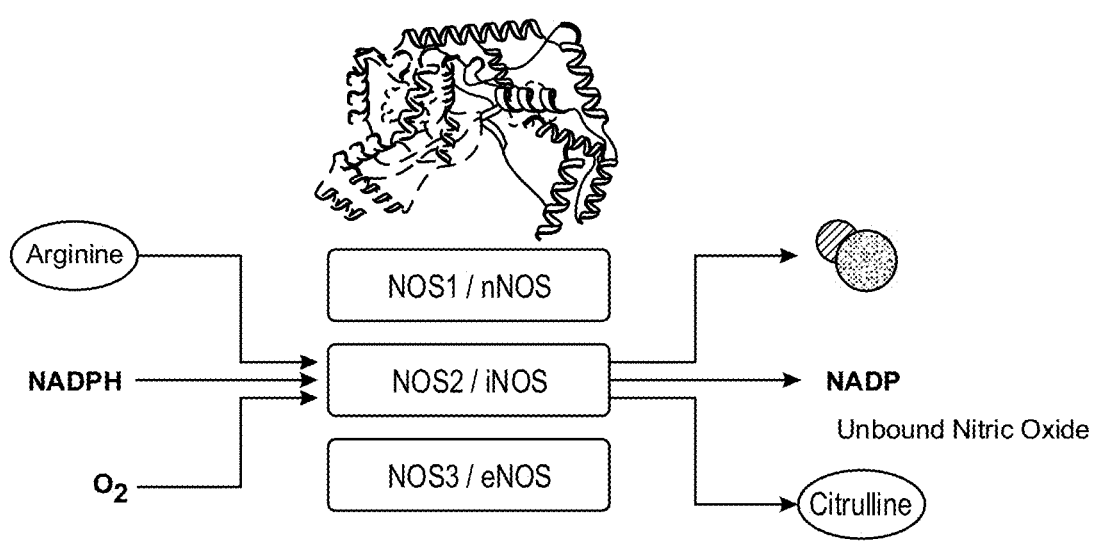
FIG. 5B is an illustration showing how arginine reacts with oxygen and NADPH, in the presence of NOS1/nNOS, NOS2/iNOS, and NOS3/eNOS, to release unbound nitric oxide, reduce the NADPH to NADP, and convert arginine to citrulline.
Figure 5C:
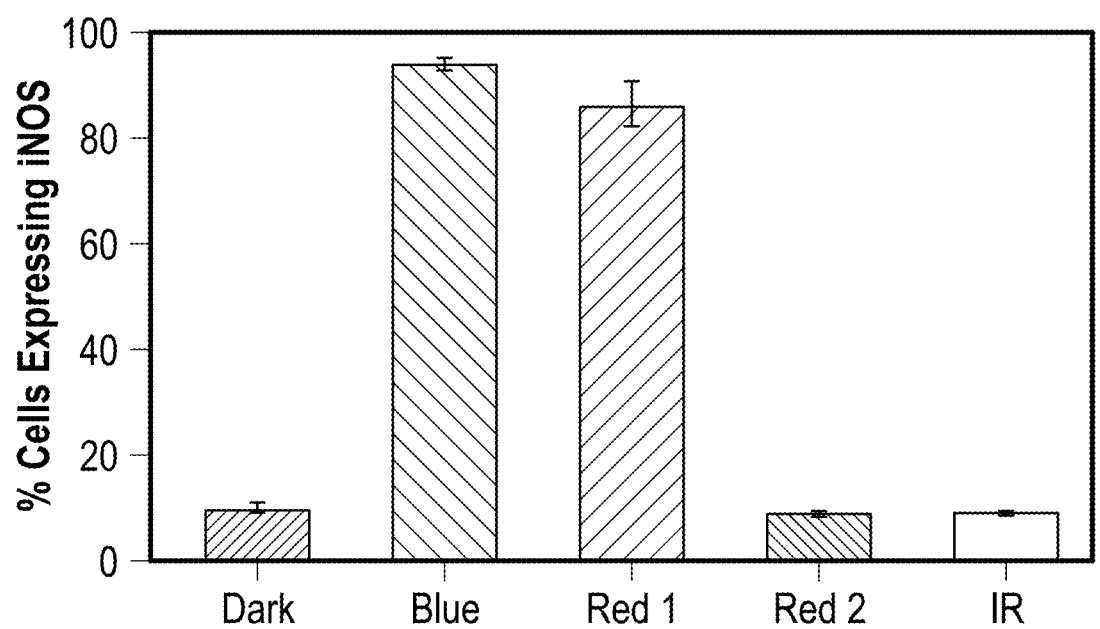
FIG. 5C is a chart showing the enzymatic generation of nitric oxide (in keratinocytes), in terms of % cells expressing iNOS, when exposed to various wavelengths of light, 24 hours after exposure of the keratinocytes to 10 minutes of irradiation.

FIGS. 5A and 5B illustrate a reaction sequence showing photoactivated upregulation (e.g., with light 230) of inducible Nitric Oxide Synthase (iNOS) expression and subsequent production of unbound nitric oxide catalyzed by iNOS, followed by binding of nitric oxide to CCO. When nitric oxide is auto-oxidized into nitrosative intermediates (e.g., endogenous stores of nitric oxide including nitrosoglutathione, nitrosoal-bumin, nitrosohemoglobin, nitrosothiols, nitrosamines, and/or metal nitrosyl complexes), the nitric oxide may be bound covalently in the body (in a "bound" state). FIG. 5C is a chart showing the enzymatic generation of nitric oxide (in keratinocytes), in terms of % cells expressing iNOS, when exposed to no light, blue light, red light at a first wavelength, red light at a second wavelength, and to infrared light, 24 hours after exposure of the keratinocytes to 10 minutes of irradiation.

Figure 6A:
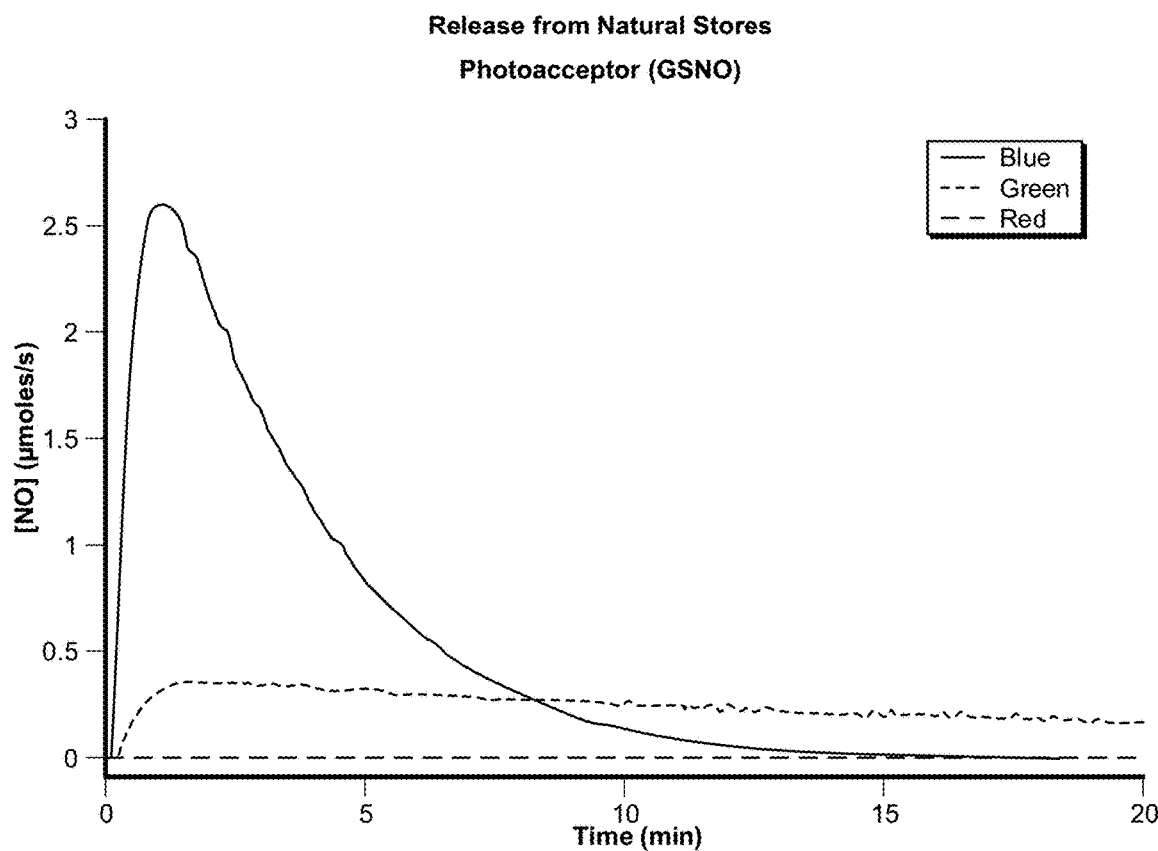
FIG. 6A is a chart showing the release of nitric oxide (μmoles/second) vs. time (minutes) from the photoacceptor GSNO, upon exposure to blue, green, and red wavelengths.
Figure 6B:
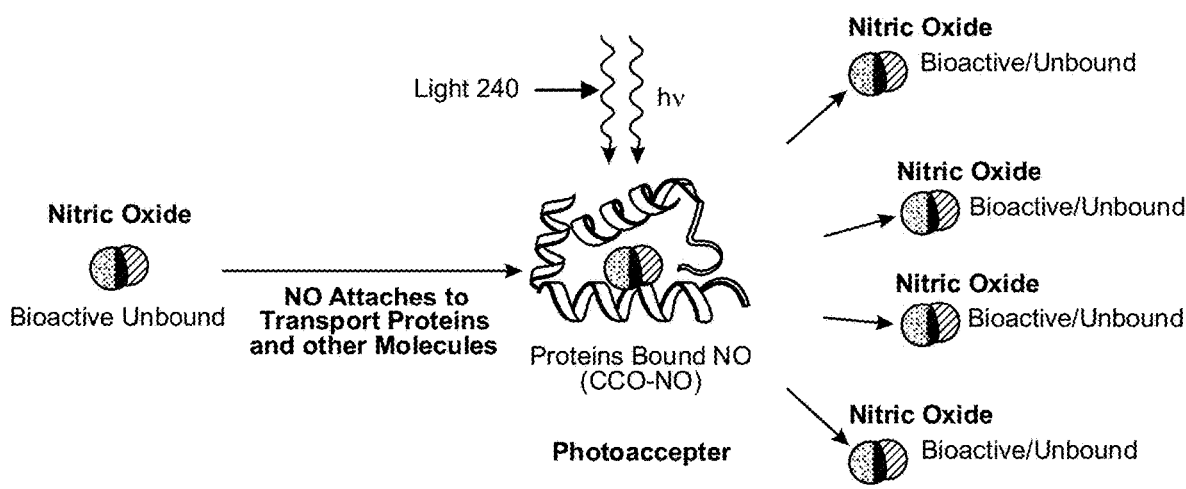
FIG. 6B is an illustration showing the attachment of nitric oxide to the photoacceptor CCO to form the complex CCO-NO, and the subsequent release of NO from this complex upon exposure to endogenous-store releasing light.

FIG. 6A is a chart showing the release of nitric oxide (μmoles/second) vs. time (minutes) from the photoacceptor GSNO, upon exposure to blue, green, and red wavelengths of light. FIG. 6B is an illustration showing the attachment of nitric oxide to the photoacceptor CCO to form the complex CCO-NO, and the subsequent release of NO from this complex upon exposure to endogenous-store releasing light 240.

The term "endogenous-store increasing light," as used herein, generally encompasses light of a wavelength or a wavelength range that photo-initiates an increase of bound nitric oxide in endogenous stores and/or that stimulates enzymatic generation of unbound nitric oxide that may be naturally bound covalently in endogenous stores. Examples of endogenous-store increasing light include, without limitation, blue light, light having a peak wavelength in a range of about 410 nm to about 440 nm, light having a peak wavelength in a range of about 400 nm to about 490 nm, light having a peak wavelength in a range of about 400 nm to about 450 nm, light having a peak wavelength in a range of about 400 nm to about 435 nm, light having a peak wavelength in a range of about 400 nm to about 420 nm, light having a peak wavelength in a range of about 420 nm to about 440 nm, light having a peak wavelength in a range of about 400 nm to about 500 nm, light having a peak wavelength in a range of about 400 nm to about 430 nm, light having a peak wavelength equal to about 415 nm, light having a peak wavelength equal to about 405 nm, and/or any combination thereof.

The term "endogenous-store releasing light," as used herein, generally encompasses light of a wavelength or a wavelength range that photo-initiates a release of unbound nitric oxide from endogenous stores of nitric oxide. Examples of endogenous-store releasing light include, without limitation, green light, light having a peak wavelength in a range of about 500 nm to about 540 nm, light having a peak wavelength in a range of about 500 nm to about 900 nm, light having a peak wavelength in a range of about 490 nm to about 570 nm, light having a peak wavelength in a range of about 510 nm to about 550 nm, light having a peak wavelength in a range of about 520 nm to about 540 nm, light having a peak wavelength in a range of about 525 nm to about 535 nm, light having a peak wavelength in a range of about 528 nm to about 532 nm, light having a peak wavelength equal to about 530 nm, and/or any combination thereof.

The term "endogenous nitric-oxide increasing and/or endogenous nitric-oxide releasing light," as used herein, encompasses light of a wavelength or a wavelength range that increases the rate of production of endogenous nitric-oxide, light of a wavelength or a wavelength range that increases the rate of release of endogenous nitric-oxide, light of a wavelength or a wavelength range that increases both the rate of production of endogenous nitric-oxide and the rate of release of endogenous nitric-oxide, and a combination of light from at least one first group of light emitters that emits light of a wavelength or a wavelength range that increases the rate of production of endogenous nitric-oxide, and light from at least one second group of light emitters that emits light of a wavelength or a wavelength range that increases the rate of release of endogenous nitric-oxide.

Returning to FIG. 2, in some embodiments, the light 240 may have a first peak wavelength and a first radiant flux to include one or more of the biological effects, and the light 230 may have a second peak wavelength and a second radiant flux to include one or more of the biological effects.

In certain embodiments, the second peak wavelength may be greater than the first peak wavelength by at least 25 nm, at least 40 nm, at least 50 nm, at least 60 nm, at least 75 nm, at least 85 nm, at least 100 nm, or another threshold specified herein. Such peak wavelength differences may be present for inducing any of the above-described biological effects, including embodiments where the light 230 is endogenous-store increasing light and the light 240 is endogenous-store releasing light.

Exemplary embodiments are provided below in the context of nitric oxide modulating light, including endogenous-store increasing light endogenous-store releasing light. It is understood that any of the below-described embodiments may equally relate to any light and/or combination of light that induces one or more of the biological effects previously described, including inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect in tissue. Different combinations of light and induced biological effects may be tailored to different body tissues and different targeted microorganisms and/or pathogens.

In certain embodiments, each of endogenous-store increasing light 230 and endogenous-store releasing light 240 (and/or the light 130) may have a radiant flux in a range of at least 5 mW, or at least 10 mW, or at least 15 mW, or at least 20 mW, or at least 30 mW, or at least 40 mW, or at least 50 mW, or at least 100 mW, or at least 200 mW, or at least 500 mW, or at least 2500 mW, or at least 5000 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in a range of from 5 mW to 5000 mW, or in a range of from 5 mW to 2500 mW, or in another range specified herein. Higher fluxes, for example, between 0.1 W and 10 W, or between 10

W and 10 GW, including those where pulsed light is used, can be used to increase penetration, and effect microbial decontamination, if need be, in another range specified herein.

Each of endogenous-store increasing light 230 and endogenous-store releasing light 240 (and the light 130) may be administered with irradiances to target tissues in a range from 0.1 mW/cm$^2$ to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including LED-based photonic devices that are configured with suitable power (radiant flux) to irradiate a target tissue with any of the above-described ranges. Depending on the configuration of one or more of the light source, the corresponding illumination device, and the distance away from a target tissue, the radiant flux value for the light source may be higher than the irradiance value at the tissue. In certain embodiments, the radiant flux value may be configured with a value that is greater than the irradiance value to the tissue. For example, the radiant flux may be in a range from 5 to 20 times greater than the irradiance, or in a range from 5 to 15 times greater than the irradiance, among other ranges and depending on the embodiments.

In certain embodiments, endogenous-store increasing light 230 may have a greater radiant flux than endogenous-store releasing light 240. In certain embodiments, endogenous-store releasing light 240 may have a greater radiant flux than endogenous-store increasing light 230.

In certain embodiments, one or both of endogenous-store increasing light 230 and endogenous-store releasing light 240 may have a radiant flux profile that may be substantially constant during a treatment window. In certain embodiments, at least one of endogenous-store increasing light 230 and endogenous-store releasing light 240 may have a radiant flux profile that increases with time during a treatment window. In certain embodiments, at least one of endogenous-store increasing light 230 and endogenous-store releasing light 240 may have a radiant flux profile that decreases with time during a treatment window. In certain embodiments, one of endogenous-store increasing light 230 or endogenous-store releasing light 240 may have a radiant flux profile that decreases with time during a treatment window, while the other of endogenous-store increasing light 230 or endogenous-store releasing light 240 may have a radiant flux profile that increases with time during a treatment window.

In certain embodiments, endogenous-store releasing light 240 may be applied to tissue during a first time window, endogenous-store increasing light 230 may be applied to the tissue during a second time window, and the second time window may overlap with the first time window. In other embodiments, endogenous-store releasing light 240 may be applied to tissue during a first time window, endogenous-store increasing light 230 may be applied to the tissue during a second time window, and the second time may be non-overlapping or may be only partially overlapping with the first time window. In certain embodiments, the second time window may be initiated more than one minute, more than 5 minutes, more than 10 minutes, more than 30 minutes, or more than one hour after conclusion of the first time window. In certain embodiments, endogenous-store releasing light 240 may be applied to tissue during a first time window, endogenous-store increasing light 230 may be applied to the tissue during a second time window, and the first time window and the second time window may be substantially the same. In other embodiments, the second time window may be longer than the first time window. Aspects of these embodiments where UVA/UVB/UVC light is administered in the same or different time windows, or to the same or different tissue, are also contemplated.

In certain embodiments, one or both of endogenous-store increasing light 230 and endogenous-store releasing light 240 may be provided by a steady state source providing a radiant flux that may be substantially constant over a prolonged period without being pulsed.

In certain embodiments, one or both of endogenous-store increasing light 230 and endogenous-store releasing light 240 may include more than one discrete pulse (e.g., a plurality of pulses) of light. In certain embodiments, more than one discrete pulse of endogenous-store releasing light 240 may be impinged on tissue during a first time window, and/or more than one discrete pulse of endogenous-store increasing light 230 may be impinged on tissue during a second time window. In certain embodiments, the first time window and the second time window may be coextensive, may be overlapping but not coextensive, or may be non-overlapping.

In certain embodiments, at least one of the radiant flux and the pulse duration of endogenous-store releasing light 240 may be reduced from a maximum value to a non-zero reduced value during a portion of a first time window. In certain embodiments, at least one of the radiant flux and the pulse duration of endogenous-store releasing light 240 may be increased from a non-zero value to a higher value during a portion of a first time window. In certain embodiments, at least one of the radiant flux and the pulse duration of endogenous-store increasing light 230 may be reduced from a maximum value to a non-zero reduced value during a portion of a second time window. In certain embodiments, at least one of the radiant flux and the pulse duration of endogenous-store increasing light 230 may be increased from a non-zero value to a higher value during a portion of a second time window.

In certain embodiments, each of endogenous-store increasing light 230 and endogenous-store releasing light 240 may consist of non-coherent light. In certain embodiments, each of endogenous-store increasing light 230 and endogenous-store releasing light 240 may consist of coherent light. In certain embodiments, one of endogenous-store increasing light 230 or endogenous-store releasing light 240 may consist of non-coherent light, and the other of endogenous-store increasing light 230 or endogenous-store releasing light 240 may consist of coherent light.

In certain embodiments, endogenous-store releasing light 240 may be provided by at least one first light emitting device and endogenous-store increasing light 230 may be provided by at least one second light emitting device. In certain embodiments, endogenous-store releasing light 240 may be provided by a first array of light emitting devices and endogenous-store increasing light 230 may be provided by a second array of light emitting devices.

In certain embodiments, at least one of endogenous-store increasing light 230 or endogenous-store releasing light 240 may be provided by at least one solid state light emitting device. Examples of solid state light emitting devices include (but are not limited to) light emitting diodes, lasers, thin film electroluminescent devices, powdered electroluminescent devices, field induced polymer electroluminescent devices, and polymer light-emitting electrochemical cells. In certain embodiments, endogenous-store releasing light 240 may be provided by at least one first solid state light emitting device and endogenous-store increasing light 230 may be provided by at least one second solid state light emitting device. In certain embodiments, endogenous-store increasing light 230 and endogenous-store releasing light 240 may be generated by different emitters contained in a single solid state emitter package, where close spacing between adjacent emitters may provide integral color mixing. In certain embodiments, endogenous-store releasing light 240 may be provided by a first array of solid state light emitting devices and endogenous-store increasing light 230 may be provided by a second array of solid state light emitting devices. In certain embodiments, an array of solid state emitter packages each including at least one first emitter and at least one second emitter may be provided, where the array of solid state emitter packages embodies a first array of solid state emitters arranged to generate endogenous-store releasing light 240 and embodies a second array of solid state emitters arranged to generate endogenous-store increasing light 230. In certain embodiments, an array of solid state emitter packages may embody packages further including third, fourth, and/or fifth solid state emitters, such that a single array of solid state emitter packages may embody three, four, or five arrays of solid state emitters, wherein each array may be arranged to generate emissions with a different peak wavelength.

In certain embodiments, at least one of endogenous-store increasing light 230 or endogenous-store releasing light 240 may be provided by at least one light emitting device devoid of a wavelength conversion material. In other embodiments, at least one of endogenous-store increasing light 230 or endogenous-store releasing light 240 may be provided by at least one light emitting device arranged to stimulate a wavelength conversion material, such as a phosphor material, a fluorescent dye material, a quantum dot material, and a fluorophore material.

In certain embodiments, endogenous-store increasing light 230 and endogenous-store releasing light 240 may consist of substantially monochromatic light. In certain embodiments, endogenous-store releasing light 240 may include a first spectral output having a first full width at half maximum value of less than 25 nm (or less than 20 nm, or less than 15 nm, or in a range of from 5 nm to 25 nm, or in a range of from 10 nm to 25 nm, or in a range of from 15 nm to 25 nm), and/or endogenous-store increasing light 230 may include a second spectral output having a second full width at half maximum value of less than 25 nm (or less than 20 nm, or less than 15 nm, or in a range of from 5 nm to 25 nm, or in a range of from 10 nm to 25 nm, or in a range of from 15 nm to 25 nm). In certain embodiments, less than 5% of the first spectral output may be in a wavelength range of less than 400 nm, and less than 1% of the second spectral output may be in a wavelength range of less than 400 nm.

In certain embodiments, endogenous-store releasing light 240 may be produced by one or more first light emitters having a single first peak wavelength, and endogenous-store increasing light 230 may be produced by one or more second light emitters having a single second peak wavelength. In other embodiments, endogenous-store increasing light 230 may be produced by at least two light emitters having different peak wavelengths (e.g., differing by at least 5 nm, at least 10 nm, at least 15 nm, at least 20 nm, or at least 25 nm), and/or endogenous-store releasing light 240 may be produced by at least two light emitters having different peak wavelengths (e.g., differing by at least 5 nm, at least 10 nm, at least 15 nm, at least 20 nm, or at least 25 nm).

Ultraviolet light (e.g., UV-A light having a peak wavelength in a range of from 350 nm to 395 nm, and UV-B light having a peak wavelength in a range of from 320 nm to 350 nm) may be effective as ES increasing light; however, overexposure to ultraviolet light may lead to detrimental health effects including premature skin aging and potentially elevated risk for certain types of cancer. UVC light can also be particularly effective at treating microbial infections. While damage to the tissue being exposed to these wavelengths should be minimal during the course of antimicrobial therapy, it may cause some detrimental effects on long-term exposure. It may therefore be desirable to use shorter cycles of UV light than non-UV light. In certain embodiments, UV light (e.g., having peak wavelengths in a range of from 320 nm to 399 nm) may be used as ES increasing light; however, in other embodiments, UV light may be avoided. The combination of light at these (UVA, UVB, and/or UVC) wavelengths with the anti-inflammatory light can minimize these effects.

In certain embodiments, endogenous-store increasing light 230 and endogenous-store releasing light 240 may be substantially free of UV light. In certain embodiments, less than 5% of endogenous-store increasing light 230 may be in a wavelength range of less than 400 nm, and less than 1% of endogenous-store releasing light 240 output may be in a wavelength range of less than 400 nm. In certain embodiments, endogenous-store increasing light 230 includes a peak wavelength in a range of from 400 nm to 490 nm, or from 400 nm to 450 nm, or from 400 nm to 435 nm, or from 400 nm to 420 nm, or from 410 nm to 440 nm, or from 420 nm to 440 nm.

In certain embodiments, endogenous-store increasing light 230 may include a wavelength range and an irradiance that may alter the presence, concentration, or growth of pathogens (e.g., bacteria, viruses, fungi, protists, and/or other microbes) in or on living mammalian tissue receiving the light. UV light and near-UV light in particular may affect microbial growth. Effects on microbial growth may depend on the wavelength range and dose. In certain embodiments, ES increasing or endogenous-store releasing light 240 may include near-UV light having a peak wavelength in a range of from 400 nm to 420 nm to provide a bacteriostatic effect (e.g., with pulsed light having an irradiance of <9 mW/cm$^2$), provide a bactericidal effect (e.g., with substantially steady state light having an irradiance in a range of from 9 mW/cm$^2$ to 17 mW/cm$^2$), or provide an antimicrobial effect (e.g., with substantially steady state light having an irradiance in a range of greater than 17 mW/cm$^2$, such as in a range of from 18 mW/cm$^2$ to 60 mW/cm$^2$). In certain embodiments, the irradiance values and ranges may extend higher, to about 60 to about 100 mW/cm$^2$ or to about 100 to about 200 mW/cm$^2$.

With respect to certain tissues and certain wavelengths, irradiances up to 1 W/cm$^2$ may be applied without causing significant damage to the tissues. If the light is pulsed, the irradiance can be applied at a significantly higher range, so long as the average irradiance falls within these ranges, and causes minimal damage to the tissue to which it is applied. The irradiance in a pulse setting may be as low as 0.1 W/cm$^2$ up to 10 W/cm$^2$, or even higher.

In certain embodiments, light in a near-UV range (e.g., from 400 nm to 420 nm) may also affect microbial growth (whether in a bacteriostatic range, bactericidal range, or an antimicrobial range) for uses such as wound healing, reduction of acne blemishes, or treatment of atopic dermatitis. Such function(s) may be in addition to the function of endogenous-store increasing light 230 that increases endogenous stores of nitric oxide in living tissue.

A combination of equal parts of 410 nm light and 530 nm light may be equally as effective as 530 nm light alone. Such a combination may be beneficial since a 410 nm blue LED may be significantly more efficient than a 530 nm green LED, such that a combination of equal parts of 410 nm LED emissions and 530 nm LED emissions may use 26% less electric power than emissions of a 530 nm LED alone, when operated to provide the same radiant flux.

Light at 660 nm may be significantly less effective than the 530 nm green light at releasing NO from Hb-NO. The release of NO from Hb-NO appears to be the same for 530 nm green light, 660 nm red light, and a combination of 530 nm green and 660 nm light for the time window of from 0 seconds to about 2000 seconds, but the effectiveness of the different sources diverges thereafter. Without intending to be bound by any particular theory or explanation of this phenomenon, it is suggested that NO binds to Hb-NO at multiple sites, and that removal of a second or subsequent NO molecule from Hb-NO may require more energy than removal of a first NO molecule, perhaps due to a change in shape of the Hb-NO after removal of a first NO molecule.

In certain embodiments, anti-inflammatory light having a first peak wavelength is impinged on living tissue, and ES increasing or ES releasing light that includes light having a second peak wavelength is impinged on the living tissue, and furthermore a light having a third peak wavelength (i.e., ES releasing or ES increasing light) may be impinged on the living tissue. In certain embodiments, the light having a third peak wavelength may be provided at substantially the same time as (or during a time window overlapping at least one time window of) one or both of the anti-inflammatory and the ES increasing and/or ES releasing light.

In certain embodiments, the light having a third peak wavelength differs from each of the first peak wavelength and the second peak wavelength by at least 10 nm. In certain embodiments, the light having a third peak wavelength exceeds the second peak wavelength by at least 20 nm. In certain embodiments, the light having a third peak wavelength provides an irradiance in a range of from 5 mW/cm$^2$ to 60 mW/cm$^2$, or between 60 and 100 mW/cm$^2$, or between 100 and 200 mW/cm$^2$, or even higher. With respect to certain tissues and certain wavelengths, irradiances up to 1 W/cm$^2$ can be applied without causing significant damage to the tissues. If the light is pulsed, the irradiance can be applied at a significantly higher range, so long as the average irradiance falls within these ranges, and causes minimal damage to the tissue to which it is applied. The irradiance in a pulse setting may be as low as 0.1 W/cm$^2$ up to 10 W/cm$^2$, or even higher.

In certain embodiments, the anti-inflammatory light is in a range of from about 630 nm to 670 nm (e.g., including specific wavelengths of about 630 nm and about 660 nm) may be useful to provide anti-inflammatory effects and/or to promote vasodilation. Anti-inflammatory effects may be useful in treating disorders, particularly microbial disorders that result in inflammation of the nasal cavity, or in the mouth.

Antiviral doses of light can be administered in a range of from 5 mW/cm$^2$ to 60 mW/cm$^2$, about 60 to about 100 mW/cm$^2$ or about 100 to about 200 mW/cm$^2$. With respect to certain tissues and certain wavelengths, irradiances up to 1 W/cm$^2$ can be applied without causing significant damage to the tissues. If the light is pulsed, the irradiance can be applied at a significantly higher range, so long as the average irradiance falls within these ranges, and causes minimal damage to the tissue to which it is applied. The irradiance in a pulse setting may be as low as 0.1 W/cm$^2$ up to 10 W/cm$^2$, or even higher.

For visible light, roughly 400 to 700 nm, phototherapy has been suggested to provide therapeutic benefits which include increasing circulation (e.g., by increasing formation of new capillaries); stimulating the production of collagen; stimulating the release of adenosine triphosphate (ATP); enhancing porphyrin production; reducing excitability of nervous system tissues; modulating fibroblast activity; increasing phagocytosis; inducing thermal effects; stimulating tissue granulation and connective tissue projections; reducing inflammation; and stimulating acetylcholine release In certain embodiments, endogenous-store increasing light 230 may include a peak wavelength in a range of from 500 nm to 900 nm, or in a range of from 490 nm to 570 nm, or in a range of from 510 nm to 550 nm, or in a range of from 520 nm to 540 nm, or in a range of from 525 nm to 535 nm, or in a range of from 528 nm to 532 nm, or in a range of about 530 nm. The wavelength at 660 nm may be both anti-inflammatory, and NO-releasing.

Figure 7:
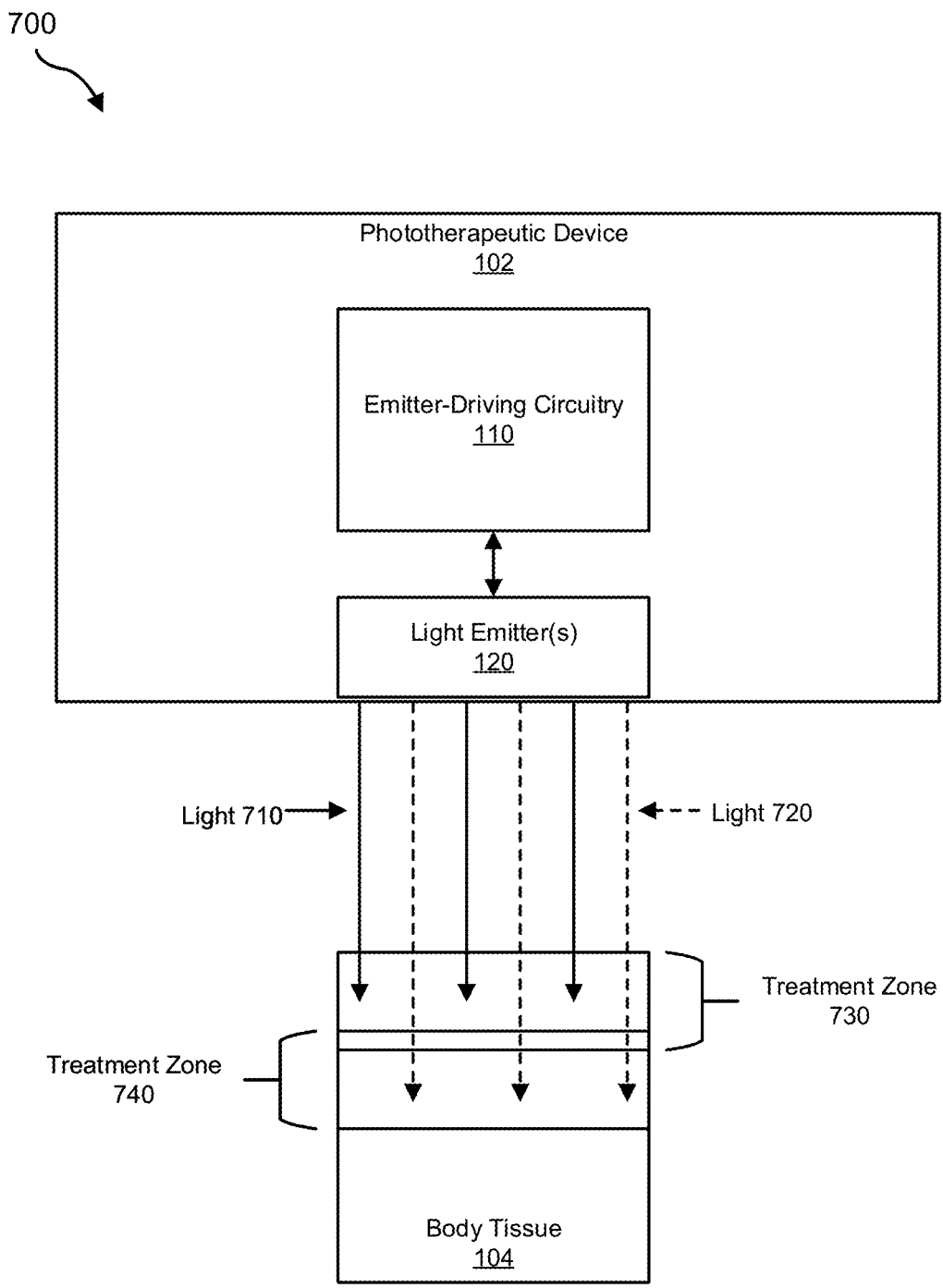
FIG. 7 is another block diagram of the exemplary illumination device of FIG. 1, according to some embodiments.

FIG. 7 is an illustration of an exemplary configuration 700 of illumination device 102 that is operable to induce biological effects in overlapping treatment zones 730 and 740 of the body tissue 104 by photomodulation. By way of example, the light emitter(s) 120 may supply photons of a first energy and/or peak wavelength (e.g., light 710) to the body tissue 104 to stimulate enzymatic generation of nitric oxide to increase endogenous stores of nitric oxide in treatment zone 730 and the light emitter(s) 120 may also supply photons of a second energy to the body tissue 104 and/or peak wavelength (e.g., light 720) in a region within or overlapping the treatment zone 730 to trigger release of nitric oxide from endogenous stores, thereby creating the treatment zone 740. In certain embodiments, sequential or simultaneous impingement of increasing wavelengths of light (e.g., nitric-oxide modulating light 710 and/or nitric-oxide modulating light 720) may serve to "push" a nitric oxide diffusion zone deeper within body tissue 104 than might otherwise be obtained by using a single (e.g., long) wavelength of light. As illustrated, the treatment zones 730 and 740 may be provided at different depths within the body tissue 104. The light emitter(s) 120 may further supply photons of additional energies and/or peak wavelengths to the same or different treatment zones, including at different depths within the body tissue 104. As with previous embodiments, while examples are provided in the context of nitric-oxide modulating light, the illumination device 102 may be configured to induce any of the previously-described biological effects in the treatment zones 730, 740. In this regard, the light 710 may be provided at a first depth, the light 720 may be provided at a second depth that greater than the first depth within the body tissue 104. One or more additional light emissions may further be supplied at further depths within the body tissue 104. In certain embodiments, the treatment zones 730 and 740 may be provided at substantially different depths within the body tissue 104. In further embodiments, the light 710 may be configured to provide a first biological effect, the light 720 may be configured to provide a second biological effect, and any additional light may be configured to provide biological effects that are the same or different than either of the first or second biological effects.

Figure 8:
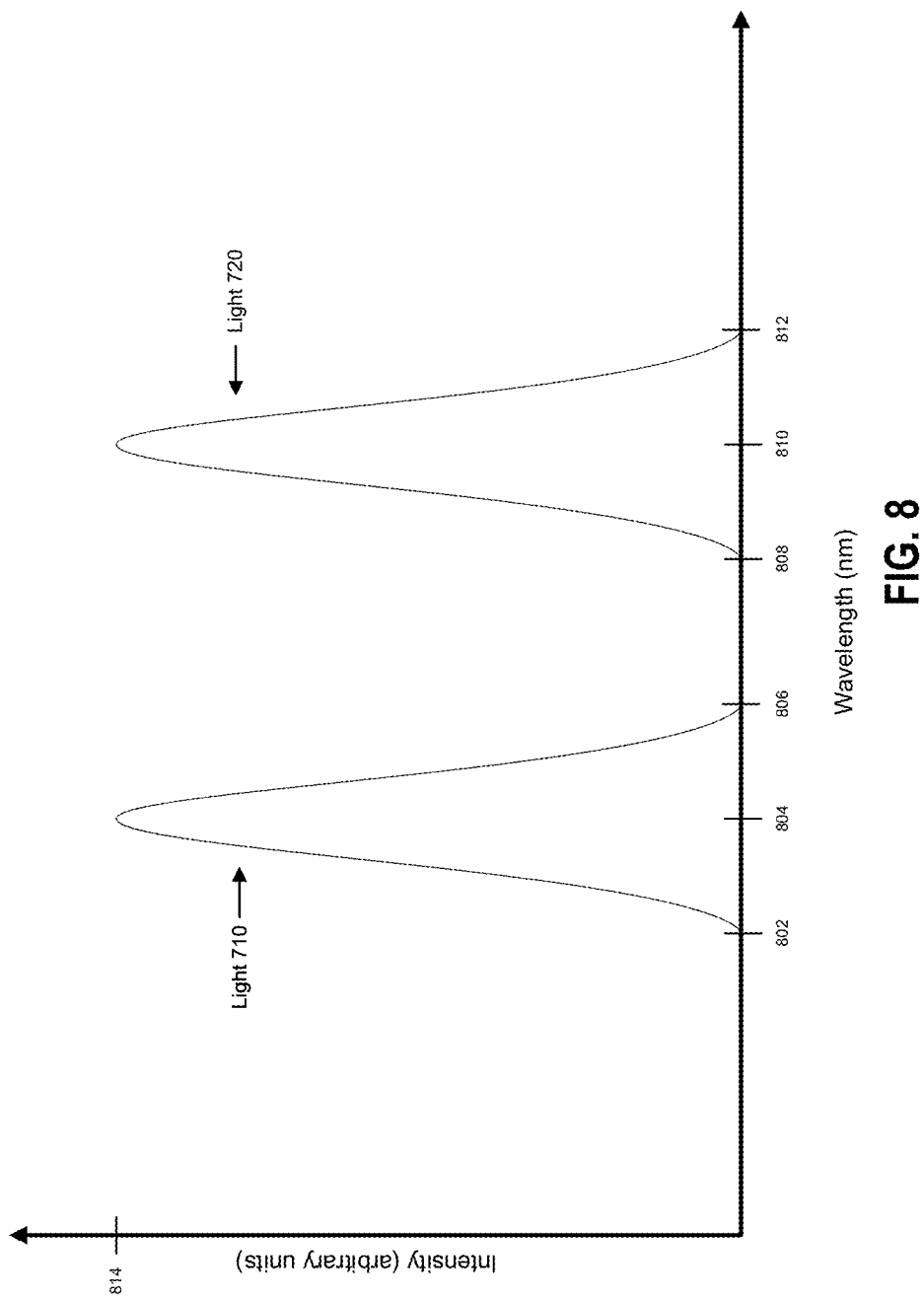
FIG. 8 is a spectral diagram showing intensity versus wavelength for the exemplary nitric-oxide modulating light illustrated in FIG. 7, according to some embodiments.

FIG. 8 is a spectral diagram showing intensity versus wavelength for exemplary nitric-oxide modulating light 710 and 720. In this example, the nitric-oxide modulating light 710 is illustrated as having a peak intensity 814 at a peak wavelength 804, the nitric-oxide modulating light 720 is illustrated as having a peak intensity 814 at a peak wavelength 810. In these examples, peak wavelength 804 may be any wavelength within a range from wavelength 802 to wavelength 806, and peak wavelength 810 may be any wavelength within a range from wavelength 808 to wavelength 812.

Figure 9:
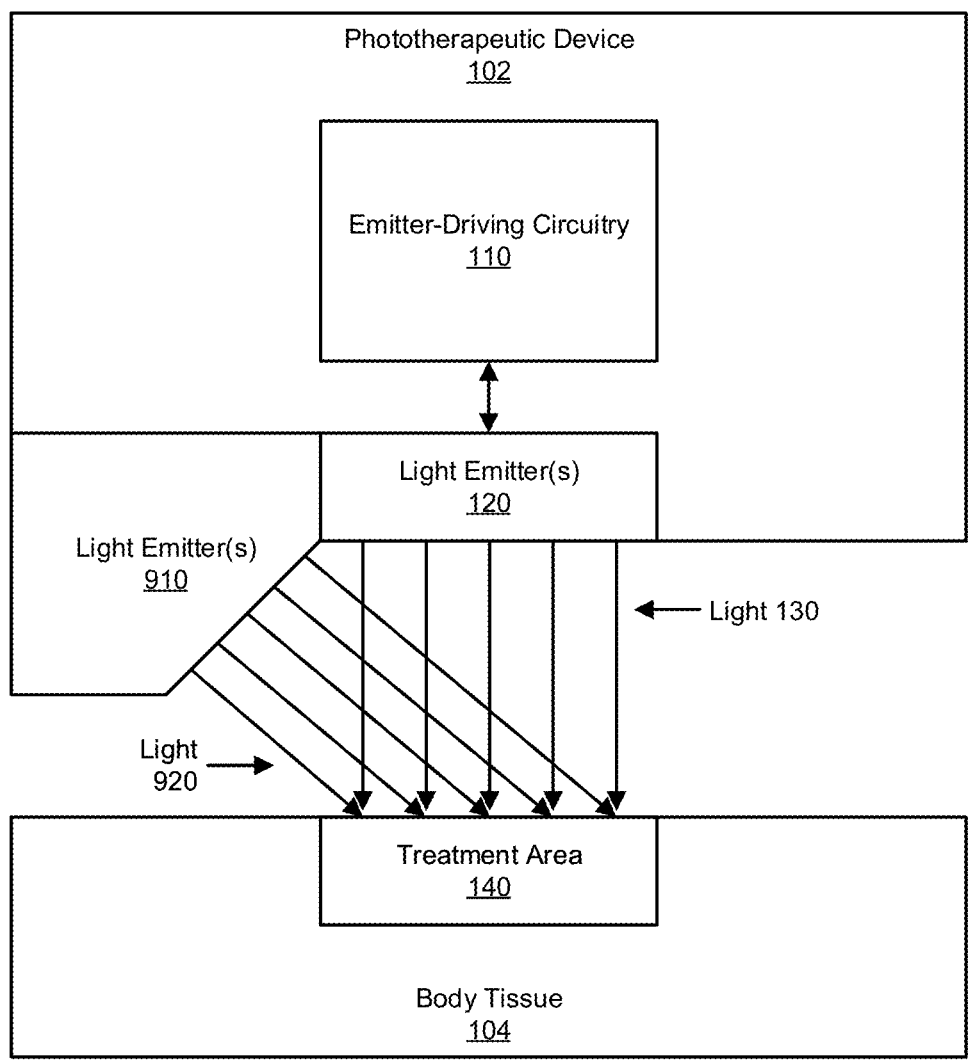
FIG. 9 is another block diagram of the exemplary illumination device of FIG. 1 including additional light emitter(s), according to some embodiments.

FIG. 9 is an illustration of an exemplary configuration 900 of illumination device 102 having additional light emitter(s) 910 operable to emit light 920. As illustrated, the additional light emitter(s) 910 may be configured to provide emissions to the treatment are 140 from a different emission angle than the light emitter(s) 120. For example, the light emitter(s) 120 may be configured with an emission angle of about 90 degrees relative to a surface of the treatment area 140 while the light emitter(s) 910 may be configured with any emission angle that is different from 90 degrees. In other configurations, the light emitter(s) 910 may be provided in a same location to provide a same emission angle to the treatment area 140 as the light emitter(s) 120. In some embodiments, light 920 may represent light that does not substantially modulate nitric oxide within body tissue 104. Examples of light 920 may include, without limitation, vasculature-controlling light for controlling blood flow within body tissue 104, microbe-controlling light for controlling biological activity of microbes on body tissue 104 including inactivating microorganisms that are in a cell-free environment and/or inhibiting replication of microorganisms that are in a cell-associated environment, anti-inflammatory light for reducing inflammation in body tissue 104, upregulating a local immune response, and/or any combination thereof.

Figure 10:
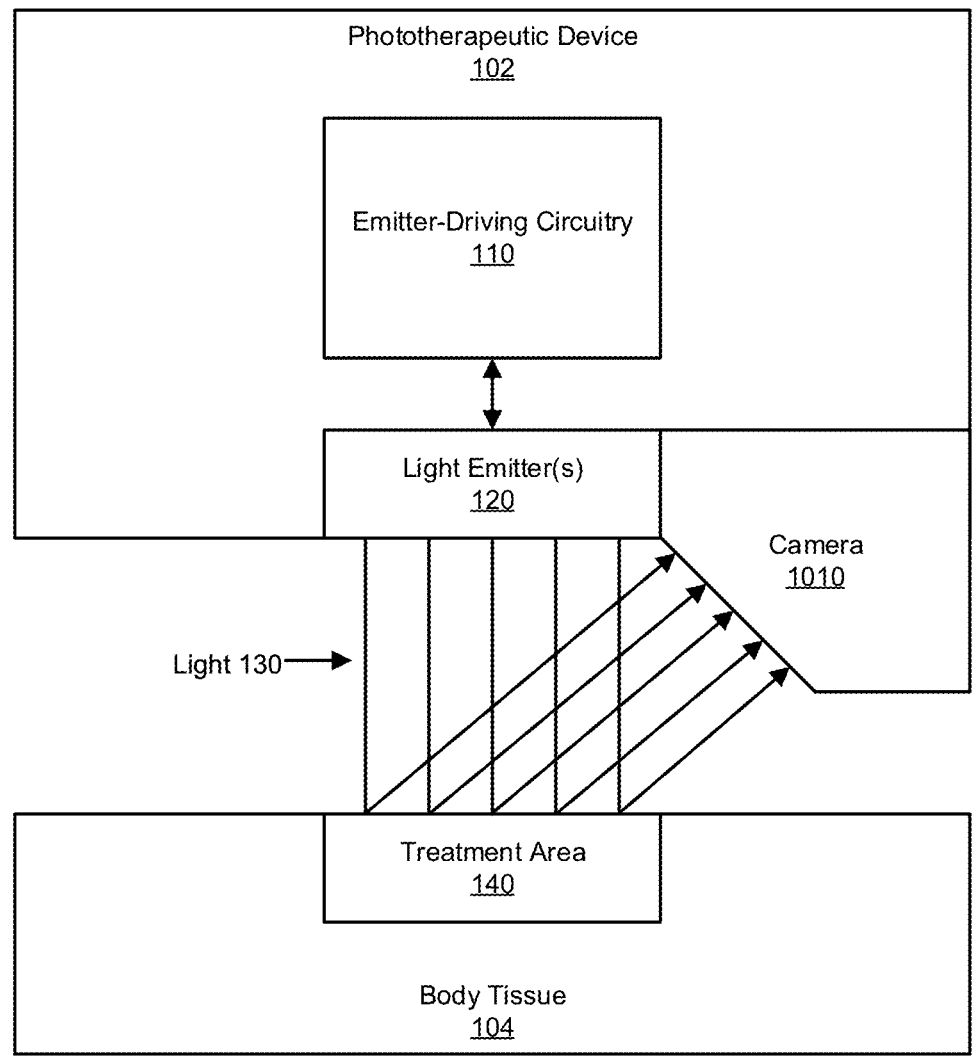
FIG. 10 is another block diagram of the exemplary illumination device of FIG. 1 including a camera sensor, according to some embodiments.
Figure 11:
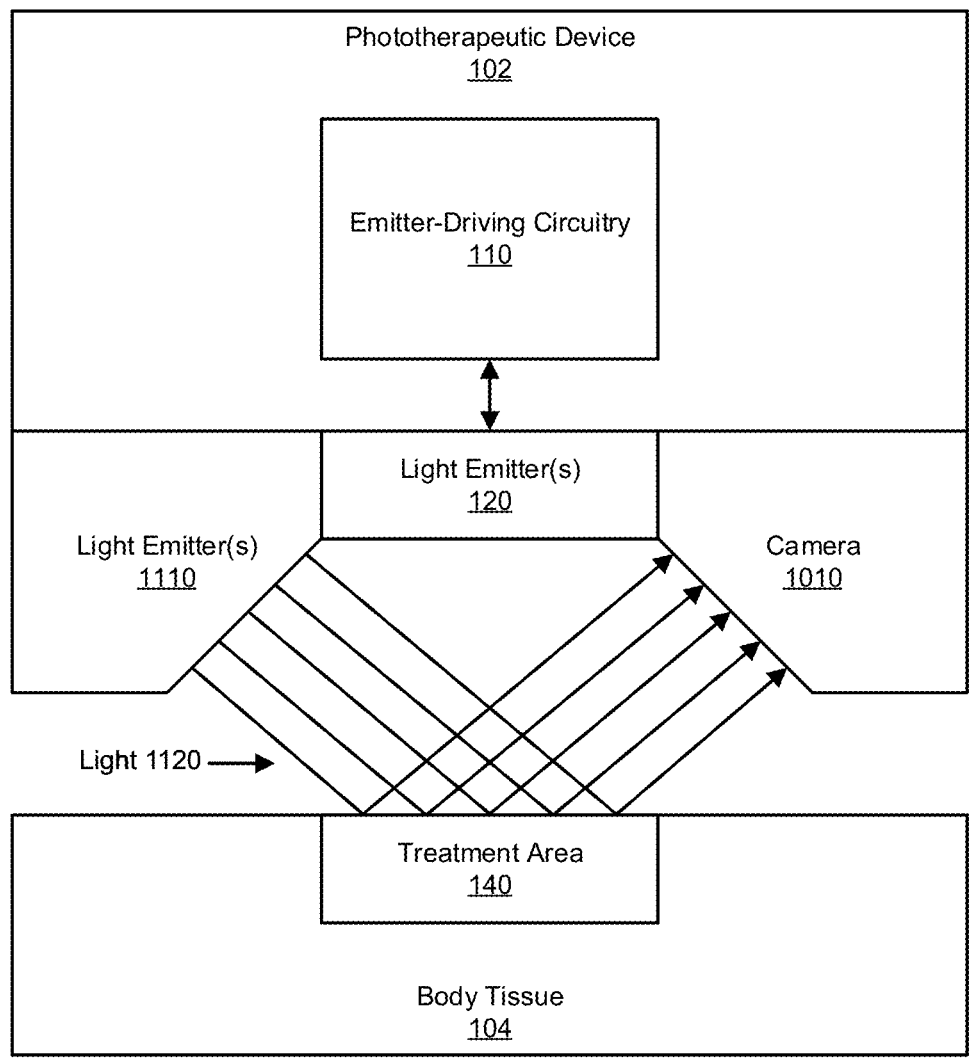
FIG. 11 is another block diagram of the exemplary illumination device of FIG. 1 including additional light emitter(s) and a camera sensor, according to some embodiments.

FIG. 10 is an illustration of an exemplary configuration 1000 of illumination device 102 having a camera sensor 1010 for acquiring images of treatment area 140 at one or more wavelengths. In some embodiments, the images may be analyzed to (1) monitor how treatment area 140 responds to light therapy, (2) monitor how much light treatment area 140 is exposed to, (3) monitor inflammation of treatment area 140, and/or (4) track which portions of body tissue 104 have or are being treated. In the embodiment illustrated in FIG. 10, camera 1010 may acquire images of treatment area 140 at the same wavelengths as the light 130. In an alternative configuration 1100 illustrated in FIG. 11, illumination device 102 may include additional light emitter(s) 1110 for illuminating treatment area 140 with imaging light 1120, which may have wavelengths that differ from those of the light 130. As illustrated, the additional light emitter(s) 1110 may be configured to provide emissions to the treatment are 140 from a different emission angle than the light emitter(s) 120. In other configurations, the additional light emitter(s) 1110 may be provided in a same location to provide a same emission angle to the treatment area 140 as the light emitter(s) 120.

The systems and devices described herein may be configured to treat tissues within a variety of body cavities. For example, the systems and devices described herein may be configured to treat, prevent, and/or reduce the biological activity of pathogens present in the oral cavity and/or auditory canal (i.e., mouth, nose and ears), as well as the throat, larynx, pharynx, oropharynx, trachea, and/or esophagus. Representative types of light delivery devices that can be used in carrying out the methods, and/or light delivery devices described herein, include devices that can be used to deliver light to (and/or that can be positioned in or pass through) any part or parts of patients' mouth, nose and ears, as well as the throat, larynx, pharynx, oropharynx, trachea and/or esophagus. In certain embodiments, exemplary illumination devices are provided that are configured to emit safe, visible light, including but not limited to light with a peak wavelength in a range from 400 nm to 490 nm to eliminate invading respiratory pathogens in and around the oropharynx and to stimulate host defenses in surrounding tissues.

Examples include, but are not limited to, light emission devices (e.g., shaped and sized so as to be inserted or insertable into a patient's oral cavity, such as the nasal cavity, and/or the auditory canal), scopes, such as ophthalmoscopes, with light emitting element(s) and/or light delivery component(s), tubes with light emitting element(s) and/or light delivery component(s), and the like. In various embodiments, the light source may be a wand, flashlight, ophthalmoscope, or light panel.

Light emission devices that are shaped and sized so as to be inserted or insertable into patients' mouths and/or nasal cavities include generally any device that is suitable for insertion into a patient's mouth and/or nasal cavity and that is capable of emitting light having desired characteristics. Examples include panels, which can be flat or curved, wands, flashlights, headphones with a light source in addition to or in place of speakers, scopes, tubes and intra-oral devices. Each of these devices may include a light emitting source, such as LEDs, OLEDs, SLDs, lasers, and combinations thereof, to shine light into the oral cavity, auditory canal, and the like.

Figure 12:
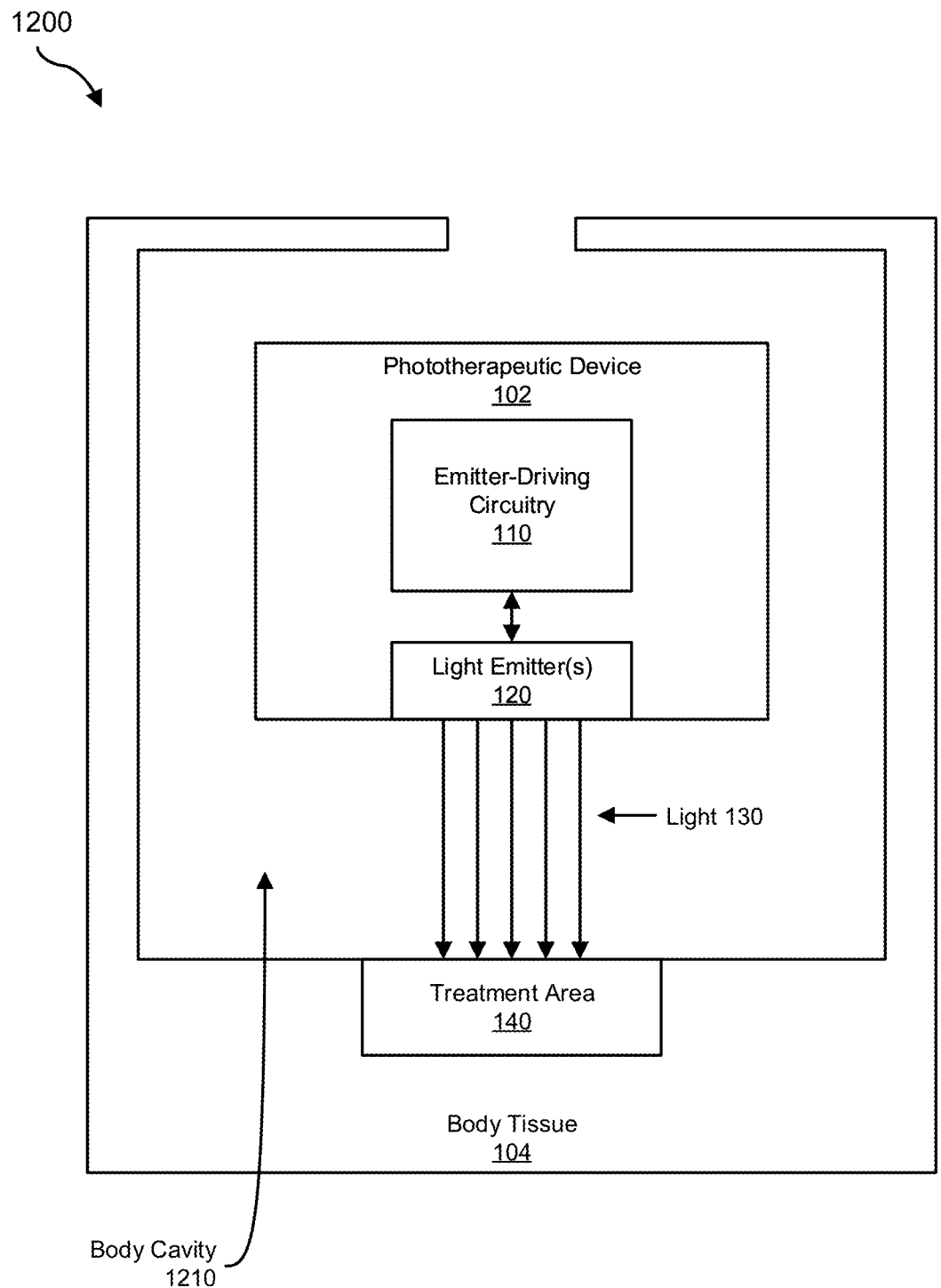
FIG. 12 is another block diagram of the exemplary illumination device of FIG. 1 sized to substantially fit within a body cavity, according to some embodiments.
Figure 13:
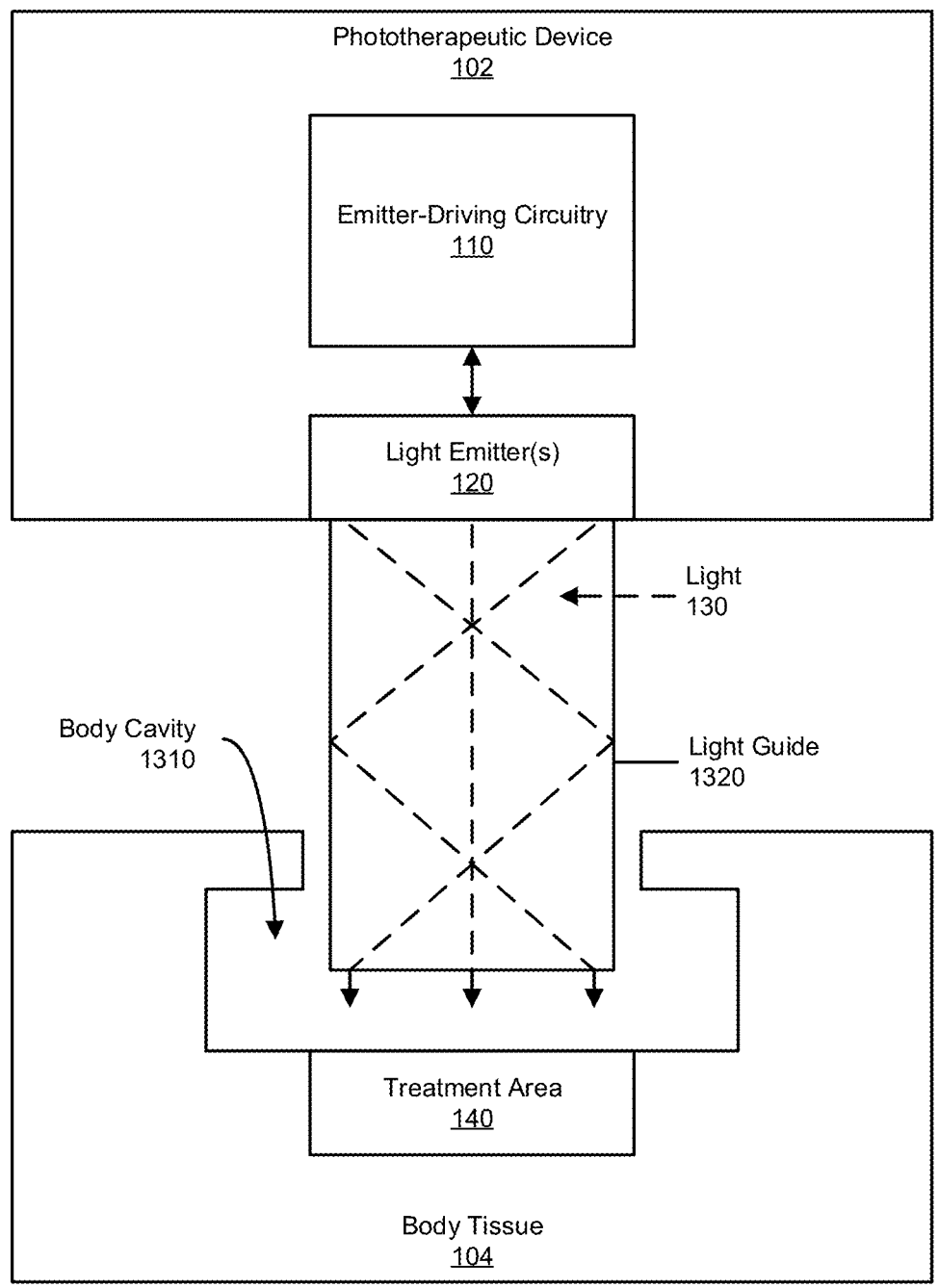
FIG. 13 is another block diagram of the exemplary illumination device of FIG. 1 including a light guide for directing nitric-oxide modulating light into a body cavity, according to some embodiments.

FIG. 12 is an illustration of an exemplary configuration 1200 of illumination device 102. In this configuration, illumination device 102 may be sized and shaped to fit partially or fully within a body cavity 1210. FIG. 13 illustrates an exemplary configuration 1300 of illumination device 102 having a light guide 1320. In this embodiment, light emitter(s) 120 may be operable to produce the light 130 outside of a body cavity 1310, and light guide 1320 may deliver the light 130 from light emitter(s) 120 to treatment area 140 within body cavity 1310. Light guide 1320 may include any light delivery component (such as fiber optic cables, waveguides, lenses, and the like) operable to deliver the light to living tissue within a body cavity. Light guide 1320 may be constructed from a thermally and/or electrically insulating material. In certain embodiments, light guide 1320 may be configured to minimize internal absorption of the light, maximize efficient transmission of the light, and/or maximize internal reflection of the light.

Light guide 1320 may be suitably shaped based on the body cavity it will be inserted into. For example, light guide 1320 may be shaped to conform to or fit within at least one of a nasal cavity, an ear cavity, a throat cavity, a laryngeal cavity, a pharyngeal cavity, a tracheal cavity, an esophageal cavity, a urethral cavity, a vaginal cavity, or a cervical cavity. In one embodiment, body cavity 1310 may be an oral cavity, and light guide 1320 may be shaped to fit through a mouth and guide the light 130 to living tissue within the oral cavity. In at least one embodiment, light guide 1320 may have a length within a range of about 85 mm to about 115 mm and a width within a range of about 10 mm to about 20 mm. As with previous embodiments, while examples are provided in the context of the light, the illumination device 102 and the light guide 1320 may be configured to induce any of the previously-described biological effects in the treatment area 140 within the body cavity 1310.

Certain embodiments of devices for use in carrying out the methods described herein (and certain embodiments of the devices described herein) may include one or more features and/or components to scatter light or enhance scattering of light. Representative examples of such features and components include (1) digital light processors (e.g., which can be positioned at the end of a fiber optic element and disseminate the light exiting the fiber optic element, e.g., 320 degrees spherically), (2) light diffusion and/or scattering materials (e.g., zinc oxide, silicon dioxide, titanium dioxide, etc.), (3) textured light scattering surfaces, (4) patterned light scattering surfaces, and/or (5) phosphors or other wavelength-conversion materials (which tend to re-emit light spherically). In certain embodiments, low-absorption light scattering particles, liquids, and/or gases can be positioned inside a low-absorption element that prevents the particles, liquids and/or gases from escaping.

Figure 14:
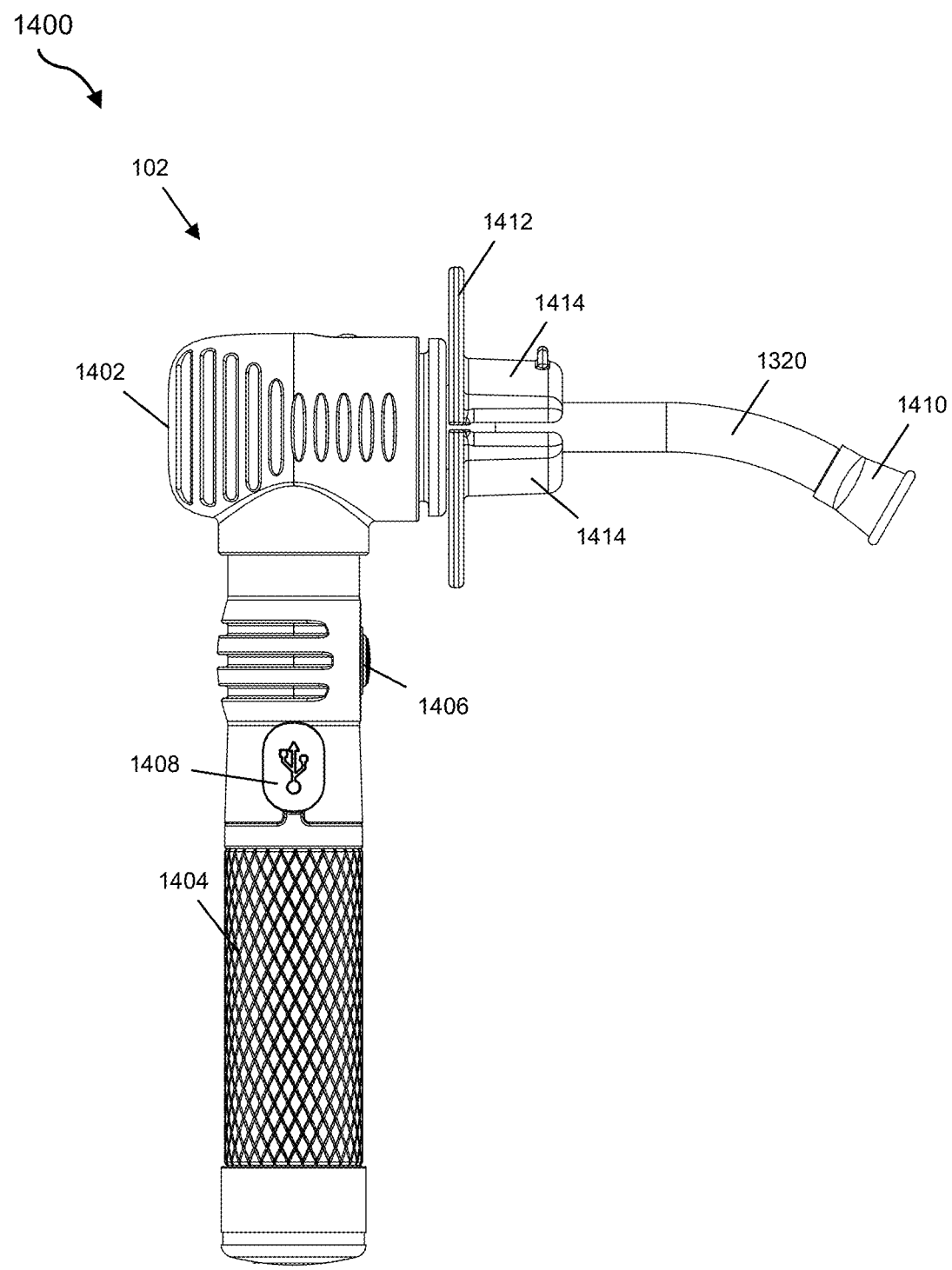
FIG. 14 is a side view of an exemplary handheld configuration of the exemplary illumination device of FIG. 13, according to some embodiments.
Figure 15:
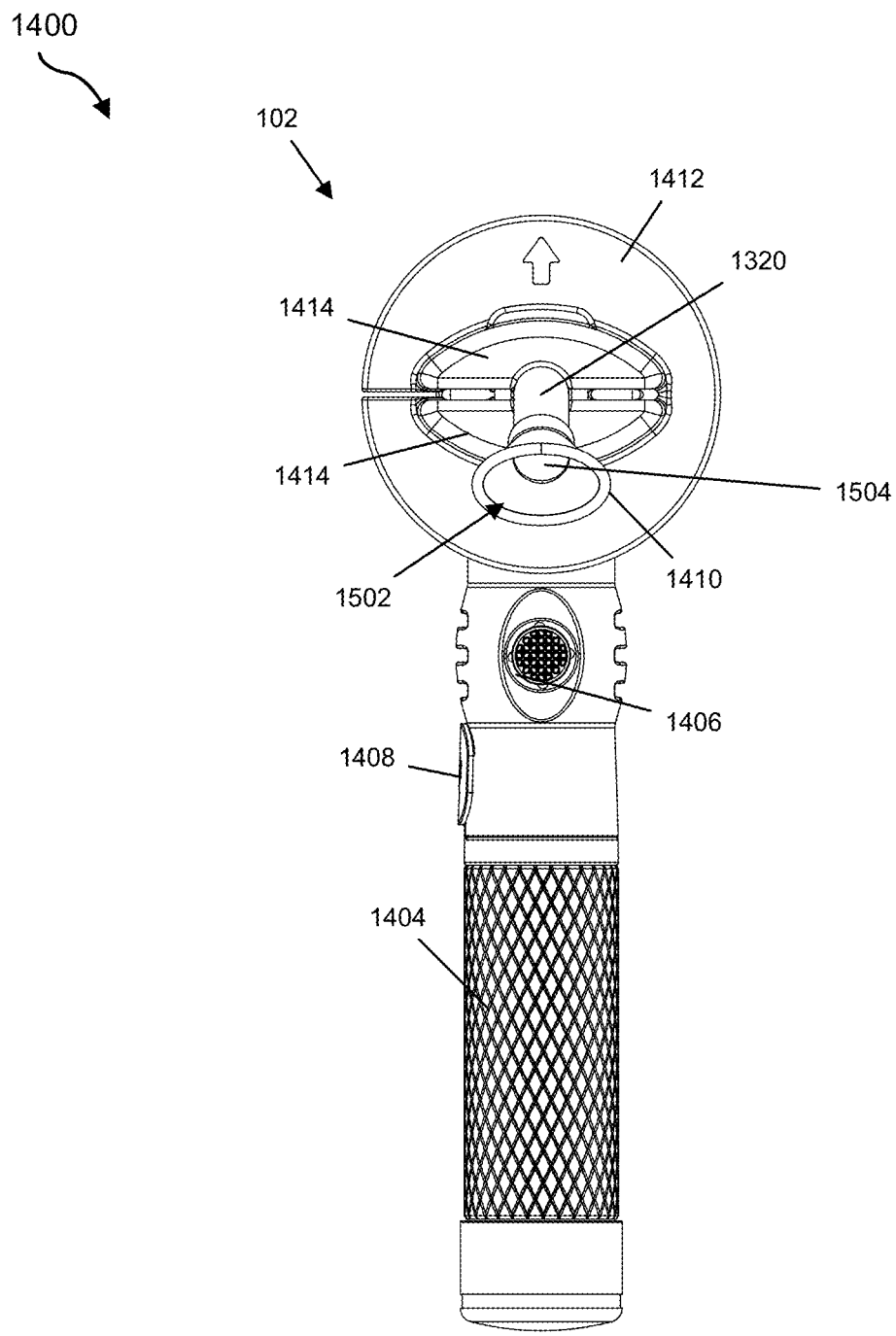
FIG. 15 is a front view of the exemplary handheld configuration of FIG. 14, according to some embodiments.

FIGS. 14 and 15 illustrate respective side and front views of an exemplary handheld configuration 1400 of illumination device 102 for delivering light to living tissue within or near a user's oral cavity, including the oropharynx. In various aspects, the light may be configured to induce one or more of the previously-described biological effects within or near the user's oral cavity, including at least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In FIGS. 14 and 15, illumination device 102 may include an outer housing 1402 for containing and protecting one or more of the light emitter(s), the emitter-driving circuitry, and/or the one or more sensors as previously-described. In some embodiments, outer housing 1402 may include a hand grip 1404, a button 1406 for energizing the illumination device 102 and/or light emitter(s) 120, and a port 1408 for charging illumination device 102 and/or accessing or updating data stored to illumination device 102. As shown in FIG. 14, the light guide 1320 may have a bent profile suitably sized and shaped for insertion into a user's oral cavity. In some embodiments, the length of light guide 1320 may be sufficient to convey light from outside of the user's oral cavity to the back of a user's oral cavity and/or at or near the oropharynx. In some embodiments, a conical shield 1410 having an oval opening 1502 may be affixed or removably attached to light-emitting end 1504 of light guide 1320. In some embodiments, illumination device 102 may include a positioning plate 1412 with which a user of illumination device 102 may gauge proper insertion depth of light guide 1320 and/or upper and lower bite guards 1414 for protecting light guide 1410 and/or enabling a user to secure light guide 1320 by biting against bite guards 1414. In some embodiments, positioning plate 1412 may, when touching an outer surface of a user's mouth, help index a light-transmissive surface of light guide 1320 at an appropriate depth within the user's oral cavity. In one embodiment, positioning plate 1412 may index light guide 1320 at a depth within a user's oral cavity at which an area of tissue exposed to the light 130 is equal to about 25 cm2. In one embodiment, positioning plate 1412 may index light guide 1320 at a depth within a user's oral cavity at which an irradiance of the light 130 onto tissue is less than about 160 mW/cm2.

Figure 16:
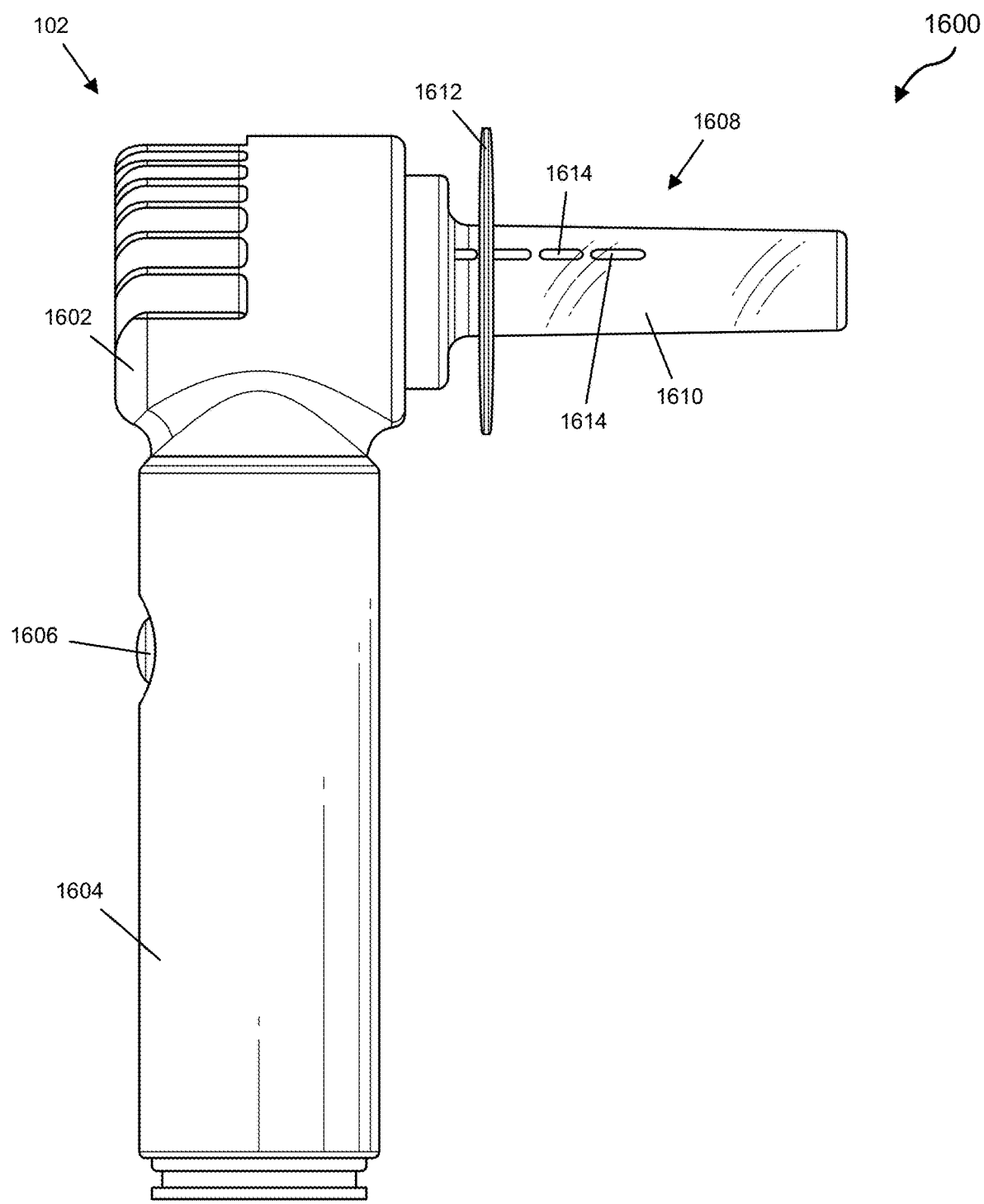
FIG. 16 is a side view of an exemplary handheld configuration of the exemplary illumination device of FIG. 13, according to some embodiments.
Figure 17:
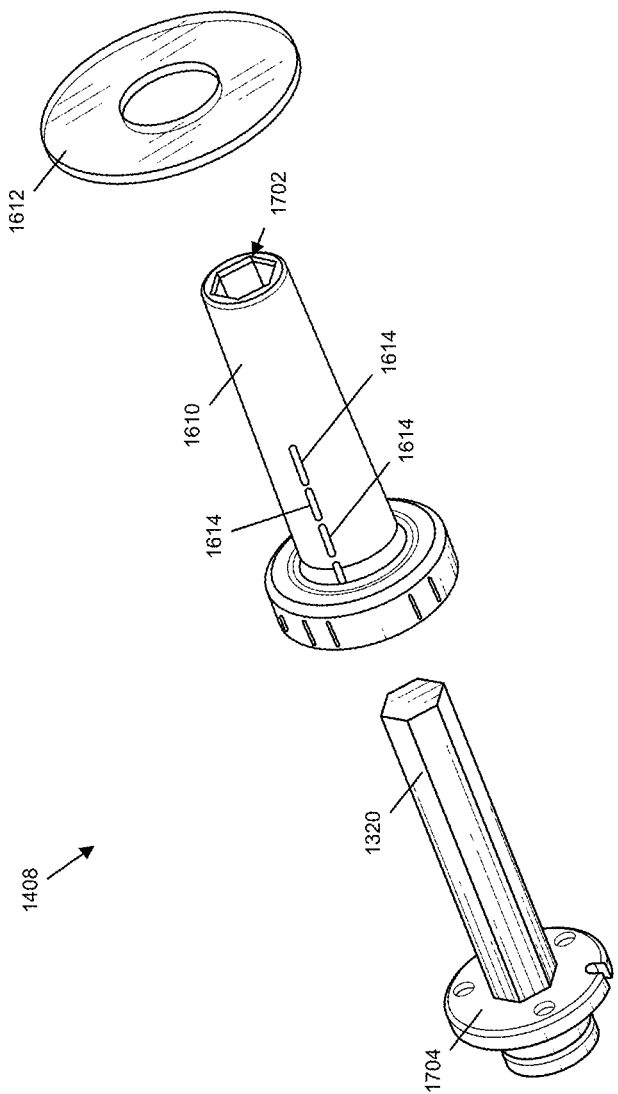
FIG. 17 is a perspective view of various components of the exemplary handheld configuration of FIG. 16, according to some embodiments.
Figure 18:
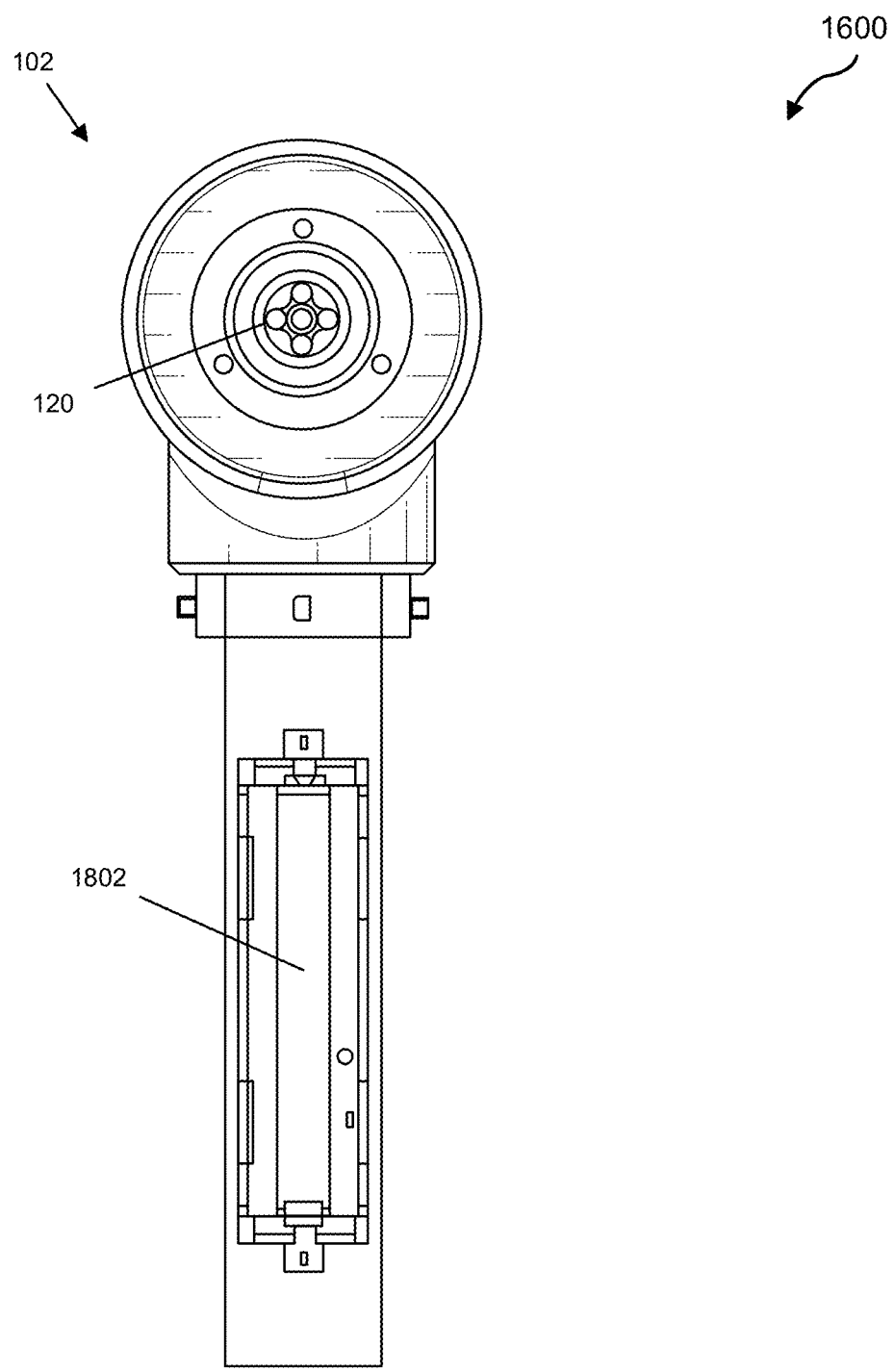
FIG. 18 is a front view of the exemplary handheld configuration of FIG. 16, according to some embodiments.

FIGS. 16-18 illustrate another exemplary handheld configuration 1600 of illumination device 102 for delivering light to living tissue within or near a user's oral cavity, including the oropharynx. FIG. 16 is a side view of the illumination device 102. In these figures, illumination device 102 may include an outer housing 1602 for containing and protecting one or more of the light emitter(s), the emitter-driving circuitry, and/or one or more of the sensors. In some embodiments, illumination device 102 may include a hand grip 1604 and/or a button 1606 for energizing illumination device 102 and/or light emitter(s) 120. As shown in FIG. 16-18, illumination device 102 may include a straight light-guide assembly 1608 suitably sized and shaped for insertion into a user's oral cavity. As best illustrated in the exploded view of FIG. 17, the light-guide assembly 1608 of FIG. 16 may include a mouthpiece housing 1610 surrounding and protecting light guide 1320. Mouthpiece housing 1610 may be formed from any suitable transparent or opaque material. Mouthpiece housing 1610 may have a hexagonal hollow core 1702 shaped to accept light guide 1320 having a similar cross-sectional shape. In some embodiments, a retaining ferrule 1704 may be affixed to light guide 1320. In some embodiments, illumination device 102 may include an adjustable positioning plate 1612 with which a user of illumination device 102 may gauge proper insertion depth of light guide 1320. In some embodiments, positioning plate 1612 may be repositionable at any one of notches 1614 integrated into mouthpiece housing 1610. In some embodiments, positioning plate 1612 may, when touching an outer surface of a user's mouth, help index a light-transmissive surface of light guide 1320 at an appropriate depth within the user's oral cavity. As shown in the front view of FIG. 18, the hand grip 1604 may be removable and may allow access to a battery 1802 within the illumination device 102.

Figure 19:
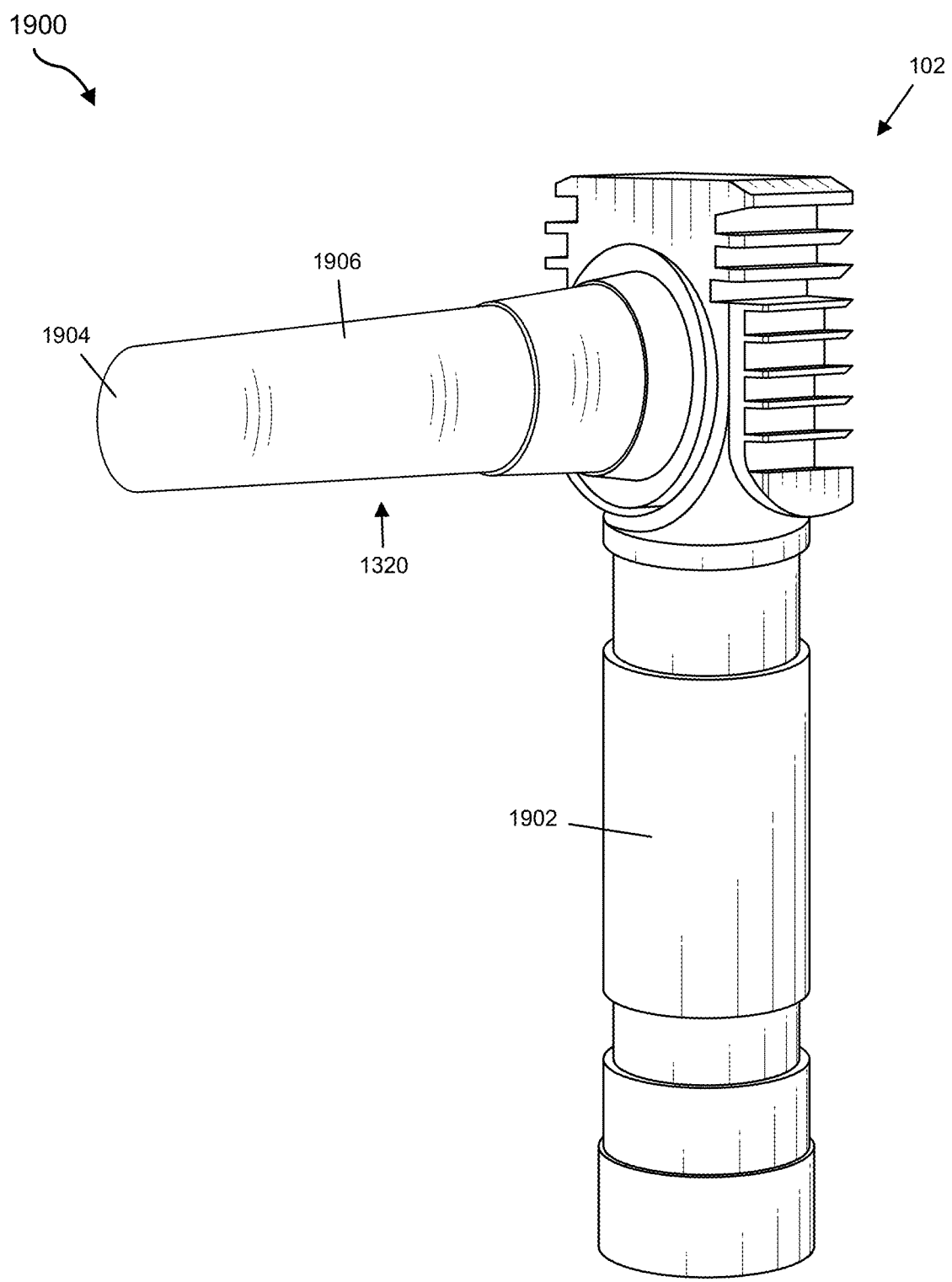
FIG. 19 is a perspective view of an exemplary handheld configuration of the exemplary illumination device of FIG. 13, according to some embodiments.

FIG. 19 illustrates another exemplary handheld configuration 1900 of illumination device 102 for delivering light to living tissue within or near a user's oral cavity, including the oropharynx. In this figure, illumination device 102 may include an outer housing 1902 for containing and protecting one or more of the light emitter(s), the emitter-driving circuitry, and/or the one or more sensors as previously described. In this embodiment, light guide 1320 may have a tapered profile and may include a rounded light-emitting tip 1904 and exposed light-emitting sides 1906.

Figure 20:
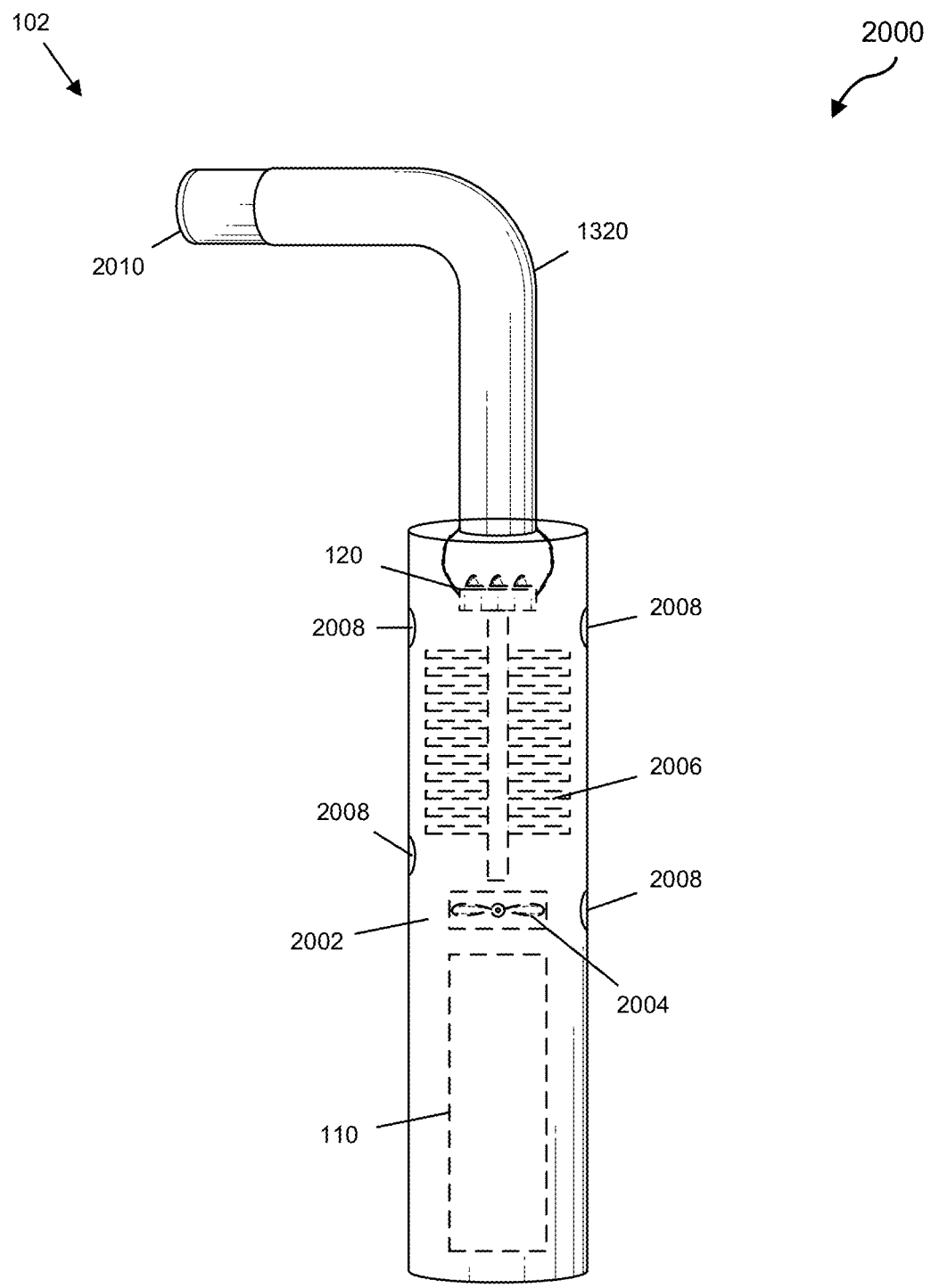
FIG. 20 is a partially transparent view of an exemplary handheld configuration of the exemplary illumination device of FIG. 13, according to some embodiments.

FIG. 20 illustrates another exemplary handheld configuration 2000 of illumination device 102 for delivering light to living tissue within or near a user's oral cavity, including the oropharynx. In this embodiment, illumination device 102 may include an outer housing 2002 for containing and protecting one or more of the light emitter(s) 120, emitter-driving circuitry 110, a fan 2004, and a heatsink 2006 coupled to light emitter(s). In some embodiments, outer housing 2002 may include one or more vents 2008 through which fan 2004 may draw air over heatsink 2006. As shown in FIG. 20, light guide 1320 may have a bent profile suitably sized and shaped for insertion into a user's oral cavity. In some embodiments, the length of light guide 1320 may be sufficient to convey light from outside of the user's oral cavity to the back of a user's oral cavity and/or to the oropharynx. In some embodiments, illumination device 102 may include a butt dome cap 2010.

FIG. 21A-21E illustrate other exemplary configurations of illumination device 102 for delivering the light to tissue in an internal cavity (e.g., vaginal cavity) of a patient. In the embodiment illustrated in FIG. 21A, illumination device 102 may include a body 2101 that may be rigid, semi-rigid, or articulated. A treatment head 2103 may include therein or thereon one or more light-emitting features 2105, which may be formed from or encapsulated in silicone or another suitable light transmissive material. In certain embodiments, light-emitting features 2105 may represent light emitter(s) 120 encapsulated within treatment head 2103. In an alternative embodiment, light emitter(s) 120 may be external to body 2101, and body 2101 and treatment head 2103 may form all or a portion of light guide 1320. In this embodiment, light emissions of light emitter(s) 120 may be transmitted within body 2101 and may exit treatment head 2103 at apertures or positions corresponding to light-emitting features 2105.

In the embodiment illustrated in FIG. 21B, illumination device 102 may include a concave light emitting surface 2114 including one or more light-emitting features 2115 for delivering the light to cervical tissue of a patient according to one embodiment. In this embodiment, illumination device 102 may include a body 2111 that may be rigid, semi-rigid, or articulated. A joint 2112 may be arranged between body 2111 and a treatment head 2113. The treatment head 2113 may have arranged therein or thereon the one or more light-emitting features 2115, which may be formed from or encapsulated in silicone or another suitable light transmissive material. In certain embodiments, light-emitting features 2115 may represent light emitter(s) 120 encapsulated within treatment head 2113. In an alternative embodiment, light emitter(s) 120 may be external to body 2111, and body 2111, joint 2112, and treatment head 2113 may form all or a portion of light guide 1320. In this embodiment, light emissions of light emitter(s) 120 may be transmitted through body 2111, joint 2112, and treatment head 2113 and may exit treatment head 2113 at apertures or positions corresponding to light-emitting features 2115. FIG. 21C illustrates illumination device 102 of FIG. 21B inserted into a vaginal cavity 2150 to deliver light to cervical tissue 2155 of a patient proximate to a cervical opening 2156. The concave light emitting surface 2114 may be configured to approximately match a convex profile of the cervical tissue 2155.

In the embodiment illustrated in FIG. 21D, illumination device 102 may include a light emitting surface 2124 with a protruding probe portion 2126 for delivering light to cervical tissue of a patient. The probe portion 2126 may include light-emitting features 2125 arranged to deliver the light into a cervical opening. In this embodiment, illumination device 102 may include a body 2121 that may be rigid, semi-rigid, or articulated. A joint 2122 may be arranged between body 2121 and a treatment head 2123. The treatment head 2123 may have arranged therein or thereon the one or more light-emitting features 2125, which may be formed from or encapsulated in silicone or another suitable light transmissive material. In certain embodiments, light-emitting features 2125 may represent light emitter(s) 120 encapsulated within treatment head 2123. In an alternative embodiment, light emitter(s) 120 may be external to body 2121, and body 2121, joint 2122, and treatment head 2123 may form all or a portion of light guide 1320. In this embodiment, light emissions of light emitter(s) 120 may be transmitted through body 2121, joint 2122, and treatment head 2123 and may exit treatment head 2123 at apertures or positions corresponding to light-emitting features 2125. FIG. 21E illustrates illumination device 102 of FIG. 21D inserted into a vaginal cavity 2150 to deliver light to cervical tissue 2155 of a patient proximate and within to a cervical opening 2156. The primary light emitting surface 2124 may be arranged to impinge light on cervical tissue bounding the vaginal cavity 2150, whereas the probe portion 2126 may be inserted into the cervical opening 2156 to deliver additional light therein to increase the amount of cervical tissue subject to receipt of the light for addressing one or more conditions including pathogen (e.g., HPV) neutralization.

Figure 22A:
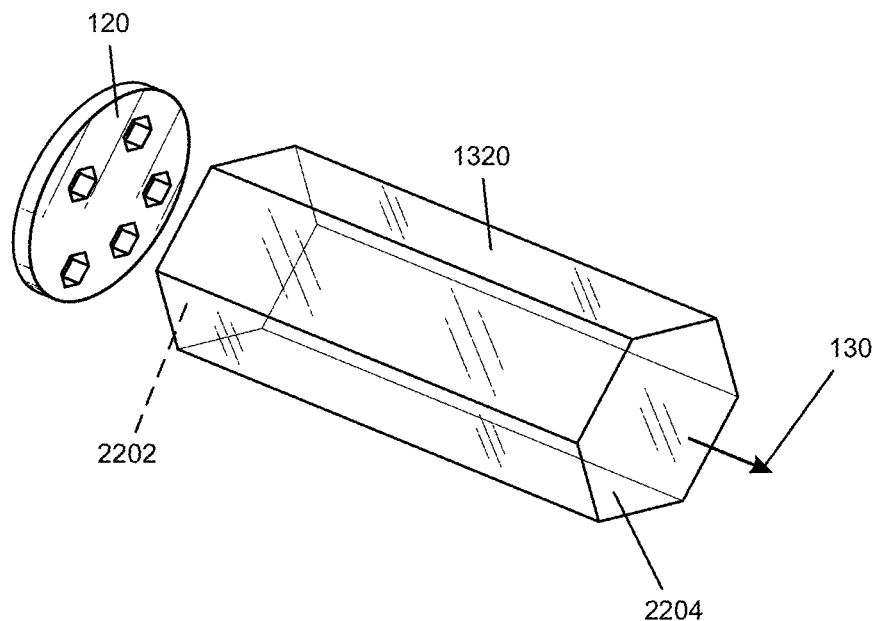
FIG. 22A is a perspective view of an exemplary straight light guide, according to at least one embodiment.
Figure 22B:
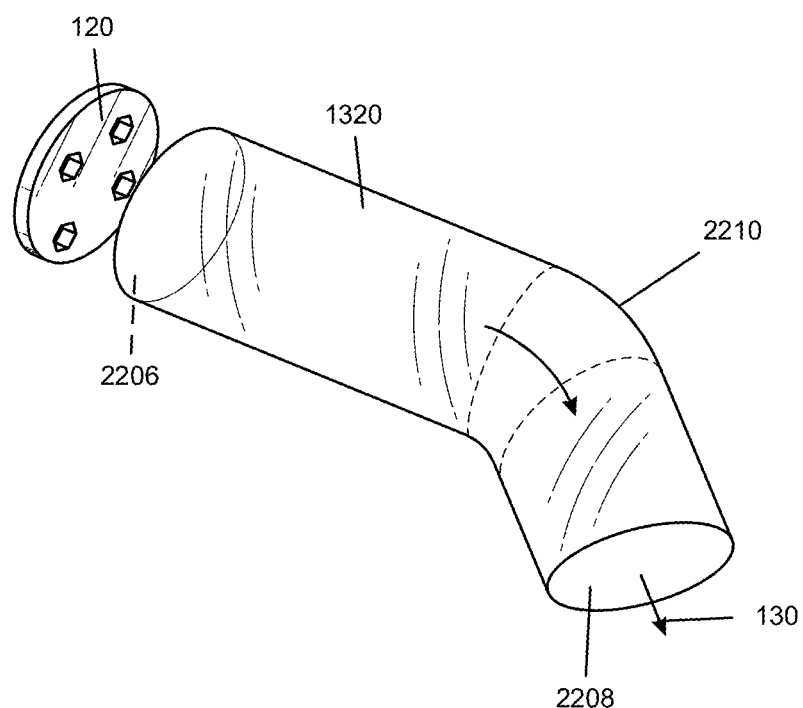
FIG. 22B is a perspective view of an exemplary bent light guide, according to at least one embodiment.
Figure 23A:
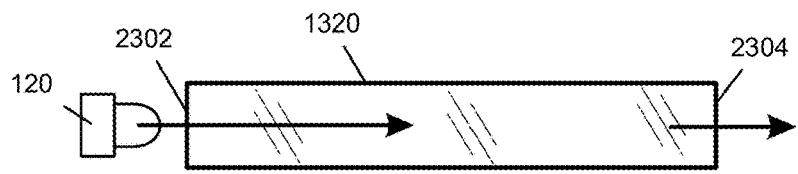
FIG. 23A is a side view of an exemplary straight light guide, according to at least one embodiment.
Figure 23B:
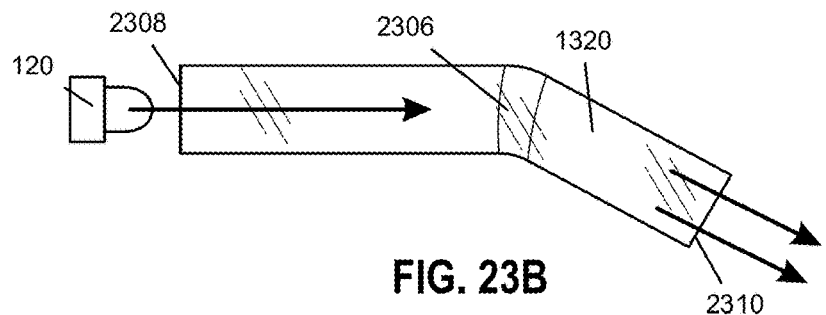
FIG. 23B is a side view of an exemplary bent light guide, according to at least one embodiment.
Figure 23C:
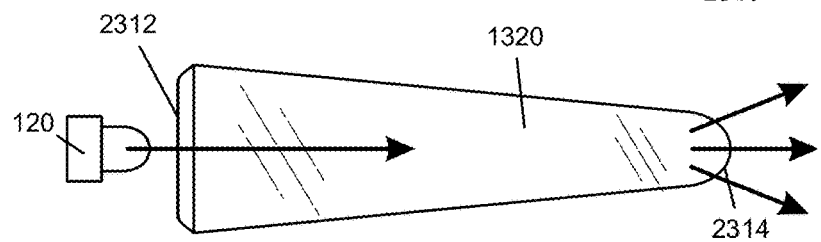
FIG. 23C is a side view of an exemplary tapered light guide, according to at least one embodiment.
Figure 23D:
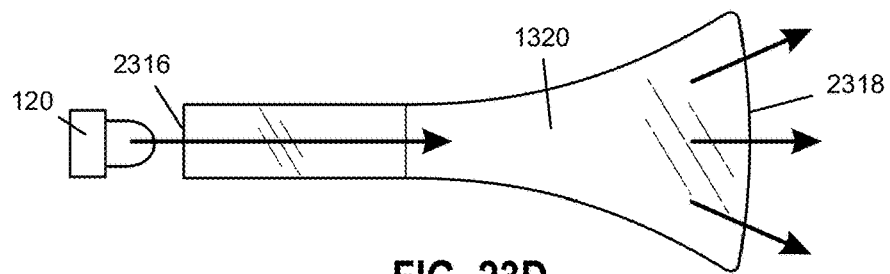
FIG. 23D is a side view of an exemplary up-tapered light guide, according to at least one embodiment.
Figure 23E:
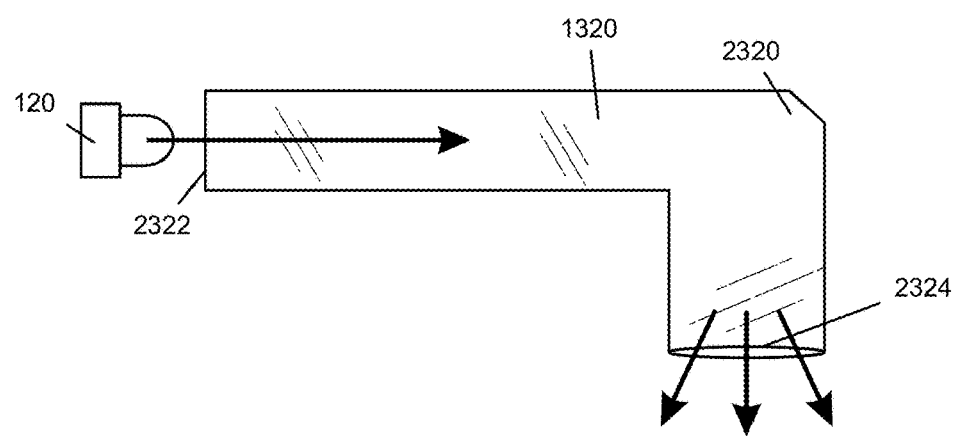
FIG. 23E is a side view of an exemplary bent light guide having a 90-degree bend, according to at least one embodiment.

Light guides according to principles of the present disclosure may be shaped in a variety of ways depending on the application. Referring to FIGS. 22A and 22B, the light guide 1320 may have various profiles and cross-sectional areas. In the embodiment illustrated in FIG. 22A, light guide 1320 may have a straight profile allowing at least some of the light from light emitter(s) 120 to enter hexagonal endface 2202 and exit hexagonal endface 2204 without being internally reflected. In the embodiment illustrated in FIG. 22B, light guide 1320 may have a bent profile. In this embodiment, light guide 1320 may have a bend 2210 that causes all of the light from light emitter(s) 120 entering circular endface 2206 and exiting circular endface 2208 to be internally reflected. In certain embodiments, bend 2210 may cause light 130 to exit light guide 1320 in a mixed and/or homogenized state.

Referring to FIGS. 23A-23E, light guide 1320 may have various profiles. In the embodiment illustrated in FIG. 23A, light guide 1320 may have a straight profile allowing at least some of the light from light emitter(s) 120 to enter endface 2302 and exit endface 2304 without being internally reflected. In the embodiment illustrated in FIG. 23B, light guide 1320 may have a bent profile. In this embodiment, light guide 1320 may have a bend 2306 that causes all of the light from light emitter(s) 120 entering endface 2308 and exiting endface 2310 to be internally reflected. In the embodiment illustrated in FIG. 23C, light guide 1320 may have a tapered profile having an endface 2312 through which light from light emitter(s) 120 enters light guide 1320 that is relatively larger than an endface 2314 through which light from light emitter(s) 120 exits light guide 1320. In the embodiment illustrated in FIG. 23D, light guide 1320 may have a uptapered profile having an endface 2316 through which light from light emitter(s) 120 enters light guide 1320 that is relatively smaller than an endface 2318 through which light from light emitter(s) 120 exits light guide 1320. In the embodiment illustrated in FIG. 23E, light guide 1320 may have a 90-degree bent profile. In this embodiment, light guide 1320 may have a 90-degree bend 2320 that causes all of the light from light emitter(s) 120 entering endface 2322 and exiting endface 2324 to be internally reflected.

Figure 24A:
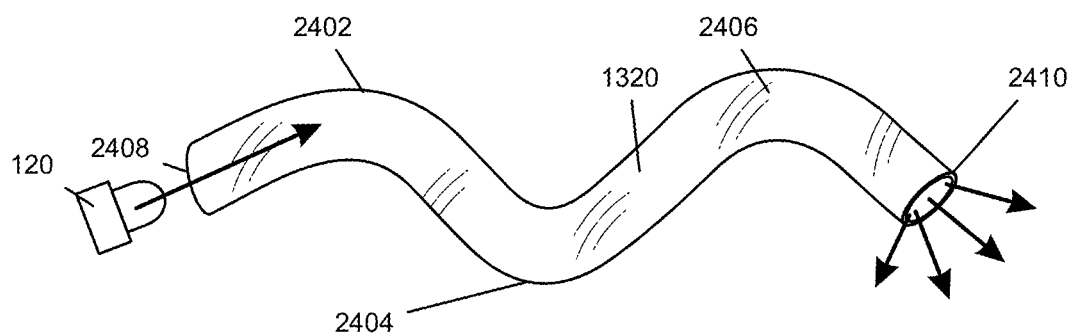
FIG. 24A is a side view of an exemplary bent light guide having multiple bends, according to at least one embodiment.
Figure 24B:
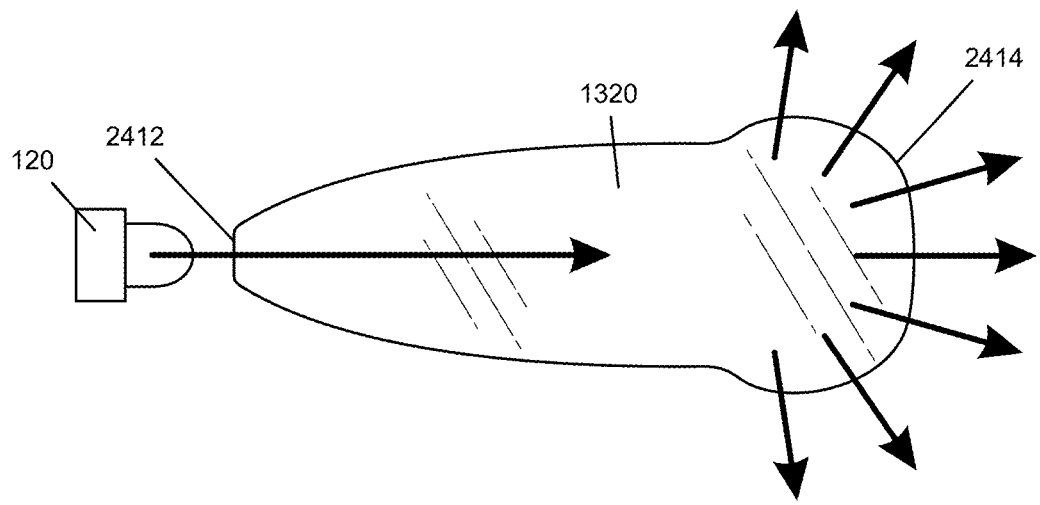
FIG. 24B is a side view of an exemplary bulbous light guide, according to at least one embodiment.
Figure 24C:
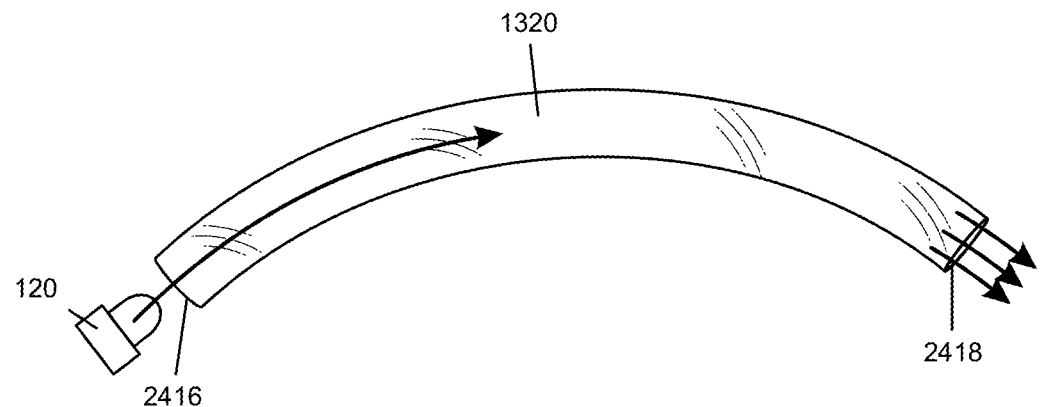
FIG. 24C is a side view of an exemplary curved light guide, according to at least one embodiment.

Referring to FIGS. 24A-24C, light guide 1320 may have various additional profiles. In the embodiment illustrated in FIG. 24A, light guide 1320 may have a bent profile. In this embodiment, light guide 1320 may have multiple bends (e.g., bends 2402, 2404, and 2406) that cause all of the light from light emitter(s) 120 entering endface 2408 and exiting endface 2410 to be internally reflected. In the embodiment illustrated in FIG. 24B, light guide 1320 may have a bulbous profile having a flat endface 2412 through which light from light emitter(s) 120 enters light guide 1320 that is relatively smaller than a bulbous endface 2414 through which light from light emitter(s) 120 exits light guide 1320. In the embodiment illustrated in FIG. 24C, light guide 1320 may have a curved profile. In this embodiment, light guide 1320 may have a uniform curvature that causes all of the light from light emitter(s) 120 entering endface 2416 and exiting endface 2418 to be internally reflected.

Referring to FIGS. 25A-25C, light guide 1320 may be tapered and/or uptapered in multiple dimensions. In this embodiment, light guide 1320 may have a tapered profile in the dimension illustrated in FIG. 25A and an uptapered profile in the dimension illustrated in FIG. 25C. In certain embodiments, a circular surface area of endface 2502 may be greater than, less than, or equal to an elliptical surface area of endface 2504.

In some embodiments, light guide 1320 may have a split configuration. In these embodiments, light guide 1320 may have a different number of light-entering endfaces and light-exiting endfaces. For example, in the embodiment illustrated in FIGS. 26A-26C, light guide 1320 may include a single light-entering endface 2602 and two light-exiting endfaces 2604. In certain embodiments, a surface area of light-entering endface 2602 may be greater than, less than, or equal to a surface area of light-exiting endfaces 2604.

Light guides of the present disclosure may include cross-sectional areas and/or endfaces with various shapes. For example, in the embodiment illustrated in FIG. 27A, light guide 1320 may have a circular cross-sectional area and a circular endface 2702. In the embodiment illustrated in FIG. 27B, light guide 1320 may have a hexagonal cross-sectional area and a hexagonal endface 2704. In the embodiment illustrated in FIG. 27C, light guide 1320 may have an elliptical cross-sectional area and an elliptical endface 2706. In the embodiment illustrated in FIG. 27D, light guide 1320 may have a rectangular cross-sectional area and a rectangular endface 2708. In the embodiment illustrated in FIG. 27E, light guide 1320 may have a pentagonal cross-sectional area and a pentagonal endface 2710. In the embodiment illustrated in FIG. 27F, light guide 1320 may have an octagonal cross-sectional area and an octagonal endface 2712. In the embodiment illustrated in FIG. 27G, light guide 1320 may have an oval cross-sectional area and an oval endface 2714. In the embodiment illustrated in FIG. 27H, light guide 1320 may have a triangular cross-sectional area and a triangular endface 2716. In the embodiment illustrated in FIG. 27I, light guide 1320 may have a semicircular cross-sectional area and a semicircular endface 2718.

Figure 28A:
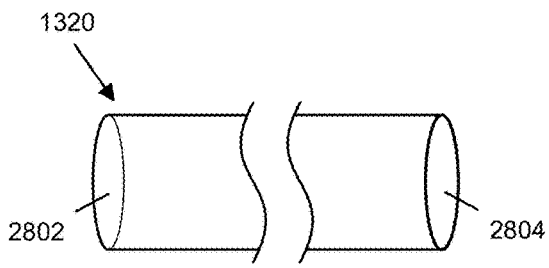
FIG. 28A is a side view of an exemplary light guide having similar faces, according to at least one embodiment.
Figure 28B:
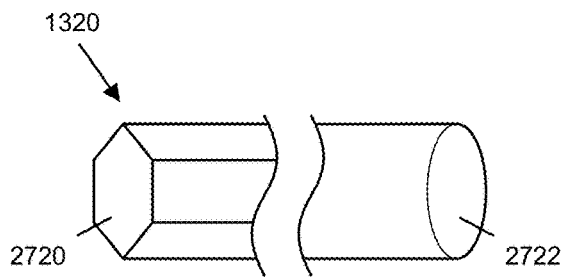
FIG. 28B is a side view of an exemplary light guide having dissimilar faces, according to at least one embodiment.

Light guides of the present disclosure may have uniformly shaped cross-sectional areas and similarly shaped endfaces. For example, in the embodiment illustrated in FIG. 28A, the light guide 1320 may have circular endfaces 2802 and 2804 with similar shapes and sizes. In other embodiments, the light guide 1320 may have differently shaped cross-sectional areas and differently shaped endfaces. For example, in the embodiment illustrated in FIGS. 27J and 28B, the light guide 1320 may have a hexagonal endface 2720 and a circular endface 2722. In this embodiment, the cross-sectional area of the light guide 1320 may be hexagonal, circular, and/or a combination of hexagonal and circular.

Figure 28C:
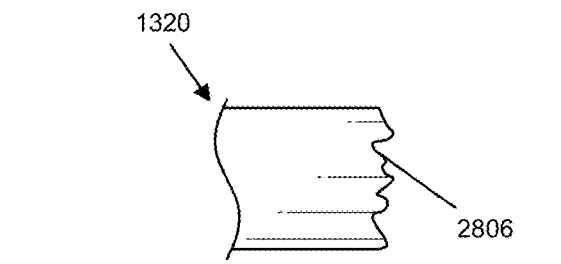
FIG. 28C is a side view of an exemplary light guide having an irregularly shaped face, according to at least one embodiment.
Figure 28D:
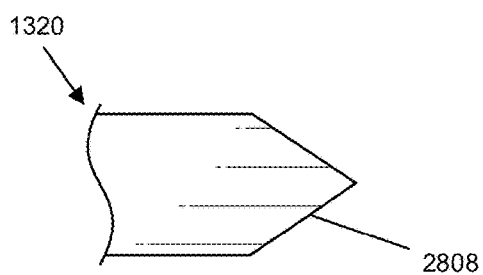
FIG. 28D is a side view of an exemplary light guide having a conical face, according to at least one embodiment.
Figure 28E:
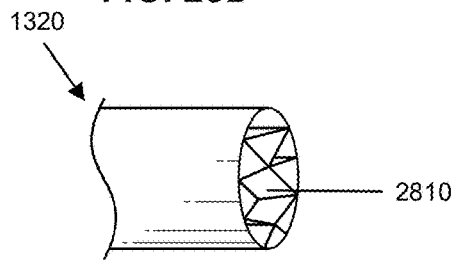
FIG. 28E is a side view of an exemplary light guide having a multifaceted face, according to at least one embodiment.
Figure 28F:
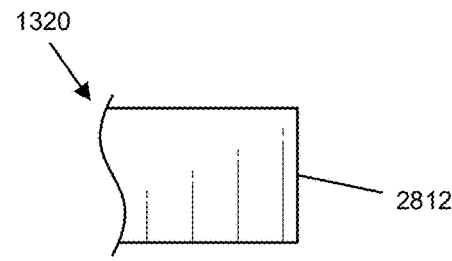
FIG. 28F is a side view of an exemplary light guide having a flat face, according to at least one embodiment.
Figure 28G:
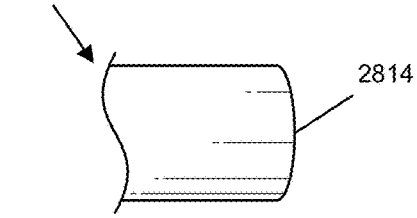
FIG. 28G is a side view of an exemplary light guide having a convex face, according to at least one embodiment.
Figure 28H:
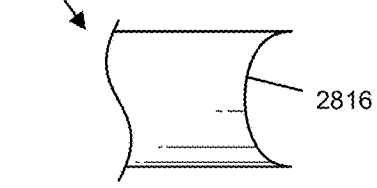
FIG. 28H is a side view of an exemplary light guide having a concave face, according to at least one embodiment.
Figure 28I:
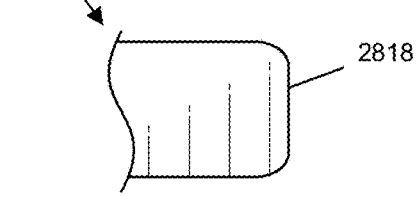
FIG. 28I is a side view of an exemplary light guide having a rounded face, according to at least one embodiment.
Figure 28J:
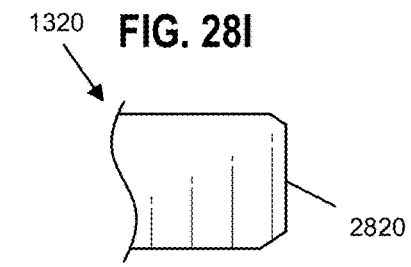
FIG. 28J is a side view of an exemplary light guide having a chamfered face, according to at least one embodiment.
Figure 28K:
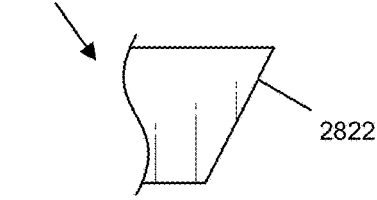
FIG. 28K is a side view of an exemplary light guide having an angled face, according to at least one embodiment.

Light guides of the present disclosure may include endfaces with various types of surfaces. For example, in the embodiments illustrated in FIGS. 28A and 28B, light guide 1320 may have substantially flat endfaces. In the embodiment illustrated in FIG. 28C, light guide 1320 may have an endface with an irregularly shaped surface 2806. In the embodiment illustrated in FIG. 28D, light guide 1320 may have an endface with a conical surface 2808. In the embodiment illustrated in FIG. 28E, light guide 1320 may have an endface with a multifaceted surface 2810. In the embodiment illustrated in FIG. 28F, light guide 1320 may have an endface with a flat surface 2812. In the embodiment illustrated in FIG. 28G, light guide 1320 may have an endface with a convex surface 2814. In the embodiment illustrated in FIG. 28H, light guide 1320 may have an endface with a concave surface 2816. In the embodiment illustrated in FIG. 28I, light guide 1320 may have an endface with a rounded surface 2818. In the embodiment illustrated in FIG. 28J, light guide 1320 may have an endface with a chamfered surface 2820. In the embodiment illustrated in FIG. 28K, light guide 1320 may have an endface with an angled surface 2822.

Light guides of the present disclosure may have one or more cores, and each core of light guide 1320 may be cladded or uncladded and/or buffered or unbuffered. For example, in the embodiment illustrated in FIGS. 29A and 29B, light guide 1320 may include a single uncladded and unbuffered circular core 2902 having a circular cross-sectional area 2904. In at least one embodiment, the index of refraction of light guide 1320 may be uniform across cross-sectional area 2904. In the embodiment illustrated in FIG. 29C, light guide 1320 may include a uncladded and unbuffered square core 2906 having a square cross-sectional area 2908. In at least one embodiment, the index of refraction of light guide 1320 may be uniform across cross-sectional area 2908. In the embodiment illustrated in FIG. 29E, light guide 1320 may include a circular core 2910 surrounded by a cladding 2912. In at least one embodiment, circular core 2910 may be designed to have a higher index of refraction than that of cladding 2912, which may cause total internal reflection of light in circular core 2910. In the embodiment illustrated in FIG. 29F, light guide 1320 may include a circular core 2914 surrounded by a cladding 2916. In at least one embodiment, cladding 2916 may be surrounded by an additional cladding or buffer 2918. In some embodiments, circular core 2914 may be designed to have a higher index of refraction than cladding 2916. Additionally, cladding 2916 may be designed to have a higher index of refraction than cladding 2918, which may cause more efficient total internal reflection of light in circular core 2914.

Figure 30A:
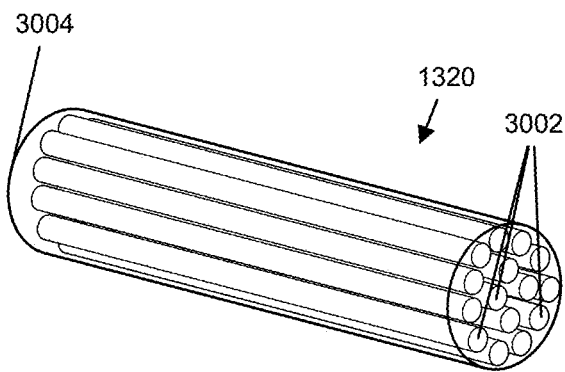
FIG. 30A is a perspective view of an exemplary multicore light guide, according to at least one embodiment.
Figure 30B:
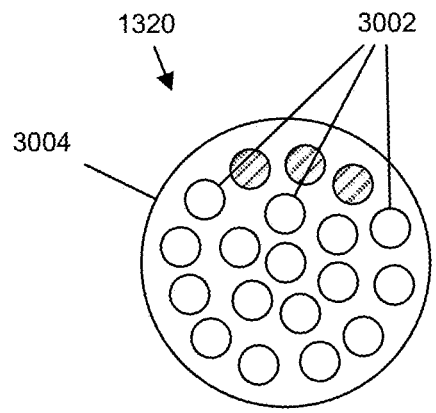
FIG. 30B is a cross-sectional view of the exemplary multicore light guide of FIG. 30A, according to at least one embodiment.
Figure 30C:
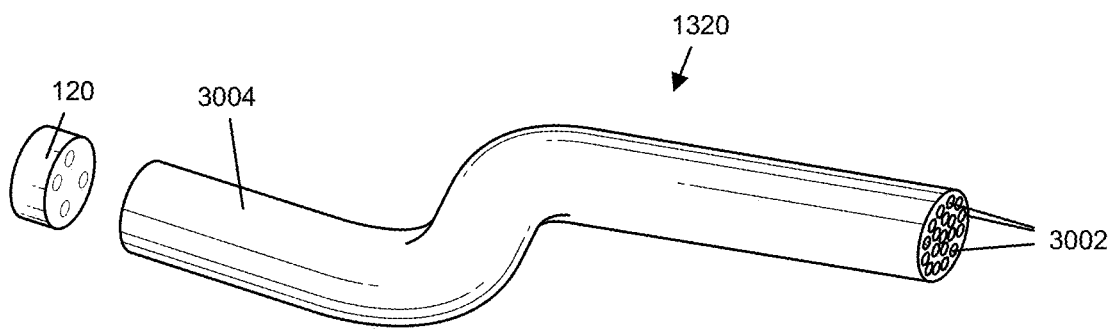
FIG. 30C is a perspective view of an exemplary flexible light guide, according to at least one embodiment.

In the embodiment illustrated in FIGS. 30A-30C, light guide 1320 may include multiple fibers 3002. In some embodiments, multiple fibers 3002 may be encapsulated in a flexible or rigid buffer 3004. If buffer 3004 is formed from a flexible material and multiple fibers 3002 are flexible, light guide 1320 may also be flexible and able to take on various bent shapes (e.g., the bent shape illustrated in FIG. 30C). In some embodiments, each of multiple fibers 3002 may be coupled to a different one of light emitter(s) 120. In other embodiments, two or more of multiple fibers 3002 may be coupled to the same light emitter(s) 120. In certain embodiments, one or more of multiple fibers 3002 may be additionally or alternatively coupled to an optical sensor.

FIG. 31A illustrates several exemplary multicore configurations of the light guide 1320 in which one or more cores 3102 are coupled to light emitter(s) 120 while one or more other cores 3104 are coupled to an optical sensor 3106. In an alternative embodiment, cores 3102 may be coupled to optical sensor 3106, and cores 3104 may be coupled to light emitter(s) 120. FIGS. 31B-31D illustrates exemplary cross-sectional areas of cores 3102 and 3104. In the embodiment illustrated in FIG. 31B, cross-sectional areas 3108 and 3110 may represent the cross-sectional areas of cores 3102 and 3104, respectively. In the embodiment illustrated in FIG. 31C, cross-sectional areas 3112 and 3114 may represent the cross-sectional areas of cores 3102 and 3104, respectively. In the embodiment illustrated in FIG. 31D, cross-sectional areas 3116 and 3118 may represent the cross-sectional areas of cores 3102 and 3104, respectively.

Figure 32A:
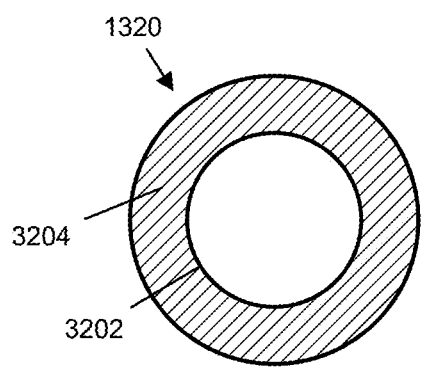
FIG. 32A is a cross-sectional view of an exemplary hollow light guide having a circular cross-sectional area, according to at least one embodiment.
Figure 32B:
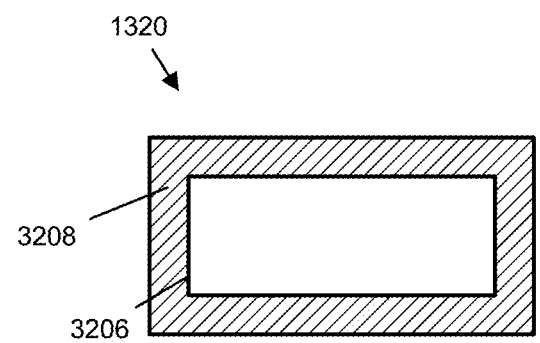
FIG. 32B is a cross-sectional view of an exemplary hollow light guide having a rectangular cross-sectional area, according to at least one embodiment.
Figure 32C:
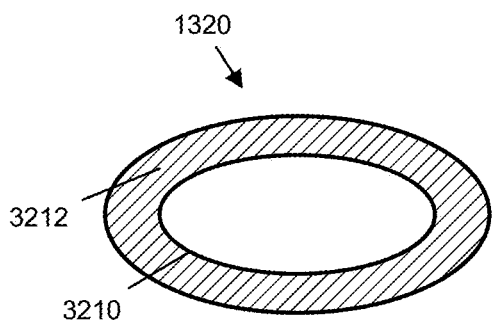
FIG. 32C is a cross-sectional view of an exemplary hollow light guide having an elliptical cross-sectional area, according to at least one embodiment.
Figure 32D:
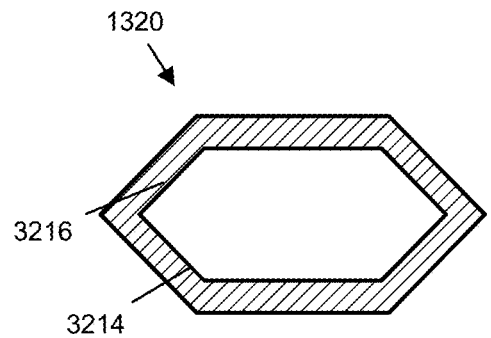
FIG. 32D is a cross-sectional view of an exemplary hollow light guide having a hexagonal cross-sectional area, according to at least one embodiment.

In certain embodiments, light guides of the present disclosure may have one or more hollow cores and/or hollow cross-sectional areas. For example, in the embodiment illustrated in FIG. 32A, light guide 1320 may have a circular hollow core 3202 and/or a circular hollow cross-sectional area 3204. In the embodiment illustrated in FIG. 32B, light guide 1320 may have a rectangular hollow core 3206 and/or a rectangular hollow cross-sectional area 3208. In the embodiment illustrated in FIG. 32C, light guide 1320 may have an elliptical hollow core 3210 and/or an elliptical hollow cross-sectional area 3212. In the embodiment illustrated in FIG. 32D, light guide 1320 may have a hexagonal hollow core 3214 and/or a hexagonal hollow cross-sectional area 3216.

Figure 33:
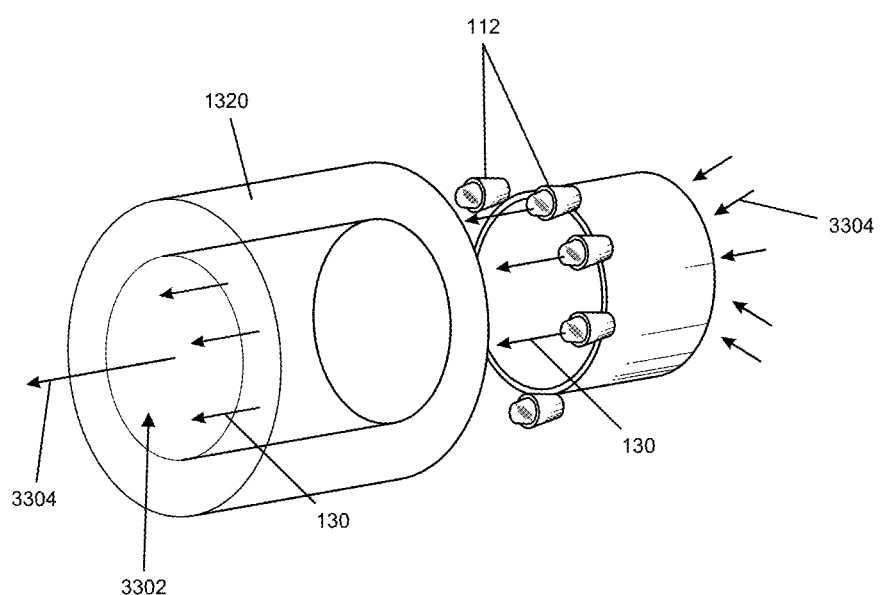
FIG. 33 is a perspective view of an exemplary hollow light guide, according to at least one embodiment.
Figure 34:
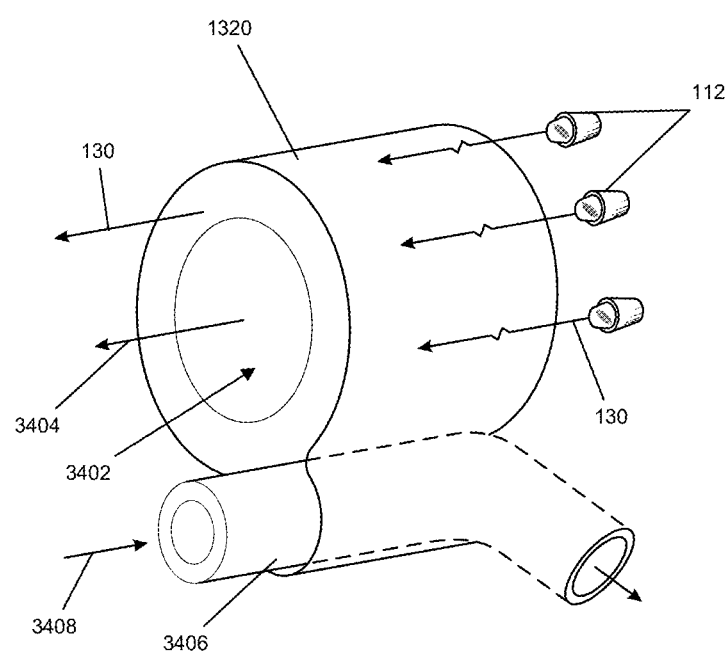
FIG. 34 is a perspective view of another exemplary hollow light guide, according to at least one embodiment.

In certain embodiments, the hollow cores 3202, 3206, 3210, and/or 3214 may have reflective surfaces, and the light guide 1320 may be configured to deliver light via the hollow cores 3202, 3206, 3210, and/or 3214. Additionally or alternatively, light guide 1320 may be configured to deliver light via cross-sectional areas 3204, 3208, 3212, or 3216. For example, in the embodiment illustrated in FIG. 33, light guide 1320 may form a part of a ventilator and may include a hollow core 3302 through which air 3304 may flow while the light 130 is transmitted from light emitter(s) 120 through light guide 1320 to tissue within a patient's oral cavity. Similarly, in the embodiment illustrated in FIG. 34, light guide 1320 may include a hollow core 3402 through which air 3404 may flow while the light 130 is transmitted from light emitter(s) 120 through light guide 1320 to tissue within a patient's oral cavity. In this embodiment, light guide 1320 may additionally include a tube 3406 through which fluids 3408 may be suctioned and/or drained while light guide 1320 is inserted within a patient's mouth (or other body cavity).

Figure 35:
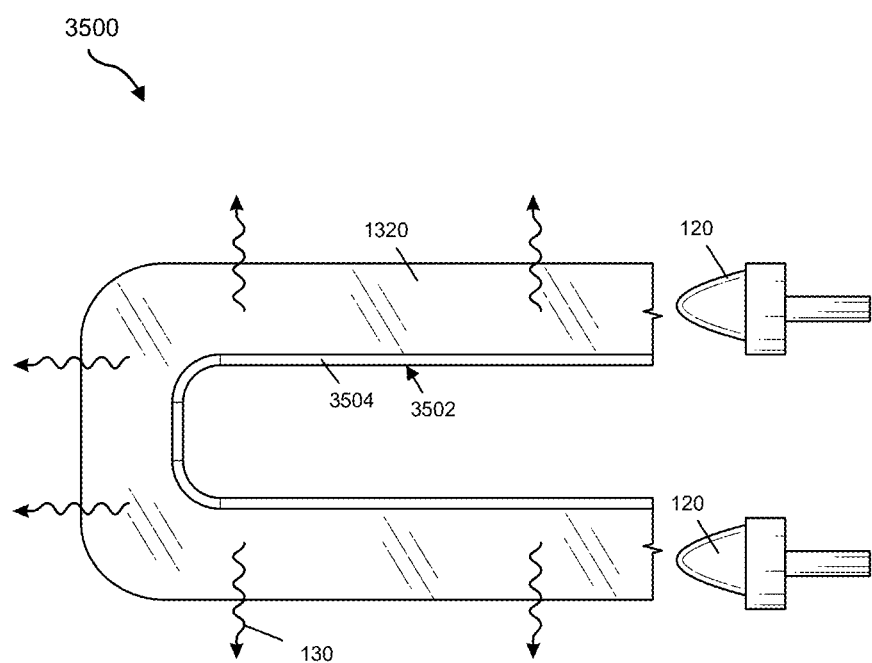
FIG. 35 is a top view of an exemplary u-shaped light guide having an inner reflective surface, according to at least one embodiment.

FIG. 35 is an illustration of an exemplary u-shaped configuration 3500 of the light guide 1320 for directing light towards a user's cheeks when inserted into the user's mouth. As shown, light guide 1320 may include an inner surface 3502 with a reflective coating 3504. Reflective coating 3504 may reflect the light 130 radially from light guide 1320 and/or in a direction transverse to the direction from which the light 130 entered light guide 1320.

Figure 36A:
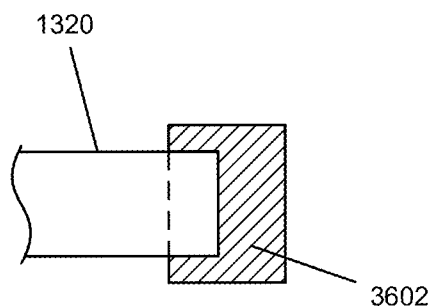
FIG. 36A is a cross-sectional view of an exemplary light guide having a covering cap, according to at least one embodiment.
Figure 36B:
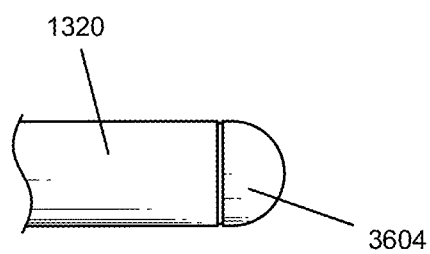
FIG. 36B is a cross-sectional view of an exemplary light guide having a butt dome cap, according to at least one embodiment.
Figure 36C:
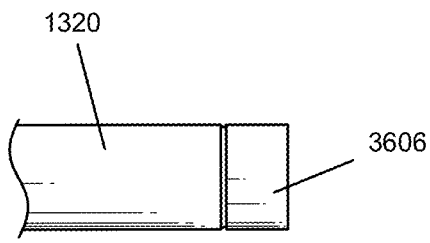
FIG. 36C is a cross-sectional view of an exemplary light guide having a butt flat cap, according to at least one embodiment.
Figure 36D:
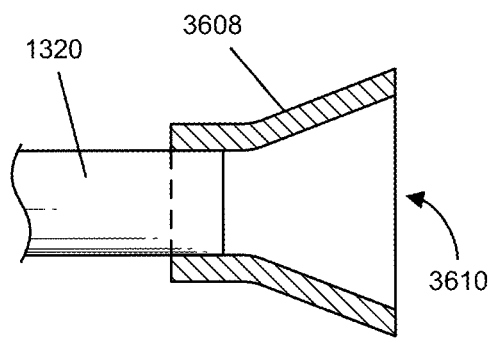
FIG. 36D is a cross-sectional view of an exemplary light guide having a conical shield, according to at least one embodiment.
Figure 36E:
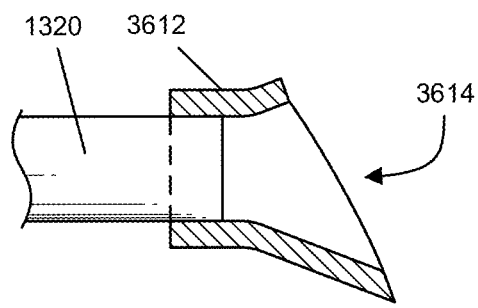
FIG. 36E is a cross-sectional view of an exemplary light guide having an angled conical shield, according to at least one embodiment.
Figure 36F:
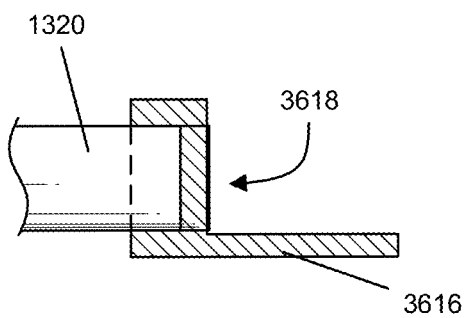
FIG. 36F is a cross-sectional view of an exemplary light guide having a one-sided shield, according to at least one embodiment.
Figure 36G:
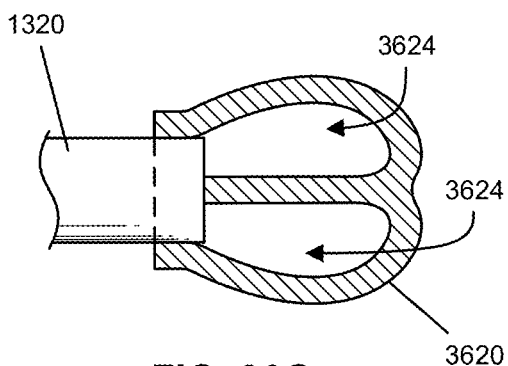
FIG. 36G is a cross-sectional view of an exemplary light guide having a perforated shield, according to at least one embodiment.

In certain embodiments, the light guide 1320 may include a cap or shield for protecting light guide 1320 and/or for protecting tissue proximate to light guide 1320 from over exposure. In the embodiment illustrated in FIG. 36A, light guide 1320 may include a covering cap 3602. In the embodiment illustrated in FIG. 36B, light guide 1320 may include a butt dome cap 3604. In the embodiment illustrated in FIG. 36C, light guide 1320 may include a butt flat cap 3606. In the embodiment illustrated in FIG. 36D, light guide 1320 may include a conical shield 3608 having an opening 3610 through which light may pass. In the embodiment illustrated in FIG. 36E, light guide 1320 may include an angled conical shield 3612 having an opening 3614 through which light may pass. In the embodiment illustrated in FIG. 36F, light guide 1320 may include a one-sided shield 3616 having an opening 3618 through which light may pass. In the embodiment illustrated in FIG. 36G, light guide 1320 may include a perforated shield 3620 having multiple openings 3624 through which light may pass.

Figure 37:
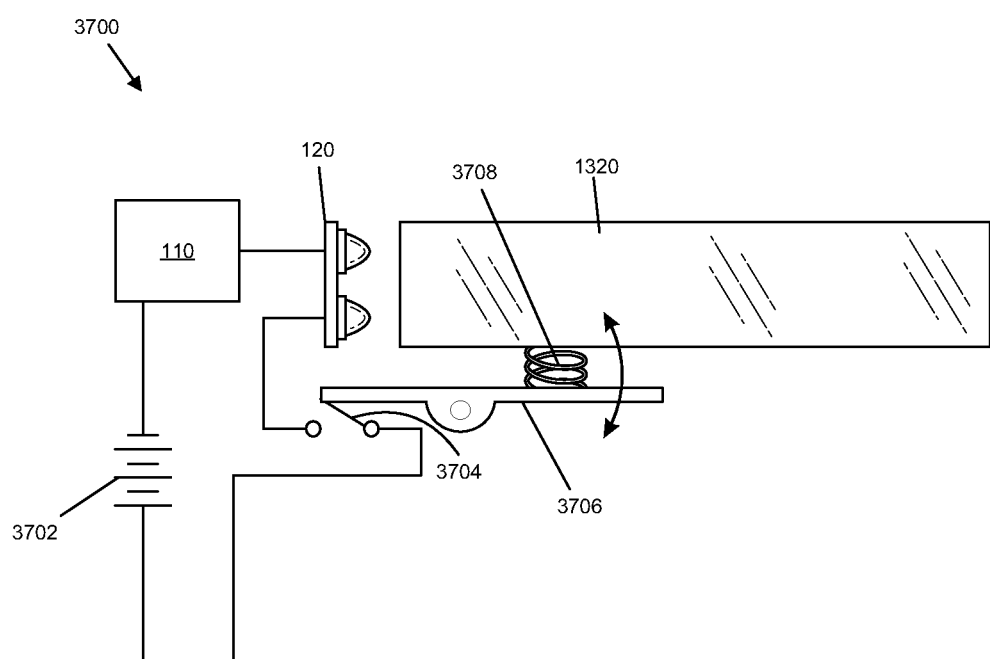
FIG. 37 is a block diagram of an exemplary switching mechanism, according to some embodiments.
Figure 38:
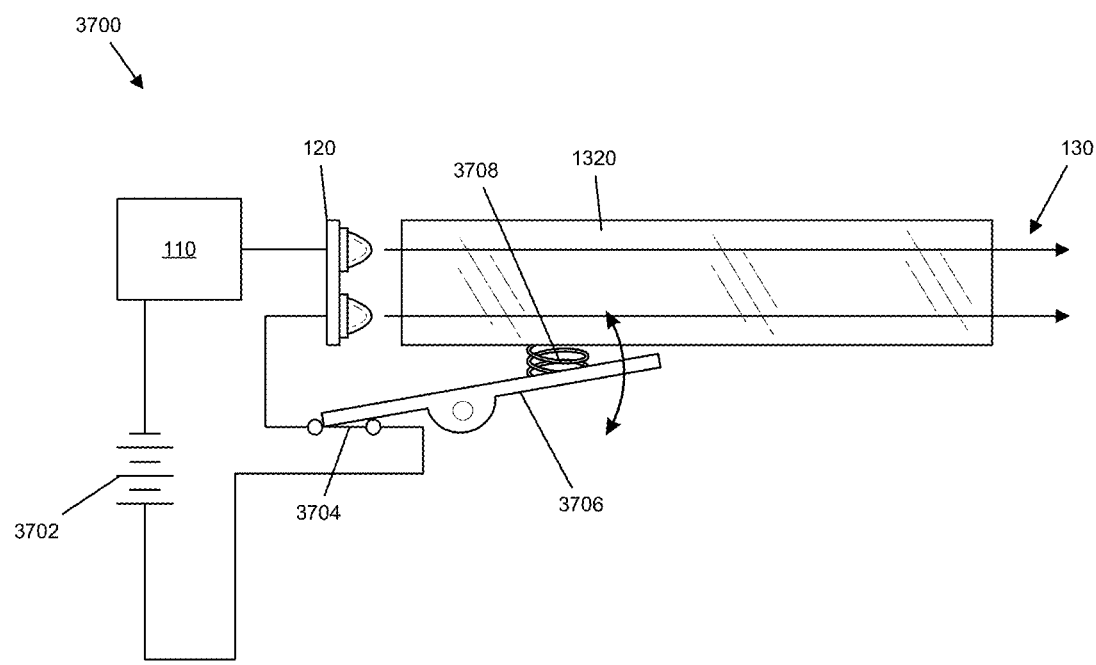
FIG. 38 is another block diagram of the exemplary switching mechanism of FIG. 37, according to some embodiments.

Illumination devices according to the present disclosure may be controlled in a variety of ways, for example illumination devices may be turned on or off via a simple on/off switch or button (e.g., via button 1406 or button 1606 discussed above), although other control mechanisms may also be provided. FIGS. 37 and 38 illustrate an exemplary lever-based switching mechanism 3700 for powering and/or controlling illumination device 102 after illumination device 102 has been inserted into a user's mouth. In this embodiment, illumination device 102 may include a power source 3702 that powers light emitter(s) 120 and/or emitter-driving circuitry 110, a switch 3704 that connects or disconnects power source 3702 from light emitter(s) 120 and/or emitter-driving circuitry 110, and a pivot lever 3706 positioned to close or open switch 3704. A spring 3708 may apply a force on pivot lever 3706 that, when not counteracted, causes pivot lever 3706 to open switch 3704. The user may counteract the force applied by spring 3708 by biting down on pivot lever 3706, thus causing pivot lever 3706 to close switch 3704 and enabling power source 3702 to apply power to light emitter(s) 120 and/or emitter-driving circuitry 110, as shown in FIG. 38.

Figure 39:
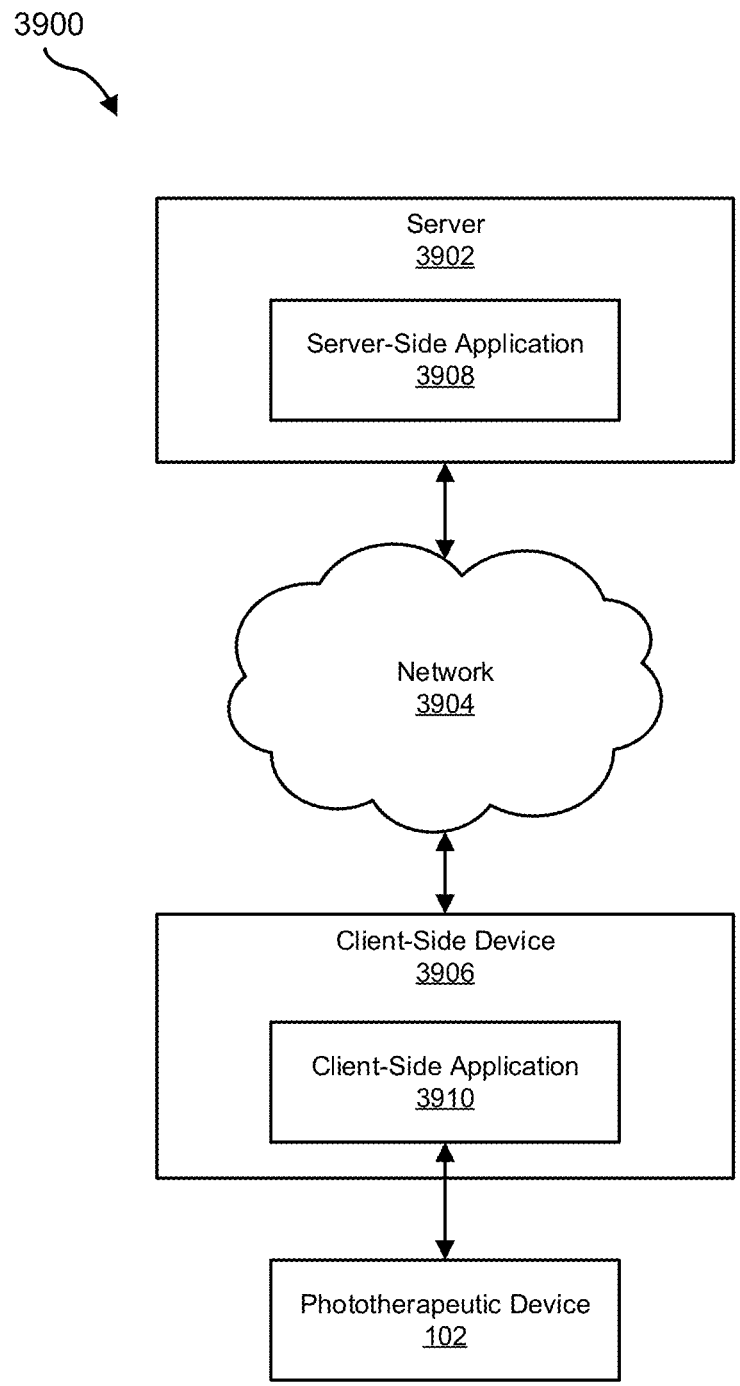
FIG. 39 is a block diagram of an exemplary system for controlling and/or managing an illumination device.

Illumination devices according to the present disclosure may be at least partially controlled or managed by an application executing on another device. In one example, illumination device 102 may be controlled or managed by all or a portion of exemplary system 3900 illustrated in FIG. 39. As shown in FIG. 39, system 3900 may include a server 3902 in communication with a client-side device 3906 via a network 3904. In one example, server 3902 may include a server-side application 3908 for managing, controlling, or communicating with illumination device 102. In at least one embodiment, server-side application 3908 may be configured to collect (e.g., as part of a clinical trial) usage data from multiple illumination devices.

Additionally or alternatively, client-side device 3906 may include a client-side application 3910 for managing, controlling, or communicating with illumination device 102. In at least one embodiment, client-side application 3910 may be configured to collect (e.g., as part of a clinical trial) sensor data from illumination devices and/or user feedback.

Server 3902 and client-side device 3906 generally represent any type or form of computing device capable of reading computer-executable instructions. Examples of server 3902 and client-side device 3906 include, without limitation, laptops, tablets, desktops, servers, cellular phones, Personal Digital Assistants (PDAs), multimedia players, embedded systems, wearable devices (e.g., smart watches, smart glasses, etc.), routers, switches, gaming consoles, combinations of one or more of the same, or any other suitable computing device. In at least one example, client-side device 3906 may represent a user's computing device to which the user has paired illumination device 102.

Network 3904 generally represents any medium or architecture capable of facilitating communication or data transfer. Examples of network 3904 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), or the like. Network 3904 may facilitate communication or data transfer using wireless or wired connections. In one embodiment, network 3904 may facilitate communication between server 3902 and either client-side device 3906 or illumination device 102.

Figure 40:
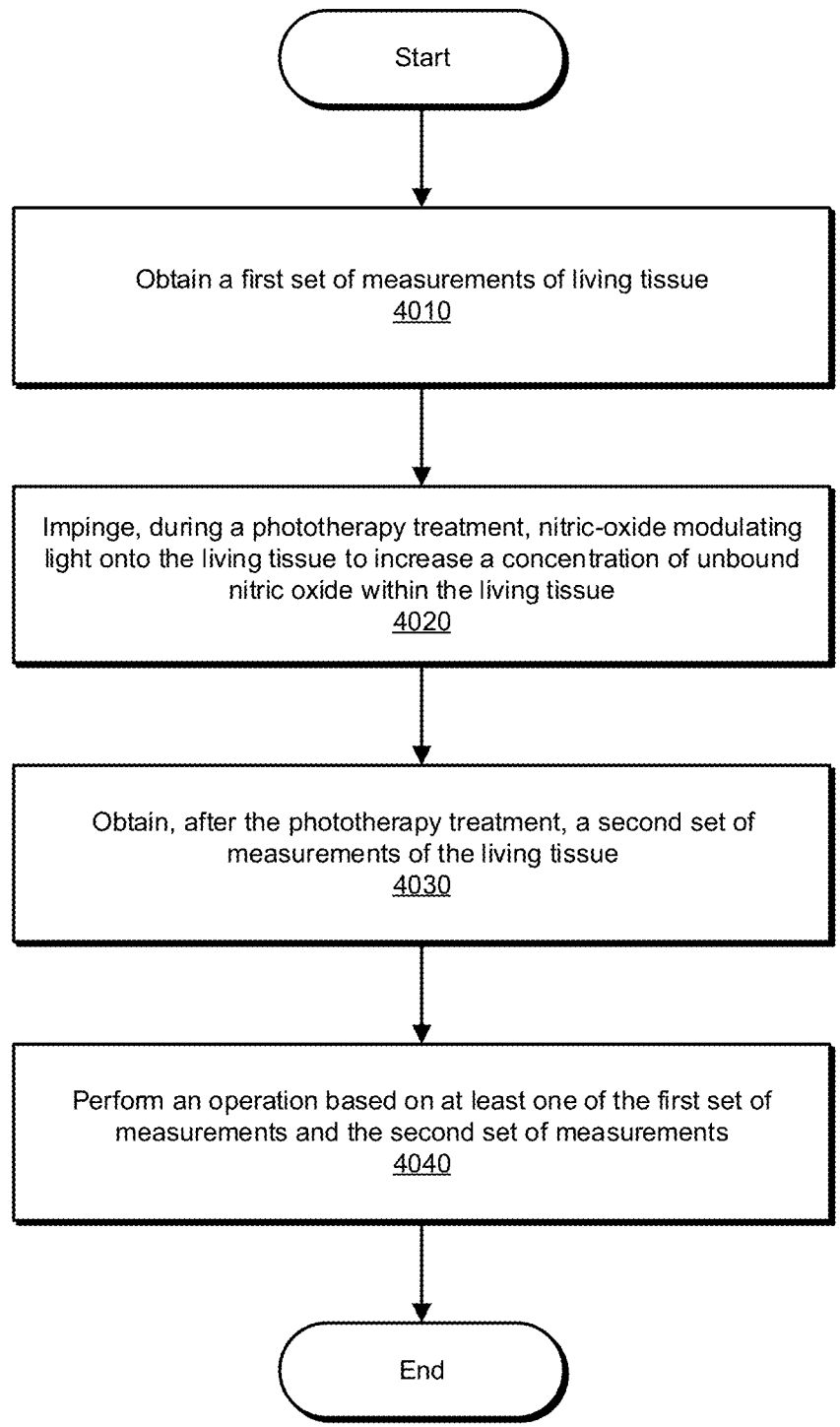
FIG. 40 is a flow diagram of an exemplary method for performing phototherapy operations based on measurements of living tissue, in accordance with some embodiments.

FIG. 40 is a flow diagram of an exemplary computer-implemented method 4000 for performing phototherapy operations based on sensor measurements. The steps shown in FIG. 40 may be performed by any suitable computer-executable code and/or computing system, including the system(s) illustrated in FIG. 39. In one example, each of the steps shown in FIG. 40 may represent an algorithm whose structure includes and/or is represented by multiple sub-steps, examples of which will be provided in greater detail below.

As illustrated in FIG. 40, at step 4010, one or more of the systems described herein may obtain a first set of measurements of living tissue. For example, as illumination device according to any of the previously-described embodiments may obtain a temperature of a target body tissue via a temperature sensor and/or may capture one or more images of the target body tissue via a camera sensor. In at least one embodiment, the illumination device may capture one or more visible-light images, one or more infrared images, one or more ultraviolet images, one or more images measuring light within a predetermined range of wavelengths, and/or one or more images measuring light within two or more different predetermined ranges of wavelengths. In some embodiments, one or more of the systems described herein may use a first set of measurements to establish a baseline measurement from which the safety or efficacy of a subsequent phototherapy treatment may be validated and/or the health of a user may be monitored.

At step 4020, one or more of the systems described herein may impinge, during a phototherapy treatment, the light onto the living tissue. Then at step 4030, one or more of the systems described herein may obtain a second set of measurements of the living tissue. In some embodiments, the second set of measurements may include the same types of measurement included in the first set of measurements. While the exemplary computer-implemented method 4000 is provided in the context of the light, the principles disclosed are applicable to any light that may induce any of previously described biological effects.

At step 4040, one or more of the systems described herein may perform an operation based on at least one of the first set of measurements and the second set of measurements. In one example, client-side application (e.g., 3910 of FIG. 39) may relay the first set of measurements and the second set of measurements from illumination device (e.g., 102 of FIG. 39) to server-side application (e.g., 3908 of FIG. 39) for analysis. In one embodiment, server-side application may use the first set of measurements and/or the second set of measurements to validate the safety or efficacy of impinging the light onto the living tissue based on a comparison of the first set of measurements and the second set of measurements.

In another example, the illumination device 102 and/or client-side application 3910 as illustrated in FIG. 39 may adjust a parameter of a subsequent phototherapy treatment based on a comparison of the first set of measurements and the second set of measurements. For example, the illumination device 102 and/or the client-side application 3910 may adjust a duration of the subsequent phototherapy treatment, an intensity, a peak wavelength, or a range of wavelengths of the light.

Figure 41:
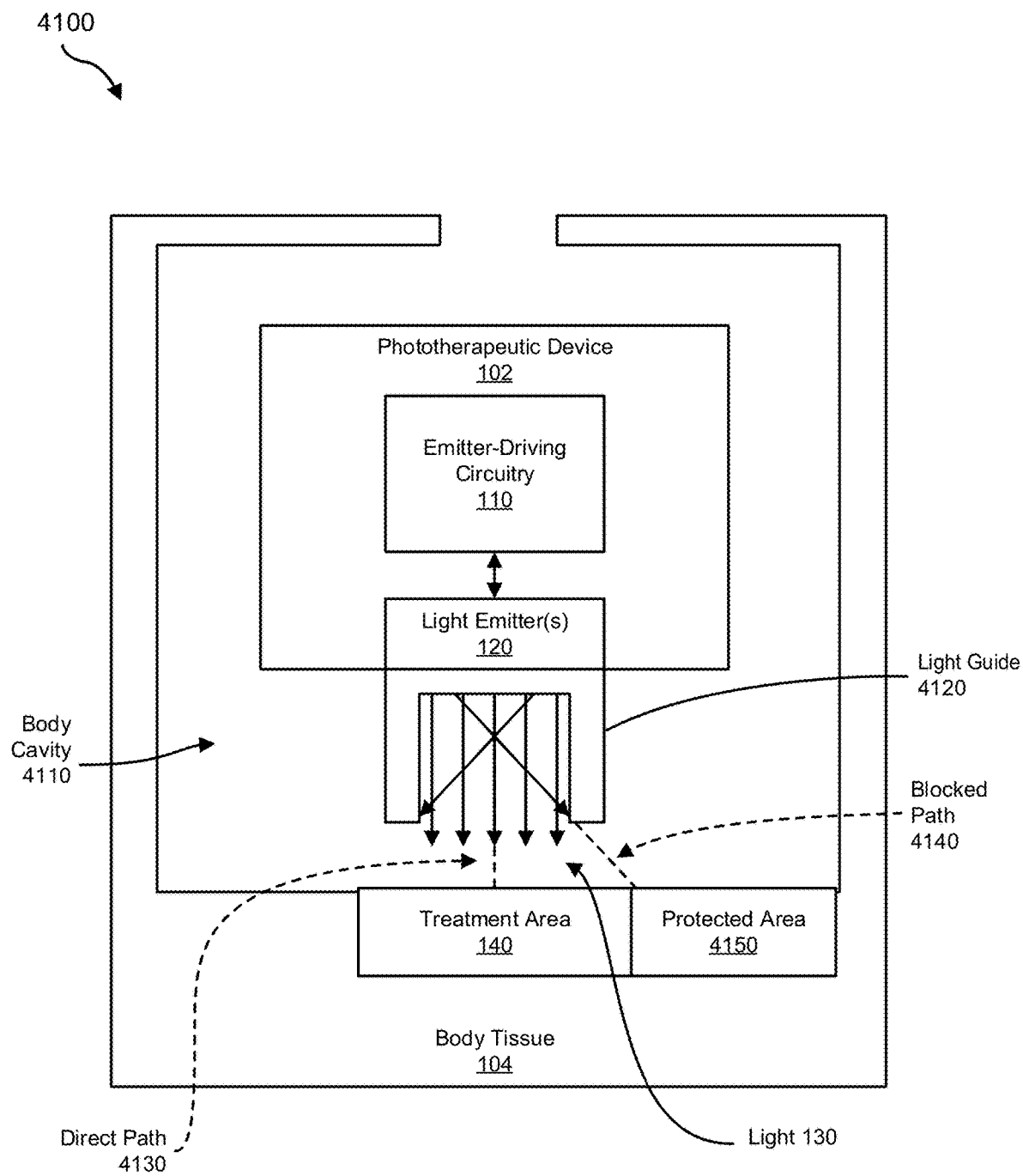
FIG. 41 is another block diagram of the exemplary illumination device of FIG. 1 including a light-blocking light guide, according to some embodiments.
Figure 42:
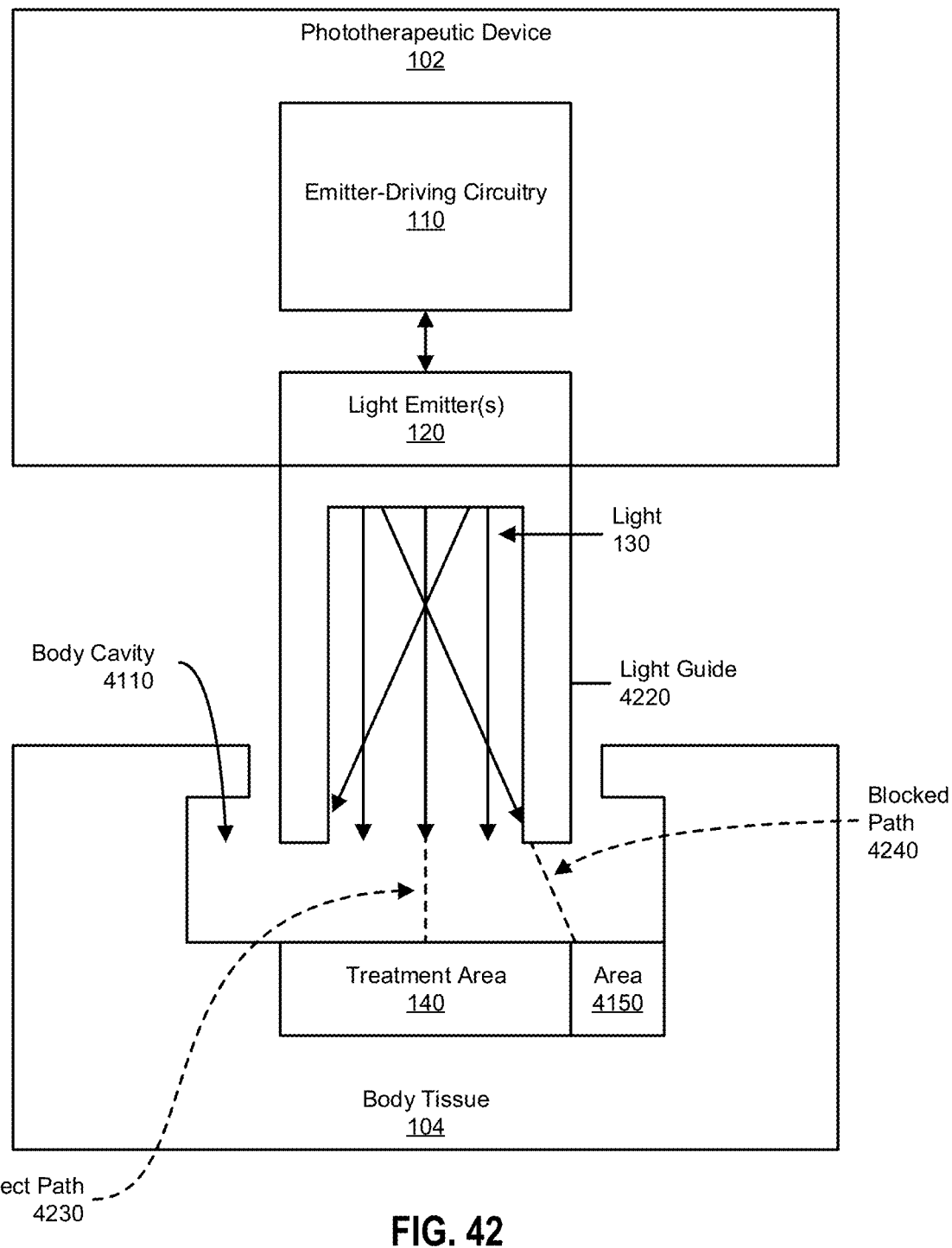
FIG. 42 is another block diagram of the exemplary illumination device of FIG. 1 including a light-blocking light guide, according to some embodiments.

In some embodiments, the illumination device 102 may include one or more light-blocking elements that prevent the light 130 from reaching portions of body tissue 104 not intended to receive the light 130 (e.g., any portions of body tissue 104 not considered treatment area 140, such as protected area 4150 in FIGS. 41 and 42). FIG. 41 is an illustration of an exemplary configuration 4100 of illumination device 102 having a light-blocking light guide 4120. In this configuration, illumination device 102 may be sized and shaped to fit partially or fully within a body cavity 4110. In this embodiment, light emitter(s) 120 may be operable to emit the light 130 inside of body cavity 4110 along one or more paths (e.g., paths 4130 and 4140), and light-blocking light guide 4120 may be shaped to (1) allow the light 130 to travel along direct path 4130 to treatment area 140 but (2) prevent the light 130 from travelling along a blocked path 4140 to protected area 4150. FIG. 42 illustrates an exemplary configuration 4200 of illumination device 102 having a light-blocking light guide 4220. In this embodiment, light emitter(s) 120 may be operable to the light 130 outside of a body cavity 4210 along multiple paths (e.g., paths 4230 and 4240), and light-blocking light guide 4220 may be shaped to (1) allow the light 130 to travel along direct path 4230 to treatment area 140 within body cavity 4210 but (2) prevent the light 130 from traveling along blocked path 4240 to protected area 4150.

Light-blocking light guides 4120 and/or 4220 may include any light blocking component operable to prevent light from reaching certain portions of a user's body by blocking, reflecting, or absorbing a substantial amount of the light. In some examples, light-blocking light guides 4120 and/or 4220 may include one or more hollow or transparent regions that allow the light to be transmitted freely through the regions and/or one or more solid, reflective, or opaque regions that prevent the light from being freely transmitted through the region. Examples of light-blocking light guides 4120 and/or 4220 include, without limitation, hollow cylinders, tubes, pipes, shrouds, funnels, snoots, and collimators. In some examples, light-blocking light guides 4120 and/or 4220 may perform additional functions, such as expanding a body cavity or spreading or displacing tissue. For example, the mouthpieces and/or light guides illustrated in connection with FIGS. 43-53 may include one or more light blocking regions (e.g., to prevent portions of a user's cheeks or tongue from being exposed to the light.

Light-blocking light guide 4220 may be suitably shaped based on the body cavity it will be inserted into. For example, light-blocking light guide 4220 may be shaped to conform to or fit within at least one of a nasal cavity, an ear cavity, a throat cavity, a laryngeal cavity, a pharyngeal cavity, a tracheal cavity, an esophageal cavity, a urethral cavity, a vaginal cavity, or a cervical cavity. In one embodiment, body cavity 4110 may be an oral cavity, and light-blocking light guide 4220 may be shaped to fit through a mouth and direct the light 130 to living tissue within the oral cavity.

FIGS. 43-52 illustrate various views of an exemplary handheld configuration 4300 of illumination device 102 for delivering light (e.g., nitric-oxide modulating light and/or light to induce any of the previously described biological effects) to living tissue within or near a user's oral cavity, including the oropharynx. As shown, illumination device 102 may include an outer housing having (1) a housing 4302 for containing and protecting the light emitter(s) 120, (2) a housing 4304 for containing and protecting at least light emitter-driving circuitry 110, a button 4306 for energizing illumination device 102 and/or light emitter(s) 120, and/or a carrier 4308, and (3) a housing 4310 for containing and protecting at least a battery 4312. In some embodiments, housing 4304 may be encased by a sleeve or overmolding 4314 having a tactile element 4316 for engaging button 4306 and a port 4318 for charging illumination device 102 and/or accessing data stored to illumination device 102. In the exploded view FIG. 46, light emitter(s) 120 may be affixed to a printed circuit board 4320, which may be secured to housing 4302 by screws 4322 (or any other suitable fasteners). Additionally, illumination device 102 may include a lens 4324 for light 130 into and/or near a user's oral cavity. In some embodiments, a retaining ring 4326 may secure lens 4324 to housing 4302. In this example, a lens washer 4328 may be positioned between retaining ring 4326 and lens 4324, and a lens gasket 4330 may be positioned between lens 4324 and housing 4302. As shown, illumination device 102 may include a light guide 4332 and a mouthpiece 4334 suitably sized and shaped for insertion into a user's oral cavity.

As shown in FIGS. 48A-48D, mouthpiece 4334 may include an outer surface 4802 for interfacing or engaging with the surfaces of a user's oral cavity (e.g., the user's lips and cheeks), a biting surface 4804 for interfacing with the user's teeth, and protrusions 4806 for engaging the backs of the user's teeth. In some embodiments, outer surface 4802 may apply an outward force on a user's lips and/or cheeks in order to expand the user's oral cavity during a phototherapy treatment. In some embodiments, biting surface 4804 and/or protrusions 4806 may enable a user to secure illumination device 102 in the user's mouth by biting against biting surface 4804. In some embodiments, mouthpiece 4334 may help index illumination device 102 at an appropriate depth within the user's oral cavity. In one embodiment, mouthpiece 4334 may index illumination device 102 at a depth within a user's oral cavity at which an area of tissue exposed to the light 130 is equal to about 25 cm2. In one embodiment, mouthpiece 4334 may index light guide 1320 at a depth within a user's oral cavity at which an irradiance of the light onto tissue is less than about 160 mW/cm2. In this regard, the mouthpiece 4334 may be referred to as a light guide positioner that is configured to position and hold the light guide 4332 at least partially in or near the oral cavity to ensure that light emitting from the light emitter(s) 120 exits the light guide 4332 in a suitable location for irradiating a target tissue, e.g., the oropharynx. In at least some embodiments, mouthpiece 4334 may function to block the light from reaching portions of a user's oral cavity and may be suitably shaped and sized for that purpose. In some embodiments, mouthpiece 4334 may be removable from illumination device 102.

As shown in FIGS. 49A-49D, light guide 4332 may include a tongue depressor 4900 for depressing a user's tongue when inserted into the user's mouth. In some embodiments, tongue depressor 4900 may displace the user's tongue to expose the back of the user's throat, the oropharynx (or another treatment area) to the light emitted by light emitter(s) 120. Tongue depressor 4900 may have any suitable size and shape and may function to block the light from reaching a user's tongue. In some embodiments, light guide 4332 may include cylindrical walls 4902 defining a light transmissive pathway 4904 through which the light may pass. In at least some embodiments, cylindrical walls 4902 may function to block the light from reaching portions of a user's oral cavity and may be suitably shaped and sized for that purpose. In some embodiments, light guide 4332 may be removable. In the embodiments illustrated in FIGS. 49A-49D, light guide 4332 may include securing tabs 4906 shaped to interface with notches 5102 and 5104 of housing 4302. In the alternative embodiment illustrated in FIG. 52, light guide 4332 may include securing notches (e.g., notch 5204) shaped to securely engage corresponding protrusions of housing 4302 (e.g., protrusion 5202).

In some embodiments, the mouthpiece 4334, which may also be referred to as a light guide positioner, and the light guide 4332 may be parts of a single inseparable structure. Alternatively, the mouthpiece 4334 and the light guide 4332 may be separable structures that are securely joined together to form removable assembly. In either case, the combination of the mouthpiece 4334 (e.g., the light guide positioner) and the light guide 4332 may form a combined assembly that may be removably attached to the illumination device 102. FIGS. 50A-50D illustrate an exemplary removable assembly 5000 of mouthpiece 4334 and light guide 4332. In this embodiment, light guide 4332 may include securing protrusions 4908 shaped to interface with corresponding notches of mouthpiece 4334 to facilitate tool-less separation of the light guide 4332 from the mouthpiece 4334.

Figure 43:
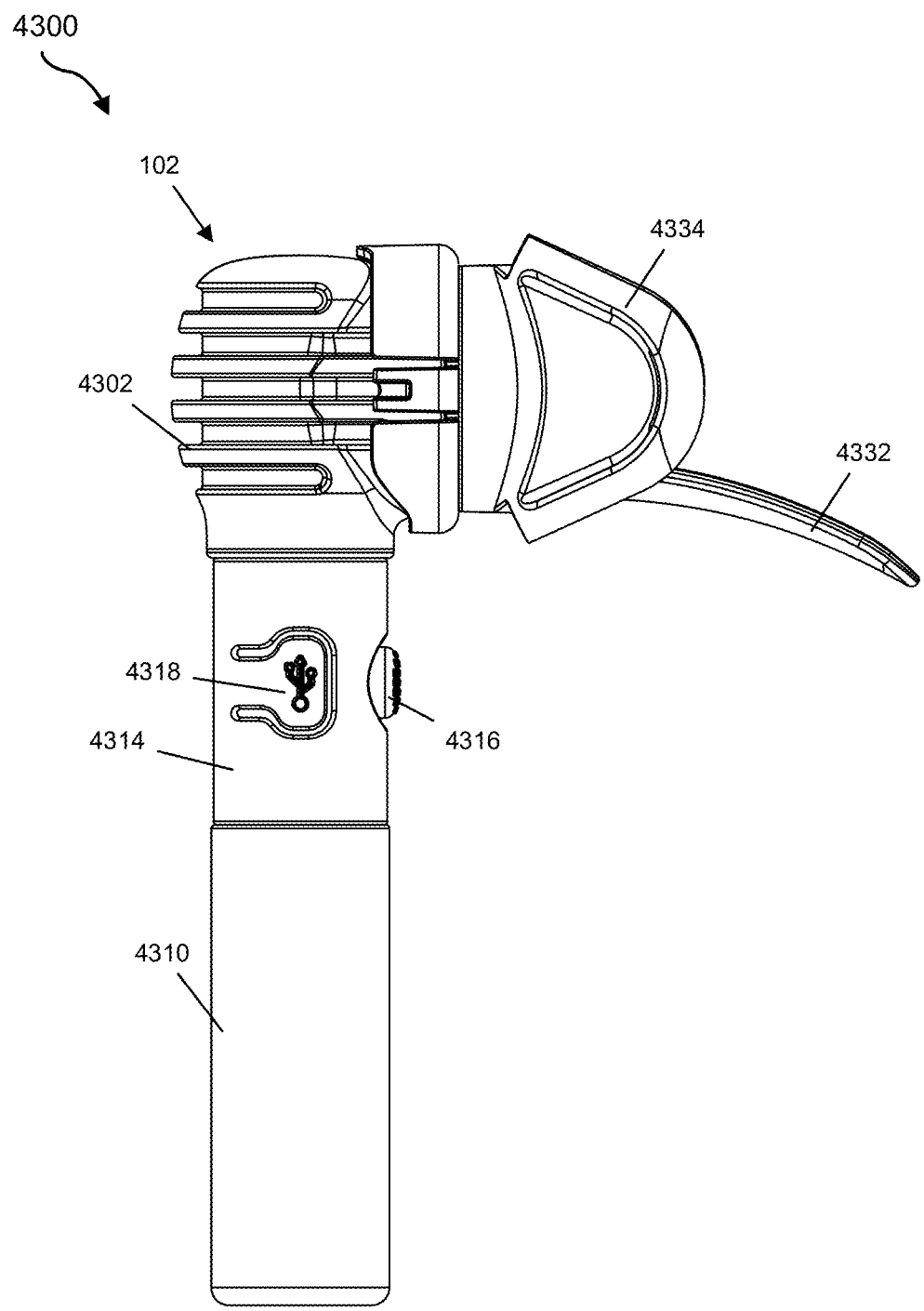
FIG. 43 is a side view of an exemplary handheld configuration of the exemplary illumination device of FIG. 1, according to some embodiments.
Figure 44:
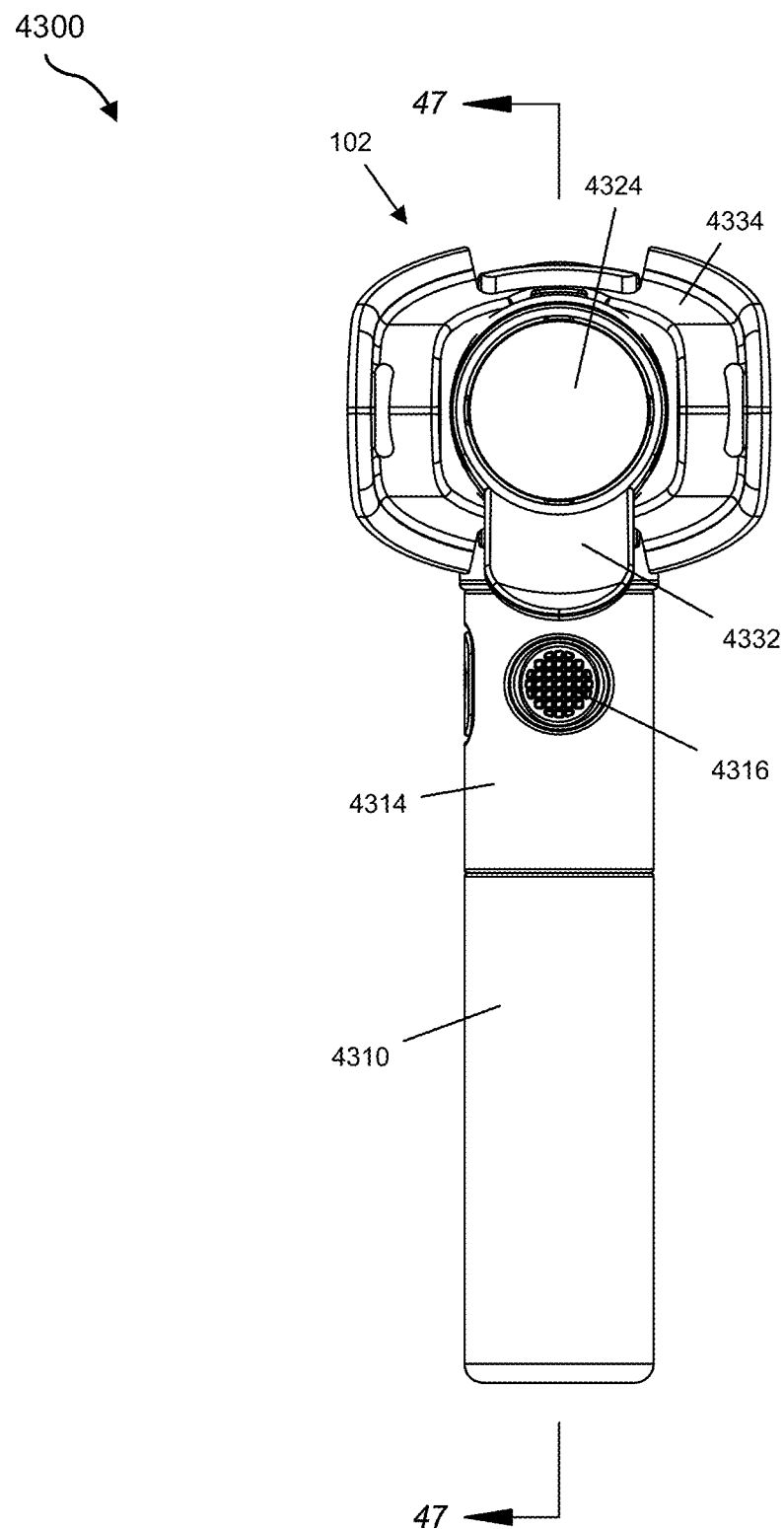
FIG. 44 is a front view of the exemplary handheld configuration of FIG. 43, according to some embodiments.
Figure 45:
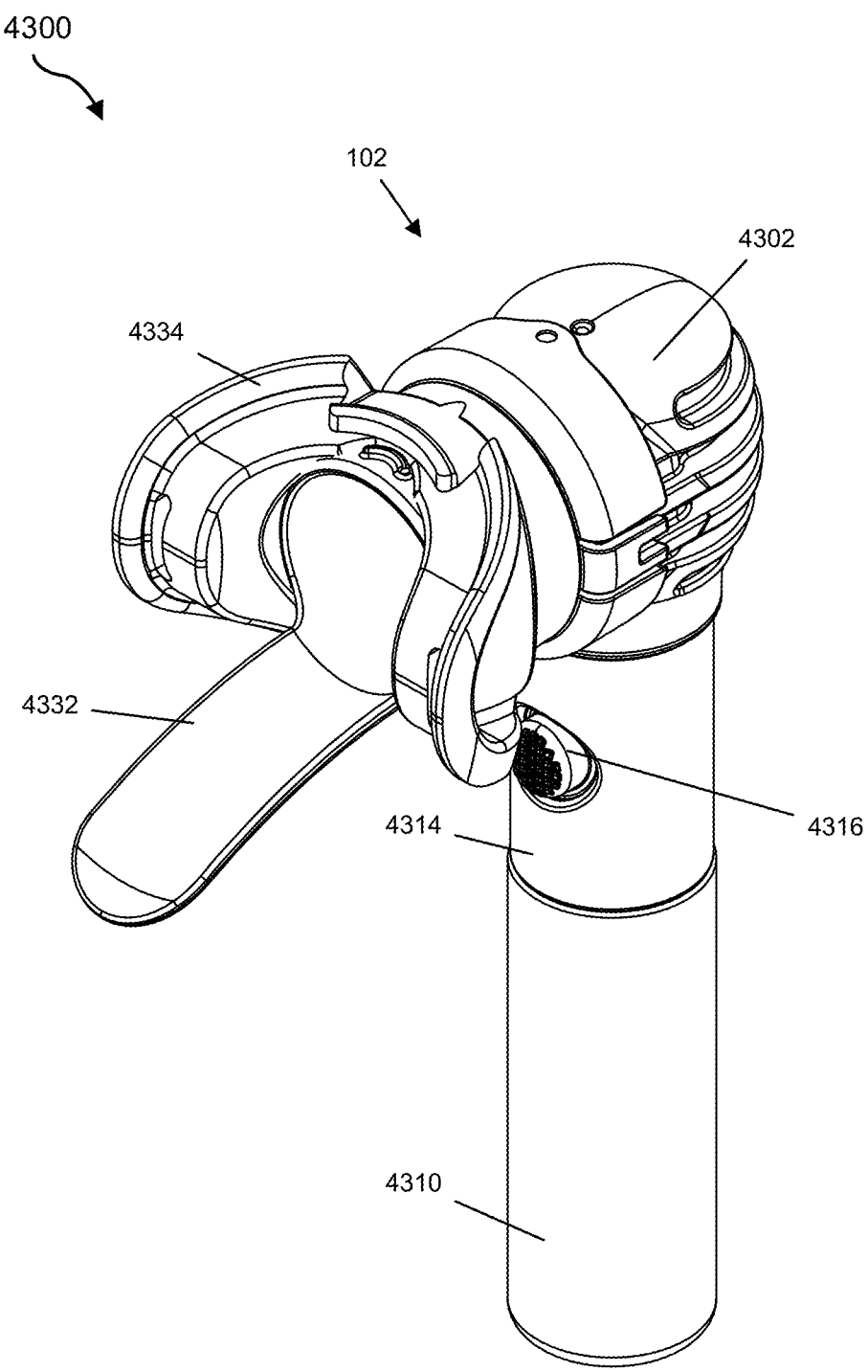
FIG. 45 is a perspective view of the exemplary handheld configuration of FIG. 43, according to some embodiments.
Figure 46:
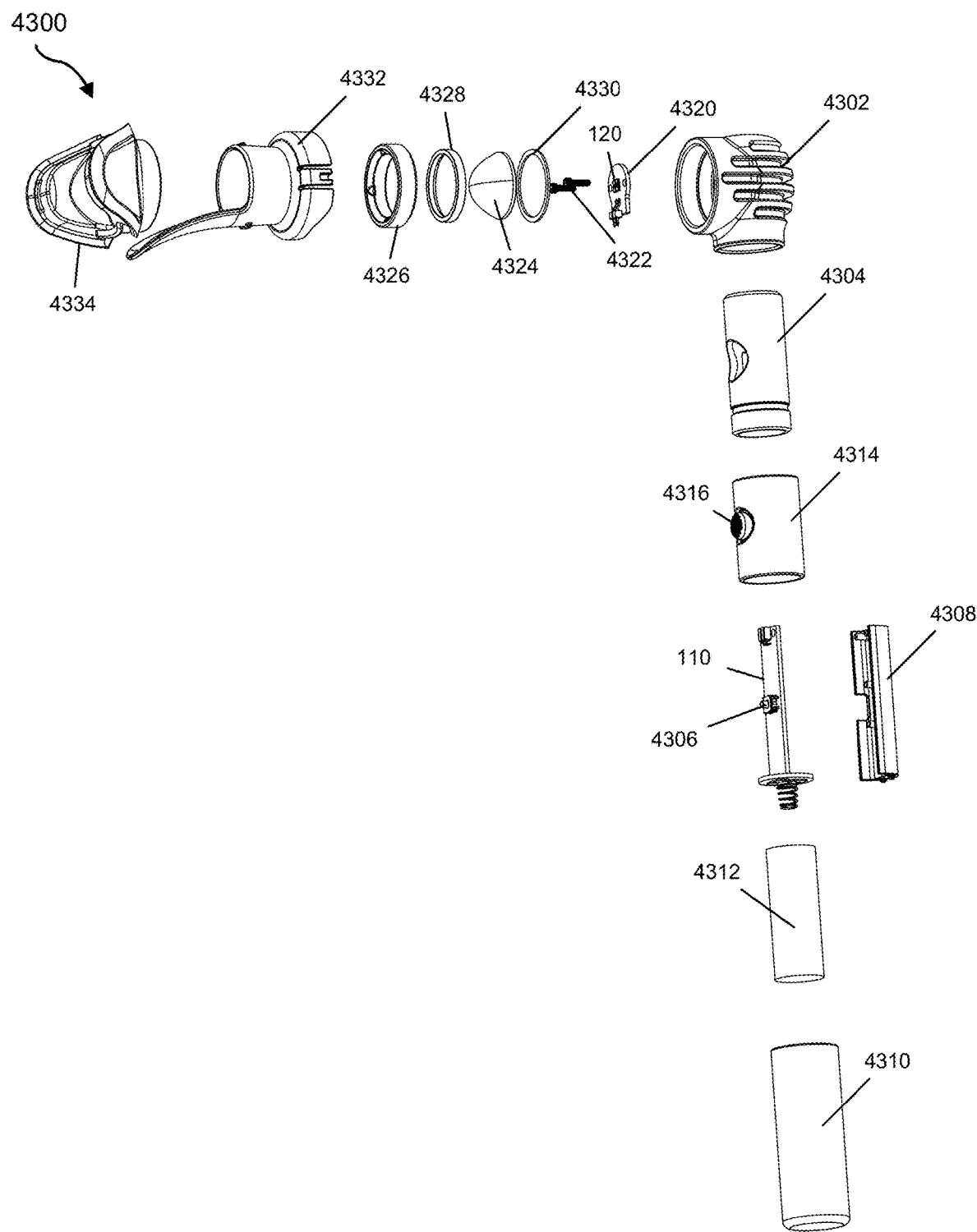
FIG. 46 is an exploded view of the exemplary handheld configuration of FIG. 43, according to some embodiments.
Figure 47:
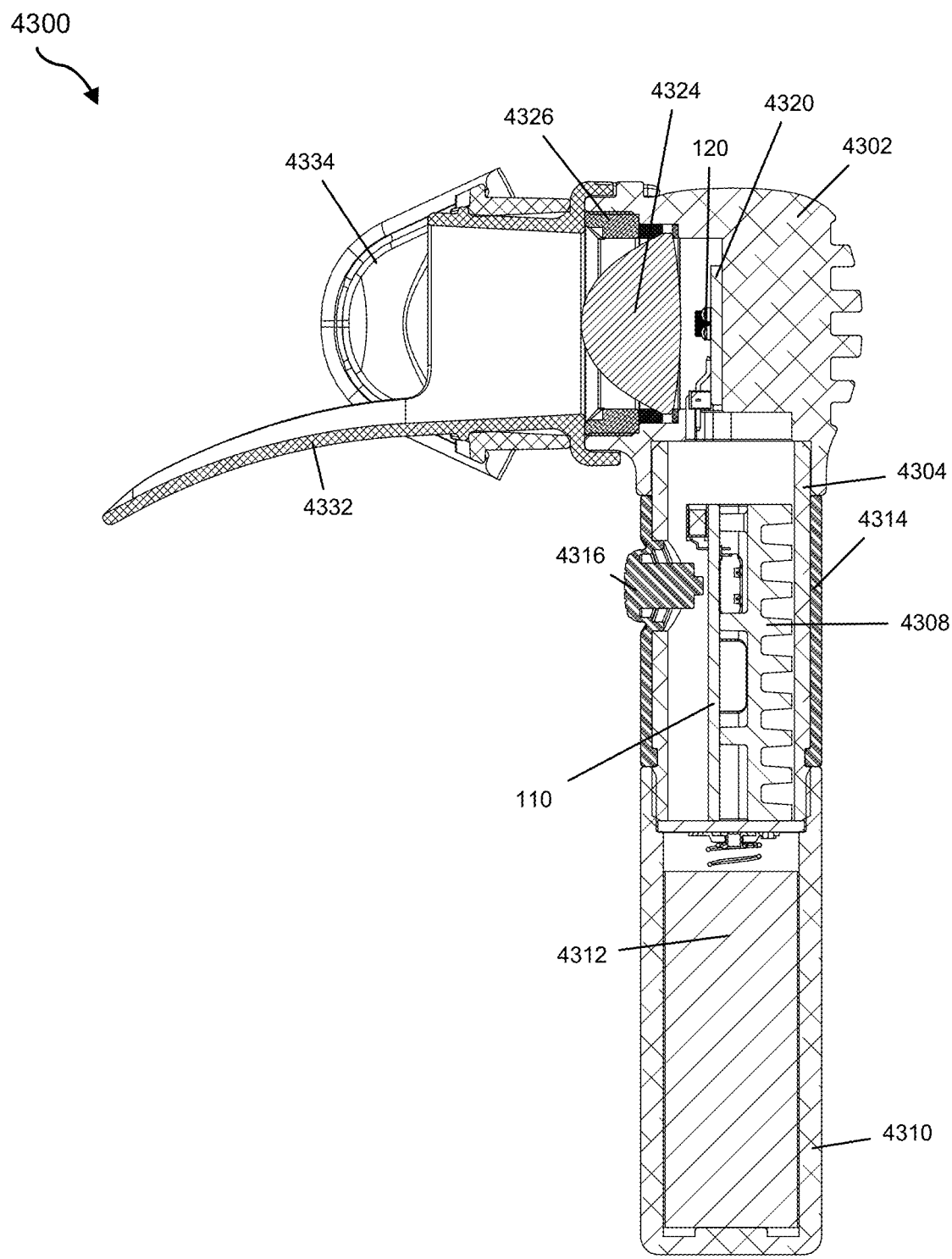
FIG. 47 is a cross-sectional view of the exemplary handheld configuration of FIG. 43, according to some embodiments.
Figure 48A:
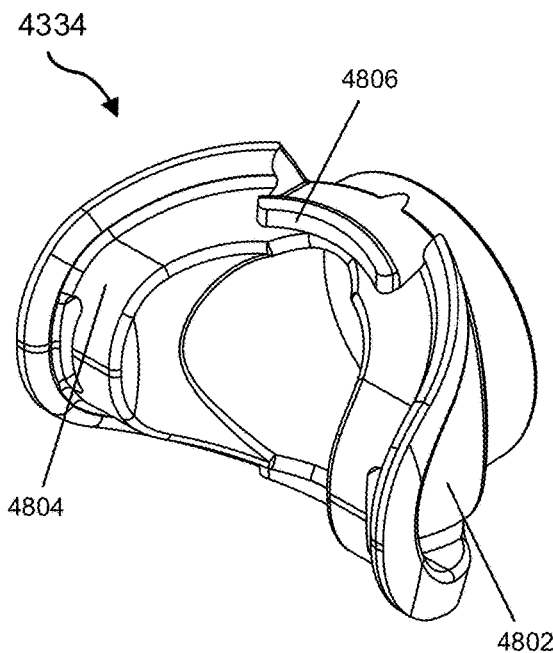
FIG. 48A is a perspective view of the exemplary mouthpiece of FIG. 43, according to some embodiments.
Figure 48B:
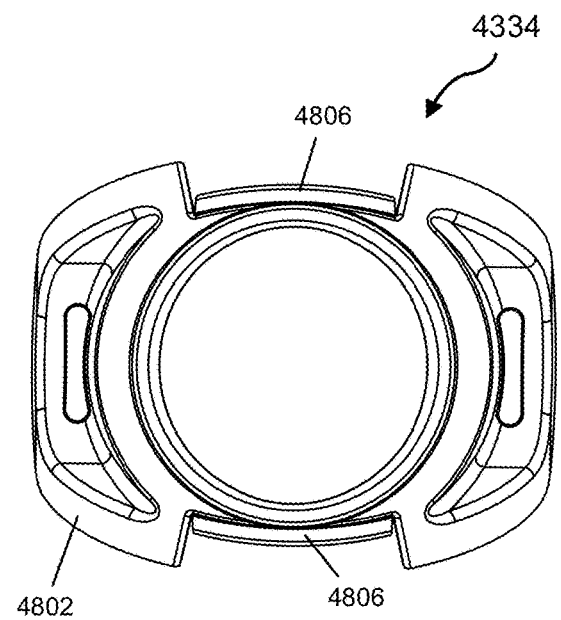
FIG. 48B is a rear view of the exemplary mouthpiece of FIG. 43, according to some embodiments.
Figure 48C:
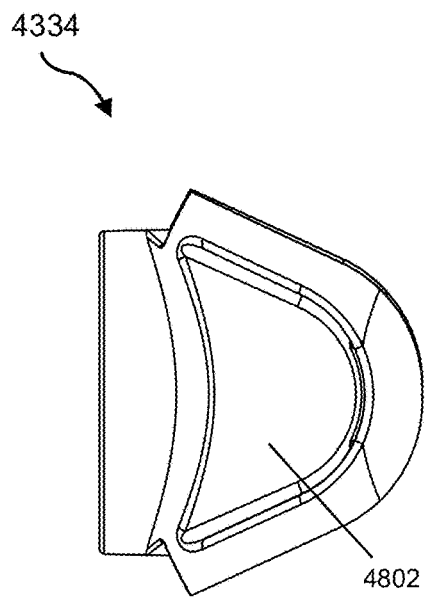
FIG. 48C is a side view of the exemplary mouthpiece of FIG. 43, according to some embodiments.
Figure 48D:
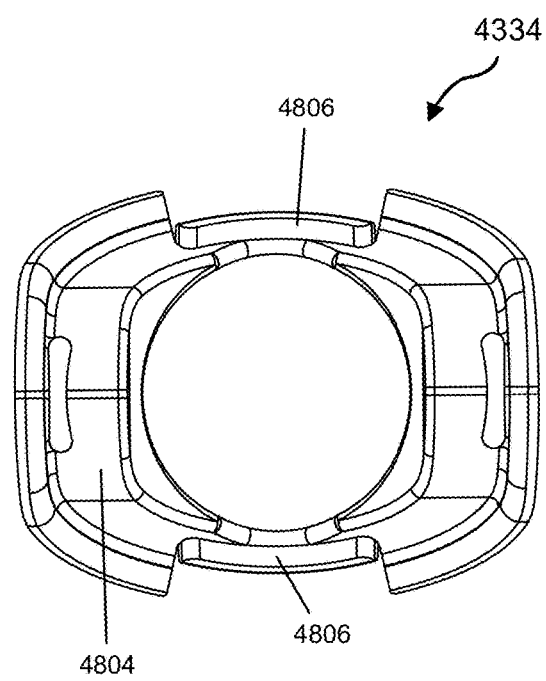
FIG. 48D is a front view of the exemplary mouthpiece of FIG. 43, according to some embodiments.
Figure 50A:
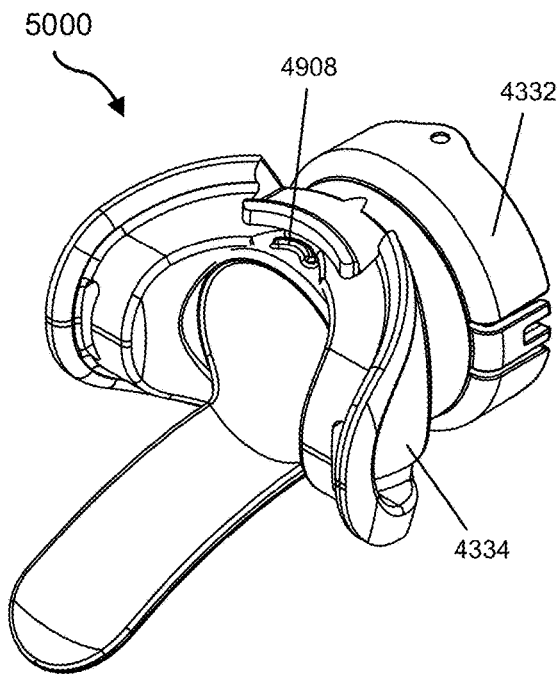
FIG. 50A is a perspective view of an exemplary removable assembly including the exemplary mouthpiece and light guide of FIG. 43, according to some embodiments.
Figure 50B:
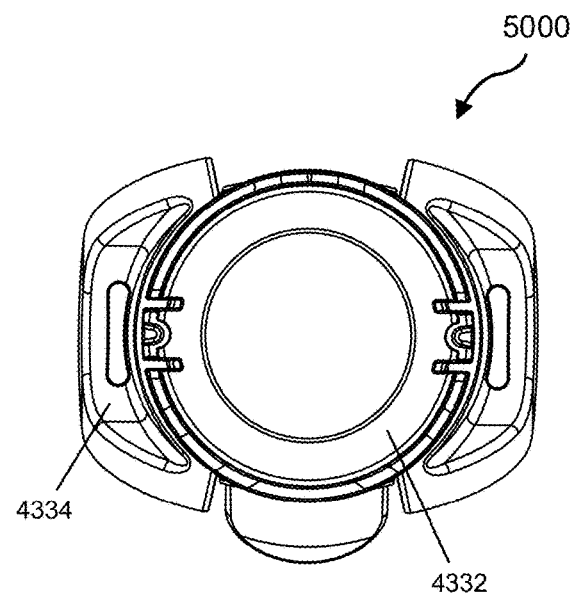
FIG. 50B is a rear view of the exemplary removable assembly of FIG. 50A, according to some embodiments.
Figure 50C:
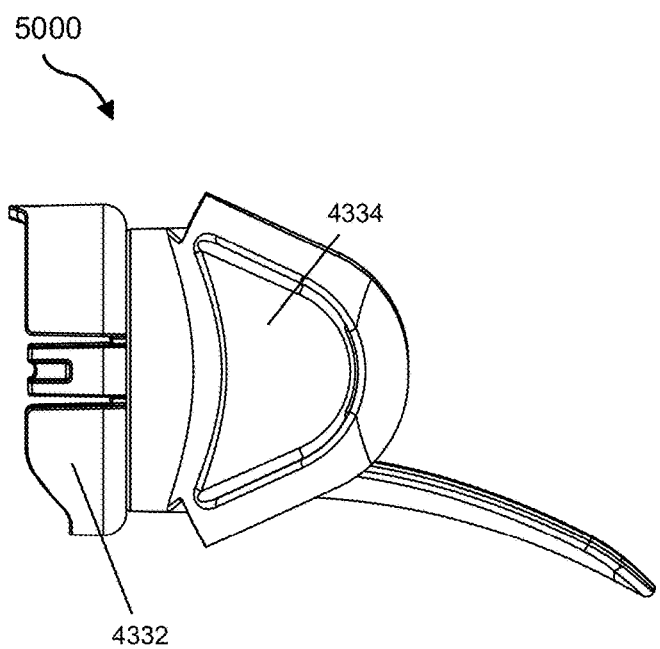
FIG. 50C is a side view of the exemplary removable assembly of FIG. 50A, according to some embodiments.
Figure 50D:
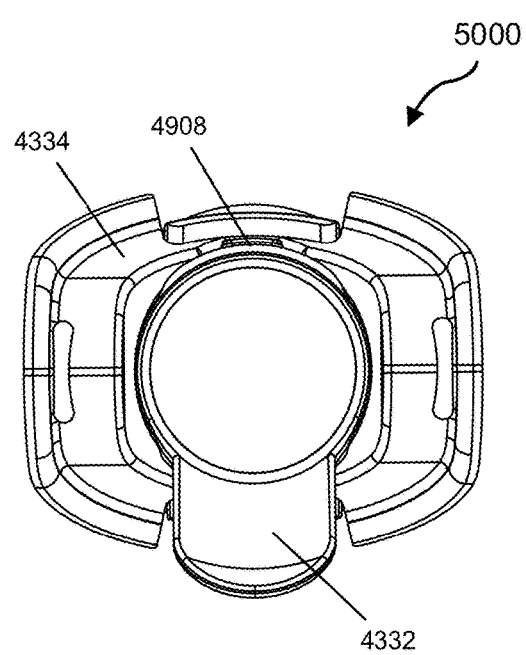
FIG. 50D is a front view of the exemplary removable assembly of FIG. 50A, according to some embodiments.
Figure 51A:
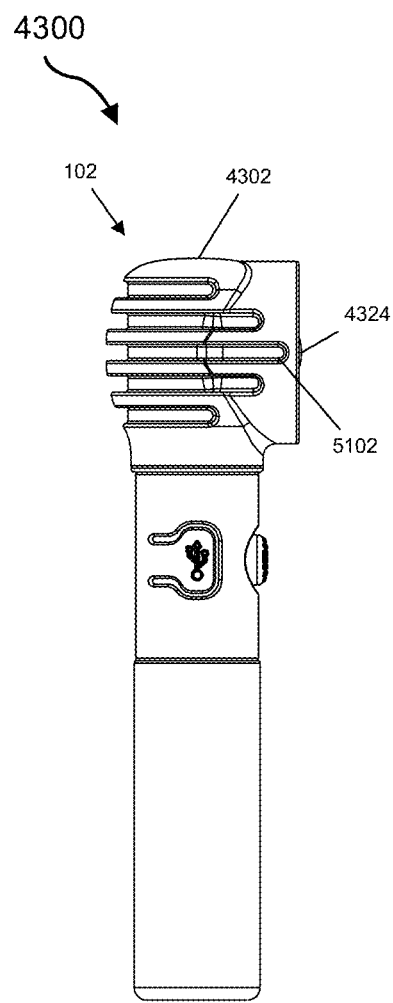
FIG. 51A is a side view of an exemplary handheld configuration of the exemplary illumination device of FIG. 43 without the removable assembly of FIGS. 50A-50D, according to some embodiments.
Figure 51B:
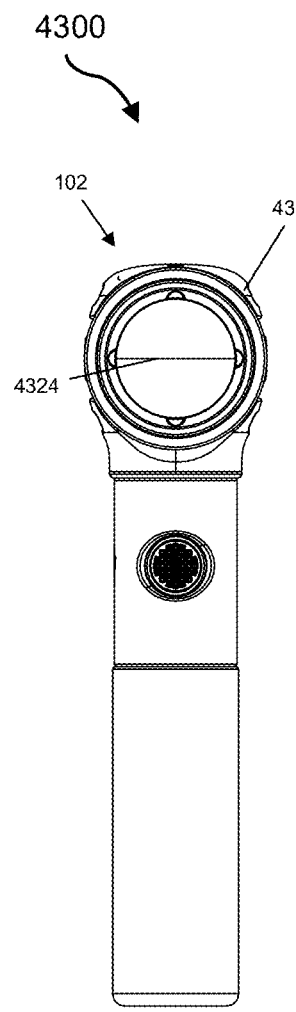
FIG. 51B is a front view of the exemplary handheld configuration of FIG. 43 without the removable assembly of FIGS. 50A-50D, according to some embodiments.
Figure 51C:
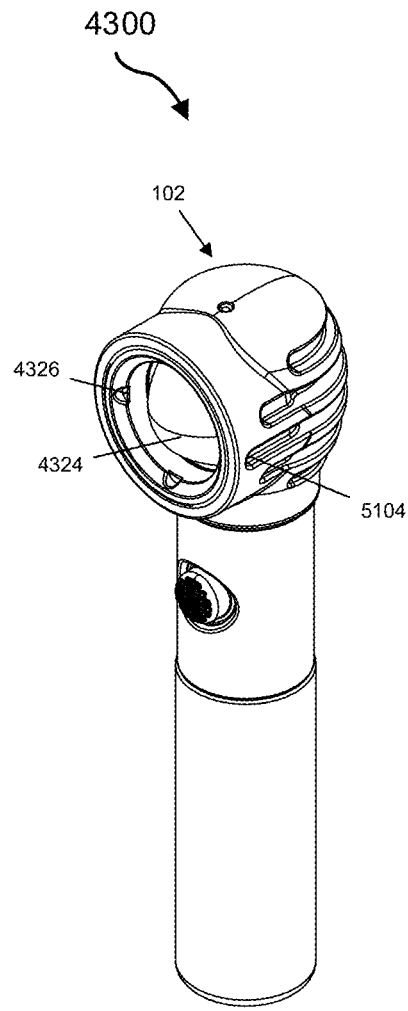
FIG. 51C is a perspective view of the exemplary handheld configuration of FIG. 43 without the removable assembly of FIGS. 50A-50D, according to some embodiments.

FIGS. 51A, 51B, and 51C are respective side, front, and perspective views of the illumination device 102 of FIG. 43 without the removable assembly 5000 of the mouthpiece 4334 and the light guide 4332 of FIGS. 50A-50D, according to some embodiments. In certain embodiments, the securing tabs 4906 as illustrated in FIGS. 49A-49D may be configured to snap fit or otherwise attach to the notches 5102 and 5104 of housing 4302. In this regard, the mouthpiece 4334 and the light guide 4332 may be easily removed from the illumination device 102 for cleaning and or replacement.

Figure 52:
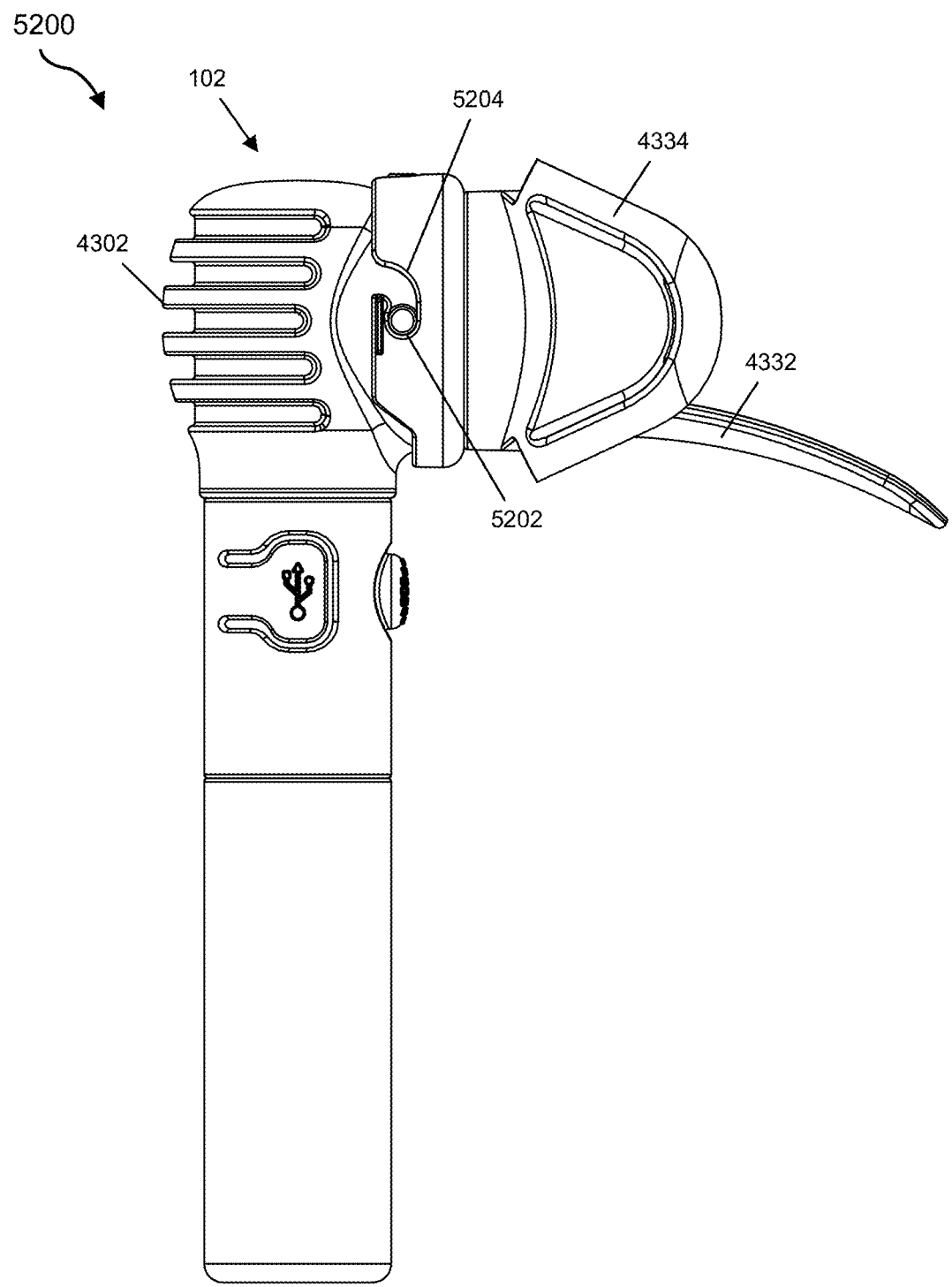

FIG. 52 is a side view of another exemplary configuration 5200 of the exemplary illumination device 102 for embodiments where the mouthpiece 4334 and the light guide 4332 may be easily removed from the illumination device 102. As illustrated, light guide 4332 may include securing notches (e.g., notch 5204) shaped to securely engage corresponding protrusions of housing 4302 (e.g., protrusion 5202).

Figure 53:
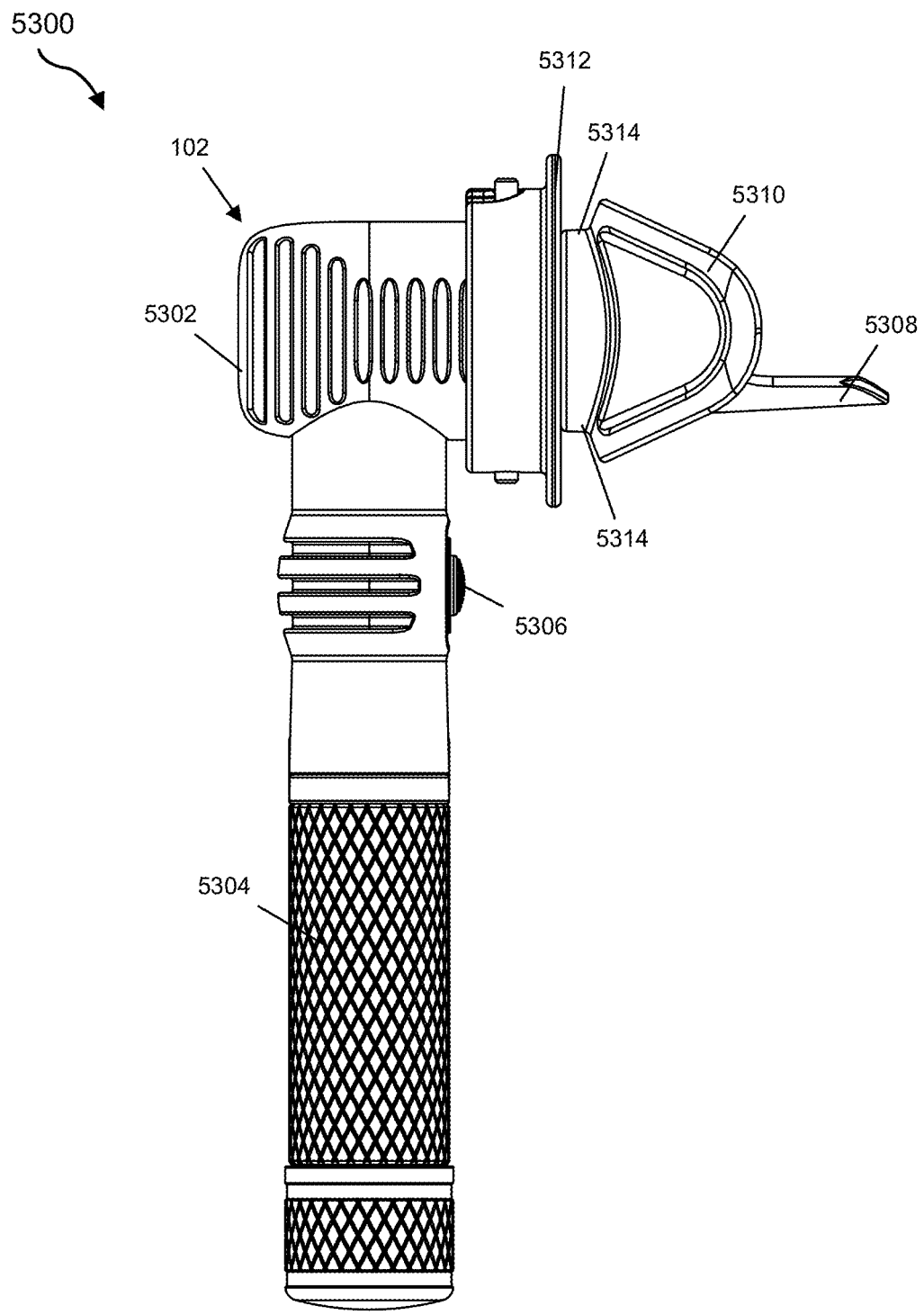

FIG. 53 illustrates an exemplary handheld configuration 5300 of illumination device 102 for delivering the light to living tissue within or near a user's oral cavity, including the oropharynx. As illustrated, the illumination device 102 may include an outer housing 5302 for containing and protecting one or more of the light emitter(s), the emitter-driving circuitry 110, and/or the one or more sensors as previously described. In some embodiments, the outer housing 5302 may include a hand grip 5304, and a button 5306 for energizing the illumination device 102 and/or the light emitter(s). In some embodiments, the illumination device 102 may include a mouthpiece 5310 for interfacing with a user's mouth, cheeks, and/or teeth and a tongue depressor 5308 for displacing the user's tongue. In some examples, illumination device 102 may include a positioning plate 5312 with which a user of illumination device 102 may gauge proper insertion depth of illumination device 102 and/or upper and lower bite guards 5314 for enabling a user to secure illumination device 102 by biting against bite guards 5314. In some embodiments, positioning plate 5312 may, when touching an outer surface of a user's mouth, help index illumination device 102 at an appropriate depth within the user's oral cavity. In one embodiment, positioning plate 5312 may index illumination device 102 at a depth within a user's oral cavity at which an area of tissue exposed to the light is equal to about 25 cm². In one embodiment, positioning plate 5312 may index light guide 1320 at a depth within a user's oral cavity at which an irradiance of the light onto tissue is less than about 160 mW/cm2.

While not illustrated in the drawings, it is noted that suitably sized and shaped mouthpieces and/or light guides (similar to the mouthpieces and light guides described in connection with FIGS. 43-53) may also be integrated into the example configurations of illumination device 102 illustrated in FIGS. 14-21. Moreover, the mouthpieces and light guides described in connection with FIGS. 43-53 may include some or all of the features of light guide 1320.

Figure 54A:
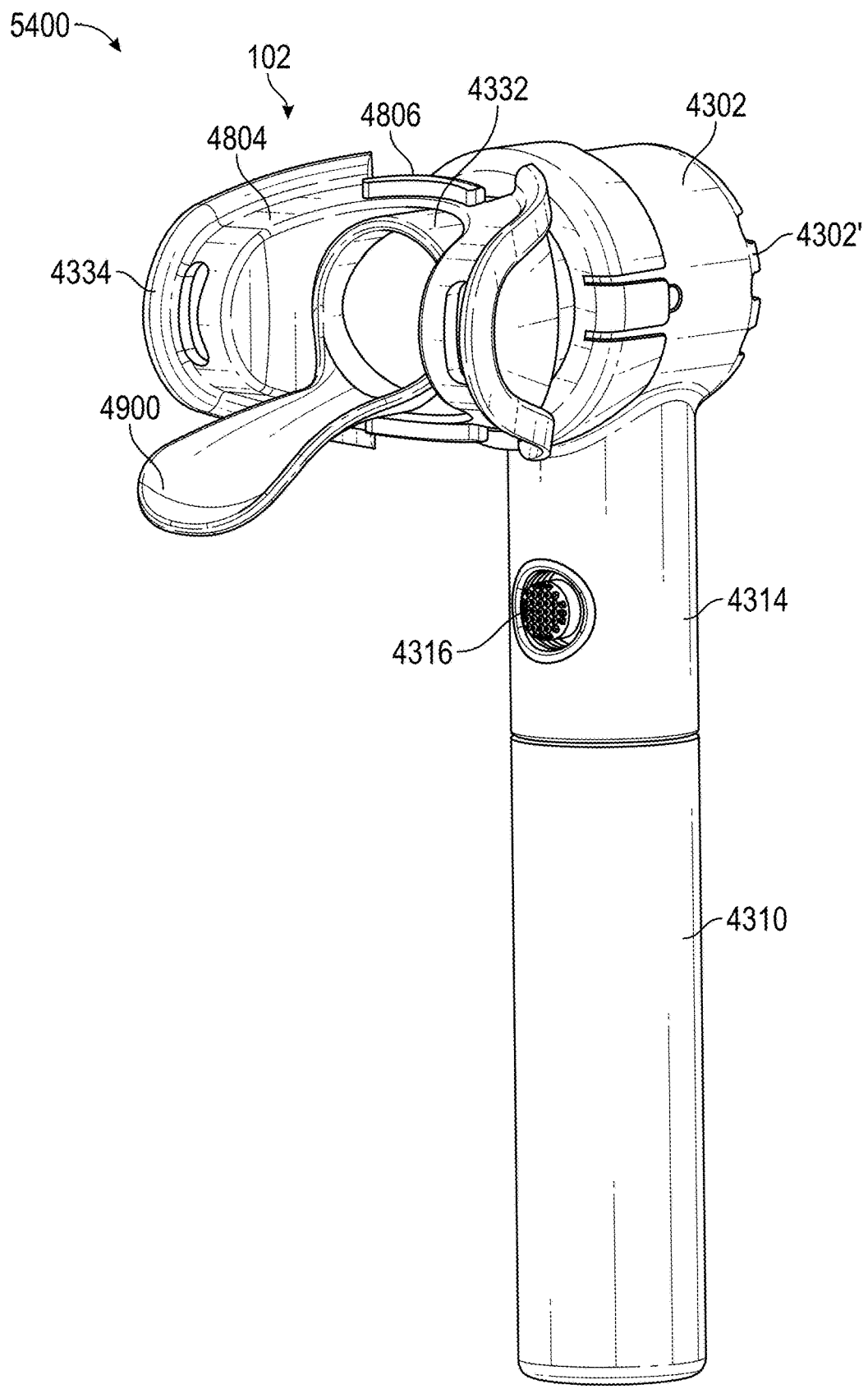
Figure 54B:
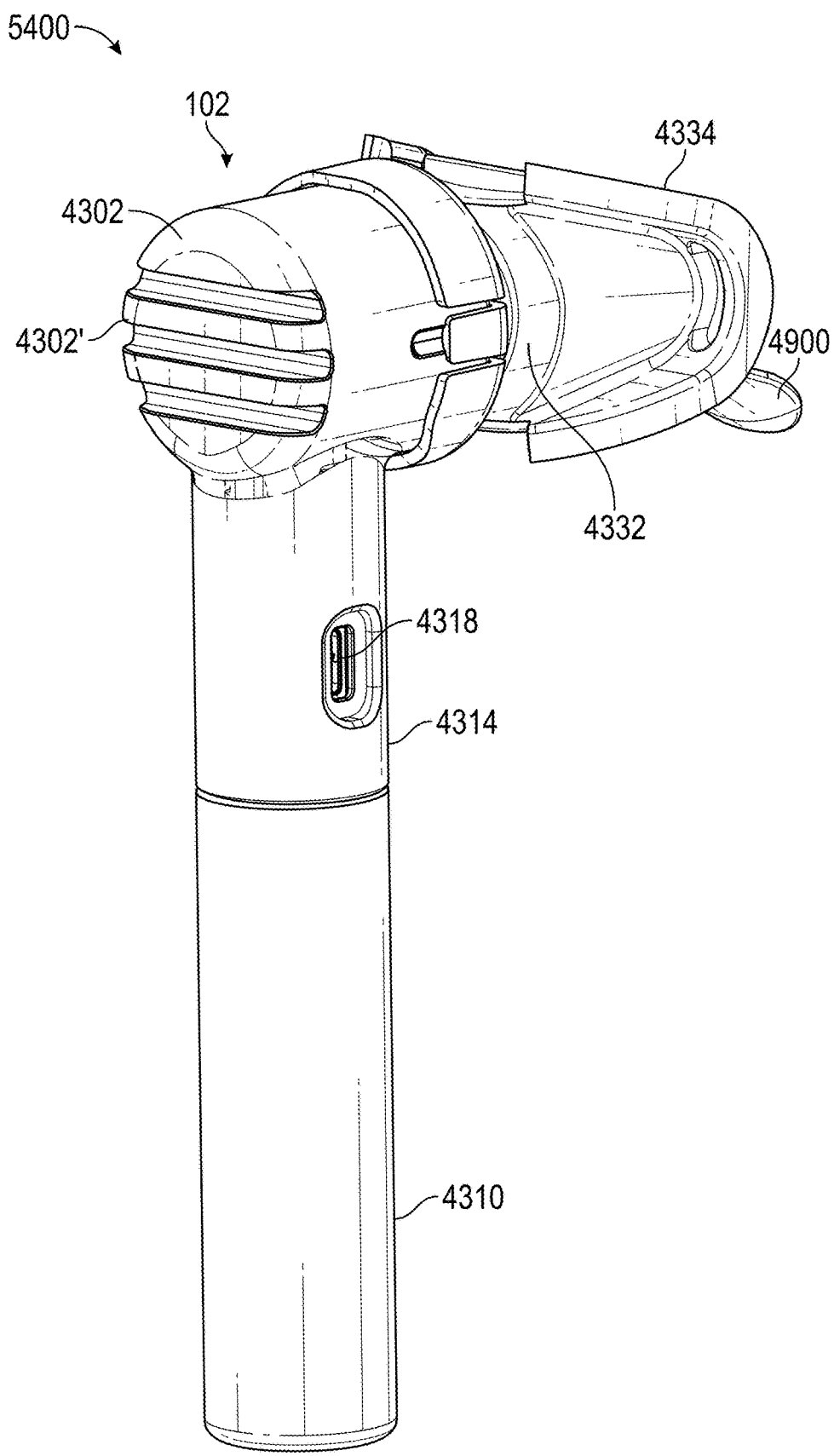
Figure 54C:
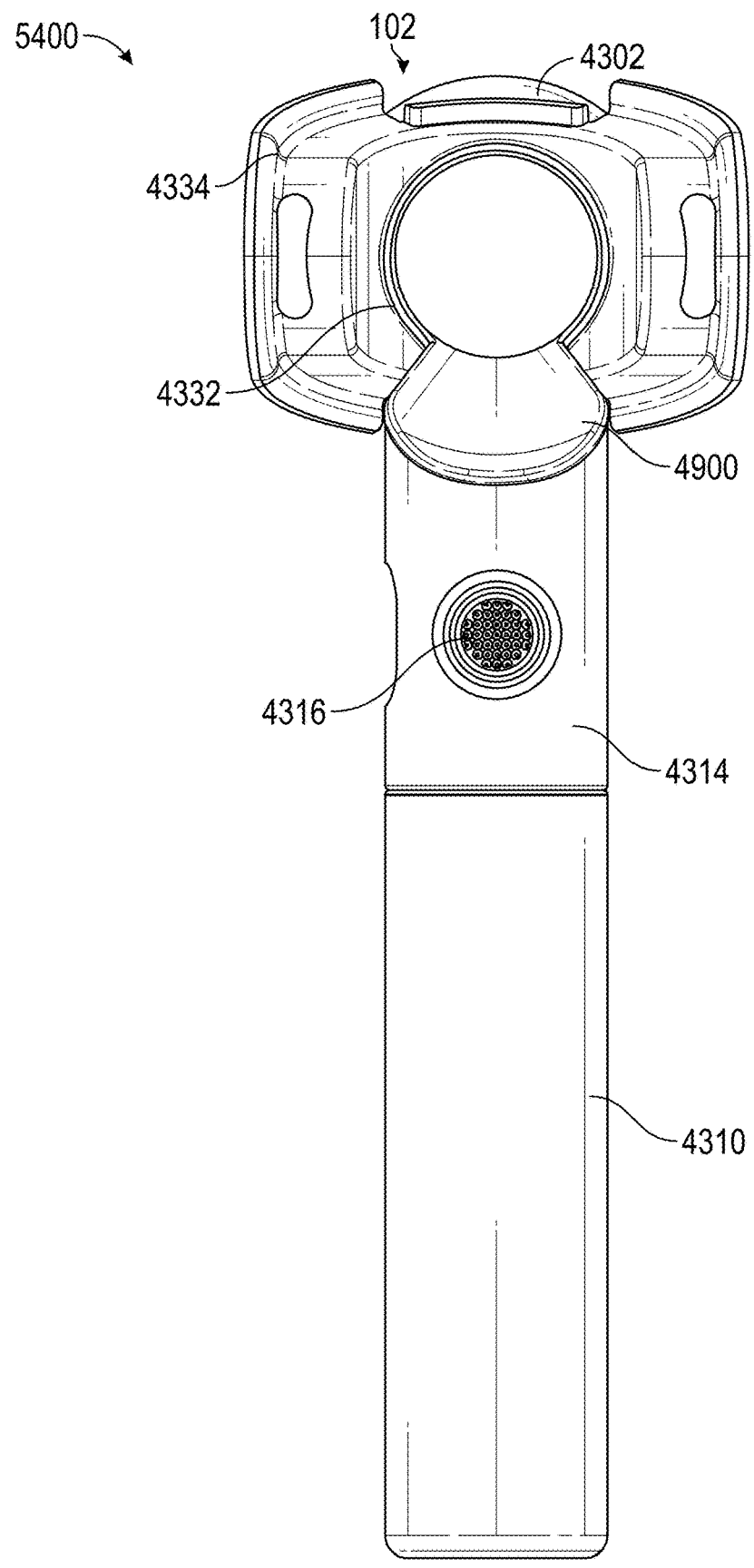
Figure 54D:
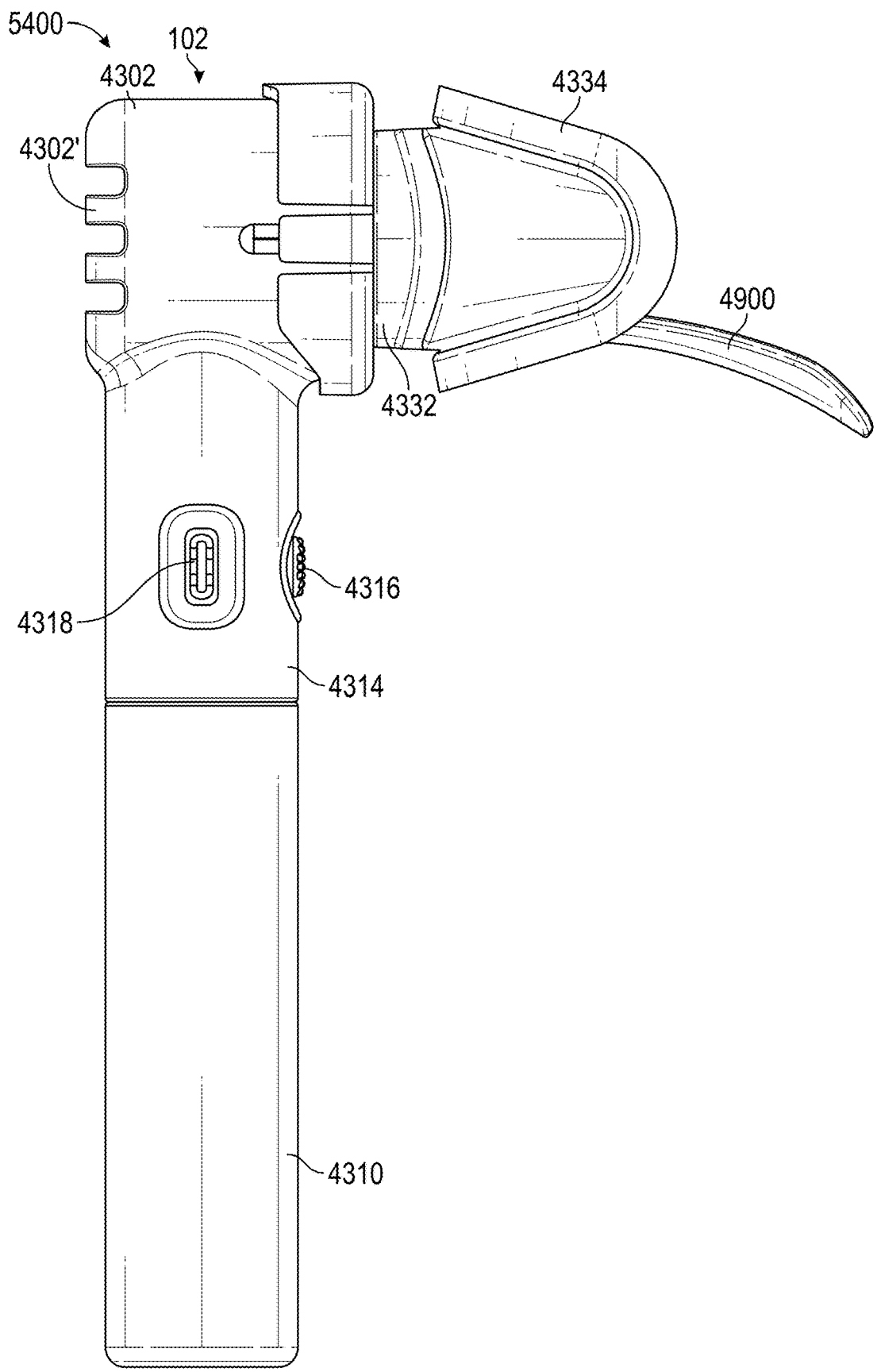
Figure 54E:
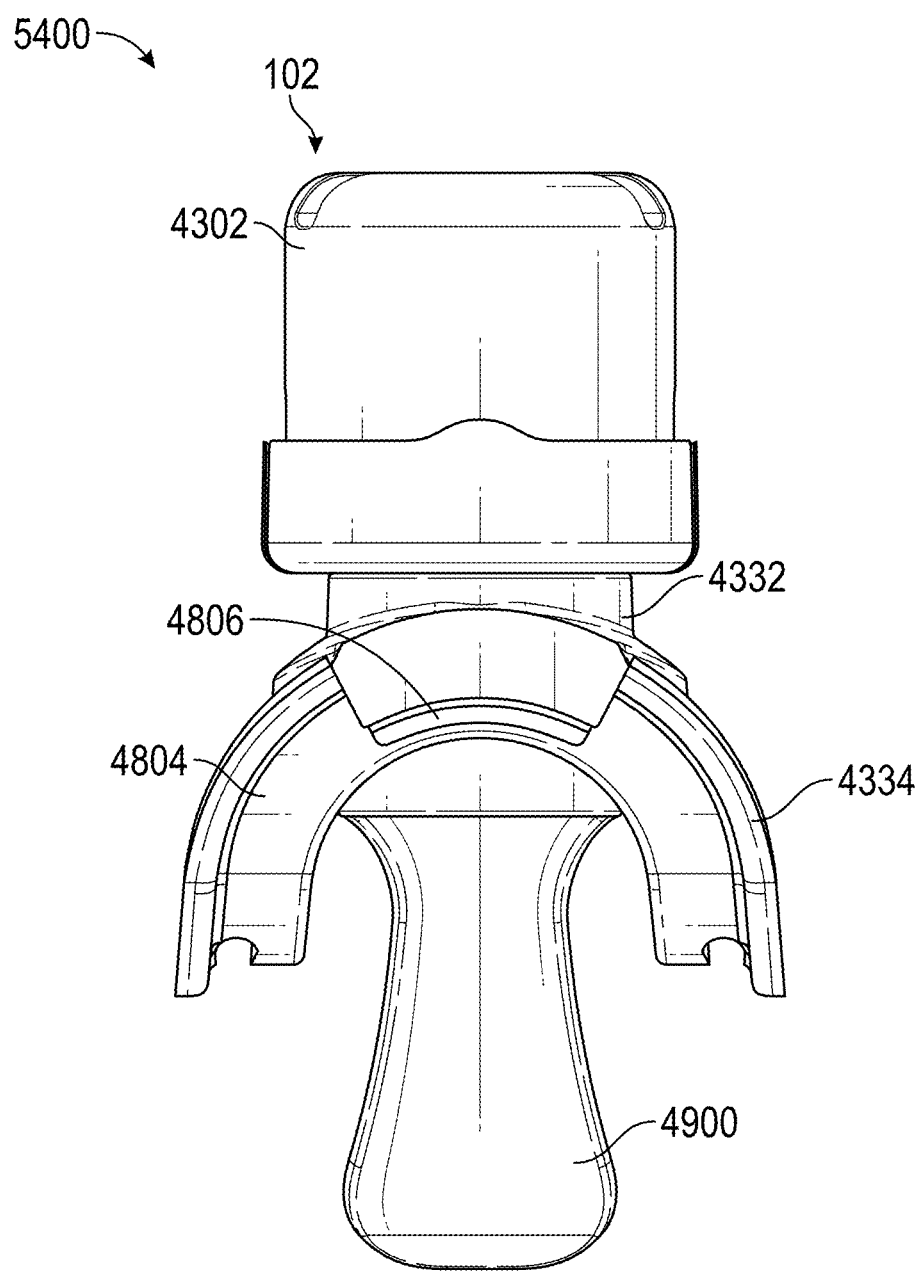

FIGS. 54A-54E illustrate various views of an exemplary handheld configuration 5400 of the illumination device 102 for delivering light (e.g., nitric-oxide modulating light and/or light to induce any of the previously described biological effects) to living tissue within or near a user's oral cavity, including the oropharynx. FIG. 54A is a front perspective view, FIG. 54B is a back perspective view, FIG. 54C is a front view, FIG. 54D is a side view, and FIG. 54E is a top view of the exemplary handheld configuration 5400 of the illumination device 102. The exemplary handheld configuration 5400 of FIGS. 54A-54E is similar to the exemplary handheld configuration 4300 of FIGS. 43-52 as previously described, and the tongue depressor 4900 further defines a shape that includes a width at an end of the tongue depressor 4900 that is larger than a corresponding width of the tongue depressor 4900 that is closer to the housing 4302. In this manner, the end of the tongue depressor 4900 may be configured to depress a larger portion of a user's tongue when inserted into the user's mouth. Additionally, the housing 4302 may form one or more features 4302' that may provide heat dissipation for the housing 4302. Similar features 4302' are illustrated in FIG. 43, but are provided in a manner that wraps around multiple sides of the housing 4302, while in the embodiment of FIGS. 54A-54E, the features 4302' may be provided along a back side of the housing 4302 with wrapping around to portions of the housing adjacent the light guide 4332.

Phototherapy as described herein may be administered to selected portions of the oral cavity, auditory canal, throat, larynx, pharynx, oropharynx, trachea and/or esophagus, using appropriate devices, the selection of which depends on the location that the light is to be administered. The treatment methods described herein can be carried out using any light delivery device or devices that is/are capable of delivering light having the desired characteristics (e.g., wavelength characteristics, radiant flux, duration, pulsing or non-pulsing, coherency, etc.) to desired regions.

In addition to the above-described illumination devices, representative types of light delivery devices that can be used in carrying out phototherapy, and/or light delivery devices described herein, include any devices that can be used to deliver light to (and/or that can be positioned in or pass through) any part or parts of patients' oral cavity, auditory canal, and the like. Examples include, but are not limited to, light emission devices (e.g., shaped and sized so as to be inserted or insertable into patients' mouths and/or nasal cavities), scopes, such as ophthalmoscopes to reach the mouth, throat, ears and nose, bronchoscopes, for reaching deeper into the throat, and to the larynx, pharynx, esophagus, trachea, and the like, tubes with light emitting element(s) and/or light delivery component(s), and the like.

Examples include, but are not limited to, light emission devices (e.g., shaped and sized so as to be inserted or insertable into patients' oral cavity, such as the nasal cavity, and/or the auditory canal), scopes, such as ophthalmoscopes, with light emitting element(s) and/or light delivery component(s), tubes with light emitting element(s) and/or light delivery component(s), and the like. In various embodiments, the light source is a wand, flashlight, ophthalmoscope, or light panel.

Light emission devices that are shaped and sized so as to be inserted or insertable into patients' mouths and/or nasal cavities include generally any device that is suitable for insertion into a patient's mouth and/or nasal cavity and that is capable of emitting light having desired characteristics. Examples include panels, which can be flat or curved, wands, flashlights, headphones with a light source in addition to or in place of speakers, scopes, tubes and intra-oral devices. Each of these has a light emitting source, such as light-emitting diodes (LEDs), OLEDs, superluminous diodes (SLDs), lasers, and combinations thereof, to shine light into the oral cavity, auditory canal, and the like.

Scopes comprising light emitting element(s) and/or light delivery component(s) can be used in the methods described herein. Such scopes include any device suitable for insertion into any region (and/or through any region) of a patient's respiratory tract. At least one light delivery component and/or at least one light emitting element is disposed within and/or supported by the scope.

Representative examples of suitable scopes include bronchoscopes, nasopharyngoscopes, fiberscopes, etc. Representative examples of suitable light delivery components include fiber optic devices and other waveguides.

In one particular embodiment, an ophthalmoscope is disclosed which, rather than permitting a physician from viewing the mouth, ears and nose of a patient, is outfitted with a light source, such as an LED, OLED, laser, and the like, which emits light at one or more specific antimicrobial wavelengths. In aspects of this embodiment, the ophthalmoscope has attachments to focus the light on the ear and/or nose.

An ophthalmoscope is a handheld, typically battery-powered device containing illumination and viewing optics intended to examine the media (cornea, aqueous, lens, and vitreous) and the retina of the eye. However, an ophthalmoscope also typically includes various attachments that enable the device to be used to illuminate the ears, nares, mouth and throat.

One such attachment is an otoscope attachment, which allows the user to illuminate the ear canal and tympanic membrane.

Another type of attachment is a nasal speculum adapter (often used in conjunction with an otoscope attachment. When using the otoscope attachment with a nasal speculum adapter, the device can illuminate the nares (nostrils) while maintaining a line of sight through the nasal passages, one nasal passage at a time.

A bent arm illuminator is a handheld light that can be used to illuminate a patient's mouth and upper throat. It can also be used for trans-illumination of the sinuses. Whereas a typical ophthalmoscope or bronchoscope includes an on/off switch, but not a timer, the bronchoscope described herein can include a timer, which allows the user to know when the treatment is completed. The timer can include different treatment times, based on the location the light is administered, the wavelength that is administered, and the like.

Certain embodiments of devices that pass through a patient's epiglottis (e.g., devices that comprise scopes and tubes that pass through a patient's mouth or nasal cavity, past the epiglottis and into the trachea) can comprise a demand valve-type component. This is similar to a demand valve in a scuba diving device, and assists in keeping the epiglottis from blocking insertion of the device (e.g., scope or tube).

Tubes with light emitting element(s) and/or light delivery component(s), for example, LED, OLED, or laser light emitting or delivering components, can be used in the methods described herein. This includes any device that is suitable for insertion into any region (and/or through any region) of a patient's oral cavity, wherein at least one light delivery component and/or at least one light emitting element is disposed within and/or supported by the tube. In another embodiment, the tube includes light sources positioned at the front of the tube, and at various positions around the tube, so as to be able to simultaneously shine light to the throat, the roof of the mouth, the tongue, the gums, and the cheeks of the user. Representative examples of suitable tubes include tracheostomy tubes, endotracheal tubes and nasogastric tubes, and representative examples of tubes with light emitting element(s) and/or light delivery components(s). Specifically included are tubes with at least one optical fiber and/or other waveguide disposed within and/or supported by the tube, and with at least one light emitting element positioned and oriented so as to feed light into the optical fiber(s) and/or other waveguide(s).

In another aspect, the light source is a panel (i.e., a light panel), which can be straight or curved, and the user can be exposed to the light by opening the mouth, for example, with a cheek retractor, and rather than hold the light source, the panel can be positioned such that the patient can sit down, or lie down, and be exposed to the panel. The panel can include a clip or a stand to facilitate orienting the panel so that the user's mouth, nose and/or ears can be exposed to the antimicrobial light.

As noted above, devices for use in carrying out methods described herein (and certain embodiments of devices described herein) comprise at least one light emitting element that is/are capable of delivering light having the desired characteristics (e.g., wavelength characteristics, radiant flux, duration, pulsing or non-pulsing, coherency, etc.) to desired regions of a patient's respiratory tract. Wavelength characteristics include saturation, wavelength spectra (e.g., range of wavelengths, full width at half maximum values), dominant wavelength, and/or peak wavelength).

In certain embodiments, at least one of the light emitting element(s) is/are solid-state light emitting devices. Examples of solid state light emitting devices include, but are not limited to, LEDs, OLEDs, SLDs, lasers, thin film electroluminescent devices, powdered electroluminescent devices, field induced polymer electroluminescent devices, and polymer light-emitting electrochemical cells.

While both LEDs and lasers are variable power light sources, LEDs are more flexible in this regard. Lasers have a threshold current, below which there is no power output, and above which the power increases exponentially as more drive current is applied. LEDs, in contrast, begin emitting light at very low drive current and then emission is roughly linear with increasing drive current. This advantage of LEDs over lasers can be important to supply sufficient flux to treat the targeted disease, while not providing so much that it damages the tissue. This feature can be particularly important in areas of the body, such as the lung, where the same medical device can be used to address different and complicated topologies.

While they are not a coherent source with a spectral width as narrow as a laser, LEDs can offer certain advantages over lasers in photobiomodulation (PBM). These advantages are directly applicable to one component of PBM—absorption by photoacceptor molecules. LEDs are more easily available over a wide range of wavelengths, from UV to IR, than lasers. In addition to being available over a wider wavelength range, LEDs are also more readily available at more discrete wavelengths within that range. LEDs are characterized by a broader spectral width than lasers, and, because of this, absorption by a targeted molecule is less likely to be missed by incorrect choice of the emission wavelength of the few nm wide laser. LEDs are also characterized by broader far fields than lasers, and this makes more uniform treatment of large areas more straightforward than it is with lasers, whether by direct emission or illumination of the target through other optical elements. Finally, from a pragmatic view, LEDs are more cost effective per mw emission, more readily available, and easier to use in optical systems than lasers. Accordingly, in one embodiment, the treatment methods described herein use LEDs as the source of light. In certain embodiments, one, some or all of the light emitting elements have full width at half maximum value of less than 25 nm (or less than 20 nm, or less than 15 nm, or in a range of from 5 nm to 25 nm, or in a range of from 10 nm to 25 nm, or in a range of from 15 nm to 25 nm).

In certain embodiments, different light emitting elements are contained in a single solid-state emitter package. In certain embodiments, light emitting elements are arranged in an array or in two or more arrays. In certain embodiments, light emitting elements comprise one or more wavelength conversion materials, examples of which include phosphor materials, fluorescent dye materials, quantum dot materials, and fluorophore materials.

Certain embodiments of devices for use in carrying out methods described herein (and certain embodiments of devices described herein) can comprise a power supply circuit arranged to provide at least one conditioned power signal for use by at least one of a microcontroller of the device.

Certain embodiments of devices for use in carrying out methods described herein (and certain embodiments of devices described herein) can comprise one or more features and/or components to scatter light or enhance scattering of light.

Persons of skill in the art are familiar with a variety of such features and components, and any of such features and components are within the scope of the present description.

Representative examples of such features and components include (1) digital light processors (e.g., which can be positioned at the end of a fiber optic and disseminate the light exiting the fiber optic, e.g., 320 degrees spherically), (2) light diffusion and/or scattering materials (e.g., zinc oxide, silicon dioxide, titanium dioxide, etc.), (3) textured light scattering surfaces, (4) patterned light scattering surfaces, (5) phosphors or other wavelength-conversion materials (which tend to re-emit light spherically).

In certain embodiments, low-absorption light scattering particles, liquids, and/or gases can be positioned inside a low-absorption element that prevents the particles, liquids and/or gases from escaping.

In certain embodiments, light extraction features can be provided, and may include different sizes and/or shapes. In certain embodiments, light extraction features may be uniformly or non-uniformly distributed over a flexible printed circuit board. In certain embodiments, light extraction features may include tapered surfaces. In certain embodiments, different light extraction features may include one or more connected portions or surfaces. In certain embodiments, different light extraction features may be discrete or spatially separated relative to one another. In certain embodiments, light extraction features may be arranged in lines, rows, zig-zag shapes, or other patterns. In certain embodiments, one or more wavelength conversion materials may be arranged on or proximate to one or more light extraction features.

Certain embodiments of devices for use in carrying out methods described herein (and certain embodiments of devices described herein) can comprise one or more sensors of any type. In certain embodiments, operation of methods disclosed herein may be responsive to one or more signals generated by one or more sensors or other elements.

Various types of sensors can be employed, including temperature sensors, photo sensors, image sensors, proximity sensors, blood pressure or other pressure sensors, chemical sensors, biosensors (e.g., heart rate sensors, body temperature sensors, sensors that detect presence or concentration of chemical or biological species, or other conditions), accelerometers, moisture sensors, oximeters, such as pulse oximeters, current sensors, voltage sensors, and the like.

Other elements that may affect impingement of light and/or operation of a device as disclosed herein include a timer, a cycle counter, a manually operated control element, such as an on-off switch, a wireless transmitter and/or receiver (as maybe embodied in a transceiver), a laptop or tablet computer, a mobile phone, or another portable digital device. Wired and/or wireless communication between a device as disclosed herein and one or more signal generating or signal receiving elements may be provided. In any of these aspects, the user can be exposed to the light at a sufficient power and for a sufficient time to result in desired antimicrobial effects, while also not overexposing the user to the light.

In certain embodiments, devices for use in carrying out methods described herein (and certain embodiments of devices described herein) can comprise one or more memory elements that are configured to store information indicative of one or more sensor signals or any other information.

Certain embodiments of devices for use in carrying out methods described herein (and certain embodiments of devices described herein) can comprise one or more communication modules configured to electronically communicate with an electronic device external to the device.

Since the user may be unable to see the wavelengths that are administered, because the user may be wearing eye protection, the light source, such as the bronchoscope, may provide an auditory or tactile signal that the light treatment has terminated. In some aspects of these embodiments, the light source can be controlled using an app. In other aspects, the light source itself includes a timer, so the user can set the time period that light is administered.

When subjects are exposed to light at antimicrobial wavelengths, it is important to protect their eyes from exposure to these wavelengths. There are several ways to do so. In one embodiment, where light at blue wavelengths or UV wavelengths is used, one can protect the subject's eyes with eye glasses, goggles, or eye shields, such as those used in tanning beds, which filter out those wavelengths. In another embodiment, the eyes are covered with an opaque cover, which can be in the form of goggles, an eye mask, and the like.

Coatings which prevent users from being subjected to certain wavelengths are well-known in the art. Examples include UV protective coatings, anti-blue coatings, and the like. In some embodiments, particularly with respect to ophthalmic lenses and goggles, one of both main faces of the lenses/goggles can include an optical filter intended to reduce the unwanted light, such as blue light, and thus reduce any light-induced phototoxic effects on the retina of a wearer. In one aspect, this is defined in terms of ranges of wavelengths and angles of incidence. As used herein, "ranging from x to y" means "within the range from x to y", both limits x and y being included within this range.

Visible light to humans extends over a light spectrum ranging from wavelengths of approximately 380 nanometers (nm) wavelength to 780 nm. The part of this spectrum, ranging from around 380 nm to around 500 nm, corresponds to a high-energy, essentially blue light. Many studies suggest that blue light has phototoxic effects on human eye health, and especially on the retina. One can limit exposure to these and other wavelengths using lenses/goggles with an appropriate filter, which prevents or limits the phototoxic blue light transmission to the retina.

Other filters efficiently transmit visible light at wavelengths higher than 465 nm, so as to maintain good vision for the wearer, while not exposing the retina to damaging wavelengths. Accordingly, in one embodiment, the lenses filter out blue light amount received by the eye in the wavelength range of from 420 nm to 450 nm, while enabling an outstanding transmission within the wavelength range of from 465 nm to 495 nm. One way to accomplish this is to use highly selective, narrow-band filters, which are typically composed of an overall thick stack, comprising a plurality of dielectric layers. Such filters can be applied to the front main face of which an optical narrow-band filter such as previously described has been deposited. In this context, the front main face of the ophthalmic lens is that main face of the ophthalmic lens, which is the most distant from the spectacle wearer's eyes. By contrast, the main face of the ophthalmic lens, which is the nearest from the spectacle wearer's eyes is the back main face.

Even if the direct light incident on the front main faces of the ophthalmic lenses is efficiently rejected through the reflection against the narrow-band filters deposited onto the front main faces, in some cases, indirect light originating from the wearer's background is reflected to the spectacle wearer's eyes. For this reason, it can be preferred to use goggles, such as the types of tanning goggles used along with tanning beds.

Ideally, sufficient eye protection is matched to the wavelengths of light that are used, such that the amount of phototoxic light, such as phototoxic blue light, reaching the wearer's retina can be significantly reduced to safe levels. In one embodiment, glasses or goggles include an ophthalmic lens having a front main face and a back main face, at least one of both main faces comprising a filter, which provides the main face comprising said filter with the following properties: an average blue reflectance factor ($R_{m,B}$) within a wavelength range of from 420 nm to 450 nm, which is higher than or equal to 5%, for an angle of incidence ranging from 0° to 15°, a spectral reflectivity curve for an angle of incidence ranging from 0° to 15°, such reflectivity curve having: a maximum reflectivity at a wavelength of less than 435 nm, and a full width at half maximum (FWHM) higher than 80 nm, and for an angle of incidence θ ranging from 0° to 15° and for an angle of incidence θ' ranging from 30° to 45°, a parameter $\Delta(\theta,\theta')$ defined by the relation $\Delta(\theta,\theta')=1-[R_{\theta'}(435 nm)/R_{\theta}(435 nm)]$, in such a way that this parameter $\Delta(\theta,\theta')$ is higher than or equal to 0.6, where: $R_{\theta}(435 nm)$ represents the reflectivity value of the main face comprising said filter, at a 435 nm-wavelength for the angle of incidence θ, and $R_{\theta'}(435 nm)$ represents the reflectivity value of the main face comprising said filter at a 435 nm-wavelength for the angle of incidence θ'.

In another embodiment, the present invention relates to an ophthalmic lens having a front main face and a back main face, at least one of both main faces comprising a filter, which provides the main face comprising said filter with the following properties: an average blue reflectance factor ($R_{m,B}$) within a wavelength range of from 420 nm to 450 nm, which is higher than or equal to 5%, for an angle of incidence ranging from 0° to 15°, a spectral reflectivity curve for an angle of incidence ranging from 0° to 15°, this reflectivity curve having: a maximum reflectivity at a wavelength of less than 435 nm, and a full width at half maximum (FWHM) higher than or equal to 70 nm, preferably higher than or equal to 75 nm, and for an angle of incidence θ ranging from 0° to 15° and for an angle of incidence θ' ranging from 30° to 45°, a parameter $\Delta(\theta,\theta')$ defined by the relation $\Delta(\theta,\theta')=1-[R_{\theta'}(435 nm)/R_{\theta}(435 nm)]$, in such a way that this parameter $\Delta(\theta,\theta')$ is higher than or equal to 0.5, where $R_{\theta}(435 nm)$ represents the reflectivity value of the main face comprising said filter at a 435 nm-wavelength for the angle of incidence θ, and $R_{\theta'}(435 nm)$ represents the reflectivity value of the main face comprising said filter at a 435 nm-wavelength for the angle of incidence θ' and or an angle of incidence ranging from 0° to 15°, a parameter $\Delta$ spectral defined by the relation $\Delta spectral=1-[R0°-15°(480 nm)/R0°-15°(435 nm)]$, in such a way that this parameter $\Delta$spectral is higher than or equal to 0.8, where $R0°-15°$ (480 nm) represents the reflectivity value of the front main face at a 480 nm-wavelength for the relevant incidence, and $R0°-15°$ (435 nm) represents the reflectivity value of the front main face at a 435 nm-wavelength for the relevant incidence. These types of ophthalmic lenses make it possible to minimize transmission of phototoxic blue light to a user's retina, by providing average reflectivity within a wavelength range of from 420 nm to 450 nanometers.

For devices that are configured for insertion into the oral cavity, a cheek retractor may be included. A cheek retractor is a medical instrument used to pull the cheeks away from the mouth and hold them in place to leave the mouth exposed during a procedure. More specifically, a cheek retractor holds mucoperiosteal flaps, cheeks, lips and tongue away from the treatment area, thus facilitating having light treat the entire mouth/oral cavity. As disclosed herein, cheek retractors may be incorporated as part of the light guide positioner and/or the mouthguard for the above-described illumination devices.

Figure 56A:
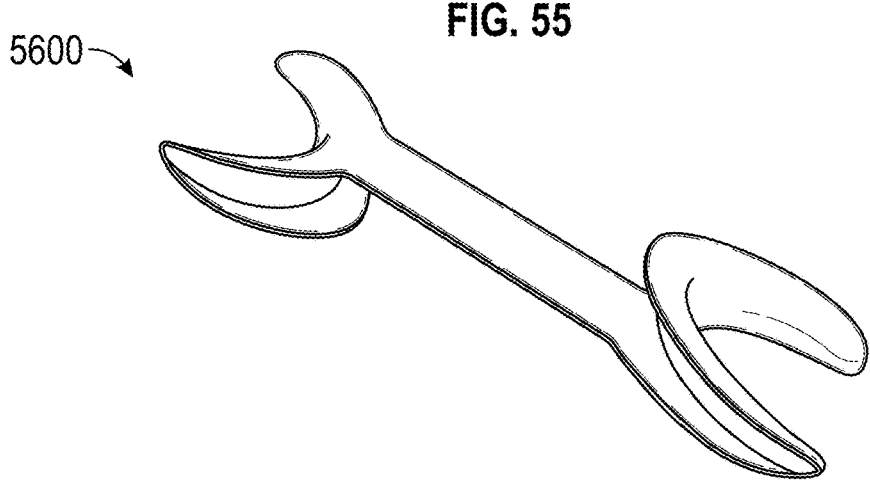
Figure 56B:
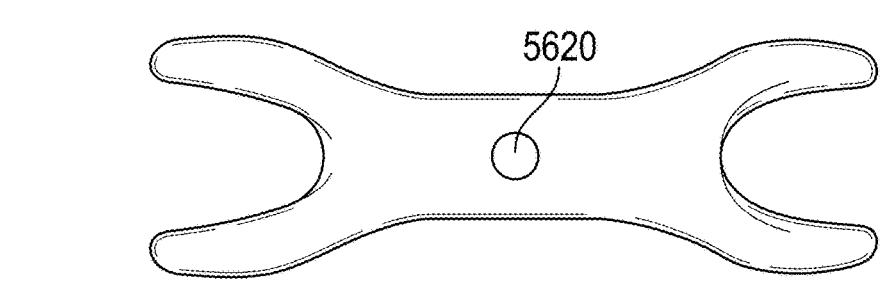

Examples of cheek retractors are shown in FIGS. 56A and 56B. FIG. 56A is a perspective view of an exemplary cheek retractor 5600. The cheek retractor 5600 may comprise a clear material, such as plastic or the like, that is designed to provide a physician or dentist with an opening wide enough to perform procedures in the mouth or other portions of the oral cavity, or in the throat. While these can be used, and while eye protection can be used to protect the user's eyes from damaging wavelengths passing through the clear plastic, it may be preferred to use a cheek retractor that is either opaque to all wavelengths, or has a coating to filter out harmful wavelengths. This is particularly true since a physician or dentist need not use the retractor to access the mouth, and all that is needed is to provide access to a source of light, and it is advantageous to minimize or prevent exposing a user's eyes to light at these wavelengths.

FIG. 56B is a perspective view of a cheek retractor 5610 that includes a material, such as a filter, that is configured block certain wavelengths of light during phototherapy. For example, if the light involves delivering blue light, or light with a peak wavelength in a range from 400 nm to 450 nm, for impinging light on or near the oropharynx, the cheek retractor 5610 may include a material that filters such blue light or light within the peak wavelength range from 400 nm to 450 nm. In other embodiments, the cheek retractor 5610 may include a material that filters and/or blocks any of the above-described peak wavelength ranges, depending on the application. In still further embodiments, the cheek retractor 5610 may include a material that is substantially opaque or even black that is configured to block most light from passing through. In certain embodiments, the material (e.g., for filtering and/or light blocking) may form the entire cheek retractor 5610 and/or the material may be embedded in a host binder material, such as plastic. In still further embodiments, the filtering and/or light blocking material may be provided as a coating on surfaces of the cheek retractor 5610.

In certain embodiments, the cheek retractor 5610 may also form a hole 5620 in the center that is adapted to receive a source of light (not shown). In this regard, one or more light sources may be adapted to fit or otherwise be positioned at or within the hole 5620 for delivery of light. One or both of the light source and the cheek retractor 5610 can be fitted with a gasket, so that a pressure-fit of the light into the hole 5620 can be affected. Alternatively, the cheek retractor 5610 may be threaded to allow the light source to be screwed in place. In either of these embodiments, the user can use the light without having to hold it in place and the cheek retractor 5610 may block light emissions from exiting the user's oral cavity. In another aspect, the cheek retractor 5610 may form a narrower shape than a traditional cheek retractor, as it is intended to allow light to enter the oral cavity, but need not serve to provide a sufficient opening for a dentist or physician to perform surgical treatments within the oral cavity. In one embodiment, the cheek retractor 5610 may be adapted to receive the light source, so that the user can maintain the light source in place by inserting the cheek retractor 5610 in the mouth. For example, the cheek retractor 5610 can be adapted to receive the light source by including an opening (e.g., the hole 5620) that receives the light source, which can be adapted to fit in the opening. In one aspect, the cheek retractor 5610 can include screw threads, and the light source is adapted to screw into these threads. In this regard, the cheek retractor 5610 may comprise an opaque, black, and/or filtering material provided within the cheek retractor 5610 or as a coating that minimizes transmission of light in undesired directions. This may sever to protect a user's eyes when a light source is inserted into the mouth, thereby reducing the amount of light which passes through the cheek retractor 5610 and out of the oral cavity. In another aspect, the cheek retractor 5610 is otherwise a solid piece of plastic, but includes an opening sized to receive a light source, so as to allow the user to keep the mouth open to receive light, while not having to hold the light source.

In other embodiments, a set of light sources adapted to transmit light to the ears is disclosed. In some aspects of these embodiments, to facilitate exposure of the light to the ears, the light source can be shaped like an in-ear headphone, or a standard headphone, but instead of, or in addition to emitting sound, the device emits light at antimicrobial wavelengths. In one aspect of this embodiment, the light source is provided in a form similar to over-the-ear headphones, which, in addition to, or in lieu of transmitting sound, includes a light source for emitting light at antimicrobial wavelengths to the ears.

In some embodiments, light sources may be adapted to facilitate light transmission into the nares (nostrils). By way of example, FIG. 57 is a perspective view of a device 5700 for securing a light source to a user's nostrils. The device may include a clip 5710, so that light source(s) in optical communication with the device 5700 may be clipped to the nostrils. Light source(s) may be included within the device 5700 or remote from the device and connected to a light receiving end 5720 of the device 5700 by way of an optical cable and/or a light guide. Dual light sources, or dual devices 5700, can be used to facilitate simultaneous administration of light to both nostrils. In these embodiments, intranasal light therapy can be used to eliminate microbes in the nasal passages.

The principles of the present disclosure may be well suited for providing a phototherapy kit for treating, preventing, or reducing the biological activity of microbes present in the mouth, nose and/or ears. Such kits may include one or more combinations of any of the illumination devices as previously described, including light sources that can be used to deliver light at antimicrobial wavelengths to the mouth, nose, and/or ears. Such phototherapy kits may also include other devices and accessories, such as protective glasses, goggles, shields, and/or masks which shield the wearer's eyes from the antimicrobial and/or from all wavelengths, the cheek retractors as described above to facilitate administering the light to the user's mouth, and/or a pillow designed to arch the user's neck, so that light transmitted into the mouth also travels a straight path to the target area for infection, such as a user's throat and/or oropharynx.

In certain embodiments, illumination devices and treatments may also be applied for infections that progress to the lungs and/or other particular lung disorders. Following treatment, the course of therapy can be followed in different ways. The treatment or prevention of microbial infections can be followed, for example, by following the severity of the symptoms, the presence of fever, the use of pulse oximetry, and the like. The prevention of pulmonary inflammatory disorders can be followed by X-ray, lung function tests, and the like. Challenge tests are lung function tests used to help confirm a diagnosis of asthma, where a patient inhales a small amount of a substance known to trigger symptoms in people with asthma, such as histamine or methacholine. After inhaling the substance, lung function is evaluated. Following light delivery to induce one or more biological effects, one can determine whether diminution of lung function following inhalation of these substances is lessened, relative to before phototherapy was initiated, which indicates that the phototherapy is effective for such a patient.

The fear of being diagnosed with coronavirus, including COVID-19, followed by rapid hospitalization and mortality from severe lung dysfunction is real. However, using the illumination devices and methods described herein, coronaviridae and coronavirus infections may be avoided, even after exposure to COVID-19, so long as an insufficient number of viral particles have traveled through the oral cavity to the lungs. The same is true of SARS-CoV-2, which infects mucosal tissue of the oropharyngeal cavity and lungs through adhesion of its spike protein to host cell receptors.

The same is also true of orthomyxoviridae (e.g., influenza) viruses, which cause the flu. Coronaviridae and orthomyxoviridae viruses cause similar symptoms, and the methods described herein are effective for preventing these viruses from traveling from the oral cavity to the lungs.

In one embodiment, coronavirus infectivity may be prevented with nitric oxide. In contrast to pharmaceutical approaches, nitric oxide may be produced by stimulating epithelial cells in the oral cavity, auditory canal, larynx, pharynx, oropharynx, throat, trachea and/or esophagus with visible blue light, for example, at peak wavelengths in a range from 400 nm to 450 nm, including 425 nm and 430 nm, among others. Light-initiated release of nitric oxide ramps up defense against SARS-CoV-2 and other coronaviruses, as well as influenza viruses such as influenza A and influenza B, by stopping entry into human cells and inactivating viral replication. If this can be accomplished after the initial infection, but before the virus particles enter the lungs in sufficient numbers to cause a respiratory infection, the result is a post-infection prevention of a coronavirus or influenza respiratory infection.

A number of widely deployable medical device countermeasures can be envisioned. One specific approach for patients exposed, or believed to be exposed, to coronavirus would utilize a routine bronchoscope procedure upfit with a thin blue light fiberoptic that is passed through the standard working channel of the bronchoscope (HopeScope) to the mouth, throat, larynx, pharynx, trachea, and esophagus. This strategy can limit infectivity, and halt progression of coronaviruses, such as SARS-CoV-2, or influenza viruses, into lung tissues. Additionally, any of the previously-described illumination devices may be well-suited for delivery of light for use against coronaviruses and influenza viruses.

Nitric oxide (NO) is a natural part of innate immune response against invading pathogens and is produced in high micromolar concentrations by inducible nitric oxide synthase (iNOS) in epithelial tissue. In vitro pre-clinical studies have shown that nitric oxide inhibits the replication of DNA viruses including herpesviruses simplex, Epstein-Barr virus and the vaccinia virus. Influenza infectivity is also diminished in the presence of nitric oxide, with results showing that when virions were exposed to nitric oxide prior to infection, a complete inhibition of infectivity was achieved for all three strains tested. Nitric oxide-based inhibition of viral replication and selective antiviral activity against HPV-18 infected human raft epithelial cultures has also been demonstrated. The broad-spectrum antiviral activity of nitric oxide has been well documented, though, previously, not in the oral cavity or auditory canal.

One way nitric oxide may be effective is that it stops SARS-CoV entry into human cells. Nitric oxide and its derivatives cause a reduction in the palmitoylation of nascently expressed spike (S) protein which affects the fusion between the S protein and its host cell receptor, angiotensin converting enzyme 2. FIG. 58 is an illustration of the nitric oxide inactivation of the active spike (S) proteins used by coronaviruses to facilitate endocytosis into human cells.

Nitric oxide may also inhibit viral replication, including replication of SARS-CoV. While not wishing to be bound to a particular theory, it is believed that one or more of the following mechanisms is implicated in the way that nitric oxide inhibits viral infections. Following exposure to nitric oxide, a reduction in viral RNA production has been observed in the early steps of viral replication, due to an effect on one or both of the cysteine proteases encoded in Orf1a of SARS-CoV. When examining the known pathogenic mechanisms that are utilized by coronaviruses, nitric oxide may also be able to inhibit other key enzymes that are utilized by the RNA virus for inducing apoptosis and rapid destruction of lung tissue (e.g. caspase). Inhibition of caspase makes coronavirus less contagious. The inhibition of caspase dependent apoptosis used for transmission of the virions offers a significant advantage to any nitric oxide-based approach for treatment or prevention. Although endogenous inhibitors of caspase activation and activity have been described, none has been shown to be more prevalent than NO. All caspase proteases contain a single cysteine at the enzyme catalytic site that can be efficiently S-nitrosylated in the presence of NO. Evidence for S-nitrosylation of caspase-3 and caspase-1 in vivo has been demonstrated.

Another mechanism by which nitric oxide is antiviral is through inhibition of NF-κB, which dampens the immunological response. The NF-κB proteins are a family of transcription factors that regulate expression of genes to control a broad range of biological processes and have been shown to play an important role in SARS-CoV infections. Inhibition of NF-κB with nitric oxide can limit the inflammatory cytokine rush that leads to death by inflammation in COVID-19 patients. Nitric oxide can directly inhibit the DNA binding activity of NF-κB family proteins, suggesting that intracellular NO provides another control mechanism for modulating the expression of NF-κB responsive genes.

Pharmacologic approaches to deliver nitric oxide have been attempted. Clinical concentrations of NO gas were safely administered to SARS patients in China, where they observed that nitric oxide gas (1) reduced the time to hospital discharge, (2) reduced the need for ventilatory support, and (3) improved appearance of infection on lungs via chest radiograph. However, nitric oxide can be produced by stimulating epithelial cells with precise colors of visible light as described in for example, U.S. Pat. No. 10,569,097, the disclosure of which is incorporated by reference in its entirety. Although other wavelengths described herein are effective at producing or releasing nitric oxide, blue light, particularly in a range from 400 nm to 450 nm, including 425 nm and 430 nm, was found to be an particular wavelength to both trigger release of bound NO from endogenous stores and to upregulate cellular enzymatic production of nitric oxide. When nitric oxide is produced naturally, the half-life of the gas is less than 1 second in physiologic tissue. Nitric oxide and its metabolites have long lasting concentration in cells as nitrosothiols and metal nitrosyl centers which can be recycled to bioactive NO following photo stimulated release. The sustained enzymatic production of nitric oxide is a completely unexpected result. Measured via upregulation of iNOS and eNOS protein in epithelial cells in culture, a single 10-minute light treatment of blue light maintained a 10× level of enzyme production for a period of 24 hours.

In certain embodiments, the wavelengths of light may not be in the UV range, and are thus separate and distinct from any disinfection approaches with UVC or UVB wavelengths, though such wavelengths are certainly contemplated in other embodiments described herein.

This groundbreaking use of targeted wavelengths of light is a rapidly deployable strategy to assist with limiting infectivity and progression of SARS-CoV-2 into deeper lung tissues. Using the illumination devices described herein, or other devices for delivering light at frequencies that can produce or release nitric oxide, among other biological effects, light can be delivered to and/or through the oral cavity, including the nasal cavity, oropharyngeal area, and the like, to stimulate mucosal epithelial cells to ramp up nitric oxide production against coronavirus. This can help inhibit entry into human cells, inhibiting viral replication, and eliminate, or at least reduce the number of viral particles, before a sufficient number of viral particles travel down the oral cavity to the lungs.

One specific device for administering the light, particularly to the throat, larynx, pharynx, oropharynx, esophagus and trachea, is a bronchoscope adapted to emit blue light. Bronchoscopes are readily available, as there are more than 500,000 bronchoscopies performed in the US every year and an abundance of these devices are already available within medical facilities across the country. Bronchoscopes can be upfit with a thin blue light fiberoptic that can be passed through the standard working channel of the bronchoscope used for fluid delivery/extraction and biopsy.

It would be advantageous to rescue recently infected patients with phototherapeutic light before they reach the "tipping point" where the virus has invaded the lungs, and eventually decline into severe acute respiratory syndrome. Since nitric oxide inhibits viral replication and reduces proliferation of the virus in or around the oral cavity, auditory canal, and the like, the efficacy of blue light against SARS-CoV-2 can be exploited by appropriately dosing light (Fluence=$J/cm^2$) and frequency of administration to safely stimulate intracellular nitric oxide production. Nitric oxide antiviral activity is dose dependent, so the most appropriate dosage is believed to be one at or near the maximum amount of phototherapeutic light that causes no visible adverse effects on the tissue, or elevation of systemic biomarkers of clinical toxicity during routine blood chemistry and hematology testing, is observed.

Representative dosing parameters include single and/or multiple exposures of 5 $J/cm^2$, 10 $J/cm^2$, 20 $J/cm^2$, or 30 $J/cm^2$, among other doses described herein, and repeat exposures once weekly, three times weekly, or once daily, or twice daily for a period of one or more days, up to two or more weeks.

Nitric oxide is a well-known and extensively researched molecule naturally present in the body. It primarily interacts with hemoglobin to form methemoglobin which denies oxygen transport. The known effects of methemoglobinemia and elevated nitrate levels are routinely observed and monitored in the clinical exploration of inhalable nitric oxide gas. These markers enable continuous patient safety monitoring. Adverse effects of gaseous nitric oxide are well known and can be mitigated by decreasing dosing upon observation of rising methemoglobin levels (>5%). Pulse co-oximetry provides a method to noninvasively and continuously measuring methemoglobin in the blood. Blood nitrate levels are also a well-known metabolite of nitric oxide within the body and can be used to monitor safety and avoid adverse effects. The toxicological consequences of elevated NOx species and MetHb have been extensively studied.

The following are desirable clinical endpoints from the use of the methods described herein:

Resolution of infection, virus undetectable at 7 days, 14 days, and/or 28 days.

Reduction in the proportion of early stage patients who progress to a severe form of the disease defined as: SpO2 <93% without oxygen supplementation sustained for more than 12 hours; or, PaO2/FiO2 ratio <300 mmHg sustained for more than 12 hours; or, necessity of high flow nasal cannula oxygen or intubation and mechanical ventilation or ECMO therapy over 7 days, 14 days, 28 days.

Reduction in the percentage of patients developing worsening symptoms, resulting from passage of viral particles from the oral cavity to the lungs.

Reduction in the percentage of patients developing SARS.

Increase in overall survival at 7 days, 14 days, 28 days, and 90 days.

Based on the discussion above, the treatment and/or prevention methods involve applying light at a sufficient wavelength to one or more regions of the oral cavity or auditory canal, or the throat, larynx, pharynx, oropharynx, esophagus and/or trachea of a patient, at a sufficient power, and for a sufficient period of time, to kill coronavirus, and thus prevent a pulmonary coronavirus infection. The same approach can be used to prevent respiratory infection by other viruses, such as influenza viruses, that are present in the oral cavity, but have not yet traveled to the lungs in sufficient numbers to result in infection.

In one embodiment, intense blue light, typically between 400 and 500 nm, and preferably at around 400-430 nm, such as 405 nm or 415 nm, can be used. A combination of 405 nm blue light and 880 nm infrared light can also be used. In aspect of this embodiment, light at wavelengths of 450-495 nm is used. Although blue light is primarily discussed above, UVA, UVB, or UVC light can also be effective at treating coronaviridae infection, with UVC light being preferred. Exposure to light at these wavelengths can be damaging to tissue if carried out for extended periods of time. Ideally, tissue is not exposed to these wavelengths for periods of time that cause significant damage. That said, since UVA/UVB/UVC light and other wavelengths operate by different mechanisms, specific wavelengths of visible light can also be used, alone or in combination with UVA/UVB/UVC light.

The light can be administered anywhere along the oral cavity, auditory canal, or throat, larynx, pharynx, oropharynx, trachea, or esophagus, depending on the status of the patient's infection. If the virus is not present in large quantities in the lung, and is largely limited to the patient's mouth, nose, and throat, phototherapy limited to those regions can prevent a respiratory infection. This approach can also be used in a prophylactic manner for patients at risk for developing a coronaviridae infection, by virtue of having been, or suspected of having been, in contact with individuals with a coronaviridae infection.

In addition to administering light at wavelengths that are antimicrobial, light can also, or alternatively, be administered at wavelengths that are anti-inflammatory. Such wavelengths can inhibit inflammation of the nasal passages or in the mouth, which can further help prevent the infection from spreading to the lung. Anti-inflammatory wavelengths, particularly in the nasal passages, can also help prevent secondary infections, such as sinus infections, which can lead to bronchitis or pneumonia, which are caused by bacteria and which frequently follow viral infections. Minimization of the risk of secondary infection can, in some cases, be even more important than treatment of the underlying viral infection.

It can be important to follow the course of treatment, particularly where a patient has an active infection that has not yet travelled to the lungs in a sufficient manner to result in pulmonary infection. The patient could experience severe adverse consequences if the prevention is not successful, so it can be important to monitor the progression of the disease.

Methods of following the progress of the treatment include taking periodic readings with a pulse oximeter and taking periodic chest X-Rays/ultrasounds/CT scans. One can also check for residual microbial infection, for example, using ELISA tests, or other tests which look for antibodies specific to certain microbial infections, as well as analyzing blood or sputum samples for residual infection. A patient's body temperature can be followed as well, particularly for following the treatment of microbial infections in the short-term.

The delivery of safe, visible wavelengths of light can be an effective, pathogen-agnostic, antiviral therapeutic countermeasure that would expand the current portfolio of intervention strategies for SARS-CoV-2 and other respiratory viral infections beyond the conventional approaches of vaccine, antibody, and drug therapeutics. Employing LED arrays, specific wavelengths of visible light may be harnessed for uniform delivery across various targeted biological surfaces. In certain aspects of the present disclosure, it is demonstrated that primary 3D human tracheal/bronchial-derived epithelial tissues exhibited differential tolerance to light in a wavelength and dose-dependent manner. Primary 3D human tracheal/bronchial tissues tolerated high doses of 425 nm peak wavelength blue light. These studies were extended to Vero E6 cells to provide understanding of how light may influence viability of a mammalian cell line conventionally used for assaying SARS-CoV-2. Exposure of single-cell monolayers of Vero E6 cells to similar doses of 425 nm blue light resulted in viabilities that were dependent on dose and cell density. Doses of 425 nm blue light that are well-tolerated by Vero E6 cells, also inhibited SARS-CoV-2 replication by greater than 99% at 24 hours post-infection after a single five-minute light exposure. Red light at 625 nm had no effect on SARS-CoV replication, or cell viability, indicating that inhibition of SARS-CoV-2 replication is specific to the antiviral environment elicited by blue light. Moreover, 425 nm visible light inactivated up to 99.99% of cell-free SARS-CoV-2 in a dose-dependent manner. Importantly, doses of 425 nm light that dramatically interfere with SARS-CoV-2 infection and replication are also well-tolerated by primary human 3D tracheal/bronchial tissue. In this regard, safe, deliverable doses of visible light may be considered part of a strategic portfolio for development of SARS-CoV-2 therapeutic countermeasures to prevent coronavirus disease 2019 (COVID-19).

Among other approaches for treating SARS-CoV-2 infection, there are nucleoside analogs such as Remdesivir, and convalescent plasma, both separately demonstrated to shorten time to recovery for Covid-19 patients; and the glucocorticoid, dexamethasone, was demonstrated to lower the mortality rate in individuals receiving oxygen alone or mechanical ventilation support. To curb the long timelines associated with clinical safety and efficacy trials for traditional drug therapeutics, researchers are briskly working to evaluate FDA-approved drug therapeutics against SARS-CoV-2. Although encouraging, many of the current strategies are SARS-CoV-2 specific and target the virus either outside (cell-free virus), or inside the cell (cell-associated, replicating virus). Expanding the therapeutic armory beyond conventional strategies may expedite the availability of therapeutic countermeasures with non-specific antiviral properties that can inactivate cell-free and cell-associated virus.

Light therapy has the potential to inactivate both cell-free and cell-associated viruses, including coronaviridae and orthomyxoviridae. Mitigating SARS-CoV-2 infection with light therapy requires knowledge of which wavelengths of light most effectively interfere with viral infection and replication, while minimizing damage to host tissues and cells. A large body of literature demonstrates that ultraviolet light, predominantly UVC at the 254 nm wavelength, is highly effective at inactivating cell-free coronaviruses on surfaces, aerosolized, or in liquid. UVC inactivates coronaviruses, as well as many other RNA and DNA viruses, through absorption of UVC photons by pyrimidines in the RNA backbone, leading to the formation of pyrimidine dimers that preclude replication of the coronavirus genome. UVC is also highly damaging to replicating mammalian cells, causing perturbations in genomic DNA that can increase the risk of mutagenic events. As such, viral inactivation with UV light is primarily limited to cell-free environmental applications. In the present disclosure, inactivating coronaviridae with safe, visible light (e.g., above 400 nm) is presented as a new approach to interfering with SARS-CoV-2 infection and replication.

Photobiomodulation (PBM), or light therapy, is an approach to mitigate outcomes of viral infection in mammals, such as humans. PBM may also refer to phototherapy as disclosed herein. PBM is the safe, low-power, illumination of cells and tissues using light-emitting diodes (LED's) or low-level laser therapy (LLLT) within the visible/near-infrared spectrum (400 nm-1050 nm). Importantly, the therapeutic effect is driven by light's interaction with photoacceptors within the biological system, and is not to be confused with photodynamic therapy (PDT), which employs the exogenous addition of photosensitizers or chemicals to induce reactive oxygen species (though the addition of photosensitizers or other chemicals to induce reactive oxygen species is another embodiment within the scope of the methods described herein).

The safe and effective use of blue light PBM in the 450-490 nm range was adopted for mainstream clinical use in the late 1960's to treat jaundice in neonates caused by hyperbilirubinemia, and continues to be employed in hospitals today as a primary treatment for hyperbilirubinemia. According to aspects of the present disclosure, changing the wavelengths of visible light based on targeted applications can broaden the scope of therapeutic applications. Studies also indicate that PBM with visible light may function to inactivate replication of RNA and DNA viruses in vitro. Importantly, several studies demonstrate that PBM therapy can be safely applied to the oral and nasal cavities to treat a spectrum of illnesses. As disclosed herein, PBM therapy in the oral and nasal cavities, as well as in the lungs or endothelial tissues, may be an effective means of mitigating replication of SARS-CoV-2 in the upper respiratory tract, so long as it can be done at doses which do not significantly affect the viability of the tissues being treated. A deeper exploration of the precise selection of optical irradiance (e.g., in mW/cm$^2$) combined with one or more monochromatic wavelengths of visible light can broaden the scope of therapeutic applications in respiratory medicine.

In this regard, embodiments of the present disclosure are provided that describe the first use of safe, visible wavelengths of blue light at low powers (<100 mW/cm$^2$) to inactivate both cell-free and cell-associated SARS-CoV-2 in in vitro cell-based assays. Importantly, doses of blue light that effectively inactivate SARS-CoV-2 are well-tolerated by primary human tracheal/bronchial respiratory tissues.

In order to evaluate the safety of visible light on cells and tissues in vitro and the efficacy of visible light in SARS-CoV-2 infectious assays, careful designs of LED arrays having narrow band emission spectra with peak wavelengths at 385 nm, 405 nm, 425 nm, and 625 nm wavelengths are provided and summarized in FIGS. 59A and 59B. In this manner, LED arrays may be properly calibrated to provide repeatable and uniform doses of light so that illumination may occur reliably across many assays and in multiple laboratories. Measuring the full emission spectrum around the peak emission wavelength is necessary to confirm proper function for each LED array and the photon density per nanometer. In this regard, such measurements are recommended as an important characterization step to help harmonize the variability of results published in literature. FIG. 59A is a chart 5900 illustrating measured spectral flux relative to wavelength for different exemplary LED arrays. Each LED array was independently characterized by measuring the spectral flux, which may be measured in W/nm, relative to the wavelength (nm). In FIG. 59A, an LED array with a peak wavelength of 385 nm is clearly within the upper bounds of the UVA spectrum (315-400 nm), whereas only a small amount (e.g., about 10%) of an LED array with a peak wavelength of 405 nm light extends into the UVA spectrum, and an LED array with a peak wavelength of 425 nm light is 99% within the visible light spectrum (400-700 nm). FIG. 59B illustrates a perspective view of a testing set-up 5910 for providing light from one or more LED arrays 5920 to a biological test article 5930. In addition to the design of the LED arrays 5920, including the emission spectrums, other important experimental conditions including a distance D of the LED arrays 5920 from the biological test article 5930 (e.g., 90 mm) an illumination power (e.g., 25 mW/cm$^2$ or 50 mW/cm$^2$ depending on the wavelength), and indicated doses (J/cm$^2$) were carefully calibrated to reduce any effects of temperature on the biological test articles 5930. Moreover, each LED array is validated to ensure that light is evenly distributed across multi-well tissue culture plates, such that the biological test articles in each replicate well receive uniform doses of light.

Understanding how target tissues in the upper airway tolerate blue light is central to the development of a light-derived antiviral approach for SARS-CoV-2. Initial evaluation of LED arrays was conducted on 3D tissue models developed from cells isolated from bronchial/tracheal region of a single donor. The 3D EpiAirway tissue models are 3-4 cell layers thick comprising a mucociliary epithelium layer with a ciliated apical surface. To assess the wavelength and doses of light most tolerated by these tissues, replicate tissue samples were exposed to 385 nm, 405 nm, or 425 nm light at various doses. Viability was assayed at 3 hours post-exposure using the indicated doses and wavelengths of light, and data is represented as +/−standard deviation. The percent viability of tissue was assessed using a well-established MTT cytotoxicity assay optimized for the 3D EpiAirway tissue models. FIG. 60A is a chart 6000 illustrating a percent viability for a peak wavelength of 385 nm for doses in a range from 0 to 120 J/cm$^2$. FIG. 60B is a chart 6010 illustrating a percent viability for a peak wavelength of 405 nm for the same doses of FIG. 60A. FIG. 60C is a chart 6020 illustrating a percent viability for a peak wavelength of 425 nm for the same doses of FIG. 60A. As illustrated in FIGS. 60A-60C, the percent viability of tissue was clearly impacted in a wavelength-dependent and a dose-dependent manner. Illumination with 385 nm light exhibited the most dramatic loss in viability with nearly a 50% decrease at a dose of 45 J/cm$^2$ (FIG. 60A). Light at 385 nm actually showed increased cell viability at doses of 15 J/cm$^2$. Although less dramatic, 405 nm exhibited a dose-dependent decrease in viability with greater than 25% loss at 60 J/cm$^2$ and about a 50% loss at 120 J/cm$^2$ (FIG. 60B). Notably, the 425 nm light was well tolerated at doses of light out to 120 J/cm$^2$ (FIG. 60C). Using 75% viability as a threshold level of acceptable cytotoxicity, 385 nm light may be safely administered to these tissues at power levels of up to 30 J/cm$^2$, and 405 nm light may be safely administered to these tissues at power levels of up to 45 J/cm$^2$, and 425 nm light may be safely administered to these tissues at power levels up to 120 J/cm$^2$ with only negligible loss of viability between 90 and 120 J/cm$^2$, and 425 nm doses up to around 75 J/cm$^2$ actually showed increased cell viability.

In this regard, 425 nm blue light is shown to have little or no impact on human upper airway-derived 3D tissue models. As such, longer wavelengths of visible light such as 425 nm and greater, that do not bleed into the UVA spectrum, may have reduced impact on tissue viability of primary human tissue derived from the upper respiratory tract. In particular, less than 20% tissue loss may be realized at higher doses with such longer wavelengths. Based on these studies visible blue light at 425 nm was chosen for subsequent evaluation in the widely available Vero E6 cell line, conventionally used to evaluate SARS-CoV-2 infection and replication.

Vero E6 cells are commonly used for preparing stocks, performing growth curves, and evaluating therapeutic countermeasures for SARS-CoV-2. Depending on the type of assay being performed it could be necessary to vary the seeding cell density and multi-well tissue culture plate format. Often, cell viability is evaluated to determine if the antiviral properties of a therapeutic can be parsed from potential therapeutic-induced cytotoxic effects. Experiments were performed to determine if cell density and multi-well plate format can influence cell viability upon exposure to 425 nm blue light. To effectively evaluate the cell viability, the cytotoxicity assay was optimized for use with Vero E6 cell densities up to $1 \times 10^6$ cells. Antiviral assays performed on 96 well plates are commonly evaluated at cell seeding densities of $1 \times 10^4$ and $2 \times 10^4$ cells.

FIG. 61A is a chart 6100 illustrating percent viability for Vero E6 cells for antiviral assays performed on 96 well plates at cell seeding densities of $1 \times 10^4$, $2 \times 10^4$, and $4 \times 10^4$ cells. Under these conditions, it is illustrated that 425 nm blue light may result in decreased cell viability (e.g., 25-50%) at doses of 30 J/cm$^2$ and 60 J/cm$^2$ by 24 hours post-illumination, whereas a seeding density of $4 \times 10^4$ cells tolerates high doses of light exposure. FIG. 61B is a chart 6110 illustrating percent viability for Vero E6 cells for antiviral assays performed on 48 well plates at cell seeding densities of $2\times10^4$, $4\times10^4$, and $8\times10^4$ cells. Unexpectedly, $4\times10^4$ cells seeded on a 48 well plate were not well tolerated, showing about a 50% reduction in cell viability at a dose of 60 J/cm$^2$ compared to $8\times10^4$ cells. These results demonstrated that the cell seeding density relative to the surface area of the culture well influences the susceptibility to 425 nm light. FIG. 61C is a chart 6120 illustrating percent viability for Vero E6 cells for antiviral assays performed on 24 well plates at cell seeding densities of $5\times10^4$, $1\times10^5$, and $2\times10^5$ cells. As illustrated, the 24 well plate format of FIG. 61C with cell seeding densities of $1\times10^5$ and $2\times10^5$ demonstrated acceptable viability at all doses tested. In contrast, illumination of Vero E6 cells to high doses of 625 nm light may have no impact on cell viability; thereby, indicating that cell density-dependent susceptibility of Vero E6 cells to 425 nm light appears to be characteristic of shorter wavelengths of light. Higher Vero E6 seeding densities resulted in 100% cell confluence prior to illumination, exhibiting cell-to-cell contact that mimics the 3D EpiAirway models. Thus, high confluence Vero E6 cell monolayers readily tolerate 425 nm blue light as well as 3D EpiAirway tissue models.

The use of visible light to inactivate cell-free and cell-associated coronaviridae is unprecedented. To assess the capability of 425 nm blue light to inactivate SARS-CoV-2, Vero E6 cells were infected with a multiplicity of infection (MOI) of 0.001 SARS-CoV-2 isolate USA-WA1/2020 for 1 hour. At 1-hour post-infection (h.p.i.) the cell-associated virus was treated with a single illumination of 425 nm blue light at doses ranging from 7.5 to 60 J/cm$^2$. FIG. 62A is a chart 6200 illustrating tissue culture infectious dose (TCID$_{50}$) per milliliter (ml) for the 425 nm light at the doses ranging from 7.5 to 60 J/cm$^2$ for the Vero E6 cells infected with a MOI of 0.001 SARS-CoV-2 isolate USA-WA1/2020 for 1 hour. At 24-hours post-infection (h.p.i), there was a clear dose-dependent decrease in SARS-CoV-2 TCID$_{50}$/ml. Low doses of 425 nm light were sufficient to reduce SARS-CoV-2 by at least 2 logs for 7.5 J/cm$^2$, at least 3 logs for 15 J/cm$^2$, and at least a 5 log reduction for 30 J/cm$^2$. A similar trend was observed at 48 h.p.i., although continued viral replication may account for the similarity in TCID$_{50}$/ml observed at low doses between 7.5 J/cm$^2$ and 15 J/cm$^2$. This data demonstrates that 425 nm blue light interferes with SARS-CoV-2 replication in a dose-dependent manner. Specific TCID$_{50}$/ml values are presented to demonstrate data trends and data values relative to on another, the actual values may vary from lab to lab and are not meant to be limiting. FIG. 62B is a chart 6210 illustrating percent reduction in SARS-CoV-2 replication versus percent cell cytotoxicity for the doses of light as illustrated in FIG. 62A. At doses of light that have little impact on the viability of Vero E6 cells (e.g., 7.5, 15, and 30 J/cm$^2$), up to a 99.99% reduction in SARS-CoV-2 replication was observed. Notably, cell viability was a bit lower at 45 J/cm$^2$ and 60 J/cm$^2$ than the data shown in FIGS. 60A-60C; however, slight variations in the cytotoxicity assay are anticipated since the SARS-CoV-2 experiments were executed in independent laboratories with differences in cell seeding, cell passage, and cell media.

FIGS. 63A and 63B represent experimental data similar to FIGS. 62A and 62B, but with the MOI increased to 0.01. FIG. 63A is a chart 6300 illustrating TCID$_{50}$/ml for 425 nm light at doses ranging from 7.5 to 60 J/cm$^2$ for Vero E6 cells infected with a MOI of 0.01 SARS-CoV-2 isolate USA-WA1/2020 for 1 hour. Specific TCID$_{50}$/ml values are presented to demonstrate data trends and data values relative to on another, the actual values may vary from lab to lab and are not meant to be limiting. FIG. 63B is a chart 6310 illustrating percent reduction in SARS-CoV-2 replication versus percent cell cytotoxicity for the doses of light as illustrated in FIG. 63A. As illustrated, increasing the MOI to 0.01 yielded a similar dose-dependent reduction in SARS-CoV-2 replication as previously illustrated for the MOI of 0.001 of FIGS. 62A and 62B. Despite increasing the amount of input virus 10-fold (e.g., from MOI 0.001 to MOI 0.01), a short, 2.5 minute dose of 7.5 J/cm$^2$ with 425 nm blue light still demonstrated reduction in SARS-CoV-2 replication by at least 2-logs at 24 h.p.i.

FIG. 63C is a table 6320 showing an evaluation of SARS-CoV-2 RNA with reverse transcription polymerase chain reaction (rRT-PCR) for samples collected for the TCID$_{50}$ assays of FIGS. 63A-63B. The cycle number for detection is the basic test result and may be referred to as a quantification cycle (Cq) where low Cq values represent higher initial amount of the target. As shown, there is a dose-dependent reduction in SARS-CoV-2 genomic RNA; further substantiating the impact of 425 nm light on SARS-CoV-2. The fold reduction between doses of 425 nm light with rRT-PCR test detection is lower than those observed for replication competent virus (TCID$_{50}$ detection), indicating that SARS-CoV-2 viral RNA is readily detectable despite decreases in infectious virions. These data imply that 425 nm blue light may have less of an impact on viral RNA replication and RNA packaging relative to the inactivation of virus particles.

FIGS. 64A and 64B represent experimental data similar to FIGS. 63A and 63B that was obtained by a second, independent laboratory evaluation using Vero 76 cells infected with a MOI of 0.01 at 48 h.p.i. FIG. 64A is a chart 6400 illustrating TCID$_{50}$/ml for 425 nm light at doses ranging from 7.5 to 60 J/cm$^2$ for Vero 76 cells infected with a MOI of 0.01 SARS-CoV-2. Specific TCID$_{50}$/ml values are presented to demonstrate data trends and data values relative to on another, the actual values may vary from lab to lab and are not meant to be limiting. FIG. 64B is a chart 6440 illustrating percent reduction in SARS-CoV-2 replication versus percent cell cytotoxicity for the doses of light as illustrated in FIG. 64A. Consistent with FIGS. 63A and 63B, a similar trend in the dose-dependent effects of 425 nm blue light on SARS-CoV-2 replication is observed in FIGS. 64A and 64B. Importantly, the dose-dependent trend showed similar log reductions despite differences in cell type (Vero 76), SARS-CoV-2 virus stock preparation, cell culture media, and viability assay.

To understand if the antiviral activity of light against SARS-CoV-2 is specific to 425 nm blue light, Vero E6 cells infected with a MOI of 0.01 were exposed to high doses red light. In this regard, FIG. 65 is a chart 6500 illustrating TCID$_{50}$/ml versus various doses of 625 nm red light for Vero E6 cells infected with a MOI of 0.01. Specific TCID$_{50}$/ml values are presented to demonstrate data trends and data values relative to on another, the actual values may vary from lab to lab and are not meant to be limiting. Extensive illumination times with doses ranging from 15 J/cm$^2$ to 240 J/cm$^2$ showed no reduction in TCID$_{50}$/ml at 24 h.p.i.; demonstrating that 425 nm blue light elicits a unique antiviral environment that results in SARS-CoV-2 inactivation. In this regard, light at 425 nm can be administered at effective, virucidal doses, which are relatively safe (e.g., less than 25% cytotoxicity) in VeroE6 cell lines, and at even higher doses in endothelial cells, like those found in the respiratory tract and all blood vessels. Red light may have little to no effect on SARS-CoV-2 replication, and/or enhances viral load, as measured by TCID$_{50}$ over 24/48 hours. However, red light may decrease inflammation resulting from exposure to blue light, which may positively impact cell viability, thereby lowering cytotoxicity. A decrease in inflammation can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Efficacy of 425 nm blue light against cell-associated SARS-CoV-2 can be a combination of blue light eliciting an antiviral environment in the cells and inactivating cell-free virions. To distinguish between these, FIGS. 66A and 66B represent cell-free SARS-CoV-2 inactivation that was evaluated by two independent laboratories. Two different virus suspensions containing the equivalent of ~$10^5$ and ~$10^6$ $TCID_{50}$/ml were illuminated with the indicated doses of 425 nm blue light. Following illumination, virus was assayed by $TCID_{50}$ on Vero E6 cells in a first laboratory as illustrated in a chart 6600 of FIG. 66A and on Vero 76 cells in a second laboratory as illustrated in a chart 6610 of FIG. 66B. As illustrated in FIG. 66A, in the first laboratory, low doses of 425 nm light were sufficient to inactivate $10^6$ $TCID_{50}$/ml SARS-CoV-2 with at least 1 log reduction at 7.5 J/cm² (or greater than 90%), with at least 2 log reduction at 15 J/cm² (or greater than 99%), with at least 3 log reduction at 30 J/cm² (or greater than 99.9%), and at least 4 log reduction at 60 J/cm² (or greater than 99.99%). A similar trend in the data was observed in the second laboratory for the Vero 76 cells as illustrated in FIG. 66B. Despite a less dramatic reduction in SARS-CoV-2 inactivation, at least a 2 log reduction was still observed at 60 J/cm² (or at least 99%). Technical differences between laboratories including SARS-CoV-2 virus stock preparation, cell culture media, and cell types used for assaying virus may be factors that influenced the magnitude of susceptibility. Overall, the results from two independent laboratories demonstrated that low doses of 425 nm blue light (e.g., ≤15 J/cm²) effectively inhibits the infection and replication of cell-free and cell-associated SARS-CoV-2, with minimal impact on cell viability. Specific $TCID_{50}$/ml values are presented to demonstrate data trends and data values relative to on another, the actual values may vary from lab to lab and are not meant to be limiting.

Figure 67A:
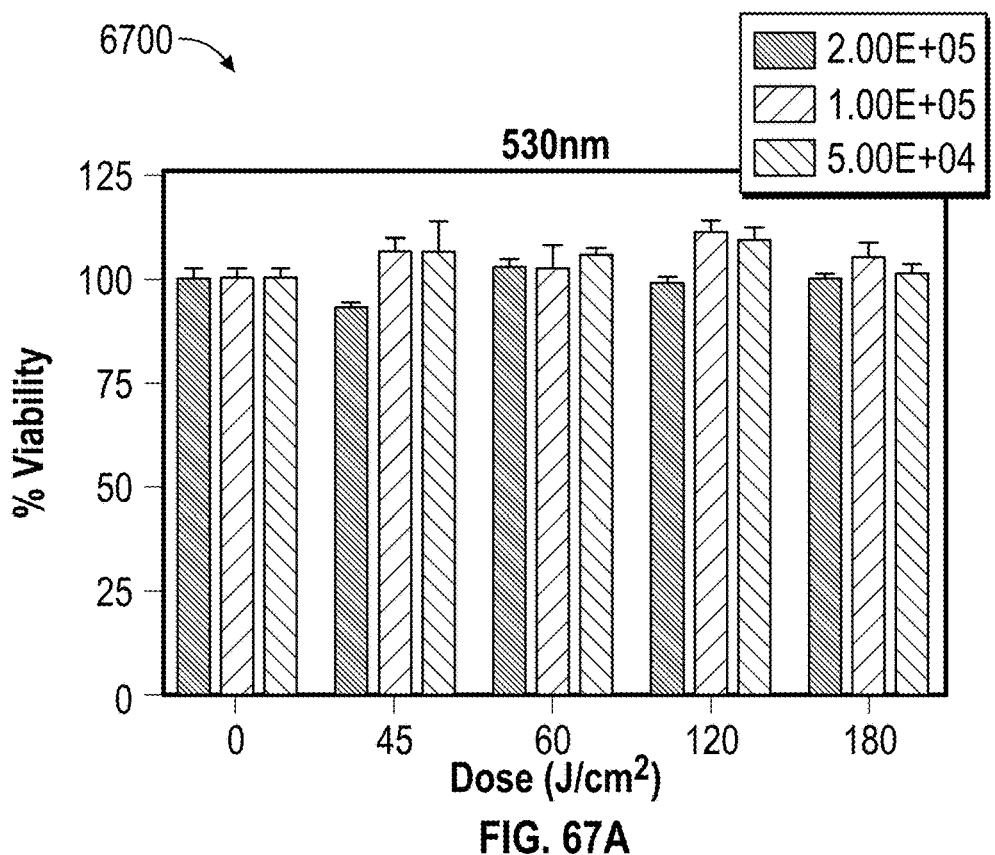
Figure 67B:
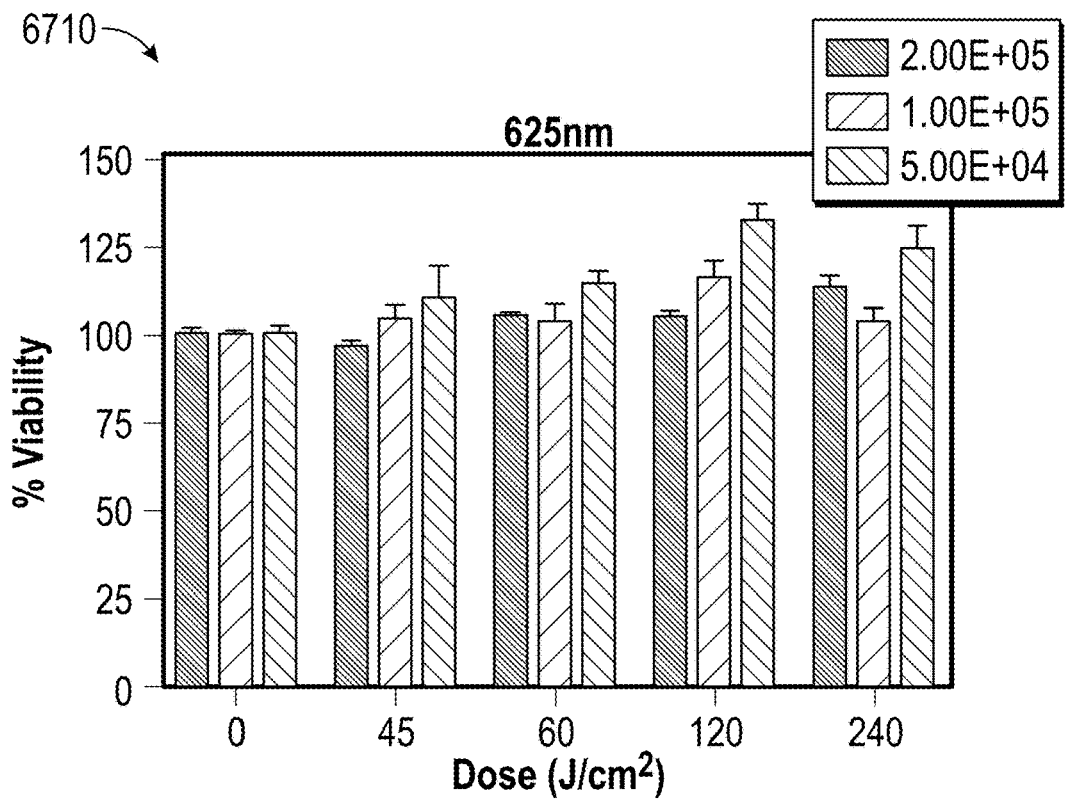

For completeness of collected data, FIGS. 67A and 67B are provided to show that Vero E6 cells do not exhibit decreased percent viability when exposed to doses of green light or doses of red light. In both FIGS. 67A and 67B, a number of cells was provided at $2 \times 10^5$ cells, $1 \times 10^5$ cells, and $5 \times 10^4$ cells. FIG. 67A is a chart 6700 indicating that Vero E6 cells do not show decreased viability under 530 nm light at doses ranging from 0-180 J/cm². FIG. 67B is a chart 6710 indicating that Vero E6 cells do not show decreased viability under 625 nm light at doses ranging from 0-240 J/cm².

The expedited need for therapeutic countermeasures against SARS-CoV-2 and other respiratory viral pathogens beckons the rapid development of novel approaches that may complement existing public health measures. As disclosed herein, LED arrays were carefully designed to demonstrate for the first time that safe, visible blue 425 nm light, can inhibit both cell-free and cell-associated SARS-CoV-2 infection and replication in a dose-dependent manner. Results from two independent laboratories demonstrate that low doses of 425 nm blue light (e.g., ≤15 J/cm²) effectively inhibit infection and replication of SARS-CoV-2 (e.g., >99%), with minimal impact on Vero E6 cell viability. Importantly, doses of 425 nm light ≤60 J/cm² were well tolerated in the 3D EpiAirway tissue models established from human tracheal/bronchial tissues.

The EpiAirway model is a commercially available in vitro organotypic model of human mucociliary airway epithelium cultured at the air/liquid interface to provide a differentiated in vivo-like epithelial structure with barrier properties and metabolic functions. There is strong global momentum to replace animal model testing with relevant in vitro human-derived test systems to reduce the number of animals used in preclinical testing. Current testing guidelines (TG403, TG433, and TG436), established by the Organization for Economic Co-operation and Development (OECD), for inhalation toxicity outline the use of animals to determine $LC_{50}$ (e.g., a concentration required to cause death of 50% of the test animals). The EpiAirway in vitro tissue model can be used to determine the $IC_{25}$ value (concentration required to reduce tissue viability by 25% of vehicle control-treated tissues) of a test article. Following 3-hours of exposure, the model have been shown to predict respiratory tissue viability using chemicals with the Globally Harmonized System (GHS) Acute Inhalation Toxicity Category 1 and 2, and Environmental Protection Agency (EPA) Acute Inhalation Toxicity Category I-II classifications. Extended exposure times (e.g., 24 and 72 hours) with toxic chemicals also reflect in vivo responses, have demonstrated the predictive value of the EpiAirway models for respiratory toxins in humans. Furthermore, such a uniform in vitro model is ideally suited to evaluate the safety doses of light applied to a fixed surface area (e.g., in J/cm²), rather than attempting to scale the optical delivery of light to the appropriate small rodent anatomy.

As previously shown in FIGS. 60A-60C, the EpiAirway model was exposed to various dose ranges at light with wavelengths of 385 nm, 405 nm, and 425 nm. Exposure to UVA light at 385 nm exhibited greater than 25% loss in viability at greater than 45 J/cm², identifying a dose that breaches the $IC_{25}$ threshold established for acute cytotoxicity in the EpiAirway model. In contrast, higher doses of the 425 nm blue light doses reached the $IC_{25}$ threshold for validated acute airway irritation. Greater than 100% tissue viability was observed following illumination with antiviral (e.g., >99.99% reduction in SARS-CoV-2) 425 nm blue light doses of 60 J/cm². The distinct viability profiles observed at 385 nm, 405 nm, and 425 nm demonstrate that the 3D EpiAirway tissue models are amenable for identifying acute respiratory effects associated with light therapy in a dose- and wavelength-dependent manner. Minimal loss in viability out to 120 J/cm² at 425 nm indicates that the 3D human respiratory tissue models are highly tolerant to this wavelength. In FIGS. 61A to 61C, 2D Vero E6 cell cultures exhibited a cell density-dependent viability response to 425 nm doses at greater than or equal to 15 J/cm², wherein low seeding densities per surface area were more susceptible to light induced cytotoxic effects. The enhanced tolerance of the 3D EpiAirway tissue models to 425 nm blue light compared to 2D Vero E6 cell cultures is not surprising, given that cells in 3D culture are often more resistant to drug treatment, drug metabolism is more effective, and there is increased resistance to drug-induced apoptosis. The characteristics of 3D tissue models more closely reflect cellular attributes observed in the context of tissues in vivo. Developing optimal conditions for SARS-CoV-2 infection and replication in 3D respiratory tissue models will help elucidate mechanisms that govern the ability of 425 nm blue light to inactivate SARS-CoV-2.

The mechanisms underlying 425 nm blue light to inactivate SARS-CoV-2 are still being developed; however, a brief introduction to putative molecular contributors is relevant. The molecular mechanisms governing the impact of blue light on non-pigmented cells are only beginning to be revealed. The effects of blue light should follow the first law of photochemistry, which states that light must be absorbed to have an effect. A handful of photoacceptors for blue light have been identified in non-pigmented cells, including cytochrome c oxidase, flavins, porphyrins, opsins, and nitrosated proteins. Light absorption by photoreceptors can lead to release of reactive oxygen species (ROS) and/or nitric oxide (NO) that may function to inactivate SARS-CoV-2 in a cell-free or cell-associated environment. Reactive oxygen species and/or bioactive NO may elicit activation of transcription factors involved in immune signaling, such as nuclear factor kappa-light-chain-enhancer of activated B cells (NF-κB) and mitogen activated protein kinase (MAPK) signaling. NFκB and MAPK pathways can lead to transcriptional activation of innate and inflammatory immune response molecules that may interfere with SARS-CoV-2 replication. Nitric oxide may also mediate inactivation of cell-associated SARS-CoV-2 through S-nitrosylation of cysteine residues in the active site of viral encoded enzymatic proteins. Reactive oxygen species and/or NO may also function to inactivate cell-free virions. Photosensitizers present in cell media may facilitate generation of ROS and/or NO that directly impact virion proteins and/or viral RNA to prevent infection and replication. It has also been demonstrated that inactivation of cell-free feline calicivirus (FCV) by 405 nm light was dependent on naturally occurring photosensitizers in media. Importantly, FCV was inactivated by 4 logs in artificial saliva and blood plasma, indicating that light-induced inactivation of cell-free virus is obtainable under biologically-relevant conditions. Evidence demonstrating that SARS-CoV can be inactivated by exogenous addition of NO donor molecules, or possibly by single oxygen substantiate the potential for SARS-CoV-2 inactivation by nitric oxide.

In the above described experiments, materials and methods are provided in more detail below for reference. With regard to cells, tissues, and viruses, Vero E6 cells were purchased from ATCC and maintained in DMEM (Sigma-Aldrich) supplemented with 10% FetalClonell (HyClone) and 1% Antibiotic-Antimycotic (Gibco). Vero 76 cells (ATCC CRL-1587) were maintained in MEM supplemented with 2 mM L-glutamine and 5% FBS. Primary human airway epithelium (EpiAirway AIR-100, MatTek Corporation) were cultured for 28 days in transwell inserts by MatTek Corporation. The cultured tissues were shipped in 24 well plates with agarose embedded in the basal compartment. Upon arrival, the transwell inserts were removed and placed in 6-well plates with cold Maintenance Media in the basal compartment; no media added to the apical surface. Cells were incubated at 37° C. and 5% $CO_2$ overnight prior to experimental use. All work with live virus was conducted in two independent Biosafety Level-3 (BSL-3) laboratories, MRI Global's Kansas City facility and the Institute for Antiviral Research at Utah State University, with adherence to established safety guidelines. At both laboratories, SARS-CoV-2 (USA_WA1/2020) was obtained from the World Reference Center for Emerging Viruses and Arboviruses (WRCEVA) and propagated with slight modifications. At MRI Global, Vero E6 cells were cultured overnight with DMEM (Gibco; 12320-032) supplemented with 10% FBS (Avantor, 97068-085), 1% nonessential amino acids (Corning 25-025-CI), and 1% penicillin/streptomycin (VWR 97063-708). To generate master stocks, cells were infected prior to infection with an approximate MOI of 0.08 in infection media (as above with 5% FBS). Cells were monitored for cytopathic effects daily and harvested at 4 days post-infection as CPE approached 100%. Working stocks were cultured in Vero E6 cells with DMEM/F12 media (Gibco; 11330-032) supplemented with 10% FBS and 1% penicillin/streptomycin at an MOI of 0.005. Cells were monitored for CPE and harvested two days post-infection as CPE approached 70%. Cell culture debris was pelleted by centrifugation at 500×g for 5 min and viral stocks were stored at −80° C. Infectivity of viral stocks was determined by $TCID_{50}$ assay. At Utah State University, SARS-CoV-2 (USA_WA1/2020) was propagated in Vero 76 cells. Infection media was Minimal Essential Media supplemented with 2 mM I-glutamine, 2% FBS, and 50 μg/mL gentamicin.

For cytotoxicity assays for human tissues, prior to illumination, the maintenance media was changed on the human tissue transwell inserts. Tissues were illuminated with 385 nm, 405 nm, or 425 nm light and incubated at 37° C. and 5% $CO_2$ for 3 hours. Cytotoxicity was determined using the EpiAirway MTT assay following manufacturer's instructions. Briefly, tissues were rinsed with TEER buffer and placed into pre-warmed MTT reagent and incubated at 37° C. and 5% $CO_2$ for 90 min. The MTT solution was extracted with MTT extractant solution by shaking for 2 hours. The tissue inserts were discarded and the extractant solution was added to a 96 well plate to be read at 570 nm. Extractant solution served as the experimental blank and cell viabilities were calculated against plates that were not illuminated.

For cytotoxicity assays for cell lines, Vero E6 cells were incubated in clear 24-well, 48-well, and 96-well plates (Corning) at varying seeding densities and incubated at 37° C. and 5% $CO_2$ overnight. Cells were illuminated with 385 nm, 405 nm, or 425 nm light and incubated at 37° C. and 5% $CO_2$ for 24 hours post-illumination. After 24 hours, cytotoxicity was determined using the CellTiterGlo One Solution (Promega) with modifications. The amount of CellTiterGlo One Solution ("CTG") was optimized in a preliminary experiment. For 24 well plates, 100 μl solution was used and 60 μl solution was used for 48 and 96 well plates. The cells were placed on an orbital shaker for 2 min and the chemiluminescent signal was stabilized for 10 min before 50 μl of the solution was added to a black well, black bottom 96-well plates and read using the CellTiterGlo program on the GloMax (Promega). CellTiterGlo One solution served as a blank and cell viabilities were calculated against plates that were not illuminated.

Cytotoxicity analysis was conducted at 48 hours post-illumination. Cells were treated for 2 hours with 0.01% neutral red for cytotoxicity. Excess dye was rinsed from cells with PBS. Absorbed dye was eluted from the cells with 50% Sorensen's citrate buffer/50% ethanol for 30 minutes. Buffer was added to 10 wells per replicate. Optical density was measured at 560 nm and cell viabilities were calculated against cells that were not illuminated.

Antiviral assays were conducted in separate laboratories with modifications. At MRI Global, cells were infected with SARS-CoV-2 at multiplicity of infections (MOI) of 0.01 and 0.001 in triplicate. At one-hour post-infection, infected cells were illuminated with 425 nm light at the specified doses. Cell culture supernatants were harvested at 24 hours and 48 hours post-infection to for $TCID_{50}$ determination and qPCR analysis. No illumination controls and no virus controls were included as a positive control for viral growth and for cytotoxicity, respectively. Cytotoxicity analysis was conducted at 24 hours post-illumination as above.

Vero 76 cells were infected with SARS-CoV-2 at MOIs of 0.01 and 0.001. At one-hour post-infection, infected cells were illuminated with 425 nm light at the specified doses. Cell culture supernatants were harvested at 48 h post-infection for $TCID_{50}$ determination. No illumination controls and no virus controls served as a positive control for viral growth and for cytotoxicity, respectively. Cytotoxicity analysis was conducted at 48 hours post-illumination.

Virucidal assays were conducted in parallel in separate laboratories. At one laboratory, 1 mL solutions containing $10^5$ and $10^6$ $TCID_{50}/ml$ were illuminated with varying doses of light. The viruses were then tittered on Vero E6 cells in triplicate via $TCID_{50}$ assay. No illumination controls served as a positive control for viral growth.

At a second laboratory, 1 mL solutions containing $10^5$ and $10^6$ $TCID_{50}/ml$ were illuminated with varying doses of light. The viruses were then tittered on Vero 76 cells in triplicate via $TCID_{50}$ assay. No illumination controls served as a positive control for viral growth.

Viral RNA levels for SARS-CoV-2 samples were determined by quantitative RT-PCR using the CDC N1 assay. Samples for the RT-PCR reactions were live virus in culture supernatants without nucleic acid extraction. Primers and probes for the N1 nucleocapsid gene target region were sourced from Integrated DNA Technologies (2019-nCoV CDC RUO Kit, No. 10006713). TaqPath 1-step RT-qPCR Master Mix, CG was sourced from ThermoFisher (No. A15299). Reaction volumes and thermal cycling parameters followed those published in the CDC 2019-Novel Coronavirus (2019-nCoV) Real-Time RT-PCR Diagnostic Panel: Instructions for Use. For the RT-PCR reaction, 15 mL of prepared master mix was added to each well followed by 5 mL of each sample, for a final total volume of 20 mL per reaction well. Reactions were run on a Bio-rad CFX real-time PCR instrument.

$TCID_{50}$ assays were conducted as follows at both laboratories with slight modifications. At one laboratory, Vero E6 cells were plated in 96 well plates at 10,000 cells/well in 0.1 ml/well of complete medium (DMEM/F12 with 10% fetal bovine serum and 1× Penicillin/Streptomycin) and incubated overnight in a 37° C., 5% $CO_2$ humidified incubator. The next day virus samples were serially diluted into un-supplemented DMEM/F12 media at 1:10 dilutions by adding 0.1 ml virus to 0.9 ml diluent, vortexing briefly and repeating until the desired number of dilutions was achieved. Media was decanted from 96 well plates and 0.1 ml of each virus dilution aliquoted into 5 or 8 wells. After 4 days of incubation at 37° C., 5% $CO_2$, plates were scored for presence of cytopathic effect. $TCID_{50}/ml$ were made using the Reed & Muench method. At the second laboratory, cell culture samples were serially diluted and plated on fresh Vero 76 cells in quadruplicate. Plates were visually examined for CPE at 6 days post-infection. Wells were indicated as positive or negative and virus titers were calculated using the Reed-Muench endpoint dilution method.

Figure 68A:
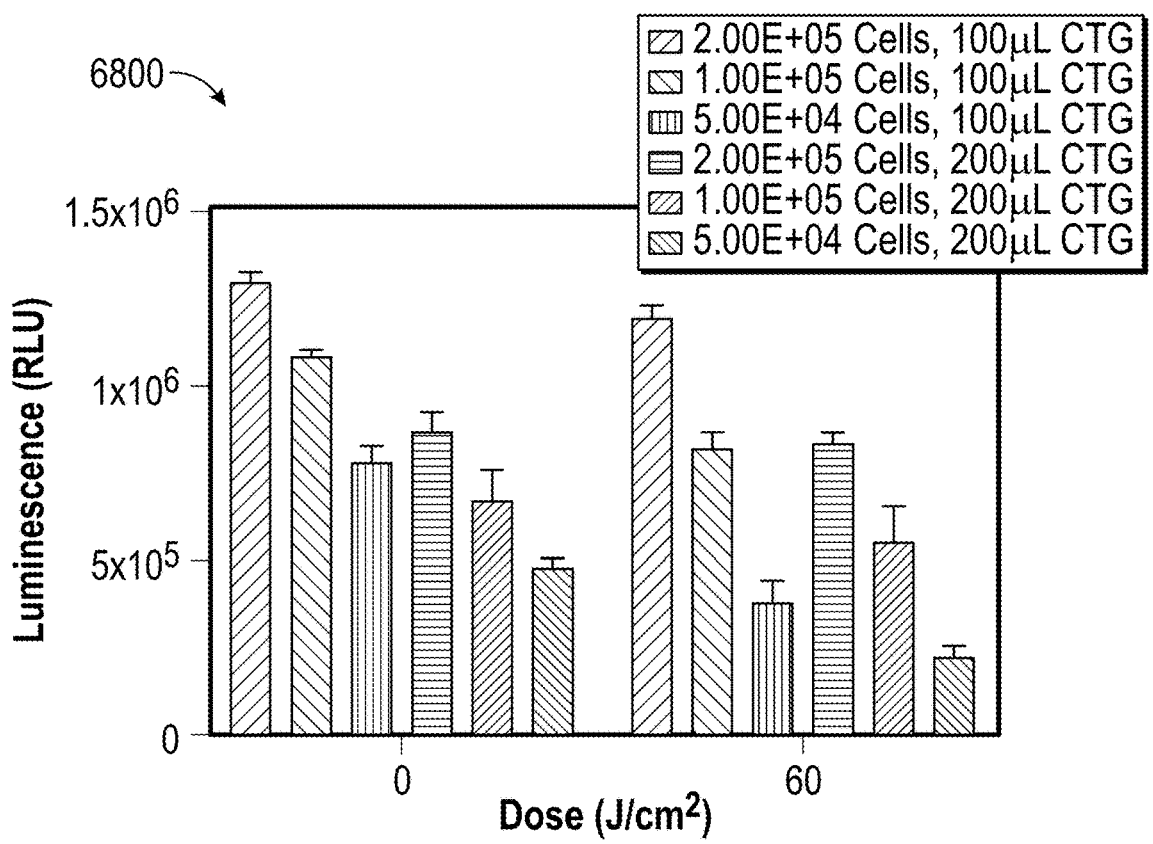
Figure 68B:
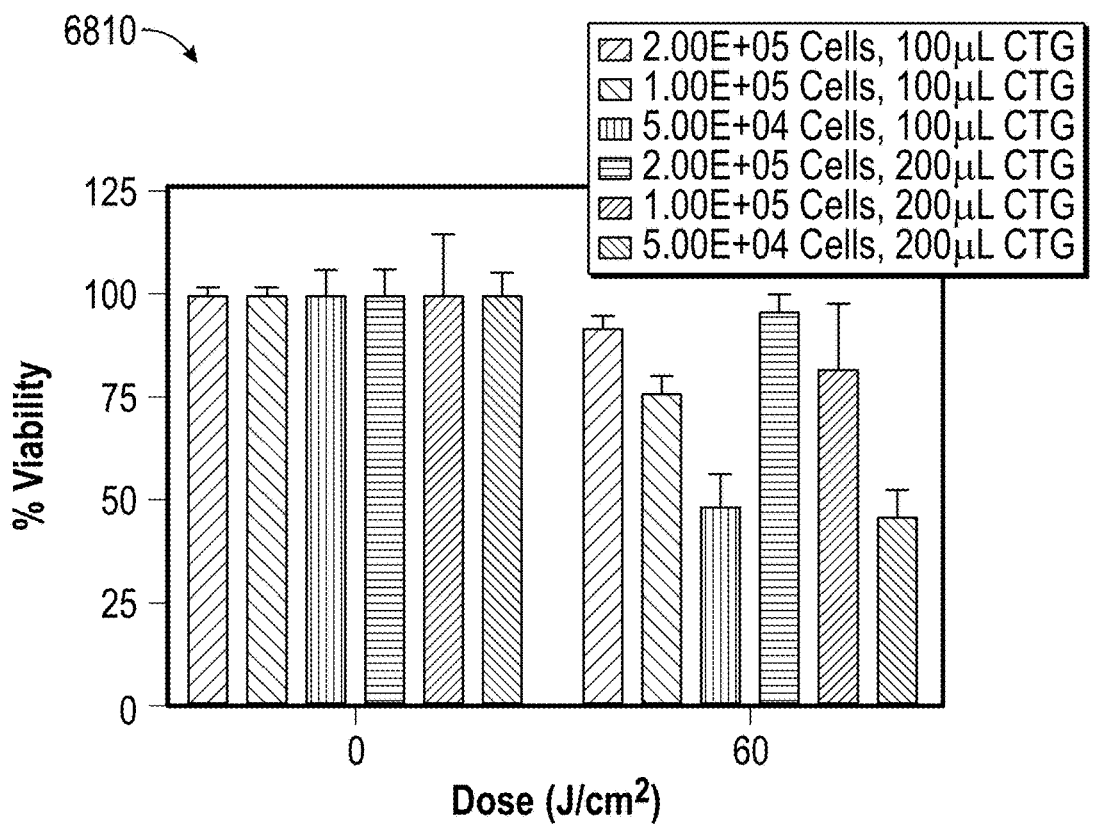
Figure 68C:
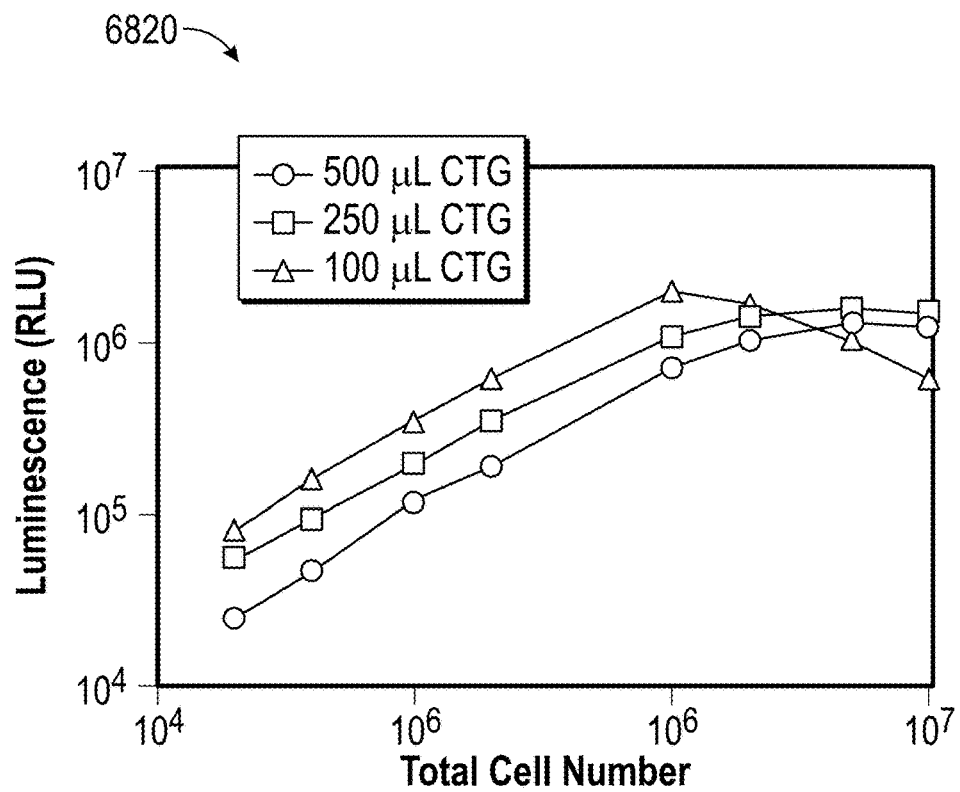

FIG. 68A is a chart 6800 showing raw luminescence values (RLU) for different seedings of Vero E6 cell densities and various doses of light ($J/cm^2$). FIG. 68B is a chart 6810 showing percent viability for the different seedings of Vero E6 cell densities and various doses of light of FIG. 68A. FIG. 68B indicates the viability of Vero E6 cells may not reach saturation until cell densities are above $10^6$ cells. RLU and percent viability based on the various doses of light demonstrate that both 100 μL and 200 μL of CellTiter-Glo (CTG) are effective volumes for measuring cell viability after seeding different Vero E6 cell densities. For FIGS. 68A and 68B, cell densities of $2\times10^5$ cells with 100 μL CTG, $1\times10^5$ cells with 100 μL CTG, $5\times10^4$ cells with 100 μL CTG, $2\times10^5$ cells with 200 μL CTG, $1\times10^5$ cells with 200 μL CTG, and $5\times10^4$ cells with 200 μL CTG are represented. FIG. 68C is a chart 6820 comparing RLU versus total cell number to show that CTG is an effective reagent for measuring cell densities of above $10^6$ Vero E6 cells. RLU values versus total cell number are provided for 500 μL CTG, 250 μL CTG, and 100 μL CTG and data is represented as +/−standard deviation.

Figure 69A:
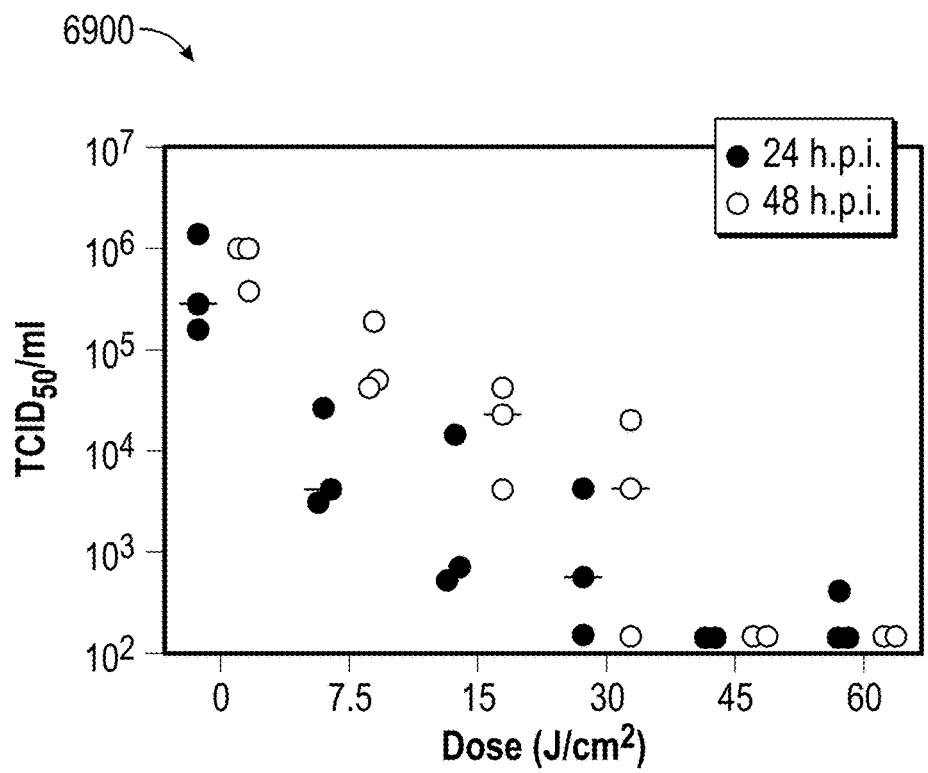
Figure 69B:
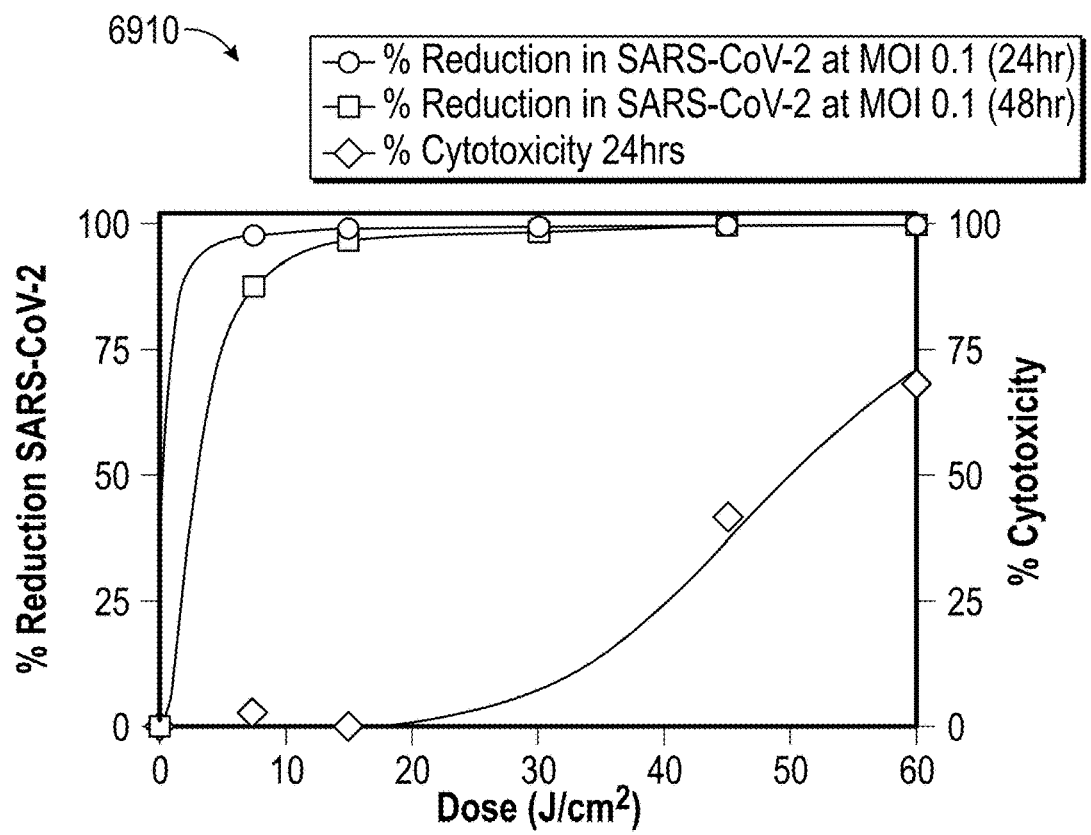

FIG. 69A is a chart 6900 of $TCID_{50}/ml$ versus dose at 24 hours and 48 hours post infection for Calu-3 cells infected with SARS-CoV-2. FIG. 69B is a chart 6910 showing the percent reduction in SARS-Cov-2 compared with percent cytotoxicity, for the Calu-3 cells of FIG. 69A. Specific $TCID_{50}/ml$ values are presented to demonstrate data trends and data values relative to on another, the actual values may vary from lab to lab and are not meant to be limiting. For FIG. 69B, the chart lines for percent reduction in SARS-Cov-2 and percent cytotoxicity are provided as nonlinear regression curves based on the doses illustrated in FIG. 69A. As shown, visible light at 425 nm inhibits viral replication of SARS-CoV-2 in the human respiratory cell line, Calu-3. The Calu-3 cells were infected with SARS-CoV-2 at an MOI of 0.1 and exposed to the indicated doses of 425 nm light at 1-hour post-infection. SARS-CoV-2 samples were harvested for $TCID_{50}$ assays at 24-hours and 48-hours post-infection. Greater than a 99% reduction in virus was observed following a single treatment for doses of 15 $J/cm^2$. Percent reduction in SARS-CoV-2 virus as shown in FIG. 69B was calculated for each dose and timepoint. As previously described, the SI (i.e., selectivity index) may be defined as ratio of the $CC_{50}$ to the $EC_{50}$ for treated cells. As shown in FIG. 69B, 50% percent reduction in SARS-CoV-2 at 24-hours and 48-hours post infection are indicated at relatively low dose values. In this regard, the doses of light that inhibit viral replication have a desirable selectivity index (SI) values of greater than 100 twenty-four hours post infection and greater than 25 when factoring in the cell viability of Calu-3 cells not infected with virus.

Figure 70A:
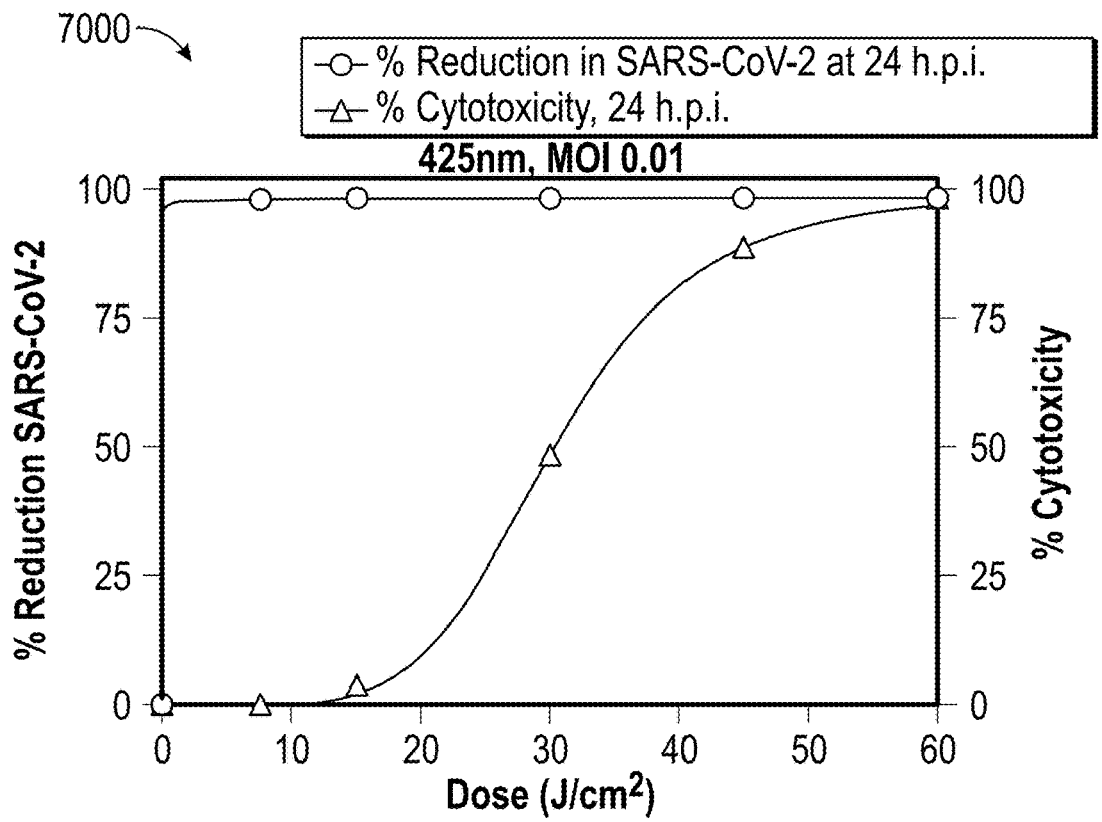
Figure 70B:
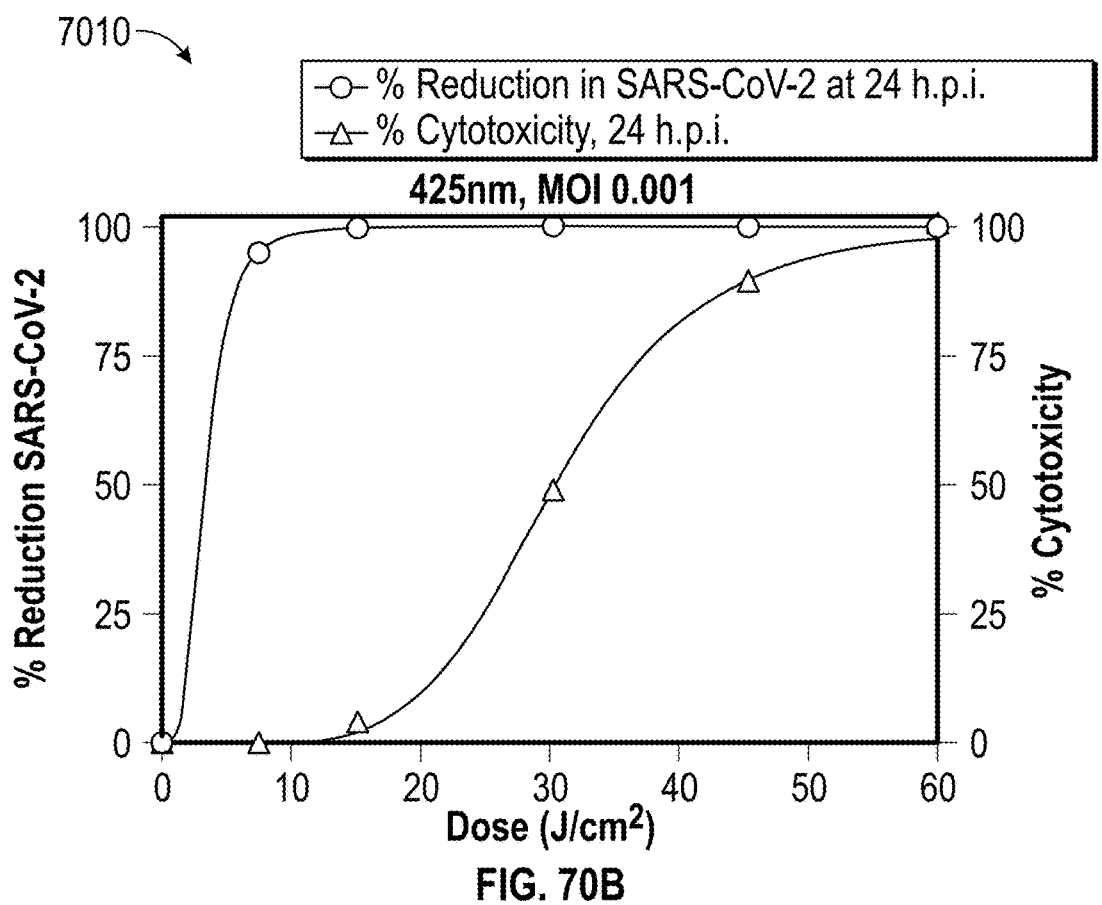

FIG. 70A is a chart 7000 illustrating percent reduction in SARS-CoV-2 replication versus percent cell cytotoxicity for Vero E6 cells infected with a MOI of 0.01. FIG. 70B is a chart 7010 illustrating percent reduction in SARS-CoV-2 replication versus percent cell cytotoxicity for Vero E6 cells infected with a MOI of 0.001. In both FIGS. 70A and 70B, the indicated doses of light were applied at 1-hour post infection and dose responses were determined at 24-hours post infection. The doses were administered by application of 425 nm light with an irradiance of 50 $mW/cm^2$ for times of 2.5 minutes (for 7.5 $J/cm^2$), 5 minutes (for 15 $J/cm^2$), 10 minutes (for 30 $J/cm^2$), 15 minutes (for 45 $J/cm^2$), and 20 mins (for 60 $J/cm^2$). Consistent with previously presented charts, similar trends are observed for dose-dependent effects of 425 nm blue light on SARS-CoV-2 replication for both MOI values. The cytotoxicity curve indicates a $CC_{50}$ of about 30.2. In FIG. 70A, the percent reduction in SARS-CoV-2 is close to 100% for doses as low as 7.5 $J/cm^2$ and the corresponding nonlinear regression curve has a sharp decrease at or near the 0 $J/cm^2$ dose. For the purposes of SI calculations, a conservative value of 1 was selected for the $EC_{50}$ value to give a SI value (e.g., $CC_{50}/EC_{50}$) of about 30. In FIG. 70B, the percent reduction in SARS-CoV-2 is farther away from 100% for the 7.5 $J/cm^2$ dose, thereby providing the corresponding nonlinear regression curve with a decrease toward 0% at a dose slightly above the 0 $J/cm^2$ dose. In this manner, a value of about 3.4 may be indicated for the $EC_{50}$ value to give a SI value (e.g., $CC_{50}/EC_{50}$) of about 9. Due to variability in experiments, slight differences in data sets may be expected. In this regard, the results illustrated in FIGS. 70A and 70B may be considered as similar and within normal experimental variations.

Figure 70C:
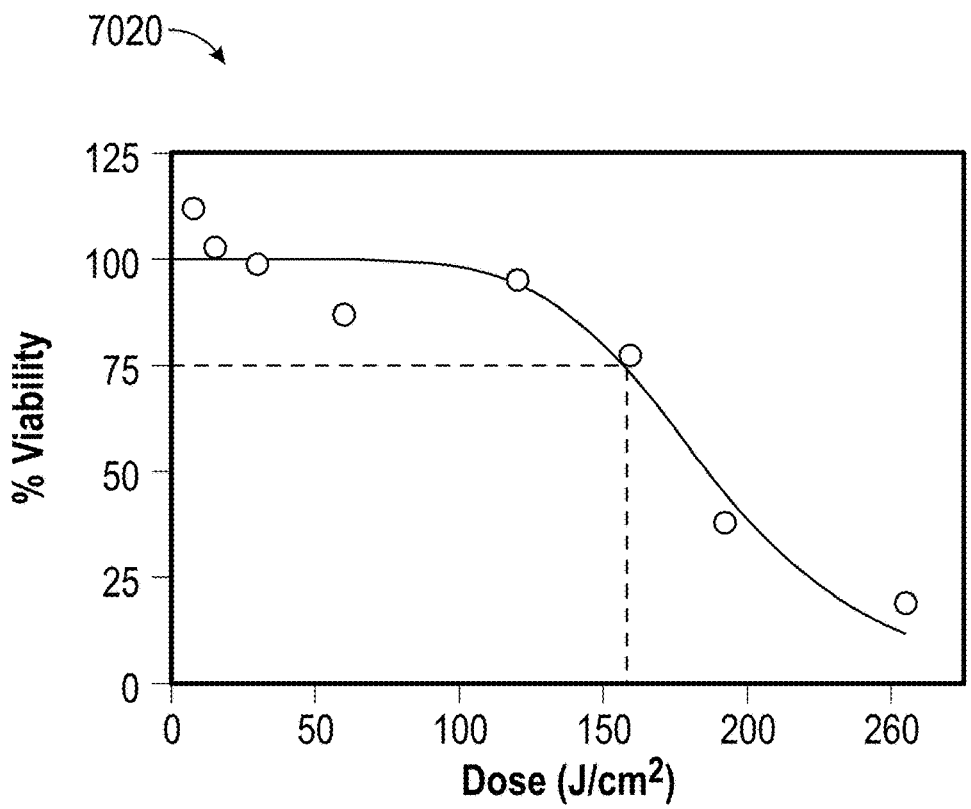

While FIGS. 70A and 70B provide percent reduction in SARS-CoV-2 at the cellular level for determining $EC_{50}$ values, $IC_{25}$ values for target tissues are needed to determine suitable LTI treatment values. FIG. 70C is a chart 7020 representing percent viability at various doses for primary human tracheal/bronchial tissue from a single donor for 425 nm light. Tissue viability is determined at 3-hours post-exposure by MTT assay, a measure of cell viability by assessing enzymatic activity of NAD(P)H-dependent cellular oxidoreductase ability to reduce MTT dye to formazan. From the chart 7020, the $IC_{25}$ value corresponds to the dose where the viability curve is at 75% (e.g., 25% reduction in tissue viability). In FIG. 70C, the $IC_{25}$ value is about 157, as indicated by the superimposed dashed lines. In combination with the $EC_{50}$ values of FIGS. 70A and 70B, the corresponding LTI values may be determined as about 157 for FIG. 70A and about 46 for FIG. 70B.

Figure 71A:
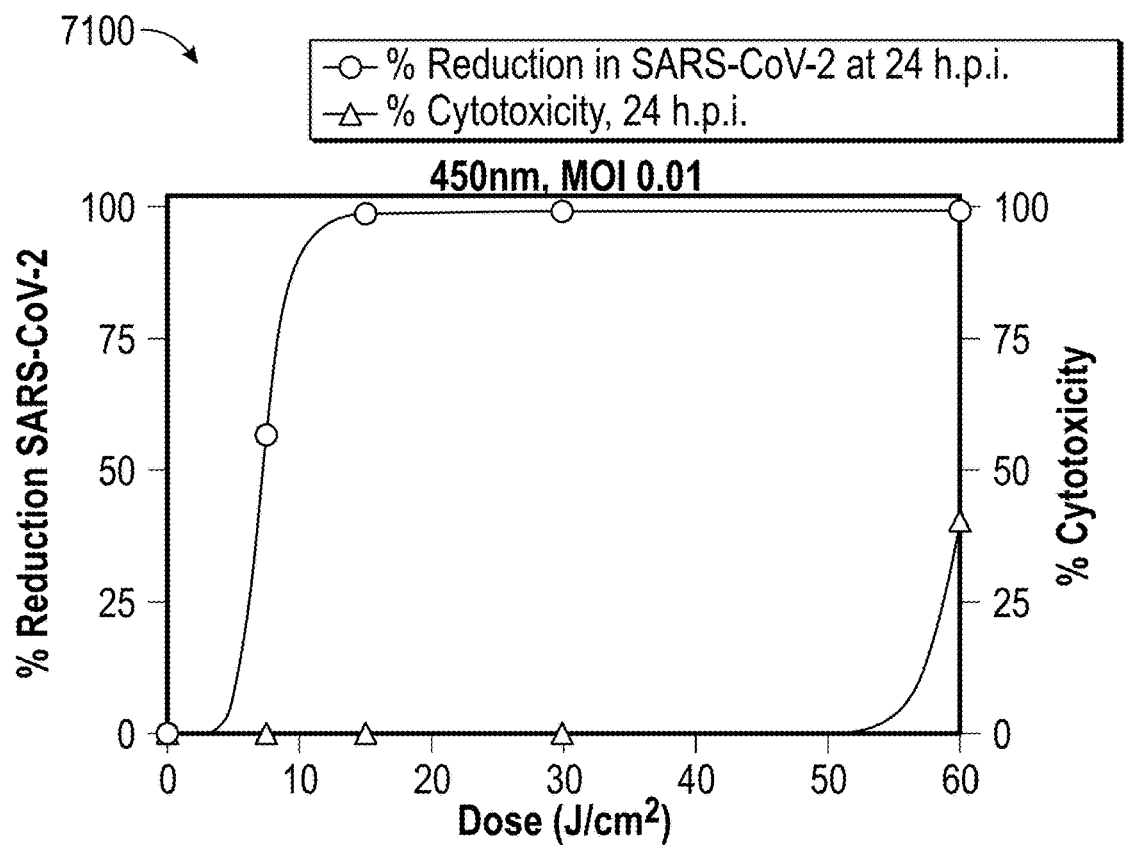
Figure 71B:
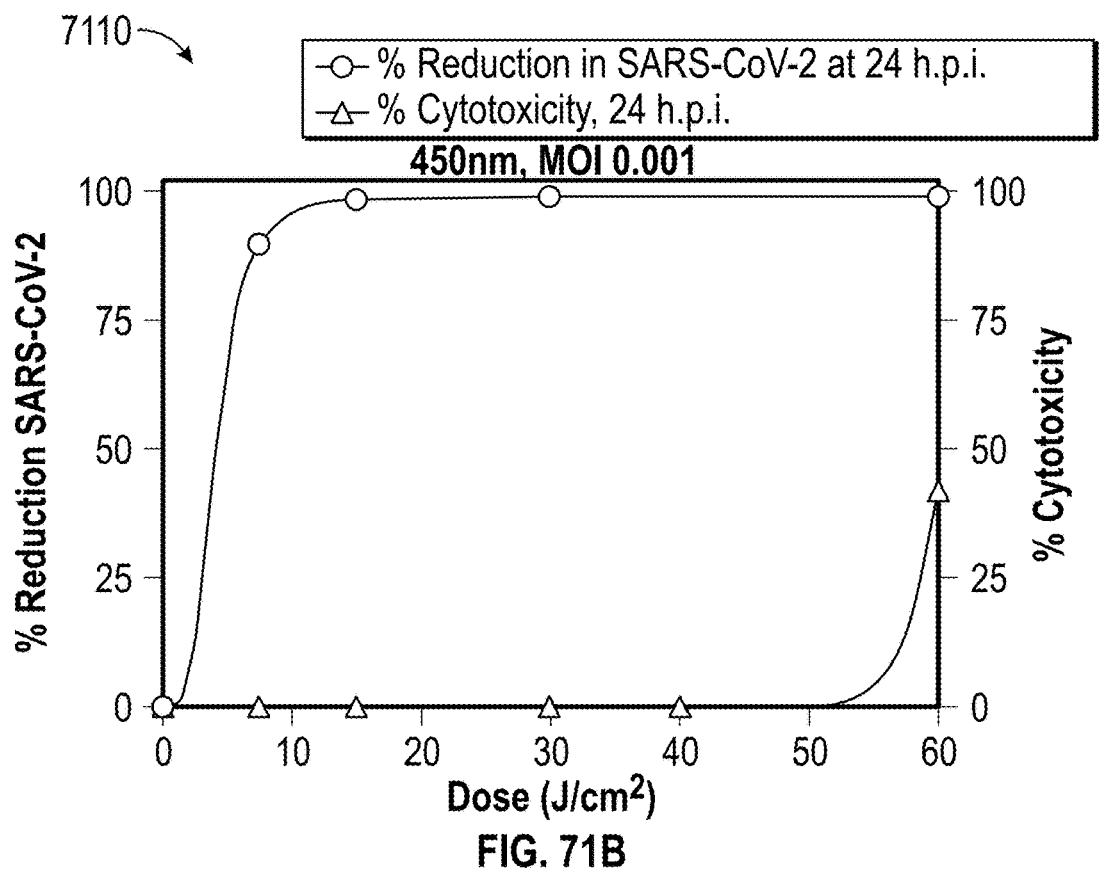
Figure 71C:
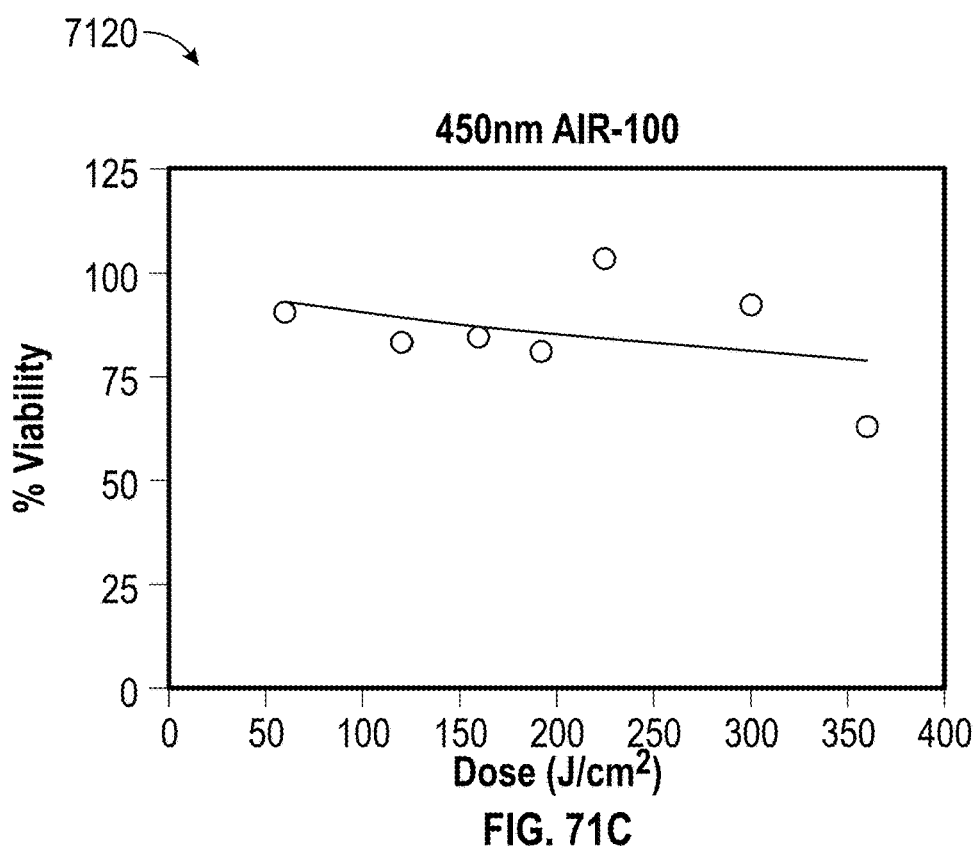

FIGS. 71A-71C repeat the experiments of FIGS. 70A-70C, but with light having a peak wavelength of 450 nm. FIG. 71A is a chart 7100 illustrating percent reduction in SARS-CoV-2 replication versus percent cell cytotoxicity for Vero E6 cells infected with a MOI of 0.01. FIG. 71B is a chart 7110 illustrating percent reduction in SARS-CoV-2 replication versus percent cell cytotoxicity for Vero E6 cells infected with a MOI of 0.001. Consistent with previously presented charts, similar trends are observed for dose-dependent effects of 450 nm blue light on SARS-CoV-2 replication for both MOI values. The cytotoxicity curves indicate a $CC_{50}$ of greater than 60 since the curve does not extend to 50% cytotoxicity. In turn, SI values based on $CC_{50}$ value of greater than 60 may also be considered as greater than the particular SI values. In FIG. 71A, a value of about 7.2 may be indicated for the $EC_{50}$ value to give a SI value (e.g., $CC_{50}/EC_{50}$) of greater than 8. In FIG. 71B, a value of about 4.1 may be indicated for the $EC_{50}$ value to give a SI value (e.g., $CC_{50}/EC_{50}$) of about greater than 15. As before, due to variability in experiments, slight differences in data sets may be expected. In this regard, the results illustrated in FIGS. 71A and 71B may be considered as similar and within normal experimental variations.

FIG. 71C is a chart 7120 representing percent viability at various doses for primary human tracheal/bronchial tissue from a single donor for light at 450 nm. As with FIG. 70C, tissue viability is determined at 3-hours post-exposure by MTT assay. From the chart 7120, the $IC_{25}$ value may be determined at about 330. In combination with the $EC_{50}$ values of FIGS. 71A and 71B, the corresponding LTI values may be determined as about 46 for FIG. 71A and about 80 for FIG. 71B. While FIG. 71C shows about 63% viability at a dose of 360 J/cm², variability between biological replicates was high at this dose. In this regard, the $IC_{25}$ values may be even greater than the approximated value of 330, indicating very high doses may be administered before significant toxicity is observed.

FIG. 72 is a table 7200 summarizing the experiments of FIGS. 70A-70C and 71A-71C. The higher SI and LTI values for 450 nm light are predominantly a consequence of lower cytotoxicity relative to 425 nm light. Lower $EC_{50}$ values demonstrate more effective virus inhibition at 425 nm, but this can be associated with higher cytotoxicity values at lower light doses than at 450 nm. Ideally, light therapy may include lower $EC_{50}$ values with $CC_{50}$ values as high as possible. Different targeted pathogens and tissue types may provide different LTI values. In this regard, LTI values according to the present disclosure may be provided at values of greater than or equal to 2, or in a range from 2 to 100,000, or in a range from 2 to 1000, or in a range from 2 to 250, depending on the application. Considering experimental variances, the exemplary data provided for treatment of SARS-CoV-2 with light in a range from 425 nm to 450 nm indicates LTI values in any of the above ranges may be achieved.

Figure 73A:
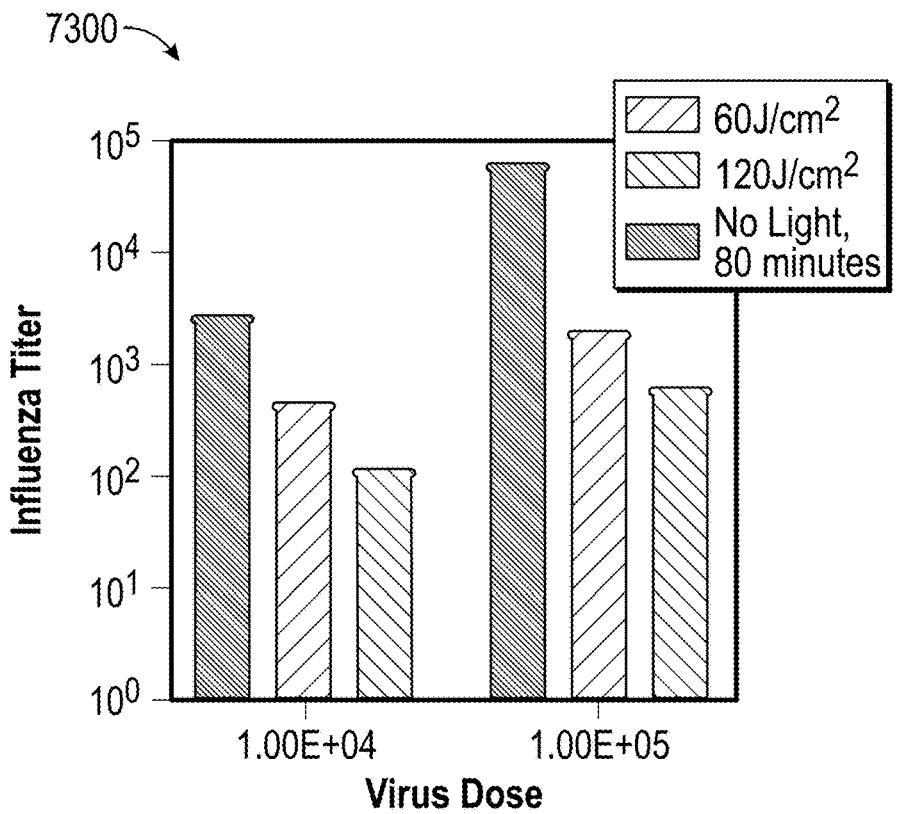

Using techniques analogous to those used to above to measure the antiviral activity of 425 to 450 nm light against SARS-CoV-2, the antiviral activity of light at 425 nm against wild-type (WT) and Tamiflu-resistant influenza A was investigated. FIG. 73A is a chart 7300 showing the titer of WT influenza A virus based on remaining viral loads for different initial viral doses after treatment with different doses of 425 nm light. The initial viral doses were set at $1 \times 10^4$ and $1 \times 10^5$, and the remaining viral load (e.g., number of copies) following treatment with light at 425 nm at dosages of 0 J/cm², 60 J/cm², and 120 J/cm² is shown. The data demonstrates significant reductions in wild-type influenza A viral loads when either 60 J/cm² or 120 J/cm² doses were administered, with an additional roughly 0.5-log reduction in viral loads observed at the higher dosage.

Figure 73B:
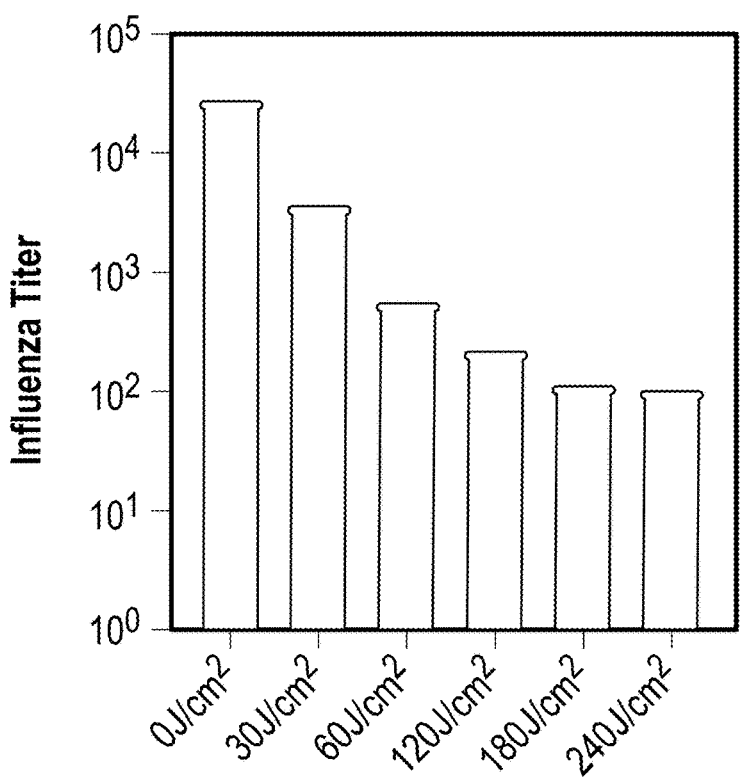

FIG. 73B is a chart 7310 showing the titer of Tamiflu-resistant influenza A virus based on remaining viral load for a single initial viral dose after treatment of different doses of 425 nm light. The initial viral dose was set at $1 \times 10^4$, the remaining viral load (e.g., number of copies) following treatment with light at 425 nm at dosages of 0 J/cm², 60 J/cm², and 120 J/cm² is shown. The initial dose is provided at about $1 \times 10^4$, and the remaining viral load (e.g., number of copies) following treatment with light at 425 nm at dosed of 0 J/cm², 30 J/cm², 60 J/cm², 120 J/cm², 180 J/cm², and 240 J/cm² is shown. The data shows an increase in viral load when no light was administered, and dose-dependent reductions in viral loads up to about 180 J/cm², totaling a roughly 2-log reduction in viral load.

Figure 74A:
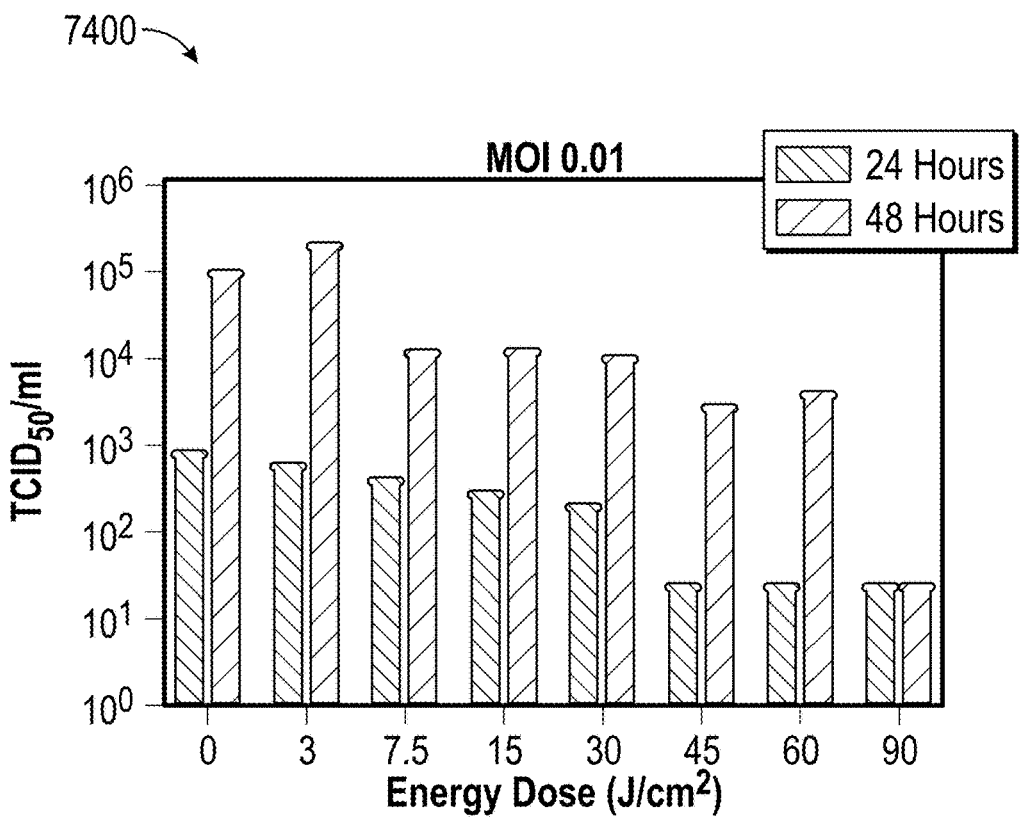

FIG. 74A is a chart 7400 showing the $TCID_{50}$/ml versus energy dose for WT-influenza A treated with light at 425 nm at various doses. The MOI for the WT-influenza A was provided at 0.01. The selected doses were provided at 0 J/cm², 3 J/cm², 7.5 J/cm², 15 J/cm², 30 J/cm², 45 J/cm², 60 J/cm² and 90 J/cm². Results were collected after 24 hours and after 48 hours. When no light was applied (e.g., dose of 0 J/cm²), viral loads increased to $10^3$ copies at 24 hours, and to $10^5$ copies at 48 hours. At doses between about 7.5 J/cm² and 60 J/cm², a dose-dependent decrease in viral loads was observed at 24 hours, though the virus significantly rebounded by 48 hours. However, at doses of 90 J/cm², the viral loads significantly decreased by 24 hours, and did not significantly increase at 48 hours. Specific $TCID_{50}$/ml values are presented to demonstrate data trends and data values relative to on another, the actual values may vary from lab to lab and are not meant to be limiting.

Figure 74B:
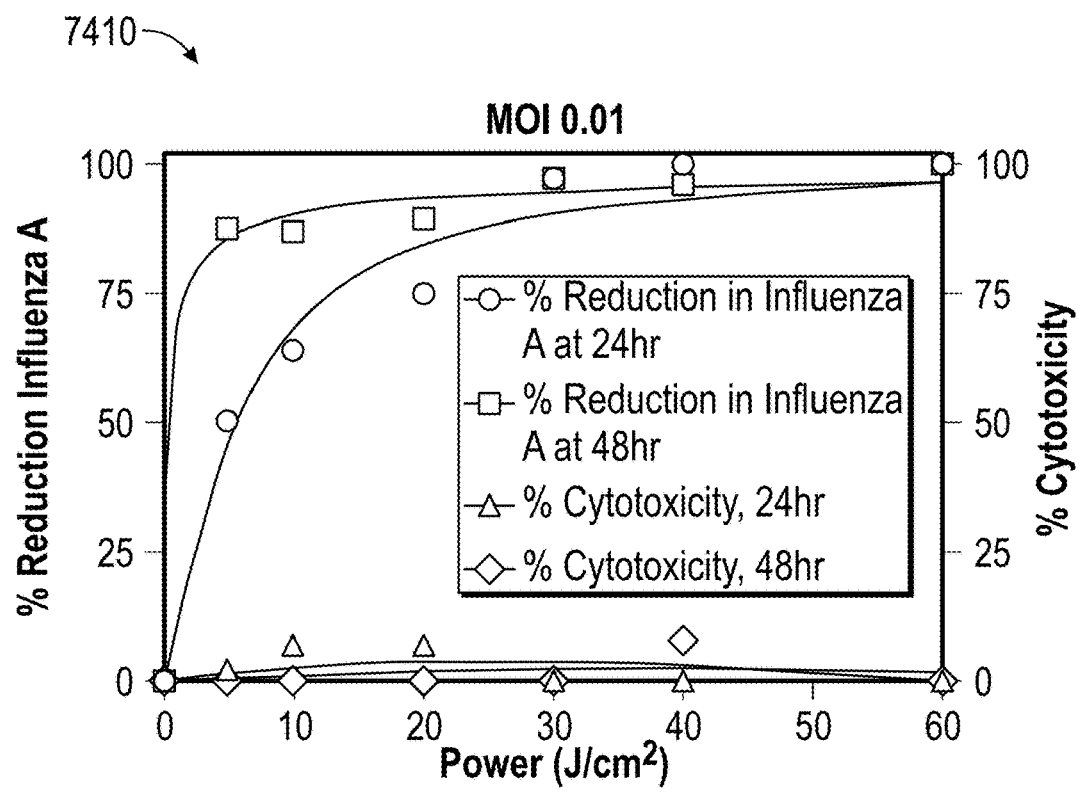

FIG. 74B is a chart 7410 showing the percent reduction in viral loads of WT-influenza A and percent cytotoxicity against the treated cells when influenza A-infected Madin-Darby Canine Kidney (MDCK) cells were exposed to 425 nm light at various doses. The MOI for the WT-influenza A was provided at 0.01. As illustrated, the doses were provided at 0 J/cm², 7.5 J/cm², 15 J/cm², 30 J/cm², 45 J/cm², 60 J/cm² and 90 J/cm². The reduction in viral loads and the cytotoxicity were monitored at 24 and 48 hours post irradiation. Virtually no cytotoxicity was observed at any time period for any of the doses. The reduction in viral loads was dose dependent, with doses of 45 J/cm², 60 J/cm², and 90 J/cm² demonstrating a nearly complete reduction in viral loads.

Figure 74C:
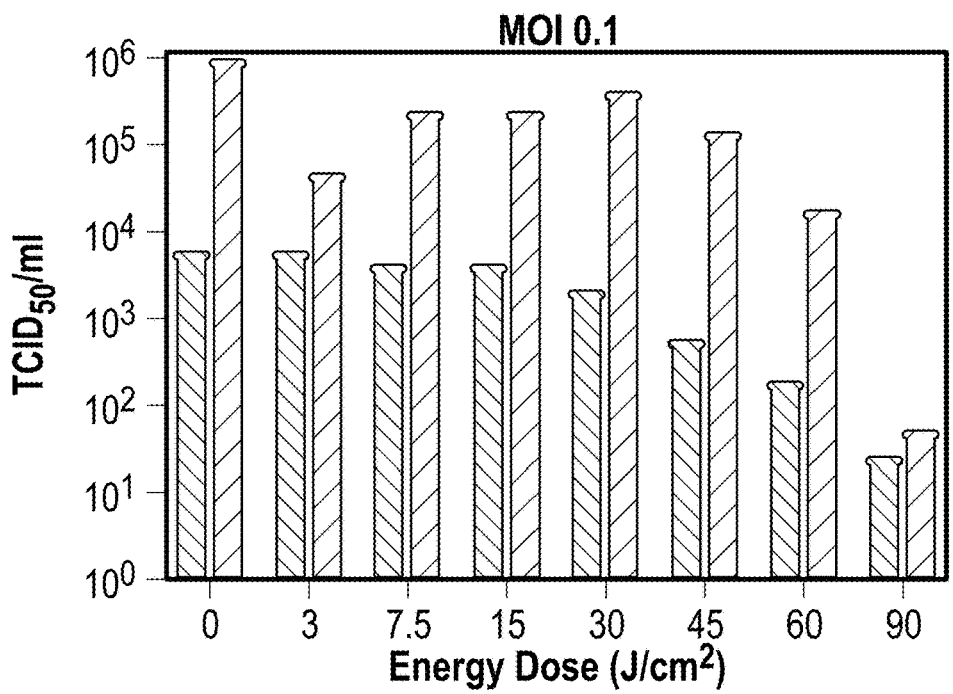

FIG. 74C is a chart 7420 that is similar to FIG. 74A, but with a starting MOI of 0.1. In this regard, FIG. 74C illustrates the $TCID_{50}$ of cells infected with WT-influenza A and treated with 425 nm light at doses of 0 $J/cm^2$, 3 $J/cm^2$, 7.5 $J/cm^2$, 15 $J/cm^2$, 30 $J/cm^2$, 45 $J/cm^2$, 60 $J/cm^2$ and 90 $J/cm^2$. Results were collected after 24 hours and after 48 hours. Viral loads stayed fairly constant at 24 hours for doses from 0 to 15 $J/cm^2$ and decreased in a dose dependent manner as the doses increased to 90 $J/cm^2$. Over the next 24 hours (i.e., a total of 48 hours post-exposure), the viral loads significantly rebounded at all dosages other than 90 $J/cm^2$.

Figure 74D:
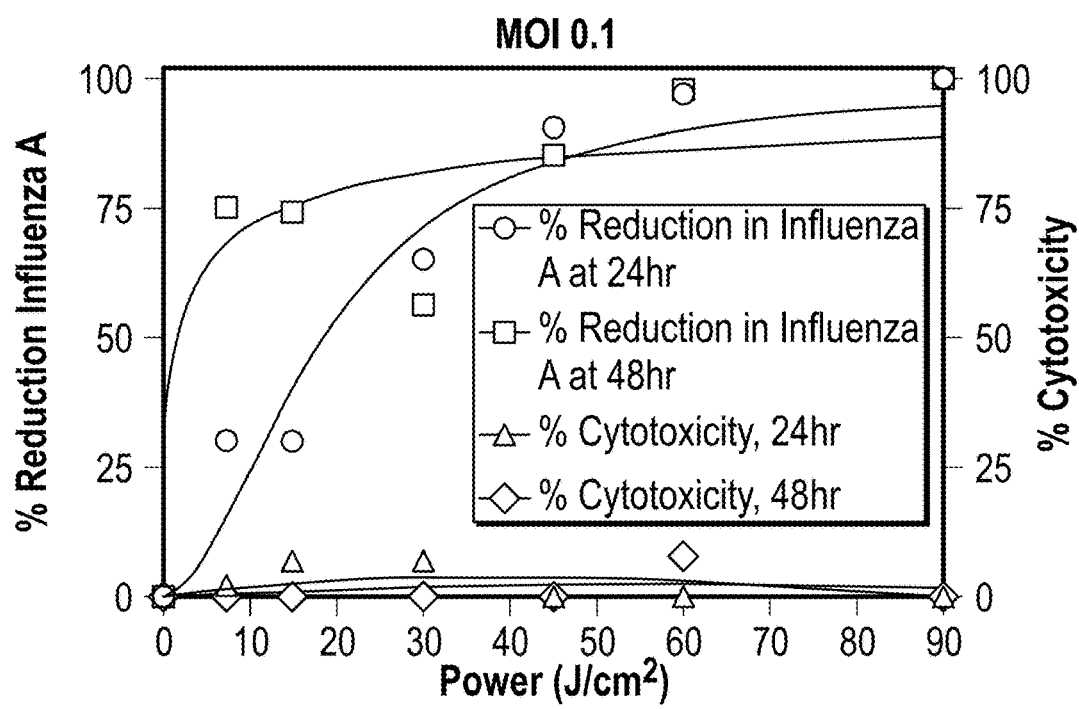

FIG. 74D is a chart 7430 that is similar to FIG. 74B, but with a starting MOI of 0.1. In this regard, FIG. 74D illustrates the percent reduction in viral loads of WT-influenza A and percent cytotoxicity against the treated cells when influenza A-infected Madin-Darby Canine Kidney (MDCK) cells were exposed to 425 nm light at various doses. The MOI for the WT-influenza A was provided at 0.1. As illustrated, the doses were provided at 0 $J/cm^2$, 7.5 $J/cm^2$, 15 $J/cm^2$, 30 $J/cm^2$, 45 $J/cm^2$, 60 $J/cm^2$ and 90 $J/cm^2$. The reduction in viral loads and the cytotoxicity were monitored at 24 and 48 hours post irradiation. As with FIG. 74B, virtually no cytotoxicity was observed at any time period for any of the doses and the reduction in viral loads was dose dependent, with doses of 45 $J/cm^2$, 60 $J/cm^2$ and 90 $J/cm^2$ demonstrating a high or nearly complete reduction in viral loads. Specific $TCID_{50}$/ml values are presented to demonstrate data trends and data values relative to on another, the actual values may vary from lab to lab and are not meant to be limiting.

As a summary of the findings, therapeutic light treatments can be selected from optimal doses including various combinations of wavelengths, irradiance, and treatment times as discussed above for various viruses, including SARS-CoV-2 and Influenza, among others. Ideally, the phototherapy may induce a dual mechanism of action on the virus, including damaging the lipid membrane using single oxygen and/or nitric oxide. The treatments demonstrate efficacy both extracellular in the absence of cells pre-infection, as well as intracellular in the presence of cells post infection. The antiviral effect can be remarkably fast. For example, inactivation of the SARS-CoV-2 virus was demonstrated within 24 to 48 hours, compared to the course of viral load reduction observed clinically as the SARS-CoV-2 virus clears the body in untreated patients, or even in patients treated with Remdesivir.

It is important to consider the "Light Therapeutic Index," or "LTI," a ratio of the $IC_{25}$ and the $EC_{50}$ values for light that is used on cells and tissues. Ideally, the light treatment will be effective at killing one or more target viruses at power levels that are not overly cytotoxic. Preferably, the ratio of $IC_{25}/EC_{50}$ is as high as possible, including greater than 2. Cell systems for each virus have a number of variables (e.g. cell density, different cell types for productive infection, media, etc.), which makes it hard to have a single LTI for all cell types. Important aspects for evaluating LTI for cell lines across all viruses, particularly for respiratory viruses, include evaluating the types of human tissue these viruses are likely to infect, such as EpiAirway from both large airway (AIR-100) and nasal (NAS-100) tissues. EpiAirway is a ready-to-use, 3D mucociliary tissue model consisting of normal, human-derived tracheal/bronchial epithelial cells, also available as a co-culture system with normal human stromal fibroblasts (EpiAirwayFT). A reduction as large as 75-fold is observed after a 2.5 min treatment dose at 50 $mW/cm^2$. The light therapy shows significant antiviral activity post infection, inhibiting about 50% of viral replication.

Additionally, this treatment shows a full log inactivation of virus on WT-Influenza A at doses of greater than 8.5 $J/cm^2$. A dose of 8.5 $J/cm^2$ was a dose that provided an $IC_{50}$ against influenza post infection. In this regard, doses of less than 10 $J/cm^2$ can provide a multi-pathogenic treatment that can eliminate different viruses via one or more separate mechanisms. In a particular example, a multi-pathogenic treatment of 425 nm light for 5 minutes and an irradiance of 50 $mW/cm^2$ may be effective for treating both SARS-CoV-2 and Influenza A. Additionally, at doses of around 60 $J/cm^2$, a greater than 2-log reduction in virucidal activity was observed using 425 nm light with a 20-minute exposure at 50 $mW/cm^2$.

Considering LTI calculations (e.g., the ratio of $IC_{25}/EC_{50}$) in antiviral assays for specific tissues for SARS-CoV-2 and Influenza at just 425 nm, it is observed that there are safe and effective doses of light that can be administered. Because the viral membranes are similar for other respiratory viruses, it is believed (based on successful results with SARS-CoV-2 and influenza A) that such treatments can be effective against all respiratory viruses. When comparing the results with light at 425 nm with the results at 405 nm or 385 nm, the LTI may be smaller, though it will be expected to vary depending on tissue types. Extrapolating the data obtained herein, the relatively high-powered light (e.g., dosed at hundreds of $J/cm^2$) used in the past to disinfect surfaces cannot safely be used in vivo. Importantly, the dosage of light ($J/cm^2$) had to be sufficiently non-cytotoxic (i.e., would not reduce viability to more than 25% at a dose that resulted in an $EC_{50}$). The resulting LTI is expected to vary depending on the type of cell exposed to the phototherapy, but for a given cell type, ideally there is an effective therapeutic window, such as an LTI of at least 2, or in a range from 2 to 100,000, or in a range from 2 to 1000, or in a range from 2 to 250, depending on the application. Because SARS-CoV-2, influenza and other viruses have lipid membranes, and part of the method by which the light kills the viruses is believed to be oxidative damage to these membranes, it is believed that this treatment will also work equally well on other respiratory viruses. Further, the treatments described herein may also work on viruses that do not have lipid membranes (e.g., rhinoviruses that cause most common colds).

Light therapies as disclosed herein may be combined with conventional pharmaceutical agents, such as antivirals, anti-coagulants, anti-inflammatories, and the like, and the antiviral wavelengths can be combined with anti-inflammatory wavelengths to reduce the inflammatory damage caused by the virus, by the cytokine storm induced by the virus, and/or by the phototherapy at the antiviral NO-producing/NO-releasing/singlet oxygen producing wavelengths.

While the above-described examples are provided in the context of viral applications, the principles of the present disclosure may also be applicable for treatment of bacterial infections. There is a current problem when treating bacterial respiratory infections, namely, AMR and recalcitrant lung infections. Antimicrobial resistance has led to many patients having their lungs infected with bacteria that are resistant to many common antibiotics. As new antibiotics become developed, bacterial resistance soon follows. One potential solution to this problem would be to use visible light as described herein, at an effective antimicrobial wavelength and dosage, alone or in combination with conventional antibiotic therapy. While bacteria can develop resistance against antibiotics, it is more difficult for them to develop resistance to antimicrobial therapy using visible light. The potential uses are far-reaching; so long as the light is delivered in a safe, therapeutic dosage, patients can be effectively treated for a number of respiratory microbial infections, such as tuberculosis, *Mycobacterium avium* complex, and the like, and specifically including those caused by spore-forming bacteria. Bacterial infections caused by spore-forming bacteria can be particularly difficult to treat with conventional antibiotics, because the antibiotics only kill bacteria when they are not in spore form. As disclosed herein, certain wavelengths of light are effective at killing spore-forming microbes not only in their active form, but also in their spore form.

As discussed below, not all light at blue wavelengths are equivalent. Some have higher cytotoxicity to the infected tissues, and some have higher antimicrobial efficacy. It is useful to consider light therapeutic index (LTI), which is a combination of antimicrobial activity and safety to the exposed tissues. Accordingly, a series of experiments were performed to identify suitable wavelengths and dosage levels to provide safe and effective antibacterial treatments.

For the experiments, bacterial cultures were prepared in 1× phosphate buffered saline (PBS) or CAMHB at 106 CFU/ml, and 200 µl were aliquoted into wells of a 96-well microtiter plate. Plates with lids were placed under a white illumination box, with an LED array placed on top such that the light shines down onto bacteria. A fan blew across the device though vents in the illumination box to minimize the heat generated by the LED lights. All setups were done inside a Class II biosafety cabinet. Lights were turned on for a given time, then bacteria were sampled, serially diluted, and plated on MHA for enumeration.

The bacterial strains used in this study were obtained from the American Type Culture Collection (ATCC), the CDC-FDA's Antimicrobial Resistance Bank (AR-BANK), from Dr. John LiPuma at the *Burkholderia cepacia* Research Laboratory and Repository (BcRLR) at the University of Michigan, or from the laboratory of Dr. Mark Schoenfisch at the University of North Carolina Chapel Hill. Strains from the BcRLR were confirmed to be *Pseudomonas aeruginosa* by 16S sequencing, and the other strains were confirmed to be *P. aeruginosa* by growth on *Pseudomonas* isolation agar. Strains were stored in 20% glycerol stocks at −80° C. Strains were cultured on tryptic soy agar (TSA) at 30° C. or 37° C. for 1-2 days, or in cation-adjusted Mueller-Hinton Broth. *Streptococcus pyogenes* and *Haemophilus influenzae* were grown using Brain Heart Infusion in a chamber with 5% CO2 packets. All bacteria were incubated at 37° C. Cytoxicity was measured as described above with respect to the antiviral data.

Figure 75A:
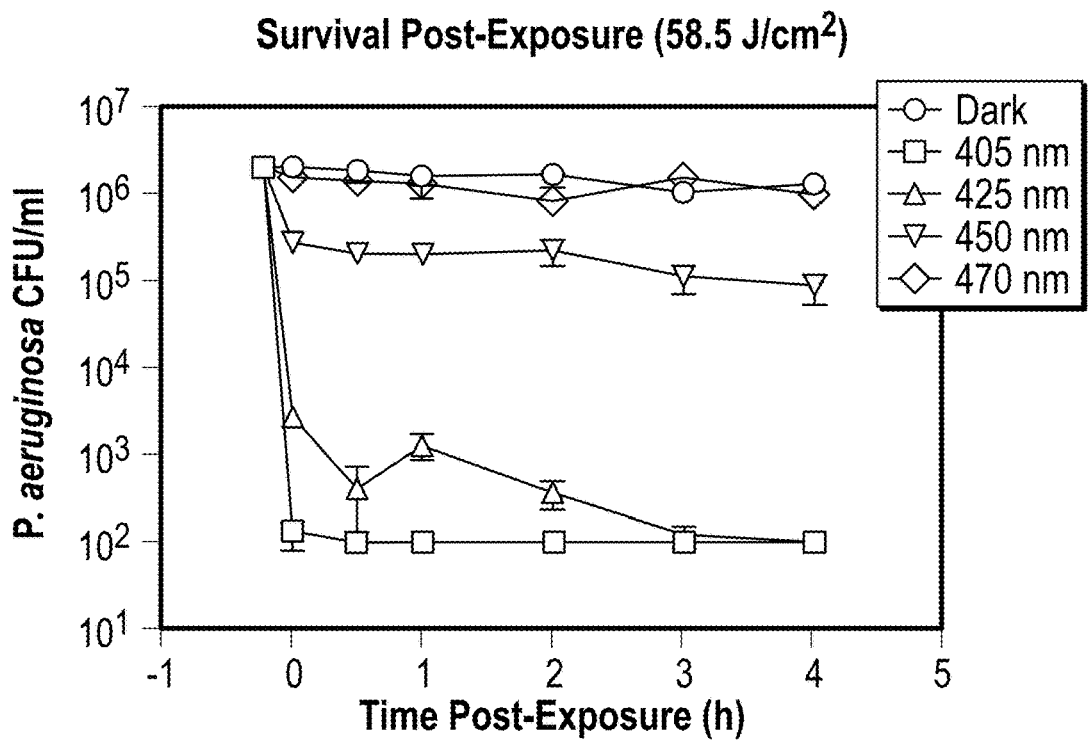

FIG. 75A is a chart 7500 showing the effectiveness of light at 405, 425, 450, and 470 nm and administered with a dose of 58.5 $J/cm^2$, in terms of hours post-exposure, at killing *P. aeruginosa* (CFU/ml). The data show that, at a wavelength of 405 nm or 425 nm, a 5-log reduction in concentration was observed almost instantaneously, and the effect was maintained for four hours post-exposure.

Figure 75B:
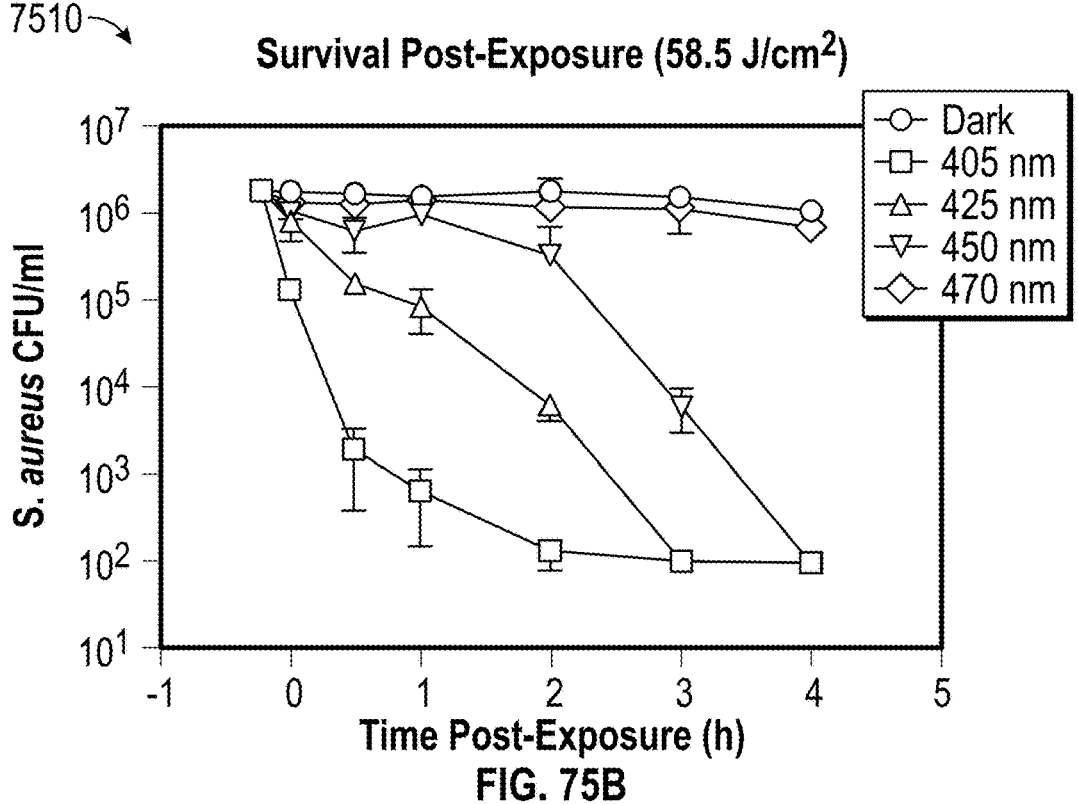

FIG. 75B is a chart 7510 showing the effectiveness of light at 405, 425, 450, and 470 nm, and administered with a dose of 58.5 $J/cm^2$, in terms of hours post-exposure, at killing *S. aeurus* (CFU/ml). The data show that, at a wavelength of 405 nm, a 3-log reduction was observed within a half hour post-exposure, and this increased to a 4-log reduction by 2 hours post-exposure. At 425 nm, a 2-log reduction in concentration was observed within two hours, and this increased to a 4-log reduction by 4 hours post-exposure. At 450 nm, a 2-log reduction in concentration was observed within three hours, and this increased to a 4-log reduction by 4 hours post-exposure. Light at 470 nm was virtually ineffective.

Figure 76A:
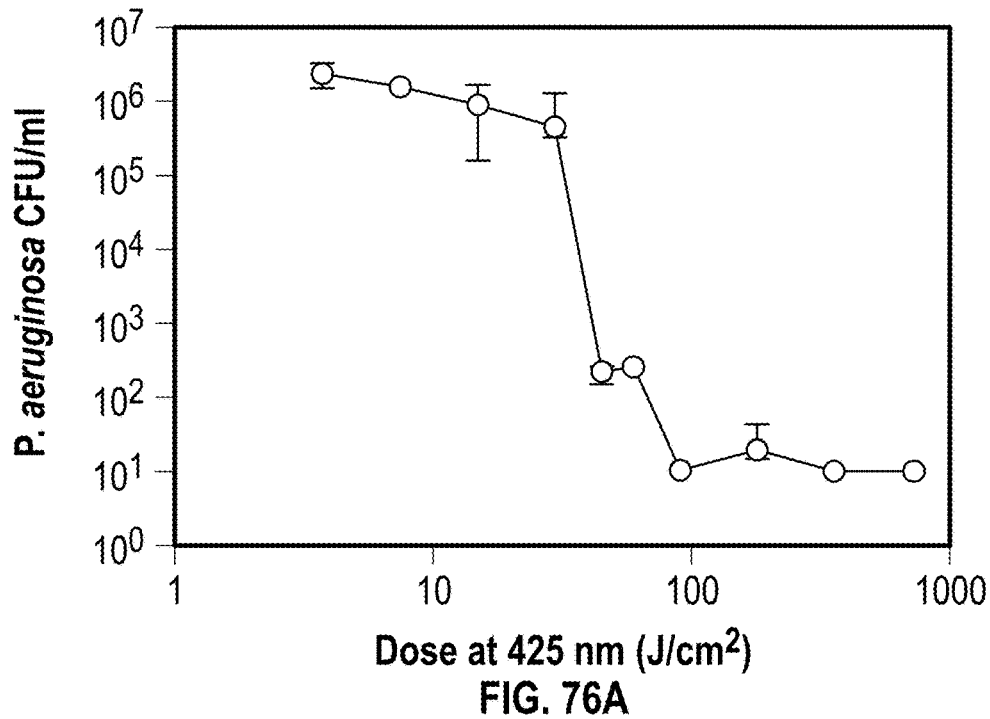

FIG. 76A is a chart 7600 showing the effectiveness of light at 425 nm and administered with doses ranging from 1 to 1000 $J/cm^2$ at killing *P. aeruginosa* (CFU/ml). The data show that, at a wavelength of 425 nm, at doses of around 60 $J/cm^2$, a 4-log reduction in concentration was observed, whereas at doses of 100 $J/cm^2$ or higher, a 5-log reduction was observed.

Figure 76B:
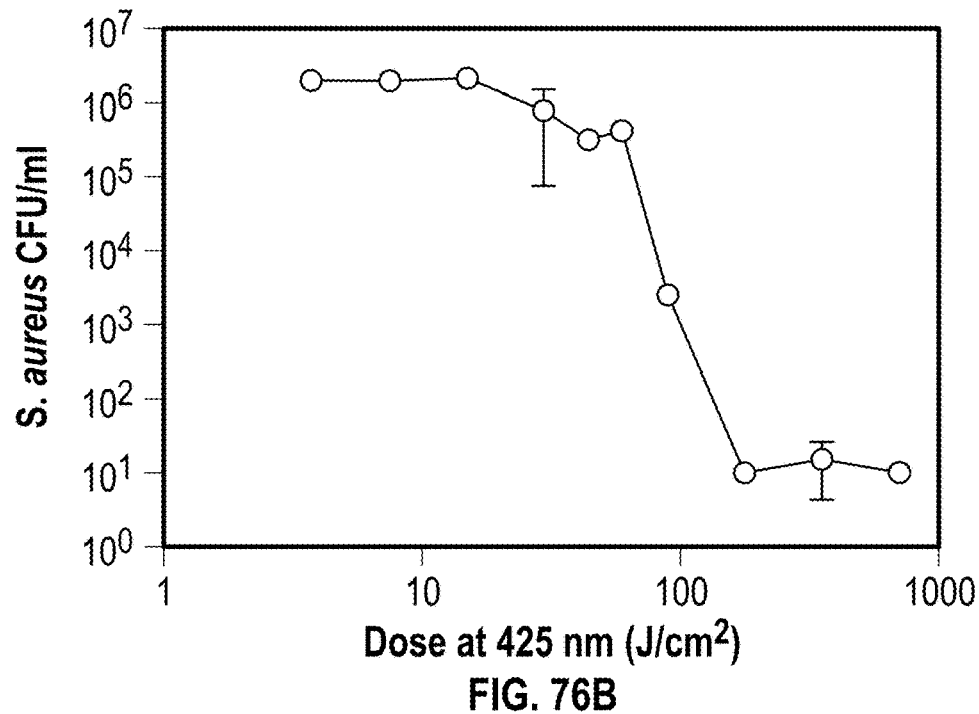

FIG. 76B is a chart 7610 showing the effectiveness of light at 425 nm and administered with doses ranging from 1 to 1000 $J/cm^2$, at killing *S. aureus* (CFU/ml). The data show that, at a wavelength of 425 nm, at doses of around 100 $J/cm^2$ or more, a 4-log or even a 5-log reduction in concentration was observed.

Figure 77A:
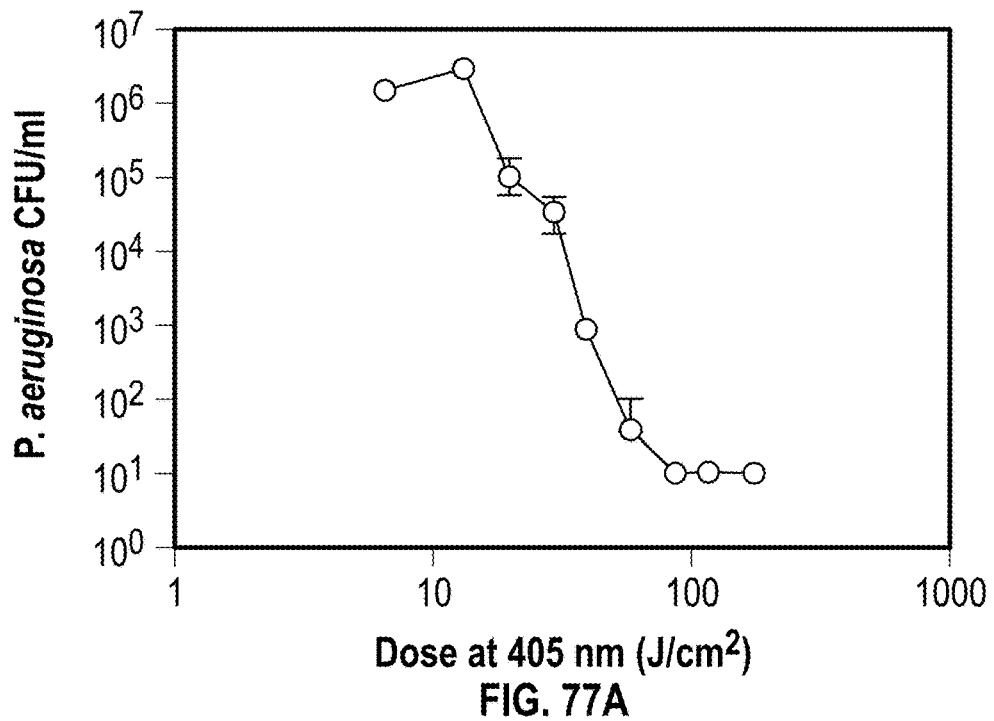

FIG. 77A is a chart 7700 showing the effectiveness of light at 405 nm and administered with doses ranging from 1 to 1000 $J/cm^2$ at killing *P. aeruginosa* (CFU/ml). The data show that, at a wavelength of 405 nm, at doses of around 60 $J/cm^2$, a 4-log reduction in concentration was observed, whereas at doses of 100 $J/cm^2$ or higher, a 5-log reduction was observed.

Figure 77B:
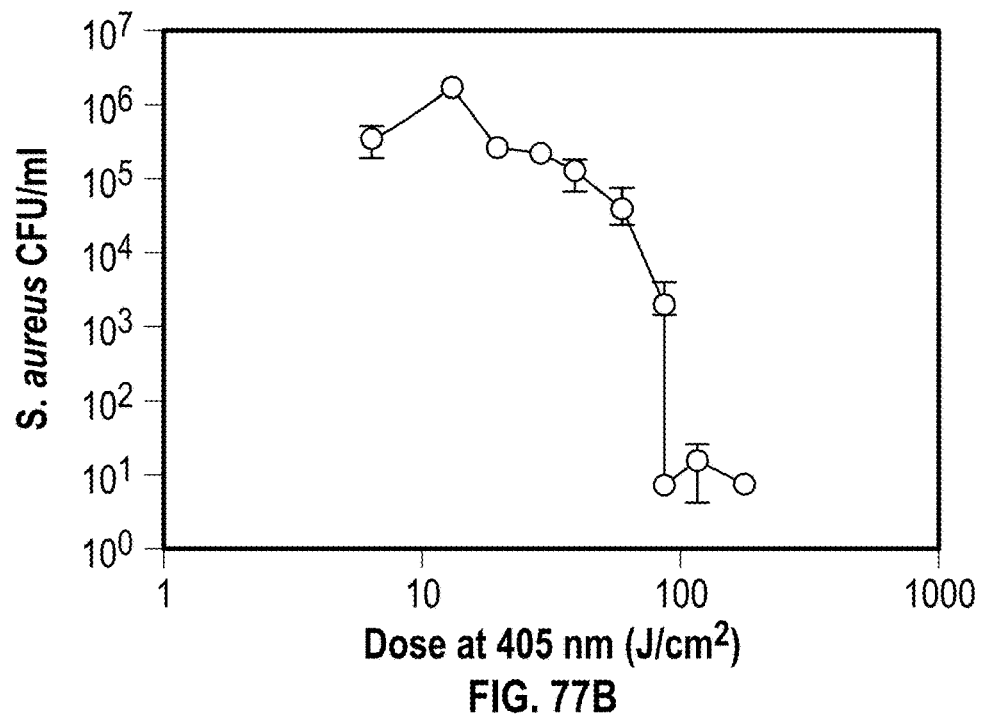

FIG. 77B is a chart 7710 showing the effectiveness of light at 405 nm and administered with doses ranging from 1 to 1000 $J/cm^2$ at killing *S. aureus* (CFU/ml). The data show that, at a wavelength of 405 nm, at doses of around 100 $J/cm^2$ or more, a 5-log reduction in concentration was observed.

Figure 78:
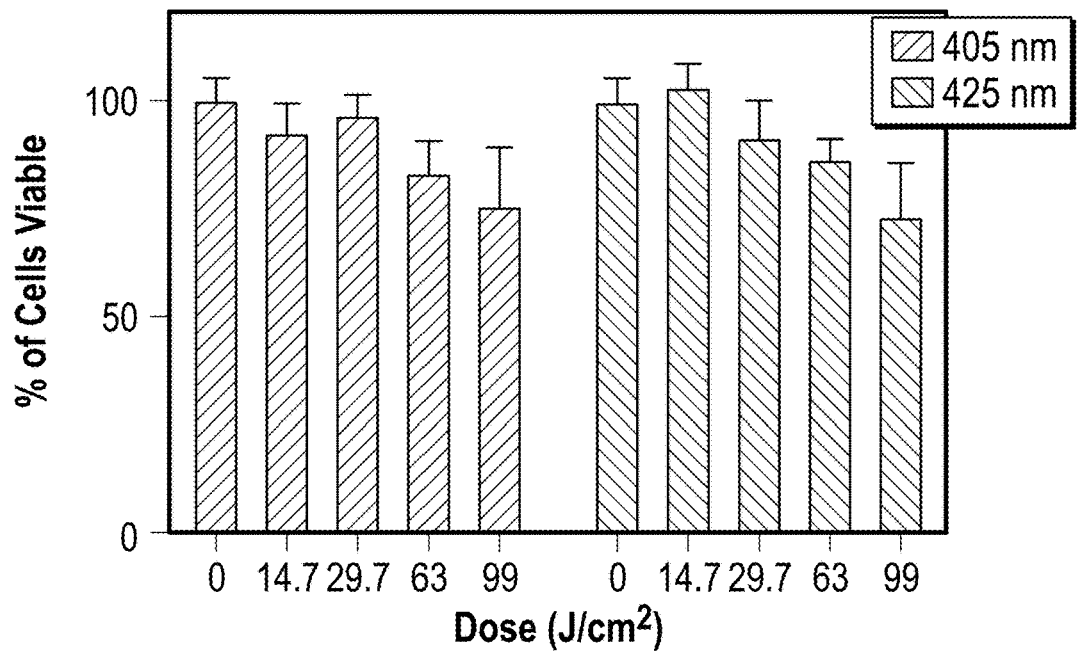

FIG. 78 is a chart 7800 showing the toxicity of 405 nm and 425 nm light in primary human aortic endothelial cells (HAEC). Data is provided showing the effect of light at 405 nm and at 425 nm for a variety of indicated doses. Even at dosages up to 99 $J/cm^2$, the viability of the cells never dropped below 75%, which is a useful threshold for determining the safety of a treatment.

FIG. 79A is a chart 7900 showing the bacterial $log_{10}$ reduction and the % loss of viability of infected AIR-100 tissues following exposure of the tissue to doses of light ranging from 4 to 512 $J/cm^2$ at 405 nm. FIG. 79B is a chart 7910 showing the bacterial $log_{10}$ reduction and the % loss of viability of infected AIR-100 tissues following exposure of the tissue to doses of light ranging from 4 to 512 $J/cm^2$ at 425 nm. At both wavelengths (405 nm and 425 nm), notable bacterial $log_{10}$ reductions are realized before dose levels reach 25% loss in tissue viability.

In a similar manner, additional data as described above for FIGS. 79A and 79B were collected and provided as shown in FIGS. 79C-79F. This data demonstrates similar results, thereby confirming identification of safe and effective operating windows. FIG. 79C is a chart 7920 showing the bacterial $log_{10}$ reduction and the % loss of viability of infected AIR-100 tissues with gram negative bacteria (e.g., *P. aeruginosa*) following exposure of the tissue to doses of light ranging from 4 to 512 $J/cm^2$ at 405 nm. FIG. 79D is a chart 7930 showing the bacterial $log_{10}$ reduction and the % loss of viability of infected AIR-100 tissues with gram negative bacteria (e.g., *P. aeruginosa*) following exposure of the tissue to doses of light ranging from 4 to 512 $J/cm^2$ at 425 nm. FIG. 79E is a chart 7940 showing the bacterial $log_{10}$ reduction and the % loss of viability of infected AIR-100 tissues with gram positive bacteria (e.g., *S. aureus*) following exposure of the tissue to doses of light ranging from 4 to 512 $J/cm^2$ at 405 nm, in a similar manner to FIGS. 79A and 79C. FIG. 79F is a chart 7950 showing the bacterial $log_{10}$ reduction and the % loss of viability of infected AIR-100 tissues with gram positive bacteria (e.g., *S. aureus*) following exposure of the tissue to doses of light ranging from 4 to 512 $J/cm^2$ at 425 nm, in a similar manner to FIGS. 79B and 79D.

Most in-vitro assays against bacteria are conducted in a cell-free system. There are two classic or industry standard measurements for anti-bacterial activity. The first is related to inhibition of growth and may be quantified in terms of a minimum inhibitory concentration (MIC). The MIC refers to the dose required to completely inhibit growth of bacteria over a 24-hour period in a broth/growth medium. Given the rapidly dividing nature of bacteria, any growth leads to high concentration of microorganism. Stated differently a 50% reduction is not sufficient for bacteria infections. A second standard is related to bactericidal results and may be quantified in terms of a minimum bactericidal concentration (MBC). The MBC refers to the dose required to result in a 3 log reduction (e.g., 99.9%) of bacteria. Assays can be run in PBS or broth/growth media and lead to different results and time is also a variable. In general, for the bacterial experiments described above, the MIC dose for a given organism has typically been greater than the MBC determined in phosphate buffered saline.

FIGS. 80A-80J are a series of charts showing the effect of light at 405 nm and 425 nm, at differing dosage levels, in terms of bacterial survival (CFU/ml) vs. dose (J/cm$^2$). The data is provided for both *P. aeruginosa* and *S. aureus* bacteria. As illustrated, light at 405 nm is particularly effective at killing these bacteria, and that light at 425 nm is also effective, though either not as effective, or not effective at higher doses. MBC values are indicated on the charts of FIGS. 80A-80J to show 3-log reductions in bacteria.

For the purposes of the present bacterial experiments, LTI calculations may be realized from the above-referenced data for providing safe and effective phototherapeutic treatments. As previously described, LTI may be determined from the relationship of $IC_{25}$ divided by the $EC_{50}$ in the context of viruses. For the bacterial data presented in FIGS. 79A-80J, the $EC_{50}$ values may be replaced or substituted with MBC values as illustrated in FIGS. 80A-80J. The $IC_{25}$ values may be determined by the horizontal dashed lines indicating 25% loss of tissue viability in FIGS. 79A-79D.

FIG. 81 is a table 8100 summarizing the LTI calculations and corresponding bactericidal doses for the bacterial experiments illustrated in FIGS. 79A-80. Notably, the bacterial pathogens are selected as those that are commonly associated with bacterial pneumonia. As illustrated, safe and effective phototherapy treatments for gram negative *P. aeruginosa* strains according to this experiment may have LTI values in a range from 1.5 to 2.5, thereby indicating LTI values for such strains may be provided with values of at least 1.5 or higher. For gram positive *S. aureus* strains, the LTI values for this experiment are lower for some of the doses than the *P. aeruginosa* strains.

FIG. 82 is a chart 8200 showing the effect of 425 nm light at various doses at killing *P. aeuriginosa* (CFU/ml) over a period of time from 0 hours, 2 hours, 4 hours, and 22.5 hours. At higher doses of light, such as 120 J/cm$^2$, the bacterial concentration actually decreases over time. Importantly, it is largely irrelevant whether the entire dosage of light (J/cm$^2$) is administered in one dose, or in a combination of smaller doses, so long as the same amount of light is administered before the bacteria rebound.

FIG. 83 is a chart 8300 showing that whether all of the light (J/cm$^2$) is administered in one dose or in a series of smaller doses, the antimicrobial effect (average CFU/ml) vs. dose (J/cm$^2$×number of treatments) is largely the same, at 8 hours and 48 hours post-administration.

FIG. 84A is a chart 8400 showing the treatment of a variety of drug-resistant bacteria (Average CFU/ml) vs. dose (J/cm$^2$) at 24 hours post-exposure. At doses of 80-120 J/cm$^2$ (a combination of two treatments of 40, 50, or 60 J/cm$^2$), all of the different drug-resistant bacterial strains were effectively killed. In this regard, the treatments described herein offer advantages over antibiotic treatments, in that a) drug resistance is not observed following treatment, and b) the treatment can be effective against drug-resistant bacteria. As shown in FIG. 84A, when the treatment was applied to a variety of drug-resistant bacteria, at doses of 80-120 J/cm$^2$ in a combination of two treatments of 40, 50, or 60 J/cm$^2$, all of the different drug-resistant bacterial strains were effectively killed.

FIG. 84B is a table 8410 summarizing the bacteria species and strains that were tested. ATCC refers to American Type Culture Collection. BcRLR refers to *Burkholderia cepacia* Research Laboratory and Repository provided by Dr. John LiPuma of the University of Michigan. MDR refers to multidrug resistant, e.g., resistant to 3 classes of antibiotics. XDR refers to extremely drug resistant, e.g., resistant to 5 classes of antibiotics, such as amikacin (AMK), aztreonam (ATM), cefepime (FEP), ceftazidime (CAZ), ceftazidime-avibactam (CZA), ceftolozane-tazobactam (C/T), ciprofloxacin (CIP), colistin (CST), doripenem (DOR), gentamicin (GEN), imipenem (IPM), levofloxacin (LVX), meropenem (MEM), piperacillin-tazobactam (TZP), or tobramycin (TOB).

FIG. 84C is a table 8420 that summarizes the efficacy of twice daily dosing of 425 nm light against difficult-to-treat clinical lung pathogens. Bactericidal doses are in PBS and for a 3-log reduction relative to dark control samples. MIC doses are in broth with no change in CFU/ml relative to starting CFU/ml. MBC doses are in broth and for a 3-log reduction in CFU/ml relative to dark control samples. Accordingly, one can use the treatments described herein to deliver safe and effective antimicrobial treatments to a number of different bacterial infections, including those caused by drug-resistant bacteria. Additionally, illumination devices and treatments as disclosed herein may provide multiple pathogenic benefits (e.g., for viruses, bacteria, and fungi) with single wavelength and/or multiple wavelength light treatments.

While various details of the above described devices and corresponding light impingement for inducing one or more biological effects have been provided, the exemplary devices may include other elements and characteristics. In certain embodiments, the devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although various modules may be provided as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive sensor data to be transformed, transform the sensor data, output a result of the transformation to control impingement of light onto living tissue, use the result of the transformation to control impingement of nitric-oxide modulating light onto living tissue, and/or store the result of the transformation to control impingement of nitric-oxide modulating light onto living tissue. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

In addition to the above-described illumination devices, the principles of the present disclosure are applicable to other devices, and kits including these devices, for treating, preventing, or reducing the biological activity of microbes present in or near the oral cavity and/or auditory canal (i.e., mouth, nose and ears), as well as the throat, larynx, pharynx, oropharynx, trachea, and esophagus, are disclosed.

Corresponding methods for treating or preventing microbial infections in the oral cavity, nasal cavity and/or ears (auditory canal), as well as the throat, larynx, pharynx, oropharynx, and esophagus, are also disclosed. Where the microbes are microbes that would result in respiratory infections when they travel from the oral cavity (which encompasses the nasal cavity) and/or auditory canal to the lungs, the devices and kits can be used to prevent such respiratory infections.

The methods involve administering light at one or more wavelengths, which are selected to a) treat the actual microbe, b) lower inflammation and/or c) improve vasculature/blood flow. Combinations of wavelengths can be used, which can, for example, inhibit microbial pathogens via one mechanism, or two or more different mechanisms, or provide a combination of antimicrobial and anti-inflammatory effects. Anti-inflammatory effects can be particularly useful to treat or prevent nasal congestion and lower the production of anti-inflammatory cytokines in the oral cavity and beyond.

Irradiances of light ($mW/cm^2$) are disclosed at a specific wavelengths of visible light for a threshold time over a given duration to yield therapeutic dosages ($J/cm^2$) which are effective for inactivating virus or treating viral infections while maintaining the viability of epithelial tissues. These treatments can be tailored to the particular tissue being treated, as well as to the various fluids in the media, such as blood, sputum, saliva, cervical fluid, and mucous. The total dosage ($J/cm^2$) to treat an infection can be spread out over multiple administrations, with each dose applied over seconds or minutes, and with multiple doses over days or weeks, at individual doses that treat the infection while minimizing damage to the particular tissue.

The present invention will be better understood with reference to the following definitions. As used herein, the oral cavity includes the part of the mouth behind the gums and teeth that is bounded above by the hard and soft palates and below by the tongue and by the mucous membrane connecting it with the inner part of the mandible. As used herein, the nasal cavity is the vaulted chamber that lies between the floor of the cranium and the roof of the mouth of higher vertebrates extending from the external nares to the pharynx, being enclosed by bone or cartilage and usually incompletely divided into lateral halves by the septum of the nose, and having its walls lined with mucous membrane that is rich in venous plexuses and ciliated in the lower part which forms the beginning of the respiratory passage and warms and filters the inhaled air and that is modified as sensory epithelium in the upper olfactory part. As used herein, the auditory canal is a tube that connects the pinna, or fleshy outer visible part of the ear, and the tympanic membrane, or eardrum.

Figure 55:
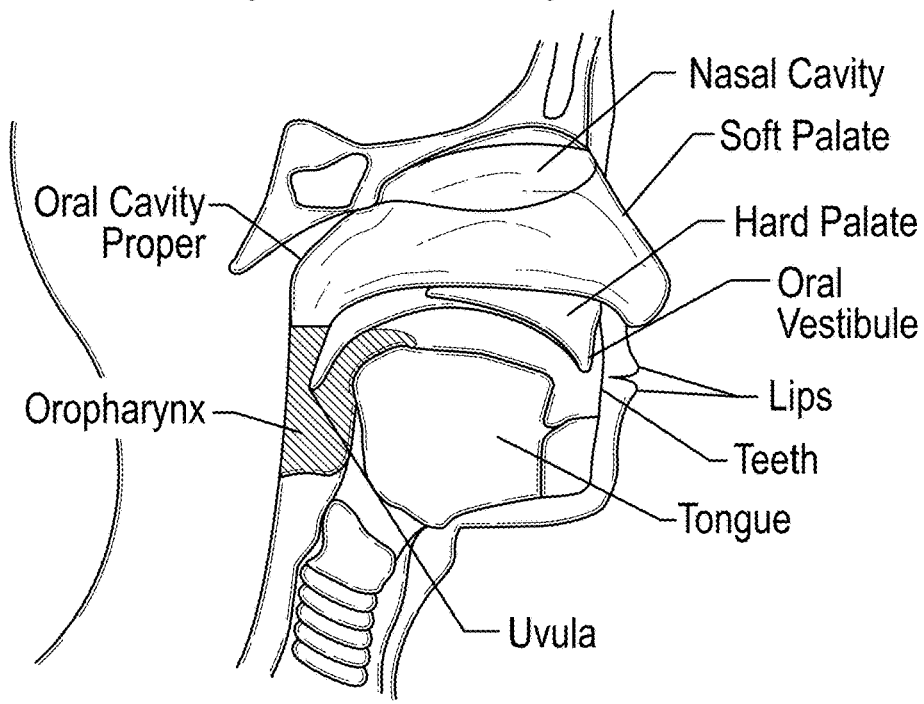

While the methods and devices described herein are described as administering light to the oral cavity, in certain embodiments it is also intended that light be administered to the throat, esophagus, larynx, pharynx, oropharynx and/or trachea. The oral cavity is illustrated in FIG. 55. As illustrated, the oropharynx is positioned as a middle portion of the throat and may include a portion of the soft palate and a portion that is connected to the oral cavity. The oropharynx may be a location for initial infection with pathogens, including bacteria, viruses, and fungi. In particular, the oropharynx may be a location for coronavirus, including the SARS-CoV-2 virus, to be positioned just after exposure and within a few days of infection. In this regard, aspects of the present disclosure, including the above-described illumination devices, may be configured for providing therapeutic light doses to the oropharynx for inactivating coronavirus in a cell-free environment at the oropharynx and surrounding tissues and/or inhibiting replication of coronavirus in a cell-associated environment at the oropharynx and surrounding tissues. With regard to all microorganisms, the principles of the present disclosure may be applicable for inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

In some embodiments, the wavelengths of light activate immune cells of the innate and/or adaptive immune responses, including macrophages.

When administering light to arrive at a suitable total dose ($J/cm^2$), it can be important to provide the therapeutic dosage of light at a suitable combination of a wavelength, irradiance ($W/cm^2$), and exposure time, and multiple exposures, at these conditions to yield total dose in $J/cm^2$.

The wavelength should be safe to the tissue being irradiated, and the irradiance should be safe to the tissue as well, ideally not heating the tissue to a temperature that is unsafe, and the cumulative exposure time should be matched with the desired clinical application. In some embodiments, the device used to administer the light can include a means for controlling the amount of light that is administered, such as a timer, actuator, dosimeter, and the like, such that the light does not exceed safe limits.

For example, light is ideally administered at a dosage that is safe and at a dosage that is effective at killing virus or other microbes. In this regard, aspects of the present disclosure provide a ratio of the $IC_{25}$ (the concentration or dose required to reduce tissue living viability by 25% when compared to control-treated tissues) to the $EC_{50}$ (dose required to kill 50% of the virus or other microbe for the specific tissue being treated as quantified at a cellular level) that is greater than or equal to 2. As disclosed herein, the $IC_{25}/EC_{50}$ ratio or fraction may be referred to as a light therapeutic index (LTI) that quantifies safe and effective light dosages. In another context, one can consider, in an in vitro setting, the ratio of the $CC_{50}$ (concentration of a therapeutic to reduce cell viability by 50%) to the $EC_{50}$ for treated cells (i.e., the Selectivity Index, or "SI"). This ratio will vary depending on the type of cells or tissue that are exposed, for example, with some cells having differential tolerance to oxidative damage than other cells.

In some embodiments, the light is administered at UVA (320-400 nm), UVB (280-320 nm), and/or UVC (200-280 nm) wavelengths. Of these, it is believed that UVC (wavelengths of 200-280 nm) may be most germicidal. UVC is absorbed by RNA and DNA bases in the microbes and can cause the photochemical fusion of two adjacent pyrimidines into covalently linked dimers, which then become non-pairing bases. UVB can also cause the induction of pyrimidine dimers, but less efficiently than UVC. UVA is weakly absorbed by DNA and RNA, and is much less effective than UVC and UVB in inducing pyrimidine dimers, but is believed to cause additional genetic damage through the production of reactive oxygen species, which cause oxidization of bases and strand breaks.

Nitric oxide is also known to be antimicrobial. The precise mechanisms by which nitric oxide (NO) kills or inhibits the replication of a variety of intracellular pathogens is not completely understood. However, it appears that the cysteine proteases are targeted. NO S-nitrosylates the cysteine residue in the active site of certain viral proteases, inhibiting protease activity and interrupting the viral life cycle. Since cysteine proteases are critical for virulence or replication of many viruses, bacteria, and parasites, NO production and release can be used to treat microbial infections. Accordingly, in some embodiments, light is administered at wavelengths effective for enhancing endogenous NO production and/or release. These wavelengths are discussed in more detail below.

In other embodiments, the light is administered at wavelengths that reduce inflammation. Following a viral infection, if the virus makes its way to the lungs, subjects are often susceptible to bacterial respiratory infections, including bronchitis and pneumonia. Secondary bacterial infections can be caused when bacteria that normally inhabit the nose and throat invade the lungs along a pathway created when the virus destroyed cells lining the bronchial tubes and lungs. Viral infections can also cause a "cytokine storm," where the body's immune system over-reacts and rapidly releases immune cells and inflammatory molecules. This can lead to severe inflammation. A build-up of fluid in the lungs, particularly the bronchial tubes, increases the chance of secondary infections.

Nitric oxide is endogenously stored on a variety of nitrosated biochemical structures. Upon receiving the required excitation energy, both nitroso and nitrosyl compounds undergo hemolytic cleavage of S—N, N—N, or M-N bonds to yield free radical nitric oxide. Nitrosothiols and nitrosamines are photoactive and can be phototriggered to release nitric oxide by wavelength specific excitation.

It has been reported that NO may diffuse in mammalian tissue by a distance of up to about 500 microns. In certain embodiments, photons of a first energy hυ1 may be supplied to the tissue to stimulate enzymatic generation of NO to increase endogenous stores of NO in a first diffusion zone 1. Photons of a second energy hυ2 may be supplied to the tissue in a region within or overlapping the first diffusion zone 1 to trigger release of NO from endogenous stores, thereby creating a second diffusion zone 2. Alternatively, or additionally, photons of a second energy hυ2 may be supplied to stimulate enzymatic generation of NO to increase endogenous stores of NO in the second diffusion zone 2. Photons of a third energy hυ3 may be supplied to the tissue in a region within or overlapping the second diffusion zone 2 to trigger release of endogenous stores, thereby creating a third diffusion zone 3. Alternatively, or additionally, photons of a third energy hυ3 may be supplied to stimulate enzymatic generation of NO to increase endogenous stores of NO in the third diffusion zone 3. In certain embodiments, the first, second, and third diffusion zones 1-3 may have different average depths relative to an outer epidermal surface. In certain embodiments, the first photon energy hυ1, the second photon energy hυ2, and the third photon energy hυ3 may be supplied at different peak wavelengths, wherein different peak wavelengths may penetrate mammalian skin to different depths—since longer wavelengths typically provide greater penetration depth. In certain embodiments, sequential or simultaneous impingement of increasing wavelengths of light may serve to "push" a nitric oxide diffusion zone deeper within mammalian tissue than might otherwise be obtained by using a single (e.g., long) wavelength of light.

Light having a first peak wavelength and a first radiant flux that stimulates enzymatic generation of nitric oxide to increase endogenous stores of nitric oxide may be referred to herein as endogenous store increasing light or ES increasing light. Light having a first peak wavelength and a first radiant flux to release nitric oxide from the endogenous stores may be referred to herein as endogenous store releasing light or ES releasing light. Light having anti-inflammatory effects may be referred to herein as anti-inflammatory light.

In certain embodiments, light at two or three peak wavelengths is used, including one peak wavelength to provide an anti-inflammatory effect, in combination with a peak wavelength of ES releasing light and/or a peak wavelength of ES increasing light. In other embodiments, in place of, or in addition to, ES increasing or ES releasing light, light at one or more wavelengths in the UVA, UVB, or UVC ranges are used.

Embodiments of the present disclosure may be used to treat a variety of viral infections. Representative viruses include Betacoronavirus (SARS-COV-2 and MERS-COV), Coronavirus, Picornavirus, influenza virus (A and B), the common cold, respiratory syncytial virus (RSV), adenovirus, parainfluenza, Legionnaire's disease, rhinoviruses, Epstein-Barr virus (EBV) (also known as human herpesvirus 4), and SARS. In addition to viruses associated with respiratory infections, causing bronchitis, sinusitis, and/or pneumonia, the human papilloma virus (HPV) is associated with certain throat cancers and laryngeal papillomas. The following is a list of viruses, one or more of which can lead to infection when virus particles enter the body through the mouth, nose, or ears, and travel to the respiratory system or gastrointestinal tract, or which can cause an infection when they are located in the mouth, nose or ears: Togaviridae, including the genus Alphavirus, examples of which include Chikungunya, Semliki Forest, Eastern equine encephalitis, Venezuelan equine encephalitis, and Western equine encephalitis; Reoviridae, including the genuses Cardiovirus and Reovirus, examples of which include Reo- and Rotaviruses; Poxviridae, including the genus Orthopoxvirus, examples of which include cowpox and Vaccinia; Picornaviridae, including the genuses Enterovirus, Cardiovirus, and Rhinovirus, examples of which include Enterovirus 71, Poliovirus Type 1, Poliovirus Type 3, Encephalomyocarditis, and ECHO 12; Phenuiviridae, including the genus Phlebovirus, examples of which include Sandfly fever, Heartland, Punta Tory, ZH501 and MP-12 viruses; Paramyxoviridae, including the genuses Morbillivirus, Respirovirus, and Pneumovirus, examples of which include Measles, Parainfluenza and RSV; Orthomyxoviridae, including the genuses Alphainfluenzavirus and Influenzavirus B, examples of which include Influenza A and Influenza B; Herpesviridae, including the genus Simplexvirus, of which herpes is an example, Hantaviridae, including the genus Orthohantavirus, of which Dobrava, Hantaan, Sin Nombre, Andes, and Maporal are examples; Coronaviridae, including the genuses Coronavirus and Betacoronavirus, examples of which include Middle Eastern Respiratory Syndrome (MERS-CoV), Corona, Sudden Acute Respiratory Syndrome (SARS-CoV), Sudden Acute Respiratory Syndrome Coronavirus 2 (SARS-CoV-2), and Covid-19; Caliciviridae, including the genus Norovirus; Arenaviridae, including the genus Arenavirus, examples of which include Junin, Tacaribe, Pichinde, and Lymphocytic choriomeningitis; and Adenoviridae, including the genus Mastadenovirus, of which adenovirus is an example. The methods described herein also include treating or preventing the individual viral infections listed above.

Currently, there are 5 recognized orders and 47 families of RNA viruses, and there are also many unassigned species and genera. Related to but distinct from the RNA viruses are the viroids and the RNA satellite viruses.

There are several main taxa: levivirus and related viruses, picornaviruses, alphaviruses, flaviviruses, dsRNA viruses, and the -ve strand viruses Positive strand RNA viruses are the single largest group of RNA viruses, with 30 families. Of these, there are three recognized groups. The picorna group (Picornavirata) includes bymoviruses, comoviruses, nepoviruses, nodaviruses, picornaviruses, potyviruses, obemoviruses and a subset of luteoviruses (beet western yellows virus and potato leafroll virus). The flavi-like group (Flavivirata) includes carmoviruses, dianthoviruses, flaviviruses, pestiviruses, statoviruses, tombusviruses, single-stranded RNA bacteriophages, hepatitis C virus and a subset of luteoviruses (barley yellow dwarf virus). The alpha-like group (Rubivirata) includes alphaviruses, carlaviruses, furoviruses, hordeiviruses, potexviruses, rubiviruses, tobraviruses, tricornaviruses, tymoviruses, apple chlorotic leaf spot virus, beet yellows virus and hepatitis E virus.

A division of the alpha-like (Sindbis-like) supergroup has been proposed, with two proposed groups. The 'altovirus' group includes alphaviruses, furoviruses, hepatitis E virus, hordeiviruses, tobamoviruses, tobraviruses, tricornaviruses and rubiviruses, and the 'typovirus' group includes apple chlorotic leaf spot virus, carlaviruses, potexviruses and tymoviruses. There are five groups of positive-stranded RNA viruses containing four, three, three, three, and one order(s), respectively. These fourteen orders contain 31 virus families (including 17 families of plant viruses) and 48 genera (including 30 genera of plant viruses). Alphaviruses and flaviviruses can be separated into two families, the Togaviridae and Flaviridae. This analysis also suggests that the dsRNA viruses are not closely related to each other but instead belong to four additional classes, Birnaviridae, Cystoviridae, Partitiviridae, and Reoviridae, and one additional order (Totiviridae) of one of the classes of positive ssRNA viruses in the same subphylum as the positive-strand RNA viruses. There are two large clades: One includes the families Caliciviridae, Flaviviridae, and Picornaviridae and a second that includes the families Alphatetraviridae, Birnaviridae, Cystoviridae, Nodaviridae, and Permutotretraviridae. Satellite viruses include Albetovirus, Aumaivirus, Papanivirus, Virtovirus, and Sarthroviridae, which includes the genus Macronovirus. Double-stranded RNA viruses (dsRNA viruses) include twelve families and a number of unassigned genera and species recognized in this group. The families include Amalgaviridae, Birnaviridae, Chrysoviridae, Cystoviridae, Endornaviridae, Hypoviridae, Megabirnaviridae, Partitiviridae, Picobirnaviridae, Reoviridae, which includes Rotavirus, Totiviridae, Quadriviridae. Botybirnavirus is one genus, and unassigned species include *Botrytis porri* RNA virus 1, *Circulifer tenellus* virus 1, *Colletotrichum camelliae* filamentous virus 1, Cucurbit yellows associated virus, *Sclerotinia sclerotiorum* debilitation-associated virus, and *Spissistilus festinus* virus 1. Positive-sense ssRNA viruses (Positive-sense single-stranded RNA viruses) include three orders and 34 families, as well as a number of unclassified species and genera. The order Nidovirales includes the families Arteriviridae, Coronaviridae, which includes Coronaviruses, such as SARS-CoV and SARS-CoV-2, Mesoniviridae and Roniviridae. The order Picornavirales includes families Dicistroviridae, Iflaviridae, Marnaviridae, Picornaviridae, which includes Poliovirus, Rhinovirus (a common cold virus), and Hepatitis A virus, Secoviridae, which includes the subfamily Comovirinae, as well as the genus Bacillariornavirus and the species Kelp fly virus. The order Tymovirales includes the families Alphaflexiviridae, Betaflexiviridae, Gammaflexiviridae, and Tymoviridae. A number of families are not assigned to any of these orders, and these include Alphatetraviridae, Alvernaviridae, Astroviridae, Barnaviridae, Benyviridae, Botourmiaviridae, Bromoviridae, Caliciviridae, which includes the Norwalk virus (i.e., norovirus), Carmotetraviridae, Closteroviridae, Flaviviridae, which includes Yellow fever virus, West Nile virus, Hepatitis C virus, Dengue fever virus, and Zika virus, Fusariviridae, Hepeviridae, Hypoviridae, Leviviridae, which includes Barley yellow dwarf virus, Polycipiviridae, Narnaviridae, Nodaviridae, Permutotetraviridae, Potyviridae, Sarthroviridae, Statoviridae, Togaviridae, which includes Rubella virus, Ross River virus, Sindbis virus, and Chikungunya virus, Tombusviridae, and Virgaviridae. Unassigned genuses include Blunervirus, Cilevirus, Higrevirus, Idaeovirus, Negevirus, Ourmiavirus, Polemovirus, Sinaivirus, and Sobemovirus. Unassigned species include *Acyrthosiphon pisum* virus, Bastrovirus, Blackford virus, Blueberry necrotic ring blotch virus, Cadicistrovirus, Chara *australis* virus, Extra small virus, Goji berry chlorosis virus, *Harmonia axyridis* virus 1, Hepelivirus, Jingmen tick virus, Le Blanc virus, Nedicistrovirus, Nesidiocoris *tenuis* virus 1, Niflavirus, Nylanderia *fulva* virus 1, Orsay virus, Osedax *japonicus* RNA virus 1, Picalivirus, Planarian secretory cell nidovirus, Plasmopara *halstedii* virus, Rosellinia necatrix fusarivirus 1, Santeuil virus. Secalivirus, *Solenopsis invicta* virus 3, and Wuhan large pig roundworm virus.

Satellite viruses include the family Sarthroviridae and the genuses Albetovirus, Aumaivirus, Papanivirus, Virtovirus, and the Chronic bee paralysis virus. Six classes, seven orders and twenty-four families are currently recognized in this group. A number of unassigned species and genera are yet to be classified Negative-sense ssRNA viruses (Negative-sense single-stranded RNA viruses) are, with the exception of the Hepatitis D virus, within a single phylum, Negarnaviricota, with two subphyla, Haploviricotina and Polyploviricotina, with four classes, Chunqiuviricetes, Milneviricetes, Monjiviricetes and Yunchangviricetes. The subphylum Polyploviricotina has two classes, Ellioviricetes and Insthoviricetes.

There are also a number of unassigned species and genera. The Phylum Negarnaviricota includes Subphylum Haploviricotina, Class Chunqiuviricetes, Order Muvirales, Family Qinviridae. The Class Milneviricetes includes Order Serpentovirales and Family Aspiviridae. The Class Monjiviricetes includes Order Jingchuvirales and Family Chuviridae. The order Mononegavirales includes families Bornaviridae, which includes the Borna disease virus, Filoviridae, which includes the Ebola virus and the Marburg virus, Mymonaviridae, Nyamiviridae, Paramyxoviridae, which includes Measles, Mumps, Nipah, Hendra, and NDV, Pneumoviridae, which RSV and Metapneumovirus, Rhabdoviridae, which Rabies, and Sunviridae, as well as genuses Anphevirus, Arlivirus, Chengtivirus, Crustavirus, and Wastrivirus. Class Yunchangviricetes includes order Goujianvirales and family Yueviridae. Subphylum Polyploviricotina includes class Ellioviricetes, order Bunyavirales, and the families Arenaviridae, which includes Lassa virus, Cruliviridae, Feraviridae, Fimoviridae, Hantaviridae, Jonviridae, Nairoviridae, Peribunyaviridae, Phasmaviridae, Phenuiviridae, Tospoviridae, as well as genus Tilapineviridae.

Class Insthoviricetes includes order Articulavirales and family Amnoonviridae, which includes the Taastrup virus, and family Orthomyxoviridae, which includes Influenza viruses. The genus Deltavirus includes the Hepatitis D virus.

Specific viruses include those associated with infection of mucosal surfaces of the respiratory tract, including Betacoronavirus (SARS-COV-2 and MERS-COV), rhinoviruses, influenza virus (including influenza A and B), parainfluenza,). Generally, orthomyxoviruses and paramyxoviruses can be treated.

A DNA virus is a virus that has DNA as its genetic material and replicates using a DNA-dependent DNA polymerase. The nucleic acid is usually double-stranded DNA (dsDNA) but may also be single-stranded DNA (ssDNA). DNA viruses belong to either Group I or Group II of the Baltimore classification system for viruses. Single-stranded DNA is usually expanded to double-stranded in infected cells. Although Group VII viruses such as hepatitis B contain a DNA genome, they are not considered DNA viruses according to the Baltimore classification, but rather reverse transcribing viruses because they replicate through an RNA intermediate. Notable diseases like smallpox, herpes, and the chickenpox are caused by such DNA viruses.

Some have circular genomes (Baculoviridae, Papovaviridae and Polydnaviridae) while others have linear genomes (Adenoviridae, Herpesviridae and some phages). Some families have circularly permuted linear genomes (phage T4 and some Iridoviridae). Others have linear genomes with covalently closed ends (Poxviridae and Phycodnaviridae).

Fifteen families are enveloped, including all three families in the order Herpesvirales and the following families: Ascoviridae, Ampullaviridae, Asfarviridae, Baculoviridae, Fuselloviridae, Globuloviridae, Guttaviridae, Hytrosaviridae, Iridoviridae, Lipothrixviridae, Nimaviridae and Poxviridae.

Of these, species of the order Herpesvirales, which includes the familes Alloherpesviridae, Herpesviridae, which includes human herpesviruses and the Varicella Zoster, and the families Adenoviridae, which includes viruses which cause human adenovirus infection, and Malacoherpesviridae, infect vertebrates.

Asfarviridae, which includes African swine fever virus, Iridoviridae, Papillomaviridae, Polyomaviridae, which includes Simian virus 40, JC virus, and BK virus, and Poxviridae, which includes Cowpox virus and smallpox, infect vertebrates. Anelloviridae and Circoviridae also infect animals (mammals and birds respectively).

The family Smacoviridae includes a number of single-stranded DNA viruses isolated from the feces of various mammals, and there are 43 species in this family, which includes six genera, namely, Bovismacovirus, Cosmacovirus, Dragsmacovirus, Drosmacovirus, Huchismacovirus and Porprismacovirus. Circo-like virus Brazil hs1 and hs2 have also been isolated from human feces. An unrelated group of ssDNA viruses includes the species bovine stool associated circular virus and chimpanzee stool associated circular virus.

Animal viruses include parvovirus-like viruses, which have linear single-stranded DNA genomes, but unlike the parvoviruses, the genome is bipartate. This group includes Hepatopancreatic parvo-like virus and Lymphoidal parvo-like virus. Parvoviruses have frequently invaded the germ lines of diverse animal species including mammals.

The human respiratory-associated PSCV-5-like virus has been isolated from the respiratory tract.

Embodiments of the present disclosure may be used to treat a variety of bacterial infections. Examples of pathogens that can be treated include *Haemophilus influenzae, Pseudomonas aeruginosa, Acinetobacter baumannii, Staphylococcus aureus, Staphylococcus warneri, Staphylococcus lugdunensis, Staphylococcus epidermidis, Streptococcus milleri/anginous, Streptococcus pyogenes*, vancomycin-resistant enterococci, nontuberculosis *mycobacterium, Mycobacterium tuberculosis, Burkholderia* spp., *Achromobacter xylosoxidans*, Pandoraeasputorum, *Stenotrophomonas maltophilia, Alcaligenes xylosoxidans, Haemophilus pittmaniae, Serratia marcescens, Candida albicans*, drug resistant *Candida albicans, Candida glabrata, Candida krusei, Candida guilliermondii, Candida auris, Candida tropicalis, Aspergillus niger, Aspergillus terreus, Aspergillus fumigatus, Aspergillus flavus, Morganella morganii, Inquilinus limosus, Ralstonia mannitolilytica, Pandoraea apista,*

*Pandoraea pnomenusa, Pandoraea sputorum, Bdellovibrio bacteriovorus, Bordetella bronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonasmendocina, Pseudomonas pseudoalcaligenes, Pseudomonas putida, Pseudomonas stutzeri, Ralstonia insidiosa, Ralstonia pickettii,* Neisseriagonorrhoeae, NDM-1 positive *E. coli, Enterobacter* cloaca, Vancomycin-resistant *E. faecium*, Vancomycin-resistant *E. faecalis, E. faecium, E. faecalis,* Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter, Agrobacterium; Bordetella; Brevundimonas; Chryseobacterium; Delftia; Enterobacter; Klebsiella; Pandoraea; Pseudomonas; Ralstonia,* and *Prevotella*. Representative non-tuberculosis mycobacterium include *Mycobacterium abscessus, Mycobacterium avium, Mycobacteriumintracellulare, Mycobacterium fortuitum, Mycobacterium gordonae, Mycobacterium kansasii, Mycobacterium avium complex, Mycobacteriummarinum, Mycobacterium terrae* and *Mycobacterium cheloni*. Representative *Burkholderia* spp. include *Burkholderia cepacia, Burkholderia cepacia* complex, *Burkholderia multivorans, Burkholderia cenocepacia, Burkholderia stabilis, Burkholderia vietnamiensis, Burkholderia dolosa, Burkholderia ambifaria, Burkholderia anthina, Burkholderia pyrrocinia, Burkholderia gladioli, Burkholderia ubonensis, Burkholderia arboris, Burkholderia latens, Burkholderia lata, Burkholderia metallica, Burkholderia seminalis, Burkholderia contaminans,* and *Burkholderia diffusa.* In some embodiments, the bacteria may be drug resistant, and in some aspects of these embodiments, the bacteria may be multi-drug resistant. For example, the bacteria may be resistant to antibiotics such as amikacin, aztreonam, methicillin, vancomycin, nafcillin, gentamicin, ampicillin, chloramphenicol, doxycycline, colistin, delamanid, pretomanid, clofazimine, bedaquiline, and/or tobramycin. While these bacteria may develop resistance to these drugs, they cannot, however, easily develop resistance to the phototherapy-based approaches described herein.

Embodiments of the present disclosure may be used to treat a variety of fungal infections. Representative fungal infections that can be treated include *Candida albicans*, drug resistant *Candida albicans, Candida glabrata, Candida krusei, Candida guilliermondii, Candida auris, Candidatropicalis, Aspergillus niger, Aspergillus terreus, Aspergillus fumigatus,* and/or *Aspergillus flavus.*

The light delivery methods described herein can be used to treat, prevent, manage or lessen the severity of symptoms and infections associated with one or more infections in the oral cavity, auditory canal, throat, larynx, pharynx, oropharynx, trachea, and/or esophagus, and/or to prevent pulmonary infections in a subject.

In some embodiments, the methods can treat an existing microbial infection with light, where the infection is in mucosal surfaces in the oral cavity, including the nasal cavity, and has not progressed to the lungs. In this respect, while the microbial infection is locally treated in these areas, it is also a post-infection prophylaxis of lung infection.

In some aspects, this treatment (or post-infection prophylaxis) operates via a nitric oxide dependent mechanism, and in other embodiments, it operates via a mechanism that is not nitric oxide dependent. In still other aspects, combinations of wavelengths are used, such that the treatment involves both types of mechanisms.

In still other embodiments, exposure to light prevents infection from occurring, by using light to boost a subject's innate immune response to microbial pathogens.

In some aspects, this boosting of the immune system operates via a nitric oxide dependent mechanism, and in other embodiments, it operates via a mechanism that is not nitric oxide dependent. In still other aspects, combinations of wavelengths are used, such that the treatment involves both types of mechanisms.

In some embodiments, the disclosed methods involve preventing infection by directly killing microbial pathogens with light. In these embodiments, the light may act on the microorganisms and not only the host.

In still other embodiments, phototherapy is used in combination with antimicrobial agents, as described herein. Depending on the type of microbial infection, this may entail combining phototherapy with antibiotics, antifungals, or antivirals. In some embodiments, the combination therapy is synergistic, rather than merely additive, as the phototherapeutic approach may render the microbe more susceptible to the antimicrobial compounds.

In some aspects, antimicrobial photodynamic inactivation is performed, using rationally designed photosensitizers combined with visible light, optionally also using potentiation by inorganic salts, such as potassium iodide. Representative photosensitizers include cationic porphyrins, chlorins, bacteriochlorins, phthalocyanines, phenothiazinium dyes, fullerenes, BODIPY-dyes, as well as some natural products. Specific examples include meso-tetra (N-methyl-4-pyridyl) porphine tetra tosylate (TMP), toluidineblue O, Photofrin, and methylene blue (MB). Representative wavelengths, photosensitizers, and salts are disclosed, for example, in and Hamblin and A brahamse, Drug Dev Res. 2019; 80:48-67.

In other aspects, porphyrins already present within microbial cells are activated by blue or violet light, and the activation of these endogenous photoactive porphyrins is effective to eliminate the microbial cells.

In other aspects, UVC light is used at wavelengths between 200 nm and 230 nm that can kill microbial cells without damaging host mammalian cells. These wavelengths can be effective against multidrug resistant bacteria, and the photochemical pathway does not induce resistance. Further, localized infections can be monitored by non-invasive bioluminescence imaging.

In other embodiments, the phototherapy serves to decrease inflammation associated with infections. In some aspects of these embodiments, in addition to or in lieu of treating the root cause of the microbial infection, the treatment provides symptomatic relief. In other aspects of these embodiments, the phototherapy decreases inflammation caused by viruses as part of their processes to multiply and divide. For example, this can involve inhibiting NF-kB and/or caspase used by Coronavirus to amplify transmission.

In some embodiments, the term "preventing" relates to preventing an infection from occurring at all. In other embodiments, preventing relates to post-exposure prophylaxis, also known as post-exposure prevention (PEP), which refers to a preventive medical treatment started after exposure to a pathogen, in order to prevent the infection from occurring. In the context of respiratory infections, post-exposure prevention refers to preventing a respiratory infection following infection of the oral cavity, auditory canal, throat, larynx, pharynx, trachea, and/or esophagus.

The methods involve administering one or more wavelengths of light to the subject, to the oral cavity, auditory canal, throat, larynx, pharynx, oropharynx, trachea, and/or esophagus. In some embodiments, the wavelengths are antimicrobial. In other embodiments, the wavelengths reduce inflammation or increase vascularization. Combinations of wavelengths can be used, and the wavelengths can be administered serially or simultaneously.

Light can be administered to the auditory canal, oral cavity, including the mouth and nasal passages, and/or to the throat, esophagus, larynx, pharynx, oropharynx, and trachea, and combinations thereof.

In some embodiments, UVC light is used to treat or prevent microbial infections, including those caused by viruses such as coronavirus. The entire range from 200 to 400 nm may be effective. In other embodiments, UVB and/or UVA light is used. The wavelength from around 400 to around 430 nm is also effective against both viruses and bacteria. Further, as discussed herein, wavelengths of light that promote production or release of endogenous nitric oxide can be used. These wavelengths may be antimicrobial via a different pathway than the UVA/UVB/UVC wavelengths, and combinations of these wavelengths can be used to provide antimicrobial effects via a combination of pathways.

Certain bacterial infections, and all fungal infections, are associated with spores. Because most pharmaceuticals are only active against the bacteria or fungus when it is not in spore form, the treatments must take place over an extended period of time, so that the spores can become active bacteria/fungi, and then be treated with the antimicrobial agents.

Certain wavelengths of light are effective not only at killing active bacteria/fungi, but also against spores. Accordingly, using the methods described herein, one can lessen the duration of treatment. By way of example, treatment of infections such as tuberculosis or NTM (non-tuberculosis mycobacterial infections) takes around 1 year for an effective treatment, largely because of the continued presence of spores. The duration of treatment often leads to poor patient compliance. The methods described herein can be used to kill these infections before they travel to the lung, therefore minimizing treatment time, and long-term exposure to antibiotics.

Examples of pulmonary infections that can be prevented include bronchiectasis infection, pneumonia, valley fever, allergic bronchopulmonary aspergillosis (ABPA), ventilator acquired pneumonia, hospital acquired pneumonia, community acquired pneumonia, ventilator associated tracheobronchitis, lower respiratory tract infection, non-tuberculous Mycobacteria, anthrax, legionellosis, pertussis, bronchitis, Bronchiolitis, COPD-associated infection, and post-lung transplantation. In some cases, pulmonary infections that are prevented would have resulted from infection by one or more bacterial or fungal pathogens.

Where the pulmonary infections are CF-related pulmonary infections, the methods described herein can be used to prevent, manage, or lessen the severity of the CF-related pulmonary infection.

The bacterial pathogen can be a gram-positive bacteria or gram-negative bacteria and can include one or more of a bacterial biofilm and planktonic bacteria.

Light can penetrate and disrupt biofilms, so in embodiments where a bacterial biofilm is present, the methods can involve (1) reducing the bacterial biofilm, (2) impairing growth of the bacterial biofilm, and (3) preventing reformation of the bacterial biofilm.

In still other embodiments, a fungal pathogen is present, which can include planktonic fungi and/or biofilm fungi.

The methods described herein can be used to prevent, manage or lessen the severity of the pulmonary infection by one or both of: prevention of the infection by the bacterial or fungal pathogen or reduction of the bacterial or fungal pathogen before it can enter the pulmonary system, or to treat or prevent infection of the oral cavity, auditory canal, and the like, by killing microbes in these tissues.

Representative pathogens that can be killed using the phototherapeutic approaches described herein include *Haemophilus influenzae, Pseudomonasaeruginosa, Staphylococcus aureus, Staphylococcus warneri Staphylococcus lugdunensis, Staphylococcus epidermidis, Streptococcus milleri/anginous, Streptococcus pyogenes*, non-tuberculosis mycobacterium, *Mycobacterium tuberculosis, Burkholderia* spp., *Achromobacter xylosoxidans, Pandoraeasputorum, Stenotrophomonas maltophilia, Alcaligenes xylosoxidans, Haemophilus pittmaniae, Serratia marcescens, Candidia albacans, Candida parapsilosis, Candida guilliermondii, Morganella morganii, Inquilinus limosus, Ralstonia mannitolilytica, Pandoraea apista, Pandoraea pnomenusa, Pandoraea sputorum, Bdellovibrio bacteriovorus, Bordetella bronchiseptica, Vampirovibrio chlorellavorus, Actinobacter baumanni, Cupriadidus metallidurans, Cupriavidus pauculus, Cupriavidus respiraculi, Delftia acidivordans, Exophilia dermatitidis, Herbaspirillum frisingense, Herbaspirillum seropedicae, Klebsiella pneumoniae, Pandoraea norimbergensis, Pandoraea pulmonicola, Pseudomonas mendocina, Pseudomonas pseudoalcaligenes, Pseudomonas putida, Pseudomonas stutzeri, Ralstonia insidiosa, Ralstonia pickettii, Neisseria gonorrhoeae*, NDM-1 positive *E. coli, Enterobacter* cloaca, Vancomycin-resistant *E. faecium*, Vancomycin-resistant *E. faecalis, E. faecium, E. faecalis*, Clindamycin-resistant *S. agalactiae, S. agalactiae, Bacteroides fragilis, Clostridium difficile, Streptococcus pneumonia, Moraxella catarrhalis, Haemophilus haemolyticus, Haemophilus parainfluenzae, Chlamydophilia pneumoniae, Mycoplasma pneumoniae, Atopobium, Sphingomonas, Saccharibacteria, Leptotrichia, Capnocytophaga, Oribacterium, Aquabacterium, Lachnoanaerobaculum, Campylobacter, Acinetobacter; Agrobacterium; Bordetella; Brevundimonas; Chryseobacterium, Delftia; Enterobacter; Klebsiella; Pandoraea; Pseudomonas; Ralstonia*, and *Prevotella*.

Common pulmonary infections include inhalation anthrax, whooping cough (also known as pertussis, and caused by *Bordetella pertussis*), streptococcus (pneumococcus, *Streptococcus pneumoniae*), mycobacteria, including mycobacteria tuberculosis and Nontuberculous mycobacterial (NTM) lung disease (*Mycobacterium avium* complex (MAC), *M. abscessus, M. kansasii, M. malmoense, M. szulgai*, and *M. xenopi*).

The phototherapeutic approaches described herein can be combined with conventional antimicrobial therapies. For example, in addition to exposing portions of the respiratory tract to wavelengths of light, for sufficient periods of time and at sufficient energy, to treat or prevent the infections, a patient can also be administered a conventional antimicrobial agent. Examples of conventional antibiotic agents include, but are not limited to, amikacin, tobramycin, gentamicin, piperacillin, mezlocillin, ticarcillin, imipenem, ciprofloxacin, ceftazidime, aztreonam, ticarcillin-clavulanate, dicloxacillin, amoxicillin, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid, Augmentin, cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meropenem, colistimethate/Colistin, methicillin, oxacillin, nafcillin, carbenicillin, azlocillin, piperacillin and tazobactam/Zosyn, cefepime, ethambutol, rifampin, and meropenem.

These antibiotics can also be combined with compounds that bind to or adsorb bacterial toxins, which can be particularly useful where bacterial toxins result in tissue damage. By way of example, *Pseudomonas aeruginosa* produces a variety of toxins that lead to cell lysis and tissue damage in the host. Type II toxins include Exotoxin U (Exo U), which degrades the plasma membrane of eukaryotic cells, leading to lysis, phospholipase C (PLC), which damages cellular phospholipids causing tissue damage and stimulates inflammation, alkaline protease, which leads to tissue damage, cytotoxin, which damages cell membranes of leukocytes and causes microvascular damage, elastase, which destroys elastin, a protein that is a component of lung tissue, and pyocyanin, a green to blue water-soluble pigment that catalyzes the formation of tissue-damaging toxic oxygen radicals, impairs ciliary function, and stimulates inflammation. Examples of compounds that bind these toxins include polyphenols and polyanionic polymers.

Antifungals can also be co-administered where the microbe is a fungus. Representative antifungal agents which can be used include fluconazole, posaconazole, viroconazole, itraconazole, echinocandin, amphotericin, and flucytosine. The choice of an appropriate antifungal agent can be made by a treating physician, and the following is a summary of fungal pulmonary infections and their treatments.

Histoplasmosis is caused by the fungus *Histoplasma capsulatum*, and conventional treatment includes Itraconazole mild and chronic pulmonary disease, and Amphotericin B (AmB) with itraconazole for moderate-to-severe histoplasmosis.

Blastomycosis is caused by *Blastomyces dermatitidis*, and conventional treatment includes itraconazole for mild-to-moderate disease and liposomal AmB (L-AmB) followed by itraconazole for life-threatening pulmonary infections.

Sporotrichosis is caused by *Sporothrix schenckii*, and conventional treatment for mild-to-moderate pulmonary disease requires itraconazole, whereas AmB followed by itraconazole is recommended for severe disease.

Coccidioidomycosis is caused by *Coccidioides immitis* and *Coccidioides posadasii*. Immunocompetent infected hosts may not require treatment, but immunocompromised patients are treated with fluconazole or itraconazole, and, in serious cases with AmB, followed by an azole. Opportunistic fungal infections primarily cause infections in patients who tend to be immunocompromised through a congenital or acquired disease process. Representative opportunistic infections are discussed below.

Aspergillosis is caused by Aspergilli, and the associated disorders include invasive pulmonary aspergillosis (IPA), chronic necrotizing aspergillosis, Aspergilloma, and allergic bronchopulmonary aspergillosis. Conventional treatments for IPA include voriconazole, lipid-based AmB formulations, echinocandins, and posaconazole.

Cryptococcosis is an opportunistic infection seen in immunocompromised individuals, including HIV or AIDS patients and organ-transplant recipients. Conventional treatments include AmB, with or without flucytosine, followed by oral fluconazole. For immunosuppressed or immunocompetent patients exhibiting mild-to-moderate symptoms, fluconazole therapy is recommended.

Candidiasis can be caused when lung parenchyma become colonized with *Candida* species. Many critically ill patients are empirically treated with broad-spectrum antibiotics. Further clinical deterioration and lack of improvement in these cases suggest the initiation of empiric antifungal therapy. Triazole antifungals and echinocandins exhibit excellent lung penetration, so, in addition to AmB formulations, can be used to treat pulmonary candidiasis.

Mucormycosis often occurs in patients with diabetes mellitus, organ or hematopoietic stem cell transplant, neutropenia, or malignancy. Pulmonary mucormycosis is primarily observed in patients with a predisposing condition of neutropenia or corticosteroid use. Due to fungal adherence to and damage of endothelial cells, fungal angioinvasion, vessel thrombosis, and successive tissue necrosis, conventional antifungal agents have a difficult time penetrating through the lung tissue. For this reason, conventional treatment includes debridement of necrotic tissue and antifungal therapy, using AmB formulations, posaconazole, and iron chelation therapy

*Pneumocystis jirovecii* Pneumonia (PCP) occurs in patients with HIV/AIDS, hematologic and solid malignancies, organ transplant, and diseases requiring immunosuppressive agents. PCP is extremely resistant to common antifungal therapy, including AmB formulations and triazole antifungals, but can be treated with Trimethoprim/sulfamethoxazole. Second-line agents primaquine plus clindamycin, atovaquone, IV pentamidine, or dapsone.

The antifungal agents identified herein can be co-administered with the phototherapy approaches described herein. However, the use of phototherapy can lessen the duration of, and/or increase the efficacy of, such antifungal treatments. When the patient has a viral pulmonary infection, conventional antiviral agents used for such viruses can be administered. The selection of antivirals typically depends on the viral infection being treated. Influenza virus is typically treated with oseltamivir (Tamiflu), zanamivir (Relenza), or peramivir (Rapivab), and RSV with ribavirin (Virazol). Coronavirus is also being treated with Tamiflu, ribavirin, certain anti-HIV compounds, and certain interferons, including Betaferon, Alferon, Multiferon, and Wellferon.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. An illumination device comprising:
   at least one light source arranged to irradiate light on tissue within a body cavity, the light configured to induce a biological effect, the biological effect comprising at least one of altering a concentration of one or more pathogens within the body cavity and altering growth of the one or more pathogens within the body cavity;
   a light guide comprising a hollow core, wherein the light guide is configured to receive the light from the at least one light source and the hollow core defines a direct path for at least some of the light to travel entirely through the light guide without being internally reflected; and
   a light guide positioner that is configured to secure the light guide at least partially within the body cavity for providing the light to the tissue within the body cavity, wherein the light guide positioner comprises a mouthpiece that is configured to engage with one or more surfaces of an oral cavity of a user, and wherein the mouthpiece comprises one or more bite guards for protecting and securing the light guide.

2. The illumination device of claim 1, wherein the biological effect comprises both altering the concentration of the one or more pathogens within the body cavity and altering the growth of the one or more pathogens within the body cavity.

3. The illumination device of claim 1, wherein the one or more pathogens comprise at least one of a virus, a bacteria, and a fungus.

4. The illumination device of claim 1, wherein the one or more pathogens comprise coronaviridae.

5. The illumination device of claim 4, wherein the coronaviridae comprises SARS-CoV-2.

6. The illumination device of claim 1, wherein the biological effect further comprises at least one of upregulating a local immune response within the body cavity, stimulating at least one of enzymatic generation of nitric oxide to increase endogenous stores of nitric oxide, and releasing nitric oxide from endogenous stores of nitric oxide.

7. The illumination device of claim 1, wherein the biological effect comprises inactivating the one or more pathogens that are in a cell-free environment in the body cavity.

8. The illumination device of claim 1, wherein the biological effect comprises inhibiting replication of the one or more pathogens that are in a cell-associated environment in the body cavity.

9. The illumination device of claim 1, further comprising a tongue depressor that is configured to depress the user's tongue for providing the light to the oropharynx.

10. The illumination device of claim 9, wherein the tongue depressor is formed by a portion of the light guide.

11. The illumination device of claim 1, further comprising a housing that includes the at least one light source and wherein the light guide and the light guide positioner are configured to be removably attached to the housing.

12. The illumination device of claim 1, further comprising a port that is configured to at least one of charge the illumination device and access data that is stored in the illumination device.

13. The illumination device of claim 1, wherein the light includes a first light characteristic comprising a peak wavelength in a range of 410 nanometers (nm) to 440 nm.

14. The illumination device of claim 1, wherein irradiating the light to the tissue within the body cavity comprises administering a dose of light in a range from 0.5 joules per square centimeter (J/cm$^2$) to 100 J/cm$^2$.

15. The illumination device of claim 1, wherein irradiating the light to the tissue within the body cavity comprises administering a dose of light with a light therapeutic index in a range from 2 to 250, the light therapeutic index being defined as a dose concentration that reduces tissue viability by 25% divided by a dose concentration that reduces cellular percentage of the one or more pathogens by 50%.

16. An illumination device comprising:
    at least one light source arranged to irradiate light on tissue of an oropharynx of a user to induce a biological effect, the biological effect comprising at least one of altering a concentration of one or more pathogens and altering growth of the one or more pathogens;
    a mouthpiece that is configured to engage with one or more surfaces of an oral cavity of the user; and
    a light guide comprising light-blocking walls that define boundaries of a hollow light transmissive pathway that provides a direct path through the light guide for the light, wherein a portion of the light guide forms a tongue depressor that is configured to depress the user's tongue for providing the light to the oropharynx.

17. The illumination device of claim 16, wherein the biological effect comprises altering the concentration of the one or more pathogens and altering the growth of the one or more pathogens.

18. The illumination device of claim 16, wherein the one or more pathogens comprise at least one of a virus, a bacteria, and a fungus.

19. The illumination device of claim 16, wherein the one or more pathogens comprise coronaviridae.

20. The illumination device of claim 19, wherein the coronaviridae comprises SARS-CoV-2.

21. The illumination device of claim 16, wherein the biological effect further comprises at least one of upregulating a local immune response, stimulating at least one of enzymatic generation of nitric oxide to increase endogenous stores of nitric oxide, and releasing nitric oxide from endogenous stores of nitric oxide.

22. The illumination device of claim 16, wherein the mouthpiece is configured to expand the oral cavity of the user.

23. The illumination device of claim 16, wherein the mouthpiece is configured to be removably attached to the light guide.

24. The illumination device of claim 16, wherein the mouthpiece comprises one or more bite guards for protecting and securing the light guide.

25. The illumination device of claim 16, wherein the light comprises a peak wavelength in a range from 410 nanometers (nm) to 440 nm and irradiating the light on the tissue of the oropharynx comprises administering a dose of light in a range from 0.5 joules per square centimeter (J/cm$^2$) to 100 J/cm$^2$.

26. The illumination device of claim 16, wherein the one or more pathogens comprise coronaviridae and irradiating the light on the tissue of the oropharynx comprises administering a dose of light with a light therapeutic index in a range from 2 to 250, the light therapeutic index being defined as a dose concentration that reduces tissue viability by 25% divided by a dose concentration that reduces cellular percentage of the one or more pathogens by 50%.

27. The illumination device of claim 16, wherein the mouthpiece and the light guide are parts of a single structure.

* * * * *

UNITED STATES PATENT AND TRADEMARK OFFICE
CERTIFICATE OF CORRECTION

PATENT NO. : 11,147,984 B2
APPLICATION NO. : 17/117889
DATED : October 19, 2021
INVENTOR(S) : David T. Emerson et al.

Page 1 of 1

It is certified that error appears in the above-identified patent and that said Letters Patent is hereby corrected as shown below:

In the Specification

Column 76, Line 17, replace "resistant to 3 classes of antibiotics" with --resistant to $\geq 3$ classes of antibiotics--.
Column 76, Lines 18-19, replace "resistant to 5 classes of antibiotics" with --resistant to $\geq 5$ classes of antibiotics--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*